United States Patent
Merighi et al.

(10) Patent No.: US 9,758,803 B2
(45) Date of Patent: Sep. 12, 2017

(54) MICROORGANISMS AND METHODS FOR PRODUCING SIALYLATED AND N-ACETYLGLUCOSAMINE-CONTAINING OLIGOSACCHARIDES

(71) Applicant: Glycosyn LLC, Waltham, MA (US)

(72) Inventors: Massimo Merighi, Somerville, MA (US); Matthew Ian Heidtman, Brighton, MA (US); John M. McCoy, Reading, MA (US)

(73) Assignee: Glycosyn LLC, Woburn, MA (US)

( * ) Notice: Subject to any disclaimer, the term of this patent is extended or adjusted under 35 U.S.C. 154(b) by 0 days.

(21) Appl. No.: 14/776,216

(22) PCT Filed: Mar. 14, 2014

(86) PCT No.: PCT/US2014/029804
§ 371 (c)(1),
(2) Date: Sep. 14, 2015

(87) PCT Pub. No.: WO2014/153253
PCT Pub. Date: Sep. 25, 2014

(65) Prior Publication Data
US 2016/0024543 A1  Jan. 28, 2016

Related U.S. Application Data

(60) Provisional application No. 61/782,999, filed on Mar. 14, 2013.

(51) Int. Cl.
| | | |
|---|---|---|
| *C07H 5/04* | (2006.01) | |
| *C12P 19/02* | (2006.01) | |
| *C12N 1/20* | (2006.01) | |
| *C12N 15/00* | (2006.01) | |
| *C07K 14/245* | (2006.01) | |
| *C12P 19/04* | (2006.01) | |
| *C12P 19/18* | (2006.01) | |
| *C12P 19/26* | (2006.01) | |
| *C12N 9/10* | (2006.01) | |
| *C12N 15/52* | (2006.01) | |
| *C07H 1/00* | (2006.01) | |
| *C07H 13/04* | (2006.01) | |
| *C07H 5/06* | (2006.01) | |

(52) U.S. Cl.
CPC ............. *C12P 19/02* (2013.01); *C07H 1/00* (2013.01); *C07H 5/06* (2013.01); *C07H 13/04* (2013.01); *C07K 14/245* (2013.01); *C12N 9/1051* (2013.01); *C12N 9/1081* (2013.01); *C12N 15/52* (2013.01); *C12P 19/04* (2013.01); *C12P 19/18* (2013.01); *C12P 19/26* (2013.01)

(58) Field of Classification Search
CPC .. C07H 1/00; C07H 13/04; C07H 5/06; Y02P 20/52; C07K 14/245; C12P 19/04; C12P 19/02; C12P 19/26; C12P 19/18; C12N 9/1051; C12N 9/1081; C12N 15/52

USPC ................. 536/55.2; 435/105, 252.8, 320.1
See application file for complete search history.

(56) References Cited

U.S. PATENT DOCUMENTS

| | | |
|---|---|---|
| 8,507,227 B2 | 8/2013 | Samain |
| 9,029,136 B2 | 5/2015 | Heidtman et al. |
| 9,453,230 B2 | 9/2016 | Merighi et al. |
| 2008/0145899 A1 | 6/2008 | Johnson et al. |
| 2008/0153133 A1* | 6/2008 | Boddy ................ C07K 14/245 435/84 |
| 2009/0082307 A1 | 3/2009 | Samain et al. |
| 2011/0014661 A1 | 1/2011 | Samain |
| 2012/0208181 A1 | 8/2012 | Merighi et al. |
| 2012/0294840 A1 | 11/2012 | Newburg et al. |
| 2014/0080201 A1 | 3/2014 | Merighi et al. |

FOREIGN PATENT DOCUMENTS

| | | |
|---|---|---|
| FR | 2796082 A1 | 1/2001 |
| WO | WO-2007101862 A1 | 9/2007 |
| WO | WO-2015175801 A1 | 11/2015 |

OTHER PUBLICATIONS

Antoine et al., Large-scale in vivo synthesis of the carbohydrate moieties of gangliosides GM1 and GM2 by metabolically engineered *E.coli*. ChemBiochem. 2003, vol. 4: 406-412.*
Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Dumon et al., Production of Lewis x tetrasaccharides by metabolically engineered *E.coli*. ChemBiochem. 2006, vol. 7: 359-365.*
Fierfort et al., Genetic engineering of *Escherichia coli* for the economical production of sialylated oligosaccharides. J. Biotechnol., 2008, vol. 134: 261-265.*
Kisselev L., Polypeptide release factors in prokaryotes and eukaryotes: same function, different structure. Structure, 2002, vol. 10: 8-9.*
Priem et al., A new fermentation process allows large-scale production of human milk oligosaccharides by metabolically engineered bacteria. Glycobiol., 2002, vol. 12(4): 235-240.*
Qaidi et al., Swithching controlof expression of ptsG from the Mlc regulon to the NagC regulon. J. Bacteriol., 2008, vol. 190(13): 4677-4686.*
Reichenbach et al., The small RNA GlmY acts upstream of the sRNA GlmZ in the activation of glmS expression and is subject to regulation by polyadenylation in *Escherichia coli*. Nuc. Acids. Res., 2008, vol. 36(8): 2570-2580.*

(Continued)

*Primary Examiner* — Ganapathirama Raghu
(74) *Attorney, Agent, or Firm* — Mintz Levin Cohn Ferris Glovsky and Popeo, P.C.

(57) ABSTRACT

The invention provides compositions and methods for engineering bacteria to produce sialylated and N-acetylglucosamine-containing oligosaccharides, and the use thereof in the prevention or treatment of infection.

26 Claims, 19 Drawing Sheets

(56) References Cited

OTHER PUBLICATIONS

Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
GenBank Database Accession No. D00067, located at www.ncbi.nlm.nih.gov/nuccore/D00067, accessed on Dec. 16, 2015, 2 pages.
GenBank Database Accession No. BAE77265, located at www.ncbi.nlm.nih.gov/protein/BAE77265, accessed on Dec. 16, 2015, 13 pages.
GenBank Database Accession No. AAG29921, located at www.ncbi.nlm.nih.gov/protein/AAG29921, accessed on Dec. 16, 2015, 2 pages.
GenBank Database Accession No. AAG29920, located at www.ncbi.nlm.nih.gov/protein/AAG29920, accessed on Dec. 16, 2015, 2 pages.
GenBank Database Accession No. ADN91474, located at www.ncbi.nlm.nih.gov/protein/ADN91474, accessed on Dec. 16, 2015, 2 pages.
GenBank Database Accession No. M84410, located at www.ncbi.nlm.nih.gov/nuccore/M84410, accessed on Dec. 16, 2015, 2 pages.
Albermann et al. "Synthesis of the Milk Oligosaccharide 2'-Fucosyllactose Using Recombinant Bacterial Enzymes." *Carbohydr. Res.* 334.2(2001):97-103.
Hamosh. "Bioactive Factors in Human Milk." *Pediatr. Clin. North Am.* 48.1(2001):69-86.
Amonsen et al. "Human Parainfluenze Viruses hPIV1 and hPIV3 Bind Oligosaccharides with α 2-3-Linked Sialic Acids That are Distinct From Those Bound by H5 Avian Influenza Virus Hemagglutinin." *J. Virol.* 81.15(2007):8341-8345.
Belfort et al. "Characterization of the *Escherichia coli* thyA Gene and its Amplified Thymidylate Synthetase Product." *PNAS.* 80.7(1983):1858-1861.
Bettler et al. "The Living Factor: In vivo Production of N-Acetyl-lactosamine Containing Carbohydrates in *E. coli*." *Glycoconj. J.* 16.3(1999):205-212.
Charlwood et al. "A Detailed Analysis of Neutral and Acidic Carbohydrates in Human Milk." *Anal. Biochem.* 273.2(1999):261-277.
Chaturvedi et al. "Fucosylated Human Milk Oligosaccharides Vary Between Individuals and Over the Course of Lactation." *Glycobiol.* 11.5(2001):365-372.
Chatuvedi et al. "Survival of Human Milk Oligosaccharides in the Intestine of Infants." *Bioactive Components of Human Milk.* Newburg, ed. New York: Kluwer Academic/Plenum Publishers. Chapter 34 (2001):315-323.
Couceiro et al. "Influenze Virus Strains Selectively Recognize Sialyloligosaccharides on Human Respiratory Epithelium; The Role of the Host Cell in Selection of Hemagglutinin Receptor Specificity." *Virus Res.* 29.2(1993):155-165.
Court et al. "Genetic Engineering Using Homologous Recombination." *Annu. Rev. Genet.* 36(2002):361-388.
Crout et al. "Glycosidases and Glycosyl Transferases in Glycoside and Oligosaccharide Synthesis." *Curr. Opin. Chem. Biol.* 2.1(1998):98-111.
Endo et al. "Large-Scale Production of N-Acetyllactosamine Through Bacterial Coupling." *Carbohydr. Res.* 316.1-4(1999):179-183.

Endo et al. "Large-Scale Production of Oligosaccharides Using Engineered Bacteria." *Curr. Opin. Struct. Biol.* 10.5(2000):536-541.
Endo et al. "Large-Scale Production of the Carbohydrate Portion of the siayl-Tn Epitope, α-Neup5Ac-(2→6)-D-GalpNAc, Through Bacterial Coupling." *Carbohydr. Res.* 330.4(2001):439-443.
Endo et al. "Large-Scale Production of the CMP-NeuAc and Sialylated Oligosaccharides Through Bacterial Coupling." *Appl. Microbiol. Biotechnol.* 53.3(2000):257-261.
Flowers. "Chemical Synthesis of Oligosaccharides." *Methods Enzymol.* 50(1978):93-121.
Johnson, K.F. "Synthesis of Oligosaccharides by Bacterial Enzymes." *Glycoconj. J.* 16.2(1999):141-146.
Koeller et al. "Synthesis of Complex Carbohydrates and Glycoconjugates: Enzyme-Based and Programmable One-Pot Strategies." *Chem. Rev.* 100.12(2000):4465-4493.
Koizumi et al. "Large-Scale Production of UDP-Galactose and Globotriose by Coupling Metabolically Engineered Bacteria." *Nat. Biotechnol.* 16.9(1998):847-850.
Kuhlenschmidt et al. "Sialic Acid Dependence and Independence of Group A Rotaviruses." *Mechanisms in the Pathogenesis of Enteric Diseases 2.* Paul et al., eds. New York: Springer Science Business Media. Chapter 33 (1999):309-317.
Mahdavi et al. "*Helicobacter pylori* SabA Adhesin in Persistent Infection and Chronic Inflammation." *Science.* 297. 5581(2002):573-578.
Martín-Sosa et al. "Sialyligosaccharides in Human and Bovine Milk and in Infant Formulas: Variations with the Progression of Lactation." *J. Dairy Sci.* 86.1(2003):52-59.
Mieschendahl et al. "A Nogel Prophage Independent TRP Regulated Lambda PL Expression System." *Nat. Biotechnol.* 4(1986):802-808.
Morrow et al. "Human Milk Oligosaccharides are Associated with Protection Against Diarrhea in Breast-Fed Infants." *J. Pediatr.* 145.3(2004):297-303.
Newburg et al. "Innate Protection Conferred by Fucosylated Oligosaccharides of Human Milk Against Diarrhea in Breastfed Infants." *Glycobiol.* 14.3(2004):253-263.
Newburg et al. "Role of Human-Milk Lactadherin in Protection Against Symptomatic Rotavirus Infection." *Lancet.* 351. 9110(1998):1160-1164.
Newburg et al. "Human Milk Gylcoconjugtes That Inhibit Pathogens." *Curr. Med. Chem.* (1999)6:117-127.
Ninoneuvo et al. "A Strategy for Annotating the Human Milk Glycome." *J. Agric. Food Chem.* 54.20(2006):7471-7480.
Palcic, M.M. "Biocatalytic Synthesis of Oligosaccharides." *Curr. Opin. Biotechnol.* 10.6(1999):616-624.
Parkkinen et al. "Isolation of Sialyl Oligosaccharides and Sialyl Oligosaccharide Phosphates From Bovine Colostrum and Human Urine." *Methods Enzymol.* 138(1987):289-300.
Ruiz-Palacios et al. "*Campylobacter jejuni* Binds Intestinal H(O) Antigen (Fucα1, 2Galβ1, 4GlcNAc), and Fucosyloligosaccharides of Human Milk Inhibit its Binding and Infection." *J. Biol. Chem.* 278.16(2003):14112-14120.
Rydell et al. "Human Noroviruses Recognize Sialyl Lewis x Neoglycoprotein." *Glycobiol.* 19.3(2009):309-320.
Scharfman et al. "Sialyl-Lex and Sulfo-Sialyl-Lex Determinants are Receptors for *P. aeruginosa.*" *Glycoconj. J.* 17.10(2000):735-740.
Seeberger. "Automated Carbohydrate Synthesis to Drive Chemical Glycomics." *Chem. Commun. (Camb.).* 10(2003):1115-1121.
Shen et al. "Resolution of Structural Isomers of Sialylated Oligosaccharides by Capillary Electrophoresis." *J. Chromatogr. A.* 921. 2(2001):315-321.
Wymer et al. "Enzyme-Catalyzed Synthesis of Carbohydrates." *Curr. Opin. Chem. Biol.* 4.1(2000):110-119.
Samain et al. "Genetic engineering of *Escherichia coli* for the economical production of sialylated oligosaccharides" Journal of Biotechnology 134 (2008) 261-265.
Newburg et al. "Bioactive Components of Human Milk" 2001 Adv Exp Med Biol, 501:3-10.
Erney, R. et al. "Human Milk Oligosaccharides" Adv Exp Med Biol (2001) 501, 285-297.

(56) References Cited

OTHER PUBLICATIONS

Bao Y. & Newburg D.S. "Capillary electrophoresis of acidic oligosaccharides from human milk" *Electrophoresis* 2008, 29, 2508-2515.

Ward et al. "In vitro fermentability of human milk oligosaccharides by several strains of bifidobacteria" Mol. Nutr. Food Res. 2007, 51, 1398-1405.

Roberfroid, M. et al. "Prebiotic Concept and Health" (2010) NS British Journal of Nutrition 104 Suppl 2, S1-63.

Sanger F. et al. "Nucleotide Sequence of Bacteriophage DNA" J. Mol. Biol. (1982) 162, 729-773.

Thomason L. et al."*E. coli* Genome Manipulation by P1 Transduction" *Current Protocols in Molecular Biology* 1.17.1-1.17.8, Jul. 2007.

Danchin, Antoine "Cells Need Safety Valves" BioEssays 31:769-773, (2009) Wiley Periodicals, Inc.

Blixt, O. et al. "High-level expression of the *Neisseria meningitidis* IgtA gene in *Escherichia coli* and characterization of the encoded N-acetylglucosaminyltransferase as a useful catalyst in the synthesis of GlcNAc® 1 3Gal and GalNAc® 1 3Gal linkages" Glycobiology vol. 9 No. 10 pp. 1061-1071, 1999.

Reichenbach, B. et al. "The small RNA GlmY acts upstream of the sRNA GlmZ in the activation of glmS expression and is subject to regulation by polyadenylation in *Escherichia coli*" 2570-2580 *Nucleic Acids Research*, 2008, vol. 36, No. 8.

McCoy, J, et al. "Expression and Purification of Thioredoxin Fusion Proteins" *Current Protocols in Molecular Biology* (1994) 16.8.1-16.8.14.

Altschul et al., Basic local alignment search tool. J Mol Biol. Oct. 5, 1990;215(3):403-10.

Altschul et al., Gapped BLAST and PSI-BLAST: a new generation of protein database search programs. Nucleic Acids Res. Sep. 1, 1997;25(17):3389-402.

Bird RE. Homology between *Escherichia coli* plasmids ColE1 and p15A. J Bacteriol. Mar. 1981;145(3):1305-9.

Drouillard et al., Efficient synthesis of 6'-sialyllactose, 6,6'-disialyllactose, and 6'-KDO-lactose by metabolically engineered *E. coli* expressing a multifunctional sialyltransferase from the *Photobacterium* sp. JT-ISH-224. Carbohydr Res. Jul. 2, 2010;345(10):1394-9.

Genbank Accession No. AAF42257.1, Mar. 29, 2017.
Genbank Accession No. AAF42258.1, Mar. 29, 2017.
Genbank Accession No. AAK91727.1, Mar. 29, 2017.
Genbank Accession No. AAK91728.1, Mar. 29, 2017.
Genbank Accession No. ACF31229.1, Mar. 29, 2017.
Genbank Accession No. AEZ55696.1, Mar. 29, 2017.
Genbank Accession No. BAA35319.1, Mar. 29, 2017.
Genbank Accession No. BAF92026.1, Mar. 29, 2017.
Genbank Accession No. M84410.1, Mar. 29, 2017.
Genbank Accession No. NP_207619.1, Mar. 29, 2017.
Genbank Accession No. NP_273962.1, Mar. 29, 2017.
Genbank Accession No. NP_418185.1, Mar. 29, 2017.
Genbank Accession No. V00295.1, Mar. 29, 2017.
Genbank Accession No. V00296.1, Mar. 29, 2017.
Genbank Accession No. YP_002392936.1, Mar. 29, 2017.
Genbank Accession No. YP_003500090.1, Mar. 29, 2017.

Han et al., Biotechnological production of human milk oligosaccharides. Biotechnol Adv. Nov.-Dec. 2012;30(6):1268-78, Mar. 29, 2017.

Sleight et al., In-Fusion BioBrick assembly and re-engineering. Nucleic Acids Res. May 2010;38(8):2624-36.

Wolfe et al., Nucleotide sequence and analysis of the purA gene encoding adenylosuccinate synthetase of *Escherichia coli* K12. J Biol Chem. Dec. 15, 1988;263(35):19147-53.

\* cited by examiner

Pathway engineering for 6'-sialyllactose production in E.coli

SEQUENCE LISTING

```
<160> NUMBER OF SEQ ID NOS: 43

<210> SEQ ID NO 1
<211> LENGTH: 5877
<212> TYPE: DNA
<213> ORGANISM: Escherichia coli

<400> SEQUENCE: 1
gcagcggaac tcacaaggca ccataacgtc ccctccctga taacgctgat actgtggtcg      60
cggttatgcc agttggcatc ttcacgtaaa tagagcaaat agtcccgcgc ctggctggcg     120
gtttgccata gccgttgcga ctgctgccag tattgccagc catagagtcc acttgcgctt     180
agcatgacca aaatcagcat cgcgaccagc gtttcaatca gcgtataacc acgttgtgtt     240
ttcatgccgg cagtatggag cgaggagaaa aaaagacgag ggccagtttc tatttcttcg     300
gcgcatcttc cggactattt acgccgttgc aggacgttgc aaaatttcgg gaaggcgtct     360
cgaagaattt aacggagggt aaaaaaaccg acgcacactg gcgtcggctc tggcaggatg     420
tttcgtaatt agatagccac cggcgcttta ttaaacctac tatgaccatg attacggatt     480
cactggccgt cgtttttacaa cgtcgtgact gggaaaaccc tggcgttacc caacttaatc     540
gccttgcagc acatcccct ttcgccagct ggcgtaatag cgaagaggcc cgcaccgatc     600
gcccttccca acagttgcgc agcctgaatg gcgaatggcg ctttgcctgg tttccggcac     660
cagaagcggg gccggaaagc tggctggagt gcgatcttcc tgaggccgat actgtcgtcg     720
tcccctcaaa ctggcagatg cacggttacg atgcgcccat ctacaccaac gtgacctatc     780
ccattacggt caatccgccg tttgttccca cggagaatcc gacgggttgt tactcgctca     840
catttaatgt tgatgaaagc tggctacagg aaggccagac gcgaattatt tttgatggcg     900
ttaactcggc gtttcatctg tggtgcaacg ggcgctgggt cggttacggc caggacagtc     960
gtttgccgtc tgaatttgac ctgagcgcat ttttacgcgc cggagaaaac cgcctcgcgg    1020
tgatggtgct gcgctggagt gacggcagtt atctggaaga tcaggatatg tggcggatga    1080
gcggcatttt ccgtgacgtc tcgttgctgc ataaaccgac tacacaaatc agcgatttcc    1140
atgttgccac tcgctttaat gatgatttca gccgcgctgt actggaggct gaagttcaga    1200
tgtgcggcga gttgcgtgac tacctacggg taacagtttc tttatggcag ggtgaaacgc    1260
aggtcgccag cggcaccgcg cctttcggcg gtgaaattat cgatgagcgt ggtggttatg    1320
ccgatcgcgt cacactacgt ctgaacgtcg aaaacccgaa actgtggagc gccgaaatcc    1380
cgaatctcta tcgtgcggtg gttgaactgc acaccgccga cggcacgctg attgaagcag    1440
aagcctgcga tgtcggtttc cgcgaggtgc ggattgaaaa tggtctgctg ctgctgaacg    1500
gcaagccgtt gctgattcga ggcgttaacc gtcacgagca tcatcctctg catggtcagg    1560
```

```
tcatggatga gcagacgatg gtgcaggata tcctgctgat gaagcagaac aactttaacg    1620
ccgtgcgctg ttcgcattat ccgaaccatc cgctgtggta cacgcgtgc gaccgctacg     1680
gcctgtatgt ggtggatgaa gccaatattg aaacccacgg catggtgcca atgaatcgtc    1740
tgaccgatga tccgcgctgg ctaccggcga tgagcgaacg cgtaacgcga atggtgcagc    1800
gcgatcgtaa tcacccgagt gtgatcatct ggtcgctggg gaatgaatca ggccacggcg    1860
ctaatcacga cgcgctgtat cgctggatca aatctgtcga tccttcccgc ccggtgcagt    1920
atgaaggcgg cggagccgac accacggcca ccgatattat ttgcccgatg tacgcgcgcg    1980
tggatgaaga ccagcccttc ccggctgtgc cgaaatggtc catcaaaaaa tggctttcgc    2040
tacctggaga gacgcgcccg ctgatccttt gcgaatacgc ccacgcgatg ggtaacagtc    2100
ttggcggttt cgctaaatac tggcaggcgt tcgtcagta tccccgttta cagggcggct     2160
tcgtctggga ctgggtggat cagtcgctga ttaaatatga tgaaaacggc aacccgtggt    2220
cggcttacgg cggtgatttt ggcgatacgc cgaacgatcg ccagttctgt atgaacggtc    2280
tggtctttgc cgaccgcacg ccgcatccag cgctgacgga agcaaaacac cagcagcagt    2340
ttttccagtt ccgtttatcc gggcaaacca tcgaagtgac cagcgaatac ctgttccgtc    2400
atagcgataa cgagctcctg cactggatgg tggcgctgga tggtaagccg ctggcaagcg    2460
gtgaagtgcc tctggatgtc gctccacaag gtaaacagtt gattgaactg cctgaactac    2520
cgcagccgga gagcgccggg caactctggc tcacagtacg cgtagtgcaa ccgaacgcga    2580
ccgcatggtc agaagccggg cacatcagcg cctggcagca gtggcgtctg gcggaaaacc    2640
tcagtgtgac gctccccgcc gcgtcccacg ccatcccgca tctgaccacc agcgaaatgg    2700
atttttgcat cgagctgggt aataagcgtt ggcaatttaa ccgccagtca ggctttcttt    2760
cacagatgtg gattggcgat aaaaaacaac tgttgacgcc gctgcgcgat cagttcaccc    2820
gtgcaccgct ggataacgac attggcgtaa gtgaagcgac ccgcattgac cctaacgcct    2880
gggtcgaacg ctgaaggcg gcgggccatt accaggccga agcagcgttg ttgcagtgca    2940
cggcagatac acttgctgat gcggtgctga ttacgaccgc tcacgcgtgg cagcatcagg    3000
ggaaaaacctt atttatcagc cggaaaaacct accggattga tggtagtggt caaatggcga    3060
ttaccgttga tgttgaagtg gcgagcgata caccgcatcc ggcgcggatt ggcctgaact    3120
gccagctggc gcaggtagca gagcgggtaa actggctcgg attagggccg caagaaaact    3180
atcccgaccg ccttactgcc gcctgttttg accgctggga tctgccattg tcagacatgt    3240
ataccccgta cgtcttcccg agcgaaaacg gtctgcgctg cgggacgcgc gaattgaatt    3300
atggcccaca ccagtggcgc ggcgacttcc agttcaacat cagccgctac agtcaacagc    3360
aactgatgga aaccagccat cgccatctgc tgcacgcgga agaaggcaca tggctgaata    3420
tcgacggttt ccatatgggg attggtggcg acgactcctg gagcccgtca gtatcggcgg    3480
aattccagct gagcgccggt cgctaccatt accagttggt ctggtgtcaa aaataagcgg    3540
ccgctttatg taggctggag ctgcttcgaa gttcctatac tttctagaga ataggaactt    3600
cggaatagga acttcaagat ccccttatta gaagaactcg tcaagaaggc gatagaaggc    3660
gatgcgctgc gaatcgggag cggcgatacc gtaaagcacg aggaagcggt cagcccattc    3720
gccgccaagc tcttcagcaa tatcacgggt agccaacgct atgtcctgat agcggtccgc    3780
cacacccagc cggccacagt cgatgaatcc tgaaaagcgg ccattttcca ccatgatatt    3840
cggcaagcag gcatcgccat gggtcacgac gagatcctcg ccgtcgggca tgcgcgcctt    3900
gagcctggcg aacagttcgg ctggcgcgag cccctgatgc tcttcgtcca gatcatcctg    3960
```

```
atcgacaaga ccggcttcca tccgagtacg tgctcgctcg atgcgatgtt tcgcttggtg    4020
gtcgaatggg caggtagccg gatcaagcgt atgcagccgc cgcattgcat cagccatgat    4080
ggatactttc tcggcaggag caaggtgaga tgacaggaga tcctgccccg gcacttcgcc    4140
caatagcagc cagtcccttc ccgcttcagt gacaacgtcg agcacagctg cgcaaggaac    4200
gcccgtcgtg gccagccacg atagccgcgc tgcctcgtcc tgcagttcat tcagggcacc    4260
ggacaggtcg gtcttgacaa aaagaaccgg gcgcccctgc gctgacagcc ggaacacggc    4320
ggcatcagag cagccgattg tctgttgtgc ccagtcatag ccgaatagcc tctccaccca    4380
agcggccgga gaacctgcgt gcaatccatc ttgttcaatc atgcgaaacg atcctcatcc    4440
tgtctcttga tcagatcttg atccctgcg ccatcagatc cttggcggca agaaagccat    4500
ccagtttact ttgcagggct tcccaacctt accagagggc gccccagctg caattccgg    4560 ttcgcttgct gtccataaaa ccgcccagtc tagctatcgc catgtaagcc cactgcaagc    4620
tacctgcttt ctctttgcgc ttgcgttttc ccttgtccag atagcccagt agctgacatt    4680
catccggggt cagcaccgtt tctgcggact ggctttctac gtgttccgct tcctttagca    4740
gcccttgcgc cctgagtgct tgcggcagcg tgagcttcaa aagcgctctg aagttcctat    4800
actttctaga gaataggaac ttcgaactgc aggtcgacgg atccccggaa tcatggttcc    4860
tcaggaaacg tgttgctgtg ggctgcgacg atatgcccag accatcatga tcacacccgc    4920
gacaatcatc gggatggaaa gaatttgccc catgctgatg tactgcaccc aggcaccggt    4980
aaactgcgcg tcgggctggc ggaaaaactc aacaatgatg cgaaacgcgc cgtaaccaat    5040
caggaacaaa cctgagacag ctcccattgg gcgtggttta cgaatataca ggttgaggat    5100
aataaacagc accacacctt ccagcagcag ctcgtaaagc tgtgatgggt ggcgcggcag    5160
cacaccgtaa gtgtcgaaaa tggattgcca ctgcgggttg gtttgcagca gcaaaatatc    5220
ttctgtacgg gagccaggga acagcatggc aaacgggaag ttcgggtcaa cgcggcccca    5280
caattcaccg ttaataaagt tgcccagacg cccggcacca agaccaaacg gaatgagtgg    5340
tgcgataaaa tcagagacct ggaagaagga acgtttagta cggcgggcga agataatcat    5400
caccacgata acgccaatca ggccgccgtg gaaagacatg ccgccgtccc agacacggaa    5460
cagatacagc ggatcggcca taaactgcgg gaaattgtag aacagaacat aaccaatacg    5520
tcccccgagg aagacgccga ggaagcccgc atagagtaag ttttcaactt cattttggt    5580 ccagccgctg cccggacgat cgcccgtcg tgttgccagc cacattgcaa aaatgaaacc    5640
caccagatac atcaggccgt accagtgaag cgccacgggt cctattgaga aaatgaccgg    5700
atcaaactcc ggaaaatgca gatagctact ggtcatctgt caccacaagt tcttgttatt    5760
tcgctgaaag agaacagcga ttgaaatgcg cgccgcaggt tcaggcgct ccaaaggtgc    5820 gaataatagc acaaggggac ctggctggtt gccggatacc gttaaaagat atgtata    5877
```

<210> SEQ ID NO 2
<211> LENGTH: 5409
<212> TYPE: DNA
<213> ORGANISM: Artificial Sequence
<220> FEATURE:
<223> OTHER INFORMATION: engineered plasmid

<400> SEQUENCE: 2

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
```

-continued

```
ttggcgggtg tcggggctgg cttaactatg cggcatcaga gcagattgta ctgagagtgc    180
accatatatg cggtgtgaaa taccgcacag atgcgtaagg agaaaatacc gcatcaggcg    240
cctcctcaac ctgtatattc gtaaaccacg cccaatggga gctgtctcag gtttgttcct    300
gattggttac ggcgcgtttc gcatcattgt tgagtttttc cgccagcccg acgcgcagtt    360
taccggtgcc tgggtgcagt acatcagcat ggggcaaatt ctttccatcc cgatgattgt    420
cgcgggtgtg atcatgatgg tctgggcata tcgtcgcagc ccacagcaac acgtttcctg    480
aggaaccatg aaacagtatt tagaactgat gcaaaaagtg ctcgacgaag gcacacagaa    540
aaacgaccgt accggaaccg gaacgctttc cattttggt catcagatgc gttttaaccc    600
gcaagatgga ttcccgctgg tgacaactaa acgttgccac ctgcgttcca tcatccatga    660
actgctgtgg tttctgcagg gcgacactaa cattgcttat ctacacgaaa caatgtcac    720
catctgggac gaatgggccg atgaaaacgg cgacctcggg ccagtgtatg gtaaacagtg    780
gcgcgcctgg ccaacgccag atggtcgtca tattgaccag atcactacgg tactgaacca    840
gctgaaaaac gacccggatt cgcgccgcat tattgtttca gcgtgaaacg taggcgaact    900
ggataaaatg gcgctggcac cgtgccatgc attcttccag ttctatgtgg cagacggcaa    960
actctcttgc cagctttatc agcgctcctg tgacgtcttc ctcggcctgc cgttcaacat   1020
tgccagctac gcgttattgg tgcatatgat ggcgcagcag tgcgatctgg aagtgggtga   1080
ttttgtctgg accggtggcg acacgcatct gtacagcaac catatggatc aaactcatct   1140
gcaattaagc cgcgaaccgc gtccgctgcc gaagttgatt atcaaacgta acccgaatc    1200
catcttcgac taccgtttcg aagactttga gattgaaggc tacgatccgc atccgggcat   1260
taaagcgccg gtggctatct aattacgaaa catcctgcca gagccgacgc cagtgtgcgt   1320
cggtttttt accctccgtt aaattcttcg agacgccttc ccgaaggcgc cattcgccat   1380
tcaggctgcg caactgttgg aagggcgat cggtgcgggc ctcttcgcta ttacgccagc    1440
tggcgaaagg gggatgtgct gcaaggcgat taagttgggt aacgccaggg ttttcccagt   1500
cacgacgttg taaaacgacg gccagtgcca agcttactgc tcacaagaaa aaaggcacgt   1560
catctgacgt gccttttta tttgtactac cctgtacgat tactgcaggt cgactctaga   1620
tgcatgctcg agtcaacggt ttttcagcaa tcggtgcaaa atgccgaagt attgcctcaa   1680
ggtaaacagc cgccgcatcc tgccgtctgc cgcaaaatcc agccacgcgc cggcgggcag   1740
cgtgtccgtc cgtttgaagc attggtacaa aaaccggcgg gcgcgttcaa aatcttcttc   1800
cggcaaatgt ttctccagca attcatacgc tactgctttt atttggcggt attcaaggct   1860
gtcgaaccgg gttttaaaac ccatagactg caaaaaatcg tttctggcgg tttttggat    1920
gccttgcgcg atttcgtgtt ggcggatgct gtatttggat gaaacctgat tggcgtgaag   1980
gcggtatttg accaaggctt cgggataata agccagcctg cccaatttgc tgacatcgta   2040
ccaaaattgg taatcttccg cccaatcccg ctccggtgttg taacgcaaac cgccgtcaat   2100
gacgctgcgc ctcataatca tcgtgttgtt gtgtatgggg ttgccgaaag ggaaaaagtc   2160
ggcaatgtct tcgtgtcggg tcggtttttt ccaaattttg ccgtgttcgt ggtgccgcgc   2220
cagccggttg ccgtccttt cttccgacaa aacttccagc cacgcaccca tcgcgatgat   2280
gctgcggtct ttttccatct cacccacgat tttctcaatc cagtcggggg cggcaatatc   2340
gtctgcatcg gtgcgcgcaa tatattcccc cccccccccc gactttgcca attcatccag   2400
cccgatgttt aaagagggaa tcagaccgga attgcgcggc tgcgcgagga tgcggatgcg   2460
gccgtcctgt tcttggaaac gctgggcaat ggcaagcgta ccgtccgtcg agccgtcatc   2520
```

-continued

```
gacaatcaaa atatccaagt tgcgccaagt tgattcacg acggcggcta atgattgggc    2580
gaaatatttt tctacgttgt aggcgcaaat caatacgctg actaaaggct gcaatttatt    2640
ctcccgatag gcacgatgcc gtctgaaggc ttcagacggc atatgtatat ctccttcttg    2700
aattctaaca attgattgaa tgtatgcaaa taaatgcata caccataggt gtggtttaat    2760
ttgatgccct ttttcagggc tggaatgtgt aagagcgggg ttatttatgc tgttgttttt    2820
ttgttactcg ggaagggctt tacctcttcc gcataaacgc ttccatcagc gtttatagtt    2880
aaaaaaatct ttcggaactg gttttgcgct taccccaacc aacagggat tgctgctttt    2940 ccattgagcc tgtttctctg cgcgacgttc gcggcggcgt gtttgtgcat ccatctggat    3000
tctcctgtca gttagctttg gtggtgtgtg gcagttgtag tcctgaacga aaaccccccg    3060
cgattggcac attggcagct aatccggaat cgcacttacg gccaatgctt cgtttcgtat    3120 cacacaccc aaagccttct gctttgaatg ctgcccttct tcagggctta attttttaaga    3180 gcgtcacctt catggtggtc agtgcgtcct gctgatgtgc tcagtatcac cgccagtggt    3240
atttatgtca acaccgccag agataattta tcaccgcaga tggttatctg tatgtttttt    3300
atatgaattt attttttgca gggggggcatt gtttggtagg tgagagatca attctgcatt    3360
aatgaatcgg ccaacgcgcg gggagaggcg gtttgcgtat tgggcgctct ccgcttcct    3420 cgctcactga ctcgctgcgc tcggtcgttc ggctgcggcg agcggtatca gctcactcaa    3480
aggcggtaat acggttatcc acagaatcag gggataacgc aggaaagaac atgtgagcaa    3540
aaggccagca aaaggccagg aaccgtaaaa aggccgcgtt gctggcgttt ttccataggc    3600 tccgccccc tgacgagcat cacaaaaatc gacgctcaag tcagaggtgg cgaaacccga    3660
caggactata aagataccag gcgtttcccc ctggaagctc cctcgtgcgc tctcctgttc    3720
cgaccctgcc gcttaccgga tacctgtccg cctttctccc ttcgggaagc gtggcgcttt    3780
ctcatagctc acgctgtagg tatctcagtt cggtgtaggt cgttcgctcc aagctgggct    3840
gtgtgcacga accccccgtt cagcccgacc gctgcgcctt atccggtaac tatcgtcttg    3900
agtccaaccc ggtaagacac gacttatcgc cactggcagc agccactggt aacaggatta    3960
gcagagcgag gtatgtaggc ggtgctacag agttcttgaa gtggtggcct aactacggct    4020
acactagaag gacagtattt ggtatctgcg ctctgctgaa gccagttacc ttcggaaaaa    4080
gagttggtag ctcttgatcc ggcaaacaaa ccaccgctgg tagcggtggt ttttttgttt    4140
gcaagcagca gattacgcgc agaaaaaaag gatctcaaga agatcctttg atcttttcta    4200
cggggtctga cgctcagtgg aacgaaaact cacgttaagg gattttggtc atgagattat    4260
caaaaaggat cttcacctag atccttttaa attaaaaatg aagttttaaa tcaatctaaa    4320
gtatatatga gtaaacttgg tctgacagtt accaatgctt aatcagtgag gcacctatct    4380
cagcgatctg tctatttcgt tcatccatag ttgcctgact ccccgtcgtg tagataacta    4440
cgatacggga gggcttacca tctggcccca gtgctgcaat gataccgcga gacccacgct    4500
caccggctcc agatttatca gcaataaacc agccagccgg aagggccgag cgcagaagtg    4560
gtcctgcaac tttatccgcc tccatccagt ctattaattg ttgccgggaa gctagagtaa    4620
gtagttcgcc agttaatagt ttgcgcaacg ttgttgccat tgctacaggc atcgtggtgt    4680
cacgctcgtc gtttggtatg gcttcattca gctccggttc ccaacgatca aggcgagtta    4740
catgatcccc catgttgtgc aaaaaagcgg ttagctcctt cggtcctccg atcgttgtca    4800
gaagtaagtt ggccgcagtg ttatcactca tggttatggc agcactgcat aattctctta    4860
```

| | |
|---|---|
| ctgtcatgcc atccgtaaga tgcttttctg tgactggtga gtactcaacc aagtcattct | 4920 |
| gagaatagtg tatgcggcga ccgagttgct cttgcccggc gtcaatacgg gataataccg | 4980 |
| cgccacatag cagaacttta aaagtgctca tcattggaaa acgttcttcg gggcgaaaac | 5040 |
| tctcaaggat cttaccgctg ttgagatcca gttcgatgta acccactcgt gcacccaact | 5100 |
| gatcttcagc atcttttact ttcaccagcg tttctgggtg agcaaaaaca ggaaggcaaa | 5160 |
| atgccgcaaa aaagggaata agggcgacac ggaaatgttg aatactcata ctcttccttt | 5220 |
| ttcaatatta ttgaagcatt tatcagggtt attgtctcat gagcggatac atatttgaat | 5280 |
| gtatttagaa aaataaacaa ataggggttc cgcgcacatt tccccgaaaa gtgccacctg | 5340 |
| acgtctaaga aaccattatt atcatgacat taacctataa aaataggcgt atcacgaggc | 5400 |
| cctttcgtc | 5409 |

<210> SEQ ID NO 3
<211> LENGTH: 6233
<212> TYPE: DNA
<213> ORGANISM: Artificial Sequence
<220> FEATURE:
<223> OTHER INFORMATION: engineered plasmid

<400> SEQUENCE: 3

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatatg cggtgtgaaa taccgcacag atgcgtaagg agaaaatacc gcatcaggcg | 240 |
| cctcctcaac ctgtatattc gtaaaccacg cccaatggga gctgtctcag gtttgttcct | 300 |
| gattggttac ggcgcgtttc gcatcattgt tgagttttt cgccagcccg acgcgcagtt | 360 |
| taccggtgcc tgggtgcagt acatcagcat ggggcaaatt cttccatcc cgatgattgt | 420 |
| cgcgggtgtg atcatgatgg tctgggcata tcgtcgcagc ccacagcaac acgtttcctg | 480 |
| aggaaccatg aaacagtatt tagaactgat gcaaaaagtg ctcgacgaag gcacacagaa | 540 |
| aaacgaccgt accggaaccg gaacgctttc cattttggt catcagatgc gttttaacct | 600 |
| gcaagatgga ttcccgctgg tgacaactaa acgttgccac ctgcgttcca tcatccatga | 660 |
| actgctgtgg tttctgcagg cgacactaa cattgcttat ctacacgaaa acaatgtcac | 720 |
| catctgggac gaatgggccg atgaaaacgg cgacctcggg ccagtgtatg gtaaacagtg | 780 |
| gcgcgcctgg ccaacgccag atggtcgtca tattgaccag atcactacgg tactgaacca | 840 |
| gctgaaaaac gacccggatt cgcgccgcat tattgtttca gcgtggaacg taggcgaact | 900 |
| ggataaaatg gcgctggcac cgtgccatgc attcttccag ttctatgtgg cagacggcaa | 960 |
| actctcttgc cagctttatc agcgctcctg tgacgtcttc ctcggcctgc cgttcaacat | 1020 |
| tgccagctac gcgttattgg tgcatatgat ggcgcagcag tgcgatctgg aagtgggtga | 1080 |
| ttttgtctgg accggtggcg acacgcatct gtacagcaac catatggatc aaactcatct | 1140 |
| gcaattaagc cgcgaaccgc gtccgctgcc gaagttgatt atcaaacgta aacccgaatc | 1200 |
| catcttcgac taccgtttcg aagactttga gattgaaggc tacgatccgc atccgggcat | 1260 |
| taaagcgccg gtggctatct aattacgaaa catcctgcca gagccgacgc cagtgtgcgt | 1320 |
| cggtttttt accctccgtt aaattcttcg agacgccttc ccgaaggcgc cattcgccat | 1380 |
| tcaggctgcg caactgttgg gaagggcgat cggtgcgggc ctcttcgcta ttacgccagc | 1440 |
| tggcgaaagg gggatgtgct gcaaggcgat taagttgggt aacgccaggg ttttcccagt | 1500 |

-continued

```
cacgacgttg taaaacgacg gccagtgcca agcttactgc tcacaagaaa aaaggcacgt    1560
catctgacgt gccttttta  tttgtactac cctgtacgat tactgcaggt cgactctaga    1620
tgcatgctcg agttattatt taatatattt acaatagatg aaggacgcaa tcgtacggat    1680
accgccgaac aggtagttaa tgttaccggt caggaagaag cacttcattt tgataaccag    1740
gtcgttaacc atcaccatgt acaggttttt ttttgcggta gactgacctt cgtgcaggcg    1800
gtagtagaac aggtattccg gcaggttttg gaacttgatt tttgccaggc tcagacggtt    1860
ccacagctcg taatcttcgg agtagttaga aaacatataa ccaccgatgc tcgcgatgac    1920
tttttacga  aacattacgc tcgggtgaac aatacaacac ttatacggca ggttttaac    1980
gatgtccagg ttctcttccg gcagtttggt cttgttgatt tcacgacctt tgtcgtcaat    2040
aaagattgcg ttggtaccca caacatctac gtacggattg ttcttcagga agtcaacctg    2100
tttagtaaaa cggtccgggt gagagatgtc gtcagagtcc atacgggcaa taaattcgcc    2160
gttgctcagt cgatcgctt  tgttcaggga gtacggcagg taagcgatgt tagtgcggat    2220
cagtttgatt ttgtcgttaa cttttgtgttt cagttcgtta tagaagtcgt cagtgcagca    2280
gttcgcaacg atgatgattt cgaagctgct gaaggtctga acaggatgc  tgttgatcgc    2340
ttcgtccaga aagggttttt tcttgttaac aggcaggata acgctcacaa ccgggtgggt    2400
agattccgcg gattccgctt catcgatgat catatgtata tctccttctt ctcgagtcaa    2460
cggttttca  gcaatcggtg caaaatgccg aagtattgcc tcaaggtaaa cagccgccgc    2520
atcctgccgt ctgccgcaaa atccagccac gcgccggcgg gcagcgtgtc cgtccgtttg    2580
aagcattggt acaaaaaccg gcgggcgcgt tcaaaatctt cttccggcaa atgtttctcc    2640
agcaattcat acgctactgc ttttatttgg cggtattcaa ggctgtcgaa ccgggtttta    2700
aaacccatag actgcaaaaa atcgtttctg gcggtttttt ggatgccttg cgcgatttcg    2760
tgttggcgga tgctgtattt ggatgaaacc tgattggcgt gaaggcgta  tttgaccaag    2820
gcttcgggat aataagccag cctgcccaat ttgctgacat cgtaccaaaa ttggtaatct    2880
tccgcccaat cccgctcggt gttgtaacgc aaaccgccgt caatgacgct gcgcctcata    2940
atcatcgtgt tgttgtgtat ggggttgccg aaagggaaaa agtcggcaat gtcttcgtgt    3000
cgggtcggtt ttttccaaat tttgccgtgt tcgtggtgcc gcgccagccg gttgccgtcc    3060
ttttcttccg acaaaacttc cagccacgca cccatcgcga tgatgctgcg gtcttttcc    3120
atctcaccca cgattttctc aatccagtcg ggggcggcaa tatcgtctgc atcggtgcgc    3180
gcaatatatt cccccccccc ccccgacttt gccaattcat ccagcccgat gtttaaagag    3240
ggaatcagac cggaattgcg cggctgcgcg aggatgcgga tgcggccgtc ctgttcttgg    3300
aaacgctggg caatggcaag cgtaccgtcc gtcgagccgt catcgacaat caaaatatcc    3360
aagttgcgcc aagtttgatt cacgacggcg gctaatgatt gggcgaaata ttttttctacg    3420
ttgtaggcgc aaatcaatac gctgactaaa ggctgcaatt tattctcccg ataggcacga    3480
tgccgtctga aggcttcaga cggcatatgt atatctcctt cttgaattct aacaattgat    3540
tgaatgtatg caaataaatg catacaccat aggtgtggtt taatttgatg ccctttttca    3600
gggctggaat gtgtaagagc ggggttattt atgctgttgt ttttttgtta ctcgggaagg    3660
gctttaccte ttccgcataa acgcttccat cagcgtttat agttaaaaaa atctttcgga    3720
actggttttg cgcttacccc aaccaacagg ggatttgctg ctttccattg agcctgtttc    3780
tctgcgcgac gttcgcggcg gcgtgtttgt gcatccatct ggattctcct gtcagttagc    3840
```

```
tttggtggtg tgtggcagtt gtagtcctga acgaaaaccc cccgcgattg gcacattggc    3900
agctaatccg gaatcgcact tacggccaat gcttcgtttc gtatcacaca ccccaaagcc    3960
ttctgctttg aatgctgccc ttcttcaggg cttaatttttt aagagcgtca ccttcatggt    4020
ggtcagtgcg tcctgctgat gtgctcagta tcaccgccag tggtatttat gtcaacaccg    4080
ccagagataa tttatcaccg cagatggtta tctgtatgtt ttttatatga atttattttt    4140
tgcaggggggg cattgtttgg taggtgagag atcaattctg cattaatgaa tcggccaacg    4200
cgcggggaga ggcggtttgc gtattgggcg ctcttccgct tcctcgctca ctgactcgct    4260
gcgctcggtc gttcggctgc ggcgagcggt atcagctcac tcaaaggcgg taatacggtt    4320
atccacagaa tcaggggata acgcaggaaa gaacatgtga gcaaaaggcc agcaaaaggc    4380
caggaaccgt aaaaaggccg cgttgctggc gtttttccat aggctccgcc ccctgacga     4440
gcatcacaaa aatcgacgct caagtcagag gtggcgaaac ccgacaggac tataaagata    4500
ccaggcgttt cccccctggaa gctccctcgt gcgctctcct gttccgaccc tgccgcttac    4560
cggatacctg tccgccttc tcccttcggg aagcgtggcg ctttctcata gctcacgctg    4620
taggtatctc agttcggtgt aggtcgttcg ctccaagctg gctgtgtgc acgaaccccc     4680
cgttcagccc gaccgctgcg ccttatccgg taactatcgt cttgagtcca acccggtaag    4740
acacgactta tcgccactgg cagcagccac tggtaacagg attagcagag cgaggtatgt    4800
aggcggtgct acagagttct tgaagtggtg gcctaactac ggctacacta aaggacagt     4860
atttggtatc tgcgctctgc tgaagccagt taccttcgga aaaagagttg gtagctcttg    4920
atccggcaaa caaaccaccg ctggtagcgg tggtttttttt gtttgcaagc agcagattac    4980
gcgcagaaaa aaaggatctc aagaagatcc tttgatcttt tctacggggt ctgacgctca    5040
gtggaacgaa aactcacgtt aagggatttt ggtcatgaga ttatcaaaaa ggatcttcac    5100
ctagatcctt ttaaattaaa aatgaagttt taaatcaatc taaagtatat atgagtaaac    5160
ttggtctgac agttaccaat gcttaatcag tgaggcacct atctcagcga tctgtctatt    5220
tcgttcatcc atagttgcct gactccccgt cgtgtagata actacgatac gggagggctt    5280
accatctggc cccagtgctg caatgatacc gcgagaccca cgctcaccgg ctccagattt    5340
atcagcaata aaccagccag ccggaagggc cgagcgcaga agtggtcctg caactttatc    5400
cgcctccatc cagtctatta attgttgccg ggaagctaga gtaagtagtt cgccagttaa    5460
tagtttgcgc aacgttgttg ccattgctac aggcatcgtg gtgtcacgct cgtcgtttgg    5520
tatggcttca ttcagctccg gttcccaacg atcaaggcga gttacatgat cccccatgtt    5580
gtgcaaaaaa gcggttagct ccttcggtcc tccgatcgtt gtcagaagta agttggccgc    5640
agtgttatca ctcatggtta tggcagcact gcataattct cttactgtca tgccatccgt    5700
aagatgcttt tctgtgactg gtgagtactc aaccaagtca ttctgagaat agtgtatgcg    5760
gcgaccgagt tgctcttgcc cggcgtcaat acgggataat accgcgccac atagcagaac    5820
tttaaaagtg ctcatcattg gaaaacgttc ttcggggcga aaactctcaa ggatcttacc    5880
gctgttgaga tccagttcga tgtaacccac tcgtgcaccc aactgatctt cagcatcttt    5940
tactttcacc agcgtttctg ggtgagcaaa aacaggaagg caaaatgccg caaaaaaggg    6000
aataagggcg acacggaaat gttgaatact catactcttc cttttcaat attattgaag    6060
catttatcag ggttattgtc tcatgagcgg atacatattt gaatgtattt agaaaaataa    6120
acaaataggg gttccgcgca catttccccg aaaagtgcca cctgacgtct aagaaaccat    6180
tattatcatg acattaacct ataaaaatag gcgtatcacg aggcccttc gtc            6233
```

<210> SEQ ID NO 4
<211> LENGTH: 6254
<212> TYPE: DNA
<213> ORGANISM: Artificial Sequence
<220> FEATURE:
<223> OTHER INFORMATION: engineered plasmid

<400> SEQUENCE: 4

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatatg cggtgtgaaa taccgcacag atgcgtaagg agaaaatacc gcatcaggcg     240
cctcctcaac ctgtatattc gtaaaccacg cccaatggga gctgtctcag gtttgttcct     300
gattggttac ggcgcgtttc gcatcattgt tgagttttc cgccagcccg acgcgcagtt      360
taccggtgcc tgggtgcagt acatcagcat ggggcaaatt ctttccatcc cgatgattgt     420
cgcgggtgtg atcatgatgg tctgggcata tcgtcgcagc ccacagcaac acgtttcctg     480
aggaaccatg aaacagtatt tagaactgat gcaaaaagtg ctcgacgaag gcacacagaa     540
aaacgaccgt accggaaccg gaacgctttc cattttggt catcagatgc gttttaacct      600
gcaagatgga ttcccgctgg tgacaactaa acgttgccac ctgcgttcca tcatccatga     660
actgctgtgg tttctgcagg gcgacactaa cattgcttat ctacacgaaa acaatgtcac     720
catctgggac gaatgggccg atgaaaaacg cgacctcggg ccagtgtatg gtaaacagtg     780
gcgcgcctgg ccaacgccag atggtcgtca tattgaccag atcactacgg tactgaacca     840
gctgaaaaac gacccggatt cgcgccgcat tattgtttca gcgtggaacg taggcgaact     900
ggataaaatg gcgctggcac cgtgccatgc attcttccag ttctatgtgg cagacggcaa     960
actctcttgc cagctttatc agcgctcctg tgacgtcttc ctcggcctgc cgttcaacat    1020
tgccagctac gcgttattgg tgcatatgat ggcgcagcag tgcgatctgg aagtgggtga    1080
ttttgtctgg accggtggcg acacgcatct gtacagcaac catatggatc aaactcatct    1140
gcaattaagc cgcgaaccgc gtccgctgcc gaagttgatt atcaaacgta acccgaatc     1200
catcttcgac taccgtttcg aagactttga gattgaaggc tacgatccgc atccgggcat    1260
taaagcgccg gtggctatct aattacgaaa catcctgcca gagccgacgc cagtgtgcgt    1320
cggttttttt accctccgtt aaattcttcg agacgccttc ccgaaggcgc cattcgccat    1380
tcaggctgcg caactgttgg gaagggcgat cggtgcgggc ctcttcgcta ttacgccagc    1440
tggcgaaagg gggatgtgct gcaaggcgat taagttgggt aacgccaggg ttttcccagt    1500
cacgacgttg taaaacgacg gccagtgcca agcttactgc tcacaagaaa aaaggcacgt    1560
catctgacgt gccttttta tttgtactac cctgtacgat tactgcaggt cgactctaga    1620
tgcatgctcg agttatacaa actgccaata tttcaaatat ttaaaatgga gttctctcat    1680
taaggcgatt ttagggctat aaggttcttc ttttcgtgct atcgtagaga tttgctcatc    1740
atcagcgatc acaaaaggtt gtaacaccag atttttcacg ccatggataa aagtagcgtc    1800
cattatcgta tccacaggaa caacccattt tcggctgcat ttcaaaaaaa ctttggcaat    1860
cttaggcgtg atcacatagc cttgagtccc caccccttcg ctataagctt taatgatccc    1920
cacacgctct tgtatctcgt ggttttatg gctcaatggc tcacttttta cactggcatc     1980
atacaataaa tgcatcaagc ggatatagcc taactcttgg atgtgttttt ctaaaaaatc    2040
```

```
caagccctct ttaaaatcct cttttcaaggt tatatcgtct tctaaaatac agatcgcttc    2100
attgagttct atgcattttt cccacaagga ataatgactc gcatagcacc caagctcccc    2160
caagctcata aacttcgcat ggtattttaa agcgtaataa aacttagaaa cctcactgat    2220
gagattggtt gtaatcccca tgtctttgat gttttgcgtg atgaaataag ggtgtaaatg    2280 cttttttcact aaggggtgca acccgccttc aaaagtttta gaataaatcg catcaaaaat    2340
ttgcgcttgg tggtgggtgg cattgatgct attgagtaaa gttgtggtgt ctctaaaaac    2400
taaaccaaat gtatcgcaca cttttgatt taaagaaatg gcaaaacac gcatatgtat       2460 atctccttct tctcgagtca acggttttc agcaatcggt gcaaaatgcc gaagtattgc      2520
ctcaaggtaa acagccgccg catcctgccg tctgccgcaa atccagcca cgcgccggcg      2580 ggcagcgtgt ccgtccgttt gaagcattgg tacaaaaacc ggcgggcgcg ttcaaaatct    2640
tcttccggca aatgtttctc cagcaattca tacgctactg cttttatttg gcggtattca    2700
aggctgtcga accgggtttt aaacccata gactgcaaaa aatcgtttct ggcggttttt      2760
tggatgcctt gcgcgatttc gtgttggcgg atgctgtatt tggatgaaac ctgattggcg    2820 tgaaggcgt atttgaccaa ggcttcggga taataagcca ggctgcccaa tttgctgaca     2880
tcgtaccaaa attggtaatc ttccgcccaa tcccgctcgg tgttgtaacg caaaccgccg    2940
tcaatgacgc tgcgcctcat aatcatcgtg ttgttgtgta tggggttgcc gaaagggaaa    3000
aagtcggcaa tgtcttcgtg tcgggtcggt tttttccaaa ttttgccgtg ttcgtggtgc    3060
cgcgccagcc ggttgccgtc ctttttcttcc gacaaaactt ccagccacgc acccatcgcg    3120
atgatgctgc ggtctttttc catctcaccc acgattttct caatccagtc ggggcggca     3180 atatcgtctg catcggtgcg cgcaatatat tccccccccc ccccgactt tgccaattca    3240 tccagcccga tgtttaaaga gggaatcaga ccggaattgc gcggctgcgc gaggatgcgg    3300
atgcggccgt cctgttcttg gaaacgctgg gcaatggcaa gcgtaccgtc cgtcgagccg    3360
tcatcgacaa tcaaaatatc caagttgcgc caagtttgat tcacgacggc ggctaatgat    3420
tgggcgaaat attttttctac gttgtaggcg caaatcaata cgctgactaa aggctgcaat   3480
ttattctccc gataggcacg atgccgtctg aaggcttcag acggcatatg tatatctcct   3540
tcttgaattc taacaattga ttgaatgtat gcaaataaat gcatacacca taggtgtggt    3600
ttaatttgat gccctttttc agggctggaa tgtgtaagag cggggttatt tatgctgttg    3660 ttttttttgtt actcgggaag ggctttacct cttccgcata aacgcttcca tcagcgttta   3720
tagttaaaaa aatctttcgg aactggtttt gcgcttaccc caaccaacag gggatttgct   3780
gctttccatt gagcctgttt ctctgcgcga cgttcgcggc ggcgtgtttg tgcatccatc    3840
tggattctcc tgtcagttag ctttggtggt gtgtggcagt tgtagtcctg aacgaaaacc    3900
ccccgcgatt ggcacattgg cagctaatcc ggaatcgcac ttacggccaa tgcttcgttt    3960
cgtatcacac accccaaagc cttctgcttt gaatgctgcc cttcttcagg gcttaatttt    4020
taagagcgtc accttcatgg tggtcagtgc gtcctgctga tgtgctcagt atcaccgcca    4080 gtggtatttta tgtcaacacc gccagagata atttatcacc gcagatggtt atctgtatgt    4140
tttttatatg aatttatttt ttgcaggggg gcattgtttg gtaggtgaga gatcaattct    4200
gcattaatga atcggccaac gcgcggggag aggcggtttg cgtattgggc gctcttccgc    4260
ttcctcgctc actgactcgc tgcgctcggt cgttcggctg cggcgagcgg tatcagctca    4320
ctcaaaggcg gtaatacggt tatccacaga atcaggggat aacgcaggaa agaacatgtg    4380
agcaaaaggc cagcaaaagg ccaggaaccg taaaaaggcc gcgttgctgg cgttttccca    4440
```

| | | | |
|---|---|---|---|
| taggctccgc | cccctgacg | agcatcacaa | aaatcgacgc tcaagtcaga ggtggcgaaa | 4500 |
| cccgacagga | ctataaagat | accaggcgtt | tccccctgga agctccctcg tgcgctctcc | 4560 |
| tgttccgacc | ctgccgctta | ccggatacct | gtccgccttt ctcccttcgg aagcgtggc | 4620 |
| gctttctcat | agctcacgct | gtaggtatct | cagttcggtg taggtcgttc gctccaagct | 4680 |
| gggctgtgtg | cacgaacccc | ccgttcagcc | cgaccgctgc gccttatccg gtaactatcg | 4740 |
| tcttgagtcc | aacccggtaa | gacacgactt | atcgccactg gcagcagcca ctggtaacag | 4800 |
| gattagcaga | gcgaggtatg | taggcggtgc | tacagagttc ttgaagtggt ggcctaacta | 4860 |
| cggctacact | agaaggacag | tatttggtat | ctgcgctctg ctgaagccag ttaccttcgg | 4920 |
| aaaaagagtt | ggtagctctt | gatccggcaa | acaaaccacc gctggtagcg gtggttttt | 4980 |
| tgtttgcaag | cagcagatta | cgcgcagaaa | aaaggatct caagaagatc ctttgatctt | 5040 |
| ttctacgggg | tctgacgctc | agtggaacga | aaactcacgt taagggattt tggtcatgag | 5100 |
| attatcaaaa | aggatcttca | cctagatcct | tttaaattaa aaatgaagtt ttaaatcaat | 5160 |
| ctaaagtata | tatgagtaaa | cttggtctga | cagttaccaa tgcttaatca gtgaggcacc | 5220 |
| tatctcagcg | atctgtctat | ttcgttcatc | catagttgcc tgactccccg tcgtgtagat | 5280 |
| aactacgata | cgggagggct | taccatctgg | ccccagtgct gcaatgatac cgcgagaccc | 5340 |
| acgctcaccg | gctccagatt | tatcagcaat | aaaccagcca gccggaaggg ccgagcgcag | 5400 |
| aagtggtcct | gcaactttat | ccgcctccat | ccagtctatt aattgttgcc gggaagctag | 5460 |
| agtaagtagt | tcgccagtta | atagtttgcg | caacgttgtt gccattgcta caggcatcgt | 5520 |
| ggtgtcacgc | tcgtcgtttg | gtatggcttc | attcagctcc ggttcccaac gatcaaggcg | 5580 |
| agttacatga | tcccccatgt | tgtgcaaaaa | agcggttagc tccttcggtc ctccgatcgt | 5640 |
| tgtcagaagt | aagttggccg | cagtgttatc | actcatggtt atggcagcac tgcataattc | 5700 |
| tcttactgtc | atgccatccg | taagatgctt | ttctgtgact ggtgagtact caaccaagtc | 5760 |
| attctgagaa | tagtgtatgc | ggcgaccgag | ttgctcttgc ccggcgtcaa tacgggataa | 5820 |
| taccgcgcca | catagcagaa | ctttaaaagt | gctcatcatt ggaaaacgtt cttcggggcg | 5880 |
| aaaactctca | aggatcttac | cgctgttgag | atccagttcg atgtaaccca ctcgtgcacc | 5940 |
| caactgatct | tcagcatctt | ttactttcac | cagcgtttct gggtgagcaa aaacaggaag | 6000 |
| gcaaaatgcc | gcaaaaaagg | gaataagggc | gacacgaaa tgttgaatac tcatactctt | 6060 |
| cctttttcaa | tattattgaa | gcatttatca | gggttattgt ctcatgagcg gatacatatt | 6120 |
| tgaatgtatt | tagaaaaata | aacaaatagg | ggttccgcgc acatttcccc gaaaagtgcc | 6180 |
| acctgacgtc | taagaaacca | ttattatcat | gacattaacc tataaaaata ggcgtatcac | 6240 |
| gaggcccttt | cgtc | | | 6254 |

<210> SEQ ID NO 5
<211> LENGTH: 7680
<212> TYPE: DNA
<213> ORGANISM: Artificial Sequence
<220> FEATURE:
<223> OTHER INFORMATION: engineered plasmid

<400> SEQUENCE: 5

| | | | |
|---|---|---|---|
| gtacccagct | tttgttccct | ttagtgaggg | ttaattgcgc gcttggcgta atcatggtca | 60 |
| tagctgtttc | ctgtgtgaaa | ttgttatccg | ctcacaattc cacacaacat acgagccgga | 120 |
| agcataaagt | gtaaagcctg | gggtgcctaa | tgagtgagct aactcacatt aattgcgttg | 180 |

```
cgctcactgc cgctttcca gtcgggaaac ctgtcgtgcc agctgcatta atgaatcggc    240
caacgcgcgg ggagaggcgg tttgcgtatt gggcgcatgc ataaaaactg ttgtaattca    300
ttaagcattc tgccgacatg gaagccatca caaacggcat gatgaacctg aatcgccagc    360
ggcatcagca ccttgtcgcc ttgcgtataa tatttgccca tggtgaaaac gggggcgaag    420
aagttgtcca tattggccac gtttaaatca aaactggtga aactcaccca gggattggct    480
gagacgaaaa acatattctc aataaaccct ttagggaaat aggccaggtt ttcaccgtaa    540
cacgccacat cttgcgaata tatgtgtaga aactgccgga atcgtcgtg gtattcactc    600 cagagcgatg aaaacgtttc agtttgctca tggaaaacgg tgtaacaagg gtgaacacta    660
tcccatatca ccagctcacc gtctttcatt gccatacgga attccggatg agcattcatc    720
aggcgggcaa gaatgtgaat aaaggccgga taaaacttgt gcttattttt ctttacggtc    780
tttaaaaagg ccgtaatatc cagctgaacg gtctggttat aggtacattg agcaactgac    840
tgaaatgcct caaaatgttc tttacgatgc cattgggata tatcaacggt ggtatatcca    900 gtgattttt tctccatttt agcttcctta gctcctgaaa atctcgataa ctcaaaaaat    960
acgcccggta gtgatcttat ttcattatgg tgaaagttgg aacctcttac gtgccgatca   1020
acgtctcatt ttcgccaaaa gttggcccag ggcttcccgg tatcaacagg gacaccagga   1080
tttatttatt ctgcgaagtg atcttccgtc acaggtattt attcgaagac gaaagggcct   1140
cgtgatacgc ctatttttat aggttaatgt catgataata atggtttctt agacgtcagg   1200
tggcactttt cggggaaatg tgcgcgcccg cgttcctgct ggcgctgggc ctgtttctgg   1260
cgctggactt cccgctgttc cgtcagcagc ttttcgccca cggccttgat gatcgcggcg   1320
gccttggcct gcatatcccg attcaacggc cccagggcgt ccagaacggg cttcaggcgc   1380
tcccgaaggt ctcgggccgt ctcttgggct tgatcggcct tcttgcgcat ctcacgcgct   1440
cctgcggcgg cctgtagggc aggctcatac ccctgccgaa ccgcttttgt cagccggtcg   1500
gccacggctt ccgcgtctc aacgcgcttt gagattccca gcttttcggc caatccctgc   1560
ggtgcatagg cgcgtggctc gaccgcttgc gggctgatgg tgacgtggcc cactggtggc   1620
cgctccaggc cctcgtagaa cgcctgaatg cgcgtgtgac gtgccttgct gcccgtcgatg   1680 ccccgttgca gccctagatc ggccacagcg gccgcaaacg tggtctggtc gcgggtcatc   1740
tgcgctttgt tgccgatgaa ctccttggcc gacagcctgc cgtcctgcgt cagcggcacc   1800
acgaacgcgg tcatgtgcgg gctggttcg tcacggtgga tgctggccgt cacgatgcga   1860
tccgccccgt acttgtccgc cagccacttg tgcgccttct cgaagaacgc cgcctgctgt   1920
tcttggctgg ccgacttcca ccattccggg ctggccgtca tgacgtactc gaccgccaac   1980
acagcgtcct tgcgccgctt ctctggcagc aactcgcgca gtcggcccat cgcttcatcg   2040
gtgctgctgg ccgcccagtg ctcgttctct ggcgtcctgc tggcgtcagc gttgggcgtc   2100
tcgcgctcgc ggtaggcgtg cttgagactg gccgccacgt tgcccatttt cgccagcttc   2160
ttgcatcgca tgatcgcgta tgccgccatg cctgcccctc ccttttggtg tccaaccggc   2220
tcgacggggg cagcgcaagg cggtgcctcc ggcgggccac tcaatgcttg agtatactca   2280
ctagactttg cttcgcaaag tcgtgaccgc ctacggcggc tgcggcgccc tacgggcttg   2340
ctctccgggc ttcgccctgc gcggtcgctg cgctcccttg ccagcccgtg gatatgtgga   2400
cgatggccgc gagcggccac cggctggctc gcttcgctcg gcccgtggac aaccctgctg   2460
gacaagctga tggacaggct gcgcctgccc acgagcttga ccacagggat tgcccaccgg   2520
ctacccagcc ttcgaccaca tacccaccgg ctccaactgc gcggcctgcg gccttgcccc   2580
```

```
atcaattttt ttaattttct ctggggaaaa gcctccggcc tgcggcctgc gcgcttcgct    2640
tgccggttgg acaccaagtg aaggcgggt  caaggctcgc gcagcgaccg cgcagcggct    2700
tggccttgac gcgcctggaa cgacccaagc ctatgcgagt gggggcagtc gaaggcgaag    2760
cccgcccgcc tgcccccga  gcctcacggc ggcgagtgcg ggggttccaa gggggcagcg    2820
ccaccttggg caaggccgaa ggccgcgcag tcgatcaaca agccccggag gggccacttt    2880
ttgccggagg gggagccgcg ccgaaggcgt ggggaaccc  gcaggggtg  cccttctttg    2940 ggcaccaaag aactagatat agggcgaaat gcgaagact  taaaaatcaa caacttaaaa    3000
aaggggggta cgcaacagct cattgcggca ccccccgcaa tagctcattg cgtaggttaa    3060
agaaaatctg taattgactg ccacttttac gcaacgcata attgttgtcg cgctgccgaa    3120
aagttgcagc tgattgcgca tggtgccgca accgtgcggc accctaccgc atggagataa    3180
gcatggccac gcagtccaga gaaatcggca ttcaagccaa gaacaagccc ggtcactggg    3240
tgcaaacgga acgcaaagcg catgaggcgt gggccgggct tattgcgagg aaacccacgg    3300
cggcaatgct gctgcatcac ctcgtggcgc agatgggcca ccagaacgcc gtggtggtca    3360
gccagaagac actttccaag ctcatcggac gttctttgcg gacggtccaa tacgcagtca    3420
aggacttggt ggccgagcgc tggatctccg tcgtgaagct caacggcccc ggcaccgtgt    3480
cggcctacgt ggtcaatgac cgcgtggcgt ggggccagcc ccgcgaccag ttgcgcctgt    3540
cggtgttcag tgccgccgtg gtggttgatc acgacgacca ggacgaatcg ctgttggggc    3600
atggcgacct cgccgcatc  ccgaccctgt atccgggcga gcagcaacta ccgaccggcc    3660
ccggcgagga gccgcccagc cagcccggca ttccgggcat ggaaccagac ctgccagcct    3720
tgaccgaaac ggaggaatgg gaacggcgcg ggcagcagcg cctgccgatg cccgatgagc    3780
cgtgttttct ggacgatggc gagccgttgg agccgccgac acgggtcacg ctgccgcgcc    3840
ggtagcactt gggttgcgca gcaacccgta agtgcgctgt tccagactat cggctgtagc    3900
cgcctcgccg ccctatacct tgtctgcctc cccgcgttgc gtcgcggtgc atggagccgg    3960
gccacctcga cctgaatgga agccggcggc acctcgctaa cggattcacc gtttttatca    4020
ggctctggga ggcagaataa atgatcatat cgtcaattat tacctccacg gggagagcct    4080
gagcaaactg gcctcaggca tttgagaagc acacggtcac actgcttccg gtagtcaata    4140
aaccggtaaa ccagcaatag acataagcgg ctatttaacg accctgccct gaaccgacga    4200
ccgggtcgaa tttgctttcg aatttctgcc attcatccgc ttattatcac ttattcaggc    4260
gtagcaccag gcgtttaagg gcaccaataa ctgccttaaa aaaattacgc cccgccctgc    4320
cactcatcgc agtcggccta ttggttaaaa aatgagctga tttaacaaaa atttaacgcg    4380
aattttaaca aaatattaac gcttacaatt tccattcgcc attcaggctg cgcaactgtt    4440
gggaagggcg atcggtgcgg gcctcttcgc tattacgcca gctggcgaaa ggggatgtg     4500 ctgcaaggcg attaagttgg gtaacgccag gttttccca  gtcacgacgt tgtaaaacga    4560
cggccagtga gcgcgcgtaa tacgactcac tatagggcga attggagctc caccgcggtg    4620
gcggccgctc tagaactagt ggatccccg  ggctgcagga attcgatatc aagcttatcg    4680
ataccgtcga cctcgagtta agtctctaat cgattgtttt ccaatggaat ggttataaaa    4740
tctttggttt ttagtcttga aaatcttcta ggattttcta tgtaagtttt tgtataaata    4800
ttatattgct ttaataaatt taatatattt ttattgcatt ttaaggttat ttttccata    4860 tctgttcaac cttttttaaa tcctccaaac agtcaatatc taaacttgag ctttcgtcca    4920
```

```
ttaaaaaatg cttggttttg ctttgtaaaa agctaggatt gtttaaaaat tcttttatct    4980
ttaaaatata aattgcacca ttgctcatat aagttttagg caattttttgc cttggcataa   5040 aaggatattc atcattacaa atccctgcta atcgccaca atcattacaa acaaaggctt    5100
ttagaatttt attatcacat tcgcttacgc taattagggc atttgcattg ctattttttat 5160 aaagattaaa agcttcatta atatgaatat ttgttcttag cggtgaagtg ggttgtaaaa  5220
aaactacatc ttcataatct ttataaaatt ttagagcatg taacagcact ttatcgcttg  5280
tggtatcatc ttgtgcaagg ctaattgggc gttttaaaat atcaacattt tgactttttg  5340
cataatttaa aatttcatca ctatcactgc ttacaacaac tttactaatg cttttagcat  5400
ttagtgcagc tttgatcgtg tagtaaatta aaggtttatt gtttaataaa accaaatttt  5460 tattttttaat acccttttgag ccaccacgag cagggattat tgctaagctc attttatatc 5520
cttaaaaact ttttgtgtgc tgagtttaaa aaaatctccg ctttgtaaat attcaaaaaa  5580
taattttgag ctatctaaaa tctctaactt agcgctaaat aaatcttgtt ttttatgaat  5640
agtgttaata gcttttagta tttcatcact atttgcatta acttttagtg tatttttcatt 5700 gccaagtctt ccattttgtc ttgagccaac taaaatccct gctgttttta agtataaggc  5760 ctctttttaaa atacaacttg aattacctat tataaaatca gcattttta acaaagttat   5820 aaaatactca aatctaagcg atggaaaaag cttaaatcta gggttatttt taaactcttc  5880
atagctttgc aagattaatt caaaacctaa atcattattt ggataaataa caatataatt  5940
tttattactt tgtatcagtg cttttactaa attgtctgct tgattttttaa tgctagtaat 6000 ttcagttgta acaggatgaa acataagcaa agcgtagttt tcataattta tatcataata  6060
tttttttgct tcgctaagtg aaattttatt atcgtttaaa agttctaaat caggcgaacc  6120
tatgataaaa atagattttt catcttctcc aagctgcatt aaacgccttt ttgcaaactc   6180
atcatttact aaatgaatat gagctagttt tgatatagcg tggcgtaagc tatcgtcaat   6240
agttcctgaa atctctccgc cttcaatatg cgctactaag atattattta atgctccaac   6300
aatagctgct gctaaaggct caattctatc tccatgtact acgattaaat caggttttag  6360
ctcatttgca taccttgaaa atccatcaat tgtagtagct aaagccttat cagtttgata  6420
atatttatca taatttataa attcataaat attttttaaag ccatttttat aaagttcttt  6480
aactgtatag ccaaaatttt tacttaagtg cattcctgtt gcaaagatgt aaagttcaaa  6540
ttcgcttgag ttttgcaccc tgtacattaa agatttaatc ttagaataat cagccctaga  6600
gcctgttata aaaaggattt ttttcacgca aaatcctcat agcttaactg agcatcattt   6660
tctatatctc ttaatgcttt tttgcctaaa atattttcaa attcagccgc actaattcca  6720
ccaagtccag gtcttttaac ccaaatatta tccatagata aaacttcgcc tttttttaata 6780 tctttaatgc taactacact tgcaaaggca aaatcaattg taacttgttc ttgtttagcc  6840
gcttttttac tttcattatt tcctcttatt atagccattt gctcactttg tataattagc  6900
tcttttaaag cctttgtatc catagaacaa actatatcag ggcccacttct atgcatacta 6960 tcagtaaaat gtctttcaag cacacaagct ccaagtacaa ctgcacctaa acacgcaaga  7020
ttatctgttg tgtggtcgct taagcctacc atacaagaaa attcttttttt taactcaagc 7080 atagcgttta atcttacaag attatgcggg gttgggtaaa gattggtcgt gtgcattaaa  7140
acaaaaggaa tttcattgtc taataagatt tttacagttg gttttatact ttcaatacta   7200
ttcattcctg tgctaactat cataggcttt ttaaaggctg ctatgtgttt aataagcgga  7260
taattattac actcacctga accaatctta aaagcactaa ctcccatatc ttctaagcgg  7320
```

-continued

```
ttcgcacctg cacgagaaaa aggtgtgcta agataaacaa gacctaatttt ttctgtgtat    7380 tctttaagtg ctagctcatc tttataatcc aaagcacatt tttgcataat ctcataaatg    7440 cttattttttg cattaccagg aattacttttt ttagcggcct tactcatctc atcttcaaca   7500
atatgagttt gatgctttat aatcttagca cctgcgctaa aggctgcatc taccataatt    7560
ttagctagtt ctaaactgcc attatgatta atgcctattt caggtacgac taagggtgct   7620
ttttcttcac ttatgattat attttgtatt tttattttctt tcatttattt tcctccttag   7680
```

<210> SEQ ID NO 6
<211> LENGTH: 4426
<212> TYPE: DNA
<213> ORGANISM: Artificial Sequence
<220> FEATURE:
<223> OTHER INFORMATION: engineered plasmid

<400> SEQUENCE: 6

```
ctaaattgta agcgttaata tttttgttaaa attcgcgtta aattttttgtt aaatcagctc    60 atttttttaac caataggccg aaatcggcaa atcccttat aaatcaaaag aatagaccga   120
gatagggttg agtgttgttc cagtttggaa caagagtcca ctattaaaga acgtggactc   180
caacgtcaaa gggcgaaaaa ccgtctatca gggcgatggc ccactacgtg aaccatcacc   240
ctaatcaagt tttttggggt cgaggtgccg taaagcacta atcggaacc ctaaagggag   300 ccccgatttt agagcttgac ggggaaagcc ggcgaacgtg gcgagaaagg aagggaagaa   360
agcgaaagga gcgggcgcta gggcgctggc aagtgtagcg gtcacgctgc gcgtaaccac   420
cacacccgcc gcgcttaatg cgccgctaca gggcgcgtcc cattcgccat tcaggctgcg   480
caactgttgg gaagggcgat cggtgcgggc ctcttcgcta ttacgccagc tggcgaaagg   540
gggatgtgct gcaaggcgat taagttgggt aacgccaggg ttttcccagt cacgacgttg   600
taaaacgacg gccagtgagc gcgcgtaata cgactcacta gggcgaat tggagctcca   660 ccgcggtggc ggccgctcta gaactagtgg atccctagac tgcaatacaa acacctgttt   720
cacaatttgg cagatcagcc caaaaaagta cattctcttc ttttacaata cctagtttta   780
tcattacttg aactaaagga cttctcaaag cagtttcacg atcagttata gtttctgtcg   840
atgtaaaaac tataaattta attttttcag ctggtatcgt gaaatataaa gagctcgcta   900
taccagcaac tgcatcagga agcatatctg tcatcatcaa acttcaaat gatatttttg   960 atggaatatc aaccattgaa ggatagttttt gcattattaa tgtattaatg ataccgccac   1020
cagggtgacc tttgaagaac aaatcataac tattgcctaa ataatgtggg ctcgattcat   1080
taattgcatt attaatgaca ttaattttgtt gtttcgcata atactctctt tcatggttac   1140
cagcccatac agtcgtacct gtaaacacaa agtttggtaa attagatgaa ttatattcat   1200
tttgtaattt ttgtttgtca aaattaacaa tcgataagaa taattcttgt tgttttgctat   1260 tgaatttttt gaaaccatcc cattgcatttt gctttaaact atcaccaata tagtctcgta   1320
actcatgtaa tgatggttct aaagttaaat aatcttttct taaaaatgg tagttagctg   1380 gatatagttt ttgccagtta taaacagatg atgttcctgt atttgaagtg tcttcattga   1440
taccattaat gacatcctca agataatctt taccaattttt taaattatct gttttattta   1500
atgtatctct ccagttatat aaatttacat attctgctga accatcatca tataaatcta   1560
tatttgttac cgtaacgtta ttaaacgaat ttaattctttt tagtattggc actaaattat   1620
caaatgaatg agcagtgtta gagctaagtt taacattcaa tctatgcttt gtttgtgctt   1680
```

```
gcttaacaat ttcttgtact aagtcagctg gtgtatggtt atttatcaat gcaaacgatg    1740
taatatttaa ctcttttcatt tgctcatcag tcggaactat tctcccccaa gctatatatc    1800
tttgtgctgt aggattttct tcttccgatt taataatatc cattagctgc tgaagagttg    1860
gaagagatgc atgatcaaca taaacctcta aagatggagc cactacgttt aatgttactt    1920
ttgttatata tttttcacct ttattactaa caccattaaa atcaaagcag tactttcat     1980 cgtcatctaa tcgtggcgcc actacagata atgatattga ctctttattt tgttctgtta    2040
atagttgttg cgtaccacaa gtttgtaccc aagagtgttt tgtaaaagag atgtttgatt    2100
gattaattgg ctctaaatta acatactcct catcaataat agttttatta atatcatttt    2160
taataataga ttgtgtattt tcttctgaca tggtctgttt cctcctcgag ggggggcccg    2220
gtacccagct tttgttccct ttagtgaggg ttaattgcgc gcttggcgta atcatggtca    2280
tagctgtttc ctgtgtgaaa ttgttatccg ctcacaattc cacacaacat acgagccgga    2340
agcataaagt gtaaagcctg gggtgcctaa tgagtgagct aactcacatt aattgcgttg    2400
cgctcactgc ccgctttcca gtcgggaaac ctgtcgtgcc agctgcatta atgaatcggc    2460
caacgcgcgg ggagaggcgg tttgcgtatt gggcgctctt ccgcttcctc gctcactgac    2520
tcgctgcgct cggtcgttcg gctgcggcga gcggtatcag ctcactcaaa ggcggtaata    2580
cggttatcca cagaatcagg ggataacgca ggaaagaaca tgtgagcaaa aggccagcaa    2640
aaggccagga accgtaaaaa ggccgcgttg ctggcgtttt tccataggct ccgcccccct    2700
gacgagcatc acaaaaatcg acgctcaagt cagaggtggc gaaacccgac aggactataa    2760
agataccagg cgtttccccc tggaagctcc ctcgtgcgct ctcctgttcc gaccctgccg    2820
cttaccggat acctgtccgc ctttctccct tcgggaagcg tggcgctttc tcatagctca    2880
cgctgtaggt atctcagttc ggtgtaggtc gttcgctcca agctgggctg tgtgcacgaa    2940
ccccccgttc agcccgaccg ctgcgcctta tccggtaact atcgtcttga gtccaacccg    3000
gtaagacacg acttatcgcc actggcagca gccactggta acaggattag cagagcgagg    3060
tatgtaggcg gtgctacaga gttcttgaag tggtggccta actacggcta cactagaagg    3120
acagtatttg gtatctgcgc tctgctgaag ccagttacct tcggaaaaag agttggtagc    3180
tcttgatccg gcaaacaaac caccgctggt agcggtggtt ttttgtttg caagcagcag    3240 attacgcgca gaaaaaaagg atctcaagaa gatcctttga tcttttctac ggggtctgac    3300
gctcagtgga acgaaaactc acgttaaggg attttggtca tgagattatc aaaaaggatc    3360
ttcacctaga tccttttaaa ttaaaaatga agttttaaat caatctaaag tatatatgag    3420
taaacttggt ctgacagtta ccaatgctta atcagtgagg cacctatctc agcgatctgt    3480
ctatttcgtt catccatagt tgcctgactc cccgtcgtgt agataactac gatacgggag    3540
ggcttaccat ctggccccag tgctgcaatg ataccgcgag acccacgctc accggctcca    3600
gatttatcag caataaacca gccagccgga agggccgagc gcagaagtgg tcctgcaact    3660
ttatccgcct ccatccagtc tattaattgt tgccgggaag ctagagtaag tagttcgcca    3720
gttaatagtt tgcgcaacgt tgttgccatt gctacaggca tcgtggtgtc acgctcgtcg    3780
tttggtatgg cttcattcag ctccggttcc caacgatcaa ggcgagttac atgatccccc    3840
atgttgtgca aaaaagcggt tagctccttc ggtcctccga tcgttgtcag aagtaagttg    3900
gccgcagtgt tatcactcat ggttatggca gcactgcata attctcttac tgtcatgcca    3960
tccgtaagat gcttttctgt gactggtgag tactcaacca agtcattctg agaatagtgt    4020
atgcggcgac cgagttgctc ttgcccggcg tcaatacggg ataataccgc gccacatagc    4080
```

```
agaactttaa aagtgctcat cattggaaaa cgttcttcgg ggcgaaaact ctcaaggatc    4140
ttaccgctgt tgagatccag ttcgatgtaa cccactcgtg cacccaactg atcttcagca    4200
tcttttactt tcaccagcgt ttctgggtga gcaaaaacag gaaggcaaaa tgccgcaaaa    4260
aagggaataa gggcgacacg gaaatgttga atactcatac tcttcctttt tcaatattat    4320
tgaagcattt atcagggtta ttgtctcatg agcggataca tatttgaatg tatttagaaa    4380
aataaacaaa taggggttcc gcgcacattt ccccgaaaag tgccac                   4426
```

<210> SEQ ID NO 7
<211> LENGTH: 22
<212> TYPE: DNA
<213> ORGANISM: Artificial Sequence
<220> FEATURE:
<223> OTHER INFORMATION: chemically synthesized oligonucleotide

<400> SEQUENCE: 7

```
ctcgaggagg aaacagacca tg                                               22
```

<210> SEQ ID NO 8
<211> LENGTH: 28
<212> TYPE: DNA
<213> ORGANISM: Artificial Sequence
<220> FEATURE:
<223> OTHER INFORMATION: chemically synthesized oligonucleotide

<400> SEQUENCE: 8

```
ctcgaggaaa gagggacaa actagatg                                          28
```

<210> SEQ ID NO 9
<211> LENGTH: 4432
<212> TYPE: DNA
<213> ORGANISM: Artificial Sequence
<220> FEATURE:
<223> OTHER INFORMATION: engineered plasmid

<400> SEQUENCE: 9

```
ctaaattgta agcgttaata ttttgttaaa attcgcgtta aatttttgtt aaatcagctc      60 atttttaac caataggccg aaatcggcaa atcccttat aaatcaaaag aatagaccga       120
gatagggttg agtgttgttc cagtttggaa caagagtcca ctattaaaga acgtggactc     180
caacgtcaaa gggcgaaaaa ccgtctatca gggcgatggc ccactacgtg aaccatcacc    240
ctaatcaagt tttttggggt cgaggtgccg taaagcacta atcggaacc ctaaagggag     300 cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat tggagctcca    660
ccgcggtggc ggccgctcta gaactagtgg atccctagac tgcaatacaa acacctgttt    720
cacaatttgg cagatcagcc caaaaaagta cattctcttc ttttacaata cctagtttta    780
tcattacttg aactaaagga cttctcaaag cagtttcacg atcagttata gtttctgtcg    840
atgtaaaaac tataaattta attttttcag ctggtatcgt gaaatataaa gagctcgcta    900
taccagcaac tgcatcagga agcatatctg tcatcatcaa aacttcaaat gatattttg     960
```

| | |
|---|---|
| atggaatatc aaccattgaa ggatagtttt gcattattaa tgtattaatg ataccgccac | 1020 |
| cagggtgacc tttgaagaac aaatcataac tattgcctaa ataatgtggg ctcgattcat | 1080 |
| taattgcatt attaatgaca ttaatttgtt gtttcgcata atactctctt tcatggttac | 1140 |
| cagcccatac agtcgtacct gtaaacacaa agtttggtaa attagatgaa ttatattcat | 1200 |
| tttgtaattt ttgtttgtca aaattaacaa tcgataagaa taattcttgt tgtttgctat | 1260 |
| tgaatttttt gaaaccatcc cattgcattt gctttaaact atcaccaata tagtctcgta | 1320 |
| actcatgtaa tgatggttct aaagttaaat aatcttttct taaaaatgg tagttagctg | 1380 |
| gatatagttt ttgccagtta taaacagatg atgttcctgt atttgaagtg tcttcattga | 1440 |
| taccattaat gacatcctca agataatctt taccaatttt taaattatct gttttattta | 1500 |
| atgtatctct ccagttatat aaatttacat attctgctga accatcatca tataaatcta | 1560 |
| tatttgttac cgtaacgtta ttaaacgaat ttaattcttt tagtattggc actaaattat | 1620 |
| caaatgaatg agcagtgtta gagctaagtt taacattcaa tctatgcttt gtttgtgctt | 1680 |
| gcttaacaat ttcttgtact aagtcagctg gtgtatggtt atttatcaat gcaaacgatg | 1740 |
| taatatttaa ctcttcatt tgctcatcag tcggaactat tctcccccaa gctatatatc | 1800 |
| tttgtgctgt aggattttct tcttccgatt taataatatc cattagctgc tgaagagttg | 1860 |
| gaagagatgc atgatcaaca taaacctcta aagatggagc cactacgttt aatgttactt | 1920 |
| ttgttatata ttttcacct ttattactaa caccattaaa atcaaagcag tacttttcat | 1980 |
| cgtcatctaa tcgtggcgcc actacagata tgatattga ctctttattt tgttctgtta | 2040 |
| atagttgttg cgtaccacaa gtttgtaccc aagagtgttt tgtaaaagag atgtttgatt | 2100 |
| gattaattgg ctctaaatta acatactcct catcaataat agttttatta atatcatttt | 2160 |
| taataataga ttgtgtattt tcttctgaca tctagtttgt cccctctttc ctcgagggg | 2220 |
| ggcccggtac ccagcttttg ttccctttag tgagggttaa ttgcgcgctt ggcgtaatca | 2280 |
| tggtcatagc tgtttcctgt gtgaaattgt tatccgctca caattccaca caacatacga | 2340 |
| gccggaagca taaagtgtaa agcctggggt gcctaatgag tgagctaact cacattaatt | 2400 |
| gcgttgcgct cactgcccgc tttccagtcg ggaaacctgt cgtgccagct gcattaatga | 2460 |
| atcggccaac gcgcggggag aggcggtttg cgtattgggc gctcttccgc ttcctcgctc | 2520 |
| actgactcgc tgcgctcggt cgttcggctg cggcgagcgg tatcagctca ctcaaaggcg | 2580 |
| gtaatacggt tatccacaga atcaggggat aacgcaggaa agaacatgtg agcaaaaggc | 2640 |
| cagcaaaagg ccaggaaccg taaaaaggcc gcgttgctgg cgtttttcca taggctccgc | 2700 |
| ccccctgacg agcatcacaa aaatcgacgc tcaagtcaga ggtggcgaaa cccgacagga | 2760 |
| ctataaagat accaggcgtt tcccctggaa gctccctcg tgcgctctcc tgttccgacc | 2820 |
| ctgccgctta ccggatacct gtccgccttt ctcccttcgg gaagcgtggc gctttctcat | 2880 |
| agctcacgct gtaggtatct cagttcggtg taggtcgttc gctccaagct gggctgtgtg | 2940 |
| cacgaacccc ccgttcagcc cgaccgctgc gccttatccg gtaactatcg tcttgagtcc | 3000 |
| aacccggtaa gacacgactt atcgccactg gcagcagcca ctggtaacag gattagcaga | 3060 |
| gcgaggtatg taggcggtgc tacagagttc ttgaagtggt ggcctaacta cggctacact | 3120 |
| agaaggacag tatttggtat ctgcgctctg ctgaagccag ttaccttcgg aaaaagagtt | 3180 |
| ggtagctctt gatccggcaa acaaaccacc gctggtagcg tggtttttt tgtttgcaag | 3240 |
| cagcagatta cgcgcagaaa aaaaggatct caagaagatc ctttgatctt ttctacgggg | 3300 |
| tctgacgctc agtggaacga aaactcacgt taagggattt tggtcatgag attatcaaaa | 3360 |

```
aggatcttca cctagatcct tttaaattaa aaatgaagtt ttaaatcaat ctaaagtata    3420
tatgagtaaa cttggtctga cagttaccaa tgcttaatca gtgaggcacc tatctcagcg    3480
atctgtctat ttcgttcatc catagttgcc tgactcccg tcgtgtagat aactacgata     3540
cgggagggct taccatctgg ccccagtgct gcaatgatac cgcgagaccc acgctcaccg    3600
gctccagatt tatcagcaat aaaccagcca gccggaaggg ccgagcgcag aagtggtcct    3660
gcaactttat ccgcctccat ccagtctatt aattgttgcc gggaagctag agtaagtagt    3720
tcgccagtta atagtttgcg caacgttgtt gccattgcta caggcatcgt ggtgtcacgc    3780
tcgtcgtttg gtatggcttc attcagctcc ggttcccaac gatcaaggcg agttacatga    3840
tcccccatgt tgtgcaaaaa agcggttagc tccttcggtc ctccgatcgt tgtcagaagt    3900
aagttggccg cagtgttatc actcatggtt atggcagcac tgcataattc tcttactgtc    3960
atgccatccg taagatgctt ttctgtgact ggtgagtact caaccaagtc attctgagaa    4020
tagtgtatgc ggcgaccgag ttgctcttgc ccggcgtcaa tacgggataa taccgcgcca    4080
catagcagaa ctttaaaagt gctcatcatt ggaaaacgtt cttcggggcg aaaactctca    4140
aggatcttac cgctgttgag atccagttcg atgtaaccca ctcgtgcacc caactgatct    4200
tcagcatctt ttactttcac cagcgtttct gggtgagcaa aacaggaag gcaaaatgcc     4260 gcaaaaagg aataagggc gacacggaaa tgttgaatac tcatactctt ccttttcaa       4320 tattattgaa gcatttatca gggttattgt ctcatgagcg gatacatatt tgaatgtatt    4380
tagaaaaata acaaataggg gttccgcgc acatttcccc gaaaagtgcc ac             4432

<210> SEQ ID NO 10
<211> LENGTH: 19
<212> TYPE: DNA
<213> ORGANISM: Artificial Sequence
<220> FEATURE:
<223> OTHER INFORMATION: chemically synthesized oligonucleotide

<400> SEQUENCE: 10
ctttattaaa cctactatg                                                  19

<210> SEQ ID NO 11
<211> LENGTH: 19
<212> TYPE: DNA
<213> ORGANISM: Artificial Sequence
<220> FEATURE:
<223> OTHER INFORMATION: chemically synthesized oligonucleotide

<400> SEQUENCE: 11
ctttcttcaa cctactatg                                                  19

<210> SEQ ID NO 12
<211> LENGTH: 7916
<212> TYPE: DNA
<213> ORGANISM: Artificial Sequence
<220> FEATURE:
<223> OTHER INFORMATION: engineered plasmid

<400> SEQUENCE: 12
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc     180
accatatatg cggtgtgaaa taccgcacag atgcgtaagg agaaaatacc gcatcaggcg    240
```

```
ccactagtgt tgaggaaaac gattggctga acaaaaaaca gactgatcga ggtcattttt    300
gagtgcaaaa agtgctgtaa ctctgaaaaa gcgatggtag aatccatttt taagcaaacg    360
gtgattttga aaaatgggta acaacgtcgt cgtactgggc acccaatggg gtgacgaagg    420
taaaggtaag atcgtcgatc ttctgactga acgggctaaa tatgttgtac gctaccaggg    480
cggtcacaac gcaggccata ctctcgtaat caacggtgaa aaaaccgttc tccatcttat    540
tccatcaggt attctccgcg agaatgtaac cagcatcatc ggtaacggtg ttgtgctgtc    600
tccggccgcg ctgatgaaag agatgaaaga actggaagac cgtggcatcc ccgttcgtga    660
gcgtctgctg ctgtctgaag catgtccgct gatccttgat tatcacgttg cgctggataa    720
cgcgcgtgag aaagcgcgtg gcgcgaaagc gatcggcacc accggtcgtg gtatcgggcc    780
tgcttatgaa gataaagtag cacgtcgcgg tctgcgtgtt ggcgaccttt tcgacaaaga    840
aaccttcgct gaaaaactga agaagtgat ggaatatcac aacttccagt tggttaacta    900
ctacaaagct gaagcggttg attaccagaa agttctggat gatacgatgg ctgttgccga    960
catcctgact tctatggtgg ttgacgtttc tgacctgctc gaccaggcgc gtcagcgtgg   1020
cgatttcgtc atgtttgaag gtgcgcaggg tacgctgctg gatatcgacc acggtactta   1080
tccgtacgta acttcttcca acaccactgc tggtggcgtg gcgaccggtt ccggcctggg   1140
cccgcgttat gttgattacg ttctgggtat cctcaaagct tactccactc gtgtaggtgc   1200
aggtccgttc ccgaccgaac tgtttgatga aactggcgag ttcctctgca agcagggtaa   1260
cgaattcggc gcaactacgg ggcgtcgtcg tcgtaccggc tggctggaca ccgttgccgt   1320
tcgtcgtgcg gtacagctga actccctgtc tggcttctgc ctgactaaac tggacgttct   1380
ggatggcctg aaagaggtta aactctgcgt ggcttaccgt atgccggatg gtcgcgaagt   1440
gactaccact ccgctggcag ctgacgactg gaaaggtgta gagccgattt acgaaaccat   1500
gccgggctgg tctgaatcca ccttcggcgt gaaagatcgt agcggcctgc cgcaggcggc   1560
gctgaactat atcaagcgta ttgaagagct gactggtgtg ccgatcgata tcatctctac   1620
cggtccggat cgtactgaaa ccatgattct gcgcgacccg ttcgacgcgt aattctggta   1680
cgcctggcag atattttgcc tgccgggcga acagtgtgat acattgctgt gtcgggtaag   1740
ccattacgct atccgacaca gtgttaaatc ctcgcttttt tccttcccca gatctggcgc   1800
cattcgccat tcaggctgcg caactgttgg gaagggcgat cggtgcgggc ctcttcgcta   1860
ttacgccagc tggcgaaagg gggatgtgct gcaaggcgat taagttgggt aacgccaggg   1920
ttttcccagt cacgacgttg taaaacgacg gccagtgcca gcttactgc tcacaagaaa    1980 aaaggcacgt catctgacgt gccttttta tttgtactac cctgtacgat tactgcaggt   2040
cgacttaatt ttccagcaaa tgctggagca aaataccgtt gagcatgcg cgttttacca    2100 gcgcaaaagc gccgattgcc gagcggtgat ccagctcaga acgtaccacc ggcagattag   2160
tgcgaaacgc cttcagcgcc tgggtattaa tgcagctttc aatagcaggg agcagcactt   2220
tatcggcttc ggtgatttca ccggcaataa caattttttg cggattaaat aagttgatag   2280
caatggcgat ggttttaccc agatgacgac cgacatactc aattacttcc gacgccagac   2340
tatcgccttt gttcgcggct ttgcagatag ttttgatggt gcagtcgtcc agcggcacgc   2400
ggctctggta gccctgcttt aacagattca acacccgttg ttcaatggca gcgttggcag   2460
cgatagtttc caggcagcca agttgccgc agtggcagcg ttcacccagc ggttcgacct    2520
gaatatggcc aatttcaccg acgttgccgt tgcggccaat aaaaatgcgc ccgttagaga   2580
taatcccggc cccggttccg cgatggacac gcaccagaat ggagtcttcg caatcctgac   2640
```

-continued

```
ttgcaccgaa gtagtgctcc gccagcgcca gactacggat atcgtgacca acgaaacagg    2700
tcactttaaa acgttcttcc agagcttcta ccagccccca gttttctacc tgaatatgcg    2760
gcatgtaatg aattttgccg ctgtccgggt caacaagccc tggcaggatc accgaaatcg    2820
cgatcagctc gcgcagtttg cgctggtagc tatcaataaa ctgagcaatg cattcaaca    2880
gggcatgttc cagcgtttgc tgggtacgtt ccggcagcgg gtaatgttct tctgccagca    2940
cttttgctgct gagatcaaac agagtgatgg tggcgtcatg acgaccaagc cgtacgccga    3000
ttgcgtggaa attgcgggtt tcggtgacga tggagatagc gcggcggccc ccggtggagg    3060
cctgctgatc aacttctttg atcagcccgc gttcgataag ctgacgcgta attttggtta    3120
cgctggcggg ggcaagctgg ctttgctcgg caatctgaat ccgcgagatt ggcccgtact    3180
ggtcaatcag gcgataaacc gccgcgctgt taagctgttt tacgagatca acattaccta    3240
tctgagcttg tccgcctggt gtcatatgta tatctccttc ttgtcgactc tagatgcatg    3300
ctcgagatta ctcaaccgta accgattttg ccaggttacg cggctggtca acgtcggtgc    3360
cttttgatcag cgcgacatgg taagccagca gctgcagcgg aacggtgtag aagatcggtg    3420
caatcacctc ttccacatgc ggcatctcga tgatgtgcat gttatcgcta cttacaaaac    3480
ccgcatcctg atcggcgaag acatacaact gaccgccacg cgcgcgaact tcttcaatgt    3540
tggatttcag tttttccagc aattcgttgt tcggtgcaac aacaataacc ggcatatcgg    3600
catcaattag cgccagcgga ccgtgtttca gttcgccagc agcgtaggct tcagcgtgaa    3660
tgtaagagat ctcttttcaac ttcaatgcgc cttccagcgc gattgggtac tgatcgccac    3720
ggcccaggaa cagcgcgtga tgtttgtcag agaaatcttc tgccagcgct tcaatgcgtt    3780
tgtcctgaga cagcatctgc tcaatacggc tcggcagcgc ctgcagacca tgcacgatgt    3840
catgttcaat ggaggcatcc agacctttca ggcgagacag cttcgccacc agcatcaaca    3900
gcacagttaa ctgagtggtg aatgcttag tggatgccac gccgatttct gtacccgcgt    3960
tggtcattag cgccagatcg gattcgcgca ccagagaaga acccggaacg ttacagattg    4020
ccagtgaacc aaggtaaccc agctctttcg acagacgcag gccagccagg gtatccgcgg    4080
tttcgccaga ctgtgacaag gtgatcatca ggctgttacg acgcacggca gatttgcgat    4140
agcggaattc agaggcgatt tcgacgtcgc acggaatacc tgctagcgat tcaaaccagt    4200
agcgggaaac cataccggag ttataagaag taccacaggc gaggatctga atatgctcaa    4260
ccttcgacag cagttcgtcg gcgttcggtc ccagctcgct taaatcaacc tgaccgtggc    4320
tgatgcgtcc ggtaagggtg tttttgatcg cgttcggctg ttcgtagatc tctttctgca    4380
tgtagtgacg gtaaatgcct ttatcgcccg cgtcatattg cagattggat tcgatatcct    4440
gacgttttac ttccgcgcca gttttatcga agatgtttac cgaacggcga gtgatttccg    4500
caatatcgcc ctcttcaagg aagataaagc gacgggtcac cggcaacagc gccagctggt    4560
cagaagcgat aaagttttcg cccatccca ggccaatcac cagcggacta ccagaacgtg    4620
ccgccagcag ggtatccggg tgacgggagt ccatgatcac tgtaccgtac gcaccacgca    4680
gctgcgggat agcacgcaga acggcctcac gcagagtccc gccttgtttc agctcccagt    4740
tcaccagatg ggcaatcact tcggtgtcgg tttcagaaaac gaaggtatag ccacgcgctt    4800
ttagctcttc acgcagcggt tcatggtttt cgatgatgcc gttatgcacc accacaatgt    4860
gttcagaaac atgcggatgc gcattcactt ctgaaggttc accgtgggtc gcccagcgag    4920
tgtgagcaat accagtgccg ccatgcagag gatgttcttc cgctgcctgt gccagcatct    4980
```

```
ggactttacc gaggcgacgc aggcgggtca tatgaccttc tgcatcaaca acggccagac    5040
cggcagagtc atatccgcgg tattccagac gacgtaaacc ttcaagaagg atttctgcta    5100
catcacgttg cgcgatcgcg ccaacaattc cacacatatg tatatctcct tcttgaattc    5160
taacaattga ttgaatgtat gcaaataaat gcatacacca taggtgtggt ttaatttgat    5220
gcccttttc agggctggaa tgtgtaagag cggggttatt tatgctgttg ttttttttgtt    5280
actcgggaag ggctttacct cttccgcata aacgcttcca tcagcgttta tagttaaaaa    5340
aatctttcgg aactggtttt gcgcttaccc caaccaacag gggatttgct gctttccatt    5400
gagcctgttt ctctgcgcga cgttcgcggc ggcgtgtttg tgcatccatc tggattctcc    5460
tgtcagttag ctttggtggt gtgtggcagt tgtagtcctg aacgaaaacc ccccgcgatt    5520
ggcacattgg cagctaatcc ggaatcgcac ttacggccaa tgcttcgttt cgtatcacac    5580
accccaaagc cttctgcttt gaatgctgcc cttcttcagg gcttaatttt taagagcgtc    5640
accttcatgg tggtcagtgc gtcctgctga tgtgctcagt atcaccgcca gtggtattta    5700
tgtcaacacc gccagagata atttatcacc gcagatggtt atctgtatgt ttttatatg    5760
aatttatttt ttgcaggggg gcattgtttg gtaggtgaga gatcaattct gcattaatga    5820
atcggccaac gcgcggggag aggcggtttg cgtattgggc gctcttccgc tgctagcgga    5880
gtgtatactg gcttactatg ttggcactga tgagggtgtc agtgaagtgc ttcatgtggc    5940
aggagaaaaa aggctgcacc ggtgcgtcag cagaatatgt gatacaggat atattccgct    6000
tcctcgctca ctgactcgct acgctcggtc gttcgactgc ggcgagcgga aatggcttac    6060
gaacggggcg agatttcct ggaagatgcc aggaagatac ttaacaggga agtgagaggg    6120
ccgcggcaaa gccgttttc cataggctcc gcccccctga caagcatcac gaaatctgac    6180
gctcaaatca gtggtggcga aacccgacag gactataaag ataccaggcg tttccccctg    6240
gcggctccct cgtgcgctct cctgttcctg cctttcggtt taccggtgtc attccgctgt    6300
tatgccgcg tttgtctcat tccacgcctg acactcagtt ccgggtaggc agttcgctcc    6360
aagctggact gtatgcacga accccccgtt cagtccgacc gctgcgcctt atccggtaac    6420
tatcgtcttg agtccaaccc ggaaagacat gcaaaagcac cactggcagc agccactggt    6480
aattgattta gaggagttag tcttgaagtc atgcgccggt taaggctaaa ctgaaaggac    6540
aagttttggt gactgcgctc ctccaagcca gttacctcgg ttcaaagagt tggtagctca    6600
gagaaccttc gaaaaaccgc cctgcaaggc ggttttttcg ttttcagagc aagagattac    6660
gcgcagacca aaacgatctc aagaagatca tcttattaat cagataaaat atttctaggc    6720
ggccgcgaac gaaaactcac gttaagggat tttggtcatg agattatcaa aaaggatctt    6780
cacctagatc cttttaaatt aaaaatgaag ttttaaatca atctaaagta tatatgagta    6840
aacttggtct gacagttacc aatgcttaat cagtgaggca cctatctcag cgatctgtct    6900
atttcgttca tccatagttg cctgactccc cgtcgtgtag ataactacga tacgggaggg    6960
cttaccatct ggccccagtg ctgcaatgat accgcgagac ccacgctcac cggctccaga    7020
tttatcagca ataaaccagc cagccggaag ggccgagcgc agaagtggtc ctgcaacttt    7080
atccgcctcc atccagtcta ttaattgttg ccgggaagct agagtaagta gttcgccagt    7140
taatagtttg cgcaacgttg ttgccattgc tacaggcatc gtggtgtcac gctcgtcgtt    7200
tggtatggct tcattcagct ccggttccca acgatcaagg cgagttacat gatcccccat    7260
gttgtgcaaa aaagcggtta gctccttcgg tcctccgatc gttgtcagaa gtaagttggc    7320
cgcagtgtta tcactcatgg ttatggcagc actgcataat tctcttactg tcatgccatc    7380
```

-continued

```
cgtaagatgc ttttctgtga ctggtgagta ctcaaccaag tcattctgag aatagtgtat    7440
gcggcgaccg agttgctctt gcccggcgtc aatacgggat aataccgcgc cacatagcag    7500
aactttaaaa gtgctcatca ttggaaaacg ttcttcgggg cgaaaactct caaggatctt    7560
accgctgttg agatccagtt cgatgtaacc cactcgtgca cccaactgat cttcagcatc    7620
ttttactttc accagcgttt ctgggtgagc aaaaacagga aggcaaaatg ccgcaaaaaa    7680
gggaataagg gcgacacgga aatgttgaat actcatactc ttccttttc aatattattg     7740 aagcatttat cagggttatt gtctcatgag cggatacata tttgaatgta tttagaaaaa    7800
taaacaaata ggggttccgc gcacatttcc ccgaaaagtg ccacctgacg tctaagaaac    7860
cattattatc atgacattaa cctataaaaa taggcgtatc acgaggccct ttcgtc        7916
```

<210> SEQ ID NO 13
<211> LENGTH: 372
<212> TYPE: PRT
<213> ORGANISM: Campylobacter jejuni

<400> SEQUENCE: 13

Met Lys Lys Ile Leu Phe Ile Thr Gly Ser Arg Ala Asp Tyr Ser Lys
1               5                   10                  15

Ile Lys Ser Leu Met Tyr Arg Val Gln Asn Ser Ser Glu Phe Glu Leu
            20                  25                  30

Tyr Ile Phe Ala Thr Gly Met His Leu Ser Lys Asn Phe Gly Tyr Thr
        35                  40                  45

Val Lys Glu Leu Tyr Lys Asn Gly Phe Lys Asn Ile Tyr Glu Phe Ile
    50                  55                  60

Asn Tyr Asp Lys Tyr Tyr Gln Thr Asp Lys Ala Leu Ala Thr Thr Ile
65                  70                  75                  80

Asp Gly Phe Ser Arg Tyr Ala Asn Glu Leu Lys Pro Asp Leu Ile Val
                85                  90                  95

Val His Gly Asp Arg Ile Glu Pro Leu Ala Ala Ile Val Gly Ala
            100                 105                 110

Leu Asn Asn Ile Leu Val Ala His Ile Glu Gly Gly Glu Ile Ser Gly
        115                 120                 125

Thr Ile Asp Asp Ser Leu Arg His Ala Ile Ser Lys Leu Ala His Ile
    130                 135                 140

His Leu Val Asn Asp Glu Phe Ala Lys Arg Arg Leu Met Gln Leu Gly
145                 150                 155                 160

Glu Asp Glu Lys Ser Ile Phe Ile Ile Gly Ser Pro Asp Leu Glu Leu
                165                 170                 175

Leu Asn Asp Asn Lys Ile Ser Leu Ser Glu Ala Lys Lys Tyr Tyr Asp
            180                 185                 190

Ile Asn Tyr Glu Asn Tyr Ala Leu Leu Met Phe His Pro Val Thr Thr
        195                 200                 205

Glu Ile Thr Ser Ile Lys Asn Gln Ala Asp Asn Leu Val Lys Ala Leu
    210                 215                 220

Ile Gln Ser Asn Lys Asn Tyr Ile Val Ile Tyr Pro Asn Asn Asp Leu
225                 230                 235                 240

Gly Phe Glu Leu Ile Leu Gln Ser Tyr Glu Glu Phe Lys Asn Asn Pro
                245                 250                 255

Arg Phe Lys Leu Phe Pro Ser Leu Arg Phe Glu Tyr Phe Ile Thr Leu
            260                 265                 270

Leu Lys Asn Ala Asp Phe Ile Ile Gly Asn Ser Ser Cys Ile Leu Lys

```
            275                 280                 285
Glu Ala Leu Tyr Leu Lys Thr Ala Gly Ile Leu Val Gly Ser Arg Gln
    290                 295                 300

Asn Gly Arg Leu Gly Asn Glu Asn Thr Leu Lys Val Asn Ala Asn Ser
305                 310                 315                 320

Asp Glu Ile Leu Lys Ala Ile Asn Thr Ile His Lys Lys Gln Asp Leu
                325                 330                 335

Phe Ser Ala Lys Leu Glu Ile Leu Asp Ser Ser Lys Leu Phe Phe Glu
            340                 345                 350

Tyr Leu Gln Ser Gly Asp Phe Phe Lys Leu Ser Thr Gln Lys Val Phe
        355                 360                 365

Lys Asp Ile Lys
        370

<210> SEQ ID NO 14
<211> LENGTH: 346
<212> TYPE: PRT
<213> ORGANISM: Campylobacter jejuni

<400> SEQUENCE: 14

Met Lys Glu Ile Lys Ile Gln Asn Ile Ile Ser Glu Glu Lys Lys Ala
1               5                   10                  15

Pro Leu Val Val Pro Glu Ile Gly Ile Asn His Asn Gly Ser Leu Glu
            20                  25                  30

Leu Ala Lys Ile Met Val Asp Ala Ala Phe Ser Ala Gly Ala Lys Ile
        35                  40                  45

Ile Lys His Gln Thr His Ile Val Glu Asp Glu Met Ser Lys Ala Ala
    50                  55                  60

Lys Lys Val Ile Pro Gly Asn Ala Lys Ile Ser Ile Tyr Glu Ile Met
65                  70                  75                  80

Gln Lys Cys Ala Leu Asp Tyr Lys Asp Glu Leu Ala Leu Lys Glu Tyr
                85                  90                  95

Thr Glu Lys Leu Gly Leu Val Tyr Leu Ser Thr Pro Phe Ser Arg Ala
            100                 105                 110

Gly Ala Asn Arg Leu Glu Asp Met Gly Val Ser Ala Phe Lys Ile Gly
        115                 120                 125

Ser Gly Glu Cys Asn Asn Tyr Pro Leu Ile Lys His Ile Ala Ala Phe
    130                 135                 140

Lys Lys Pro Met Ile Val Ser Thr Gly Met Asn Ser Ile Glu Ser Ile
145                 150                 155                 160

Lys Pro Thr Val Lys Ile Leu Leu Asp Asn Glu Ile Pro Phe Val Leu
                165                 170                 175

Met His Thr Thr Asn Leu Tyr Pro Thr Pro His Asn Leu Val Arg Leu
            180                 185                 190

Asn Ala Met Leu Glu Leu Lys Lys Glu Phe Ser Cys Met Val Gly Leu
        195                 200                 205

Ser Asp His Thr Thr Asp Asn Leu Ala Cys Leu Gly Ala Val Val Leu
    210                 215                 220

Gly Ala Cys Val Leu Glu Arg His Phe Thr Asp Ser Met His Arg Ser
225                 230                 235                 240

Gly Pro Asp Ile Val Cys Ser Met Asp Thr Lys Ala Leu Lys Glu Leu
                245                 250                 255

Ile Ile Gln Ser Glu Gln Met Ala Ile Ile Arg Gly Asn Asn Glu Ser
            260                 265                 270
```

-continued

Lys Lys Ala Ala Lys Gln Glu Gln Val Thr Ile Asp Phe Ala Phe Ala
            275                 280                 285

Ser Val Ser Ile Lys Asp Ile Lys Lys Gly Glu Val Leu Ser Met
    290                 295                 300

Asp Asn Ile Trp Val Lys Arg Pro Gly Leu Gly Gly Ile Ser Ala Ala
305                 310                 315                 320

Glu Phe Glu Asn Ile Leu Gly Lys Lys Ala Leu Arg Asp Ile Glu Asn
            325                 330                 335

Asp Ala Gln Leu Ser Tyr Glu Asp Phe Ala
            340                 345

<210> SEQ ID NO 15
<211> LENGTH: 221
<212> TYPE: PRT
<213> ORGANISM: Campylobacter jejuni

<400> SEQUENCE: 15

Met Ser Leu Ala Ile Ile Pro Ala Arg Gly Gly Ser Lys Gly Ile Lys
1               5                   10                  15

Asn Lys Asn Leu Val Leu Leu Asn Asn Lys Pro Leu Ile Tyr Tyr Thr
            20                  25                  30

Ile Lys Ala Ala Leu Asn Ala Lys Ser Ile Ser Lys Val Val Val Ser
        35                  40                  45

Ser Asp Ser Asp Glu Ile Leu Asn Tyr Ala Lys Ser Gln Asn Val Asp
    50                  55                  60

Ile Leu Lys Arg Pro Ile Ser Leu Ala Gln Asp Asp Thr Thr Ser Asp
65                  70                  75                  80

Lys Val Leu Leu His Ala Leu Lys Phe Tyr Lys Asp Tyr Glu Asp Val
                85                  90                  95

Val Phe Leu Gln Pro Thr Ser Pro Leu Arg Thr Asn Ile His Ile Asn
            100                 105                 110

Glu Ala Phe Asn Leu Tyr Lys Asn Ser Asn Ala Asn Ala Leu Ile Ser
        115                 120                 125

Val Ser Glu Cys Asp Asn Lys Ile Leu Lys Ala Phe Val Cys Asn Asp
    130                 135                 140

Cys Gly Asp Leu Ala Gly Ile Cys Asn Asp Glu Tyr Pro Phe Met Pro
145                 150                 155                 160

Arg Gln Lys Leu Pro Lys Thr Tyr Met Ser Asn Gly Ala Ile Tyr Ile
                165                 170                 175

Leu Lys Ile Lys Glu Phe Leu Asn Asn Pro Ser Phe Leu Gln Ser Lys
            180                 185                 190

Thr Lys His Phe Leu Met Asp Glu Ser Ser Ser Leu Asp Ile Asp Cys
        195                 200                 205

Leu Glu Asp Leu Lys Lys Val Glu Gln Ile Trp Lys Lys
    210                 215                 220

<210> SEQ ID NO 16
<211> LENGTH: 349
<212> TYPE: PRT
<213> ORGANISM: Neisseria meningitidis

<400> SEQUENCE: 16

Met Pro Ser Glu Ala Phe Arg Arg His Arg Ala Tyr Arg Glu Asn Lys
1               5                   10                  15

Leu Gln Pro Leu Val Ser Val Leu Ile Cys Ala Tyr Asn Val Glu Lys
            20                  25                  30

Tyr Phe Ala Gln Ser Leu Ala Ala Val Val Asn Gln Thr Trp Arg Asn
                35                  40                  45

Leu Asp Ile Leu Ile Val Asp Asp Gly Ser Thr Asp Gly Thr Leu Ala
 50                  55                  60

Ile Ala Gln Arg Phe Gln Glu Gln Asp Gly Arg Ile Arg Ile Leu Ala
 65                  70                  75                  80

Gln Pro Arg Asn Ser Gly Leu Ile Pro Ser Leu Asn Ile Gly Leu Asp
                 85                  90                  95

Glu Leu Ala Lys Ser Gly Gly Gly Glu Tyr Ile Ala Arg Thr Asp
            100                 105                 110

Ala Asp Asp Ile Ala Ala Pro Asp Trp Ile Glu Lys Ile Val Gly Glu
            115                 120                 125

Met Glu Lys Asp Arg Ser Ile Ile Ala Met Gly Ala Trp Leu Glu Val
130                 135                 140

Leu Ser Glu Glu Lys Asp Gly Asn Arg Leu Ala Arg His His Glu His
145                 150                 155                 160

Gly Lys Ile Trp Lys Lys Pro Thr Arg His Glu Asp Ile Ala Asp Phe
                165                 170                 175

Phe Pro Phe Gly Asn Pro Ile His Asn Asn Thr Met Ile Met Arg Arg
            180                 185                 190

Ser Val Ile Asp Gly Gly Leu Arg Tyr Asn Thr Glu Arg Asp Trp Ala
        195                 200                 205

Glu Asp Tyr Gln Phe Trp Tyr Asp Val Ser Lys Leu Gly Arg Leu Ala
    210                 215                 220

Tyr Tyr Pro Glu Ala Leu Val Lys Tyr Arg Leu His Ala Asn Gln Val
225                 230                 235                 240

Ser Ser Lys Tyr Ser Ile Arg Gln His Glu Ile Ala Gln Gly Ile Gln
                245                 250                 255

Lys Thr Ala Arg Asn Asp Phe Leu Gln Ser Met Gly Phe Lys Thr Arg
            260                 265                 270

Phe Asp Ser Leu Glu Tyr Arg Gln Ile Lys Ala Val Ala Tyr Glu Leu
        275                 280                 285

Leu Glu Lys His Leu Pro Glu Glu Asp Phe Glu Arg Ala Arg Arg Phe
    290                 295                 300

Leu Tyr Gln Cys Phe Lys Arg Thr Asp Thr Leu Pro Ala Gly Ala Trp
305                 310                 315                 320

Leu Asp Phe Ala Ala Asp Gly Arg Met Arg Arg Leu Phe Thr Leu Arg
                325                 330                 335

Gln Tyr Phe Gly Ile Leu His Arg Leu Leu Lys Asn Arg
            340                 345

<210> SEQ ID NO 17
<211> LENGTH: 273
<212> TYPE: PRT
<213> ORGANISM: Helicobacter pylori

<400> SEQUENCE: 17

Met Arg Val Phe Ala Ile Ser Leu Asn Gln Lys Val Cys Asp Thr Phe
 1               5                  10                  15

Gly Leu Val Phe Arg Asp Thr Thr Leu Leu Asn Ser Ile Asn Ala
                 20                  25                  30

Thr His His Gln Ala Gln Ile Phe Asp Ala Ile Tyr Ser Lys Thr Phe
            35                  40                  45

Glu Gly Gly Leu His Pro Leu Val Lys Lys His Leu Pro Tyr Phe
 50                  55                  60

```
Ile Thr Gln Asn Ile Lys Asp Met Gly Ile Thr Thr Asn Leu Ile Ser
 65                  70                  75                  80

Glu Val Ser Lys Phe Tyr Tyr Ala Leu Lys Tyr His Ala Lys Phe Met
                 85                  90                  95

Ser Leu Gly Glu Leu Gly Cys Tyr Ala Ser His Tyr Ser Leu Trp Glu
            100                 105                 110

Lys Cys Ile Glu Leu Asn Glu Ala Ile Cys Ile Leu Glu Asp Asp Ile
            115                 120                 125

Thr Leu Lys Glu Asp Phe Lys Glu Gly Leu Asp Phe Leu Glu Lys His
        130                 135                 140

Ile Gln Glu Leu Gly Tyr Ile Arg Leu Met His Leu Leu Tyr Asp Ala
145                 150                 155                 160

Ser Val Lys Ser Glu Pro Leu Ser His Lys Asn His Glu Ile Gln Glu
                165                 170                 175

Arg Val Gly Ile Ile Lys Ala Tyr Ser Glu Gly Val Gly Thr Gln Gly
            180                 185                 190

Tyr Val Ile Thr Pro Lys Ile Ala Lys Val Phe Leu Lys Cys Ser Arg
            195                 200                 205

Lys Trp Val Val Pro Val Asp Thr Ile Met Asp Ala Thr Phe Ile His
210                 215                 220

Gly Val Lys Asn Leu Val Leu Gln Pro Phe Val Ile Ala Asp Asp Glu
225                 230                 235                 240

Gln Ile Ser Thr Ile Ala Arg Lys Glu Glu Pro Tyr Ser Pro Lys Ile
                245                 250                 255

Ala Leu Met Arg Glu Leu His Phe Lys Tyr Leu Lys Tyr Trp Gln Phe
                260                 265                 270

Val

<210> SEQ ID NO 18
<211> LENGTH: 265
<212> TYPE: PRT
<213> ORGANISM: Escherichia coli

<400> SEQUENCE: 18

Met Ile Ile Asp Glu Ala Glu Ser Ala Glu Ser Thr His Pro Val Val
  1               5                  10                  15

Ser Val Ile Leu Pro Val Asn Lys Lys Asn Pro Phe Leu Asp Glu Ala
             20                  25                  30

Ile Asn Ser Ile Leu Ser Gln Thr Phe Ser Ser Phe Glu Ile Ile Ile
             35                  40                  45

Val Ala Asn Cys Cys Thr Asp Asp Phe Tyr Asn Glu Leu Lys His Lys
 50                  55                  60

Val Asn Asp Lys Ile Lys Leu Ile Arg Thr Asn Ile Ala Tyr Leu Pro
 65                  70                  75                  80

Tyr Ser Leu Asn Lys Ala Ile Asp Leu Ser Asn Gly Glu Phe Ile Ala
                 85                  90                  95

Arg Met Asp Ser Asp Asp Ile Ser His Pro Asp Arg Phe Thr Lys Gln
            100                 105                 110

Val Asp Phe Leu Lys Asn Asn Pro Tyr Val Asp Val Gly Thr Asn
            115                 120                 125    Asn

Ala Ile Phe Ile Asp Asp Lys Gly Arg Glu Ile Asn Lys Thr Lys Leu
        130                 135                 140

Pro Glu Glu Asn Leu Asp Ile Val Lys Asn Leu Pro Tyr Lys Cys Cys
145                 150                 155                 160
```

```
Ile Val His Pro Ser Val Met Phe Arg Lys Lys Val Ile Ala Ser Ile
                165                 170                 175

Gly Gly Tyr Met Phe Ser Asn Tyr Ser Glu Asp Tyr Glu Leu Trp Asn
            180                 185                 190

Arg Leu Ser Leu Ala Lys Ile Lys Phe Gln Asn Leu Pro Glu Tyr Leu
        195                 200                 205

Phe Tyr Tyr Arg Leu His Glu Gly Gln Ser Thr Ala Lys Lys Asn Leu
    210                 215                 220

Tyr Met Val Met Val Asn Asp Leu Val Ile Lys Met Lys Cys Phe Phe
225                 230                 235                 240

Leu Thr Gly Asn Ile Asn Tyr Leu Phe Gly Gly Ile Arg Thr Ile Ala
                245                 250                 255

Ser Phe Ile Tyr Cys Lys Tyr Ile Lys
                260                 265

<210> SEQ ID NO 19
<211> LENGTH: 406
<212> TYPE: PRT
<213> ORGANISM: Escherichia coli

<400> SEQUENCE: 19

Met Thr Pro Gly Gly Gln Ala Gln Ile Gly Asn Val Asp Leu Val Lys
1               5                   10                  15

Gln Leu Asn Ser Ala Ala Val Tyr Arg Leu Ile Asp Gln Tyr Gly Pro
            20                  25                  30

Ile Ser Arg Ile Gln Ile Ala Glu Gln Ser Gln Leu Ala Pro Ala Ser
        35                  40                  45

Val Thr Lys Ile Thr Arg Gln Leu Ile Glu Arg Gly Leu Ile Lys Glu
    50                  55                  60

Val Asp Gln Gln Ala Ser Thr Gly Gly Arg Arg Ala Ile Ser Ile Val
65                  70                  75                  80

Thr Glu Thr Arg Asn Phe His Ala Ile Gly Val Arg Leu Gly Arg His
                85                  90                  95

Asp Ala Thr Ile Thr Leu Phe Asp Leu Ser Ser Lys Val Leu Ala Glu
            100                 105                 110

Glu His Tyr Pro Leu Pro Glu Arg Thr Gln Gln Thr Leu Glu His Ala
        115                 120                 125

Leu Leu Asn Ala Ile Ala Gln Phe Ile Asp Ser Tyr Gln Arg Lys Leu
    130                 135                 140

Arg Glu Leu Ile Ala Ile Ser Val Ile Leu Pro Gly Leu Val Asp Pro
145                 150                 155                 160

Asp Ser Gly Lys Ile His Tyr Met Pro His Ile Gln Val Glu Asn Trp
                165                 170                 175

Gly Leu Val Glu Ala Leu Glu Glu Arg Phe Lys Val Thr Cys Phe Val
            180                 185                 190

Gly His Asp Ile Arg Ser Leu Ala Leu Ala Glu His Tyr Phe Gly Ala
        195                 200                 205

Ser Gln Asp Cys Glu Asp Ser Ile Leu Val Arg Val His Arg Gly Thr
    210                 215                 220

Gly Ala Gly Ile Ile Ser Asn Gly Arg Ile Phe Ile Gly Arg Asn Gly
225                 230                 235                 240

Asn Val Gly Glu Ile Gly His Ile Gln Val Glu Pro Leu Gly Glu Arg
                245                 250                 255

Cys His Cys Gly Asn Phe Gly Cys Leu Glu Thr Ile Ala Ala Asn Ala
```

```
                260               265               270
Ala Ile Glu Gln Arg Val Leu Asn Leu Leu Lys Gln Gly Tyr Gln Ser
                275               280               285
Arg Val Pro Leu Asp Asp Cys Thr Ile Lys Thr Ile Cys Lys Ala Ala
                290               295               300
Asn Lys Gly Asp Ser Leu Ala Ser Glu Val Ile Glu Tyr Val Gly Arg
305               310               315               320
His Leu Gly Lys Thr Ile Ala Ile Ala Ile Asn Leu Phe Asn Pro Gln
                325               330               335
Lys Ile Val Ile Ala Gly Glu Ile Thr Glu Ala Asp Lys Val Leu Leu
                340               345               350
Pro Ala Ile Glu Ser Cys Ile Asn Thr Gln Ala Leu Lys Ala Phe Arg
                355               360               365
Thr Asn Leu Pro Val Val Arg Ser Glu Leu Asp His Arg Ser Ala Ile
                370               375               380
Gly Ala Phe Ala Leu Val Lys Arg Ala Met Leu Asn Gly Ile Leu Leu
385               390               395               400
Gln His Leu Leu Glu Asn
                405

<210> SEQ ID NO 20
<211> LENGTH: 609
<212> TYPE: PRT
<213> ORGANISM: Escherichia coli

<400> SEQUENCE: 20

Met Cys Gly Ile Val Gly Ala Ile Ala Gln Arg Asp Val Ala Glu Ile
1               5                 10                15
Leu Leu Glu Gly Leu Arg Arg Leu Glu Tyr Arg Gly Tyr Asp Ser Ala
                20                25                30
Gly Leu Ala Val Val Asp Ala Glu Gly His Met Thr Arg Leu Arg Arg
                35                40                45
Leu Gly Lys Val Gln Met Leu Ala Gln Ala Ala Glu Glu His Pro Leu
        50                55                60
His Gly Gly Thr Gly Ile Ala His Thr Arg Trp Ala Thr His Gly Glu
65              70                75                80
Pro Ser Glu Val Asn Ala His Pro His Val Ser Glu His Ile Val Val
                85                90                95
Val His Asn Gly Ile Ile Glu Asn His Glu Pro Leu Arg Glu Glu Leu
                100               105               110
Lys Ala Arg Gly Tyr Thr Phe Val Ser Glu Thr Asp Thr Glu Val Ile
                115               120               125
Ala His Leu Val Asn Trp Glu Leu Lys Gln Gly Gly Thr Leu Arg Glu
                130               135               140
Ala Val Leu Arg Ala Ile Pro Gln Leu Arg Gly Ala Tyr Gly Thr Val
145               150               155               160
Ile Met Asp Ser Arg His Pro Asp Thr Leu Leu Ala Ala Arg Ser Gly
                165               170               175
Ser Pro Leu Val Ile Gly Leu Gly Met Gly Glu Asn Phe Ile Ala Ser
                180               185               190
Asp Gln Leu Ala Leu Leu Pro Val Thr Arg Arg Phe Ile Phe Leu Glu
                195               200               205
Glu Gly Asp Ile Ala Glu Ile Thr Arg Arg Ser Val Asn Ile Phe Asp
        210               215               220
```

```
Lys Thr Gly Ala Glu Val Lys Arg Gln Asp Ile Glu Ser Asn Leu Gln
225                 230                 235                 240

Tyr Asp Ala Gly Asp Lys Gly Ile Tyr Arg His Tyr Met Gln Lys Glu
                245                 250                 255

Ile Tyr Glu Gln Pro Asn Ala Ile Lys Asn Thr Leu Thr Gly Arg Ile
            260                 265                 270

Ser His Gly Gln Val Asp Leu Ser Glu Leu Gly Pro Asn Ala Asp Glu
        275                 280                 285

Leu Leu Ser Lys Val Glu His Ile Gln Ile Leu Ala Cys Gly Thr Ser
    290                 295                 300

Tyr Asn Ser Gly Met Val Ser Arg Tyr Trp Phe Glu Ser Leu Ala Gly
305                 310                 315                 320

Ile Pro Cys Asp Val Glu Ile Ala Ser Glu Phe Arg Tyr Arg Lys Ser
                325                 330                 335

Ala Val Arg Arg Asn Ser Leu Met Ile Thr Leu Ser Gln Ser Gly Glu
                340                 345                 350

Thr Ala Asp Thr Leu Ala Gly Leu Arg Leu Ser Lys Glu Leu Gly Tyr
            355                 360                 365

Leu Gly Ser Leu Ala Ile Cys Asn Val Pro Gly Ser Ser Leu Val Arg
        370                 375                 380

Glu Ser Asp Leu Ala Leu Met Thr Asn Ala Gly Thr Glu Ile Gly Val
385                 390                 395                 400

Ala Ser Thr Lys Ala Phe Thr Thr Gln Leu Thr Val Leu Leu Met Leu
                405                 410                 415

Val Ala Lys Leu Ser Arg Leu Lys Gly Leu Asp Ala Ser Ile Glu His
                420                 425                 430

Asp Ile Val His Gly Leu Gln Ala Leu Pro Ser Arg Ile Glu Gln Met
            435                 440                 445

Leu Ser Gln Asp Lys Arg Ile Glu Ala Leu Ala Glu Asp Phe Ser Asp
    450                 455                 460

Lys His His Ala Leu Phe Leu Gly Arg Gly Asp Gln Tyr Pro Ile Ala
465                 470                 475                 480

Leu Glu Gly Ala Leu Lys Leu Lys Glu Ile Ser Tyr Ile His Ala Glu
                485                 490                 495

Ala Tyr Ala Ala Gly Glu Leu Lys His Gly Pro Leu Ala Leu Ile Asp
            500                 505                 510

Ala Asp Met Pro Val Ile Val Ala Pro Asn Asn Glu Leu Leu Glu
            515                 520                 525

Lys Leu Lys Ser Asn Ile Glu Glu Val Arg Ala Arg Gly Gly Gln Leu
    530                 535                 540

Tyr Val Phe Ala Asp Gln Asp Ala Gly Phe Val Ser Ser Asp Asn Met
545                 550                 555                 560

His Ile Ile Glu Met Pro His Val Glu Glu Val Ile Ala Pro Ile Phe
                565                 570                 575

Tyr Thr Val Pro Leu Gln Leu Leu Ala Tyr His Val Ala Leu Ile Lys
            580                 585                 590

Gly Thr Asp Val Asp Gln Pro Arg Asn Leu Ala Lys Ser Val Thr Val
        595                 600                 605

Glu

<210> SEQ ID NO 21
<211> LENGTH: 514
<212> TYPE: PRT
<213> ORGANISM: Photobacterium sp. JT-ISH-224
```

<400> SEQUENCE: 21

```
Met Lys Asn Phe Leu Leu Leu Thr Leu Ile Leu Leu Thr Ala Cys Asn
1               5                   10                  15

Asn Ser Glu Glu Asn Thr Gln Ser Ile Ile Lys Asn Asp Ile Asn Lys
            20                  25                  30

Thr Ile Ile Asp Glu Glu Tyr Val Asn Leu Glu Pro Ile Asn Gln Ser
        35                  40                  45

Asn Ile Ser Phe Thr Lys His Ser Trp Val Gln Thr Cys Gly Thr Gln
    50                  55                  60

Gln Leu Leu Thr Glu Gln Asn Lys Glu Ser Ile Ser Leu Ser Val Val
65                  70                  75                  80

Ala Pro Arg Leu Asp Asp Glu Lys Tyr Cys Phe Asp Phe Asn Gly
                85                  90                  95

Val Ser Asn Lys Gly Glu Lys Tyr Ile Thr Lys Val Thr Leu Asn Val
                100                 105                 110

Val Ala Pro Ser Leu Glu Val Tyr Val Asp His Ala Ser Leu Pro Thr
            115                 120                 125

Leu Gln Gln Leu Met Asp Ile Ile Lys Ser Glu Glu Glu Asn Pro Thr
        130                 135                 140

Ala Gln Arg Tyr Ile Ala Trp Gly Arg Ile Val Pro Thr Asp Glu Gln
145                 150                 155                 160

Met Lys Glu Leu Asn Ile Thr Ser Phe Ala Leu Ile Asn Asn His Thr
                165                 170                 175

Pro Ala Asp Leu Val Gln Glu Ile Val Lys Gln Ala Gln Thr Lys His
            180                 185                 190

Arg Leu Asn Val Lys Leu Ser Ser Asn Thr Ala His Ser Phe Asp Asn
        195                 200                 205

Leu Val Pro Ile Leu Lys Glu Leu Asn Ser Phe Asn Asn Val Thr Val
    210                 215                 220

Thr Asn Ile Asp Leu Tyr Asp Asp Gly Ser Ala Glu Tyr Val Asn Leu
225                 230                 235                 240

Tyr Asn Trp Arg Asp Thr Leu Asn Lys Thr Asp Asn Leu Lys Ile Gly
                245                 250                 255

Lys Asp Tyr Leu Glu Asp Val Ile Asn Gly Ile Asn Glu Asp Thr Ser
            260                 265                 270

Asn Thr Gly Thr Ser Ser Val Tyr Asn Trp Gln Lys Leu Tyr Pro Ala
        275                 280                 285

Asn Tyr His Phe Leu Arg Lys Asp Tyr Leu Thr Leu Glu Pro Ser Leu
    290                 295                 300

His Glu Leu Arg Asp Tyr Ile Gly Asp Ser Leu Lys Gln Met Gln Trp
305                 310                 315                 320

Asp Gly Phe Lys Lys Phe Asn Ser Lys Gln Gln Leu Phe Leu Ser
                325                 330                 335

Ile Val Asn Phe Asp Lys Gln Lys Leu Gln Asn Glu Tyr Asn Ser Ser
            340                 345                 350

Asn Leu Pro Asn Phe Val Phe Thr Gly Thr Thr Val Trp Ala Gly Asn
        355                 360                 365

His Glu Arg Glu Tyr Tyr Ala Lys Gln Gln Ile Asn Val Ile Asn Asn
    370                 375                 380

Ala Ile Asn Glu Ser Ser Pro His Tyr Leu Gly Asn Ser Tyr Asp Leu
385                 390                 395                 400

Phe Phe Lys Gly His Pro Gly Gly Gly Ile Ile Asn Thr Leu Ile Met
```

```
                    405                 410                 415
Gln Asn Tyr Pro Ser Met Val Asp Ile Pro Ser Lys Ile Ser Phe Glu
            420                 425                 430

Val Leu Met Met Thr Asp Met Leu Pro Asp Ala Val Ala Gly Ile Ala
        435                 440                 445

Ser Ser Leu Tyr Phe Thr Ile Pro Ala Glu Lys Ile Lys Phe Ile Val
    450                 455                 460

Phe Thr Ser Thr Glu Thr Ile Thr Asp Arg Glu Thr Ala Leu Arg Ser
465                 470                 475                 480

Pro Leu Val Gln Val Met Ile Lys Leu Gly Ile Val Lys Glu Asn
                485                 490                 495

Val Leu Phe Trp Ala Asp Leu Pro Asn Cys Glu Thr Gly Val Cys Ile
            500                 505                 510

Ala Val

<210> SEQ ID NO 22
<211> LENGTH: 156
<212> TYPE: PRT
<213> ORGANISM: Escherichia coli

<400> SEQUENCE: 22

Met Lys Thr Gln Arg Gly Tyr Thr Leu Ile Glu Thr Leu Val Ala Met
1               5                   10                  15

Leu Ile Leu Val Met Leu Ser Ala Ser Gly Leu Tyr Gly Trp Gln Tyr
            20                  25                  30

Trp Gln Gln Ser Gln Arg Leu Trp Gln Thr Ala Ser Gln Ala Arg Asp
        35                  40                  45

Tyr Leu Leu Tyr Leu Arg Glu Asp Ala Asn Trp His Asn Arg Asp His
    50                  55                  60

Ser Ile Ser Val Ile Arg Glu Gly Thr Leu Trp Cys Leu Val Ser Ser
65                  70                  75                  80

Ala Ala Gly Ala Asn Thr Cys His Gly Ser Pro Leu Val Phe Val
                85                  90                  95

Pro Arg Trp Pro Glu Val Glu Met Ser Asp Leu Thr Pro Ser Leu Ala
            100                 105                 110

Phe Phe Gly Leu Arg Asn Thr Ala Trp Ala Gly His Ile Arg Phe Lys
        115                 120                 125

Asn Ser Thr Gly Glu Trp Trp Leu Val Val Ser Pro Trp Gly Arg Leu
    130                 135                 140

Arg Leu Cys Gln Gln Gly Glu Thr Glu Gly Cys Leu
145                 150                 155

<210> SEQ ID NO 23
<211> LENGTH: 37
<212> TYPE: DNA
<213> ORGANISM: Escherichia coli

<400> SEQUENCE: 23
cagtcagtca ggcgccttcg ggaaggcgtc tcgaaga                              37

<210> SEQ ID NO 24
<211> LENGTH: 84
<212> TYPE: DNA
<213> ORGANISM: Escherichia coli

<400> SEQUENCE: 24
ggcgtcggct ctggcaggat gtttcgtaat tagatagcca ccggcgcttt aggaaaccta    60
```

```
ctatgaccat gattacggat tcac                                           84
```

<210> SEQ ID NO 25
<211> LENGTH: 84
<212> TYPE: DNA
<213> ORGANISM: Escherichia coli

<400> SEQUENCE: 25

```
ggcgtcggct ctggcaggat gtttcgtaat tagatagcca ccggcgcttt attaaaccta   60
ctatgaccat gattacggat tcac                                           84
```

<210> SEQ ID NO 26
<211> LENGTH: 84
<212> TYPE: DNA
<213> ORGANISM: Escherichia coli

<400> SEQUENCE: 26

```
ggcgtcggct ctggcaggat gtttcgtaat tagatagcca ccggcgcttt cttcaaccta   60
ctatgaccat gattacggat tcac                                           84
```

<210> SEQ ID NO 27
<211> LENGTH: 84
<212> TYPE: DNA
<213> ORGANISM: Escherichia coli

<400> SEQUENCE: 27

```
ggcgtcggct ctggcaggat gtttcgtaat tagatagcca ccggcgcttt aggaaaccta   60
ctatgaccat gattacggat tcac                                           84
```

<210> SEQ ID NO 28
<211> LENGTH: 68
<212> TYPE: DNA
<213> ORGANISM: Escherichia coli

<400> SEQUENCE: 28

```
cggctctggc aggatgtttc gtaattagat agccaccggc gctttattaa acctactatg   60
accatgat                                                             68
```

<210> SEQ ID NO 29
<211> LENGTH: 1024
<212> TYPE: PRT
<213> ORGANISM: Escherichia coli

<400> SEQUENCE: 29

```
Met Thr Met Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

Pro Phe Ala Ser Trp Arg Asn Ser Glu Glu Ala Arg Thr Asp Arg Pro
        35                  40                  45

Ser Gln Gln Leu Arg Ser Leu Asn Gly Glu Trp Arg Phe Ala Trp Phe
    50                  55                  60

Pro Ala Pro Glu Ala Val Pro Glu Ser Trp Leu Glu Cys Asp Leu Pro
65                  70                  75                  80

Glu Ala Asp Thr Val Val Val Pro Ser Asn Trp Gln Met His Gly Tyr
                85                  90                  95

Asp Ala Pro Ile Tyr Thr Asn Val Thr Tyr Pro Ile Thr Val Asn Pro
            100                 105                 110
```

```
Pro Phe Val Pro Thr Glu Asn Pro Thr Gly Cys Tyr Ser Leu Thr Phe
        115                 120                 125

Asn Val Asp Glu Ser Trp Leu Gln Glu Gly Gln Thr Arg Ile Ile Phe
130                 135                 140

Asp Gly Val Asn Ser Ala Phe His Leu Trp Cys Asn Gly Arg Trp Val
145                 150                 155                 160

Gly Tyr Gly Gln Asp Ser Arg Leu Pro Ser Glu Phe Asp Leu Ser Ala
                165                 170                 175

Phe Leu Arg Ala Gly Glu Asn Arg Leu Ala Val Met Val Leu Arg Trp
            180                 185                 190

Ser Asp Gly Ser Tyr Leu Glu Asp Gln Asp Met Trp Arg Met Ser Gly
        195                 200                 205

Ile Phe Arg Asp Val Ser Leu Leu His Lys Pro Thr Thr Gln Ile Ser
    210                 215                 220

Asp Phe His Val Ala Thr Arg Phe Asn Asp Asp Phe Ser Arg Ala Val
225                 230                 235                 240

Leu Glu Ala Glu Val Gln Met Cys Gly Glu Leu Arg Asp Tyr Leu Arg
                245                 250                 255

Val Thr Val Ser Leu Trp Gln Gly Glu Thr Gln Val Ala Ser Gly Thr
            260                 265                 270

Ala Pro Phe Gly Gly Glu Ile Ile Asp Glu Arg Gly Gly Tyr Ala Asp
        275                 280                 285

Arg Val Thr Leu Arg Leu Asn Val Glu Asn Pro Lys Leu Trp Ser Ala
    290                 295                 300

Glu Ile Pro Asn Leu Tyr Arg Ala Val Val Glu Leu His Thr Ala Asp
305                 310                 315                 320

Gly Thr Leu Ile Glu Ala Glu Ala Cys Asp Val Gly Phe Arg Glu Val
                325                 330                 335

Arg Ile Glu Asn Gly Leu Leu Leu Leu Asn Gly Lys Pro Leu Leu Ile
            340                 345                 350

Arg Gly Val Asn Arg His Glu His His Pro Leu His Gly Gln Val Met
        355                 360                 365

Asp Glu Gln Thr Met Val Gln Asp Ile Leu Leu Met Lys Gln Asn Asn
    370                 375                 380

Phe Asn Ala Val Arg Cys Ser His Tyr Pro Asn His Pro Leu Trp Tyr
385                 390                 395                 400

Thr Leu Cys Asp Arg Tyr Gly Leu Tyr Val Val Asp Glu Ala Asn Ile
                405                 410                 415

Glu Thr His Gly Met Val Pro Met Asn Arg Leu Thr Asp Asp Pro Arg
            420                 425                 430

Trp Leu Pro Ala Met Ser Glu Arg Val Thr Arg Met Val Gln Arg Asp
        435                 440                 445

Arg Asn His Pro Ser Val Ile Ile Trp Ser Leu Gly Asn Glu Ser Gly
    450                 455                 460

His Gly Ala Asn His Asp Ala Leu Tyr Arg Trp Ile Lys Ser Val Asp
465                 470                 475                 480

Pro Ser Arg Pro Val Gln Tyr Glu Gly Gly Gly Ala Asp Thr Thr Ala
                485                 490                 495

Thr Asp Ile Ile Cys Pro Met Tyr Ala Arg Val Asp Glu Asp Gln Pro
            500                 505                 510

Phe Pro Ala Val Pro Lys Trp Ser Ile Lys Lys Trp Leu Ser Leu Pro
        515                 520                 525
```

-continued

```
Gly Glu Thr Arg Pro Leu Ile Leu Cys Glu Tyr Ala His Ala Met Gly
    530                 535                 540
Asn Ser Leu Gly Gly Phe Ala Lys Tyr Trp Gln Ala Phe Arg Gln Tyr
545                 550                 555                 560
Pro Arg Leu Gln Gly Gly Phe Val Trp Asp Trp Val Asp Gln Ser Leu
                565                 570                 575
Ile Lys Tyr Asp Glu Asn Gly Asn Pro Trp Ser Ala Tyr Gly Gly Asp
            580                 585                 590
Phe Gly Asp Thr Pro Asn Asp Arg Gln Phe Cys Met Asn Gly Leu Val
        595                 600                 605
Phe Ala Asp Arg Thr Pro His Pro Ala Leu Thr Glu Ala Lys His Gln
    610                 615                 620
Gln Gln Phe Phe Gln Phe Arg Leu Ser Gly Gln Thr Ile Glu Val Thr
625                 630                 635                 640
Ser Glu Tyr Leu Phe Arg His Ser Asp Asn Glu Leu Leu His Trp Met
                645                 650                 655
Val Ala Leu Asp Gly Lys Pro Leu Ala Ser Gly Glu Val Pro Leu Asp
            660                 665                 670
Val Ala Pro Gln Gly Lys Gln Leu Ile Glu Leu Pro Glu Leu Pro Gln
        675                 680                 685
Pro Glu Ser Ala Gly Gln Leu Trp Leu Thr Val Arg Val Val Gln Pro
    690                 695                 700
Asn Ala Thr Ala Trp Ser Glu Ala Gly His Ile Ser Ala Trp Gln Gln
705                 710                 715                 720
Trp Arg Leu Ala Glu Asn Leu Ser Val Thr Leu Pro Ala Ala Ser His
                725                 730                 735
Ala Ile Pro His Leu Thr Thr Ser Glu Met Asp Phe Cys Ile Glu Leu
            740                 745                 750
Gly Asn Lys Arg Trp Gln Phe Asn Arg Gln Ser Gly Phe Leu Ser Gln
        755                 760                 765
Met Trp Ile Gly Asp Lys Lys Gln Leu Leu Thr Pro Leu Arg Asp Gln
    770                 775                 780
Phe Thr Arg Ala Pro Leu Asp Asn Asp Ile Gly Val Ser Glu Ala Thr
785                 790                 795                 800
Arg Ile Asp Pro Asn Ala Trp Val Glu Arg Trp Lys Ala Ala Gly His
                805                 810                 815
Tyr Gln Ala Glu Ala Ala Leu Leu Gln Cys Thr Ala Asp Thr Leu Ala
            820                 825                 830
Asp Ala Val Leu Ile Thr Thr Ala His Ala Trp Gln His Gln Gly Lys
        835                 840                 845
Thr Leu Phe Ile Ser Arg Lys Thr Tyr Arg Ile Asp Gly Ser Gly Gln
    850                 855                 860
Met Ala Ile Thr Val Asp Val Glu Val Ala Ser Asp Thr Pro His Pro
865                 870                 875                 880
Ala Arg Ile Gly Leu Asn Cys Gln Leu Ala Gln Val Ala Glu Arg Val
                885                 890                 895
Asn Trp Leu Gly Leu Gly Pro Gln Glu Asn Tyr Pro Asp Arg Leu Thr
            900                 905                 910
Ala Ala Cys Phe Asp Arg Trp Asp Leu Pro Leu Ser Asp Met Tyr Thr
        915                 920                 925
Pro Tyr Val Phe Pro Ser Glu Asn Gly Leu Arg Cys Gly Thr Arg Glu
    930                 935                 940
Leu Asn Tyr Gly Pro His Gln Trp Arg Gly Asp Phe Gln Phe Asn Ile
```

```
                   945              950              955              960
Ser Arg Tyr Ser Gln Gln Gln Leu Met Glu Thr Ser His Arg His Leu
                965              970              975

Leu His Ala Glu Glu Gly Thr Trp Leu Asn Ile Asp Gly Phe His Met
                980              985              990

Gly Ile Gly Gly Asp Asp Ser Trp  Ser Pro Ser Val Ser  Ala Glu Phe
                995              1000             1005

Gln Leu Ser Ala Gly Arg Tyr  His Tyr Gln Leu Val  Trp Cys Gln
    1010             1015             1020

Lys

<210> SEQ ID NO 30
<211> LENGTH: 264
<212> TYPE: PRT
<213> ORGANISM: Escherichia coli

<400> SEQUENCE: 30

Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
                20                  25                  30

Asp Ala Ala Val Phe Arg Leu Ser Ala Gln Gly Arg Pro Val Leu Phe
            35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
                100                 105                 110

Val Ser Ile Met Ala Asp Ala Met Arg Arg Leu His Thr Leu Asp Pro
            115                 120                 125

Ala Thr Cys Pro Phe Asp His Gln Ala Lys His Arg Ile Glu Arg Ala
        130                 135                 140

Arg Thr Arg Met Glu Ala Gly Leu Val Asp Gln Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
                195                 200                 205

Cys Gly Arg Leu Gly Val Ala Asp Arg Tyr Gln Asp Ile Ala Leu Ala
        210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260

<210> SEQ ID NO 31
<211> LENGTH: 70
<212> TYPE: DNA
```

<213> ORGANISM: Escherichia coli

<400> SEQUENCE: 31

```
tctgggcata tcgtcgcagc ccacagcaac acgtttcctg aggaaccatg attccgggga      60
tccgtcgacc                                                             70
```

<210> SEQ ID NO 32
<211> LENGTH: 291
<212> TYPE: PRT
<213> ORGANISM: Escherichia coli

<400> SEQUENCE: 32

```
Met Thr Ser Ser Tyr Leu His Phe Pro Glu Phe Asp Pro Val Ile Phe
1               5                   10                  15

Ser Ile Gly Pro Val Ala Leu His Trp Tyr Gly Leu Met Tyr Leu Val
            20                  25                  30

Gly Phe Ile Phe Ala Met Trp Leu Ala Thr Arg Arg Ala Asn Arg Pro
        35                  40                  45

Gly Ser Gly Trp Thr Lys Asn Glu Val Glu Asn Leu Leu Tyr Ala Gly
    50                  55                  60

Phe Leu Gly Val Phe Leu Gly Gly Arg Ile Gly Tyr Val Leu Phe Tyr
65                  70                  75                  80

Asn Phe Pro Gln Phe Met Ala Asp Pro Leu Tyr Leu Phe Arg Val Trp
                85                  90                  95

Asp Gly Gly Met Ser Phe His Gly Gly Leu Ile Gly Val Ile Val Val
            100                 105                 110

Met Ile Ile Phe Ala Arg Arg Thr Lys Arg Ser Phe Phe Gln Val Ser
        115                 120                 125

Asp Phe Ile Ala Pro Leu Ile Pro Phe Gly Leu Gly Ala Gly Arg Leu
    130                 135                 140

Gly Asn Phe Ile Asn Gly Glu Leu Trp Gly Arg Val Asp Pro Asn Phe
145                 150                 155                 160

Pro Phe Ala Met Leu Phe Pro Gly Ser Arg Thr Glu Asp Ile Leu Leu
                165                 170                 175

Leu Gln Thr Asn Pro Gln Trp Gln Ser Ile Phe Asp Thr Tyr Gly Val
            180                 185                 190

Leu Pro Arg His Pro Ser Gln Leu Tyr Glu Leu Leu Glu Gly Val
        195                 200                 205

Val Leu Phe Ile Ile Leu Asn Leu Tyr Ile Arg Lys Pro Arg Pro Met
    210                 215                 220

Gly Ala Val Ser Gly Leu Phe Leu Ile Gly Tyr Gly Ala Phe Arg Ile
225                 230                 235                 240

Ile Val Glu Phe Phe Arg Gln Pro Asp Ala Gln Phe Thr Gly Ala Trp
                245                 250                 255

Val Gln Tyr Ile Ser Met Gly Gln Ile Leu Ser Ile Pro Met Ile Val
            260                 265                 270

Ala Gly Val Ile Met Met Val Trp Ala Tyr Arg Arg Ser Pro Gln Gln
        275                 280                 285

His Val Ser
    290
```

<210> SEQ ID NO 33
<211> LENGTH: 40
<212> TYPE: DNA
<213> ORGANISM: Escherichia coli

<400> SEQUENCE: 33

```
cagtcagtca ggcgcctcct caacctgtat attcgtaaac                              40
```

<210> SEQ ID NO 34
<211> LENGTH: 5877
<212> TYPE: DNA
<213> ORGANISM: Escherichia coli

<400> SEQUENCE: 34

```
gcagcggaac tcacaaggca ccataacgtc ccctccctga taacgctgat actgtggtcg        60
cggttatgcc agttggcatc ttcacgtaaa tagagcaaat agtcccgcgc ctggctggcg       120
gtttgccata gccgttgcga ctgctgccag tattgccagc catagagtcc acttgcgctt       180
agcatgacca aaatcagcat cgcgaccagc gtttcaatca gcgtataacc acgttgtgtt       240
ttcatgccgg cagtatggag cgaggagaaa aaaagacgag ggccagtttc tatttcttcg       300
gcgcatcttc cggactattt acgccgttgc aggacgttgc aaaatttcgg gaaggcgtct       360
cgaagaattt aacggagggt aaaaaaaccg acgcacactg gcgtcggctc tggcaggatg       420
tttcgtaatt agatagccac cggcgcttta ttaaacctac tatgaccatg attacggatt       480
cactggccgt cgttttacaa cgtcgtgact gggaaaaccc tggcgttacc caacttaatc       540
gccttgcagc acatcccct ttcgccagct ggcgtaatag cgaagaggcc cgcaccgatc       600
gcccttccca acagttgcgc agcctgaatg gcgaatggcg ctttgcctgg tttccggcac       660
cagaagcggt gccggaaagc tggctggagt gcgatcttcc tgaggccgat actgtcgtcg       720
tccccctcaaa ctggcagatg cacgttacg atgcgcccat ctacaccaac gtgacctatc       780
ccattacggt caatccgccg tttgttccca cggagaatcc gacgggttgt tactcgctca       840
catttaatgt tgatgaaagc tggctacagg aaggccagac gcgaattatt tttgatggcg       900
ttaactcggc gtttcatctg tggtgcaacg ggcgctgggt cggttacggc caggacagtc       960
gtttgccgtc tgaatttgac ctgagcgcat ttttacgcgc cggagaaaac cgcctcgcgg      1020
tgatggtgct gcgctggagt gacggcagtt atctggaaga tcaggatatg tggcggatga      1080
gcggcatttt ccgtgacgtc tcgttgctgc ataaaccgac tacacaaatc agcgatttcc      1140
atgttgccac tcgctttaat gatgatttca gccgcgctgt actggaggct gaagttcaga      1200
tgtgcggcga gttgcgtgac tacctacggg taacagtttc tttatggcag ggtgaaacgc      1260
aggtcgccag cggcaccgcg ccttttcggcg gtgaaattat cgatgagcgt ggtggttatg      1320
ccgatcgcgt cacactacgt ctgaacgtcg aaaacccgaa actgtggagc gccgaaatcc      1380
cgaatctcta tcgtgcggtg gttgaactgc acaccgccga cggcacgctg attgaagcag      1440
aagcctgcga tgtcggtttc cgcgaggtgc ggattgaaaa tggtctgctg ctgctgaacg      1500
gcaagccgtt gctgattcga ggcgttaacc gtcacgagca tcatcctctg catggtcagg      1560
tcatggatga gcagacgatg gtgcaggata tcctgctgat gaagcagaac aactttaacg      1620
ccgtgcgctg ttcgcattat ccgaaccatc cgctgtggta cacgctgtgc gaccgctacg      1680
gcctgtatgt ggtggatgaa gccaatattg aaacccacgg catggtgcca atgaatcgtc      1740
tgaccgatga tccgcgctgg ctaccggcga tgagcgaacg cgtaacgcga atggtgcagc      1800
gcgatcgtaa tcacccgagt gtgatcatct ggtcgctggg gaatgaatca ggccacggcg      1860
ctaatcacga cgcgctgtat cgctggatca aatctgtcga tccttcccgc ccggtgcagt      1920
atgaaggcgg cggagccgac accacggcca ccgatattat ttgcccgatg tacgcgcgcg      1980
tggatgaaga ccagcccttc ccggctgtgc cgaaatggtc catcaaaaaa tggctttcgc      2040
```

```
tacctggaga  gacgcgcccg  ctgatccttt  gcgaatacgc  ccacgcgatg  ggtaacagtc   2100
ttggcggttt  cgctaaatac  tggcaggcgt  ttcgtcagta  tccccgttta  cagggcggct   2160
tcgtctggga  ctgggtggat  cagtcgctga  ttaaatatga  tgaaaacggc  aacccgtggt   2220
cggcttacgg  cggtgatttt  ggcgatacgc  cgaacgatcg  ccagttctgt  atgaacggtc   2280
tggtctttgc  cgaccgcacg  ccgcatccag  cgctgacgga  agcaaaacac  cagcagcagt   2340
ttttccagtt  ccgtttatcc  gggcaaacca  tcgaagtgac  cagcgaatac  ctgttccgtc   2400
atagcgataa  cgagctcctg  cactggatgg  tggcgctgga  tggtaagccg  ctggcaagcg   2460
gtgaagtgcc  tctggatgtc  gctccacaag  gtaaacagtt  gattgaactg  cctgaactac   2520
cgcagccgga  gagcgccggg  caactctggc  tcacagtacg  cgtagtgcaa  ccgaacgcga   2580
ccgcatggtc  agaagccggg  cacatcagcg  cctggcagca  gtggcgtctg  gcggaaaacc   2640
tcagtgtgac  gctccccgcc  gcgtcccacg  ccatcccgca  tctgaccacc  agcgaaatgg   2700 attttttgcat  cgagctgggt  aataagcgtt  ggcaatttaa  ccgccagtca  ggctttcttt   2760
cacagatgtg  gattggcgat  aaaaaacaac  tgttgacgcc  gctgcgcgat  cagttcaccc   2820
gtgcaccgct  ggataacgac  attggcgtaa  gtgaagcgac  ccgcattgac  cctaacgcct   2880
gggtcgaacg  ctggaaggcg  gcgggccatt  accaggccga  agcagcgttg  ttgcagtgca   2940
cggcagatac  acttgctgat  gcggtgctga  ttacgaccgc  tcacgcgtgg  cagcatcagg   3000
ggaaaacctt  atttatcagc  cggaaaacct  accggattga  tggtagtggt  caaatggcga   3060
ttaccgttga  tgttgaagtg  gcgagcgata  caccgcatcc  ggcgcggatt  ggcctgaact   3120
gccagctggc  gcaggtagca  gagcgggtaa  actggctcgg  attagggccg  caagaaaact   3180
atcccgaccg  ccttactgcc  gcctgttttg  accgctggga  tctgccattg  tcagacatgt   3240
ataccccgta  cgtcttcccg  agcgaaaacg  gtctgcgctg  cgggacgcgc  gaattgaatt   3300
atggcccaca  ccagtggcgc  ggcgacttcc  agttcaacat  cagccgctac  agtcaacagc   3360
aactgatgga  aaccagccat  cgccatctgc  tgcacgcgga  agaaggcaca  tggctgaata   3420
tcgacggttt  ccatatgggg  attggtggcg  acgactcctg  gagcccgtca  gtatcggcgg   3480
aattccagct  gagcgccggt  cgctaccatt  accagttggt  ctggtgtcaa  aaataagcgg   3540
ccgctttatg  taggctggag  ctgcttcgaa  gttcctatac  tttctagaga  ataggaactt   3600
cggaatagga  acttcaagat  ccccttatta  gaagaactcg  tcaagaaggc  gatagaaggc   3660
gatgcgctgc  gaatcgggag  cggcgatacc  gtaaagcacg  aggaagcggt  cagcccattc   3720
gccgccaagc  tcttcagcaa  tatcacgggt  agccaacgct  atgtcctgat  agcggtccgc   3780
cacacccagc  cggccacagt  cgatgaatcc  tgaaaagcgg  ccattttcca  ccatgatatt   3840
cggcaagcag  gcatcgccat  gggtcacgac  gagatcctcg  ccgtcgggca  tgcgcgcctt   3900
gagcctggcg  aacagttcgg  ctggcgcgag  cccctgatgc  tcttcgtcca  gatcatcctg   3960
atcgacaaga  ccggcttcca  tccgagtacg  tgctcgctcg  atgcgatgtt  tcgcttggtg   4020
gtcgaatggg  caggtagccg  gatcaagcgt  atgcagccgc  cgcattgcat  cagccatgat   4080
ggatactttc  tcggcaggag  caaggtgaga  tgacaggaga  tcctgccccg  gcacttcgcc   4140
caatagcagc  cagtcccttc  ccgcttcagt  gacaacgtcg  agcacagctg  cgcaaggaac   4200
gcccgtcgtg  gccagccacg  atagccgcgc  tgcctcgtcc  tgcagttcat  tcagggcacc   4260
ggacaggtcg  gtcttgacaa  aaagaaccgg  gcgcccctgc  gctgacagcc  ggaacacggc   4320
ggcatcagag  cagccgattg  tctgttgtgc  ccagtcatag  ccgaatagcc  tctccaccca   4380
```

```
agcggccgga gaacctgcgt gcaatccatc ttgttcaatc atgcgaaacg atcctcatcc   4440
tgtctcttga tcagatcttg atccctgcg ccatcagatc cttggcggca agaaagccat   4500
ccagtttact ttgcagggct tcccaacctt accagagggc gccccagctg gcaattccgg   4560
ttcgcttgct gtccataaaa ccgcccagtc tagctatcgc catgtaagcc cactgcaagc   4620
tacctgcttt ctctttgcgc ttgcgttttc ccttgtccag atagcccagt agctgacatt   4680
catccgggt cagcaccgtt tctgcggact ggctttctac gtgttccgct tcctttagca   4740
gcccttgcgc cctgagtgct gcggcagcg tgagcttcaa aagcgctctg aagttcctat   4800
actttctaga gaataggaac ttcgaactgc aggtcgacgg atccccggaa tcatggttcc   4860
tcaggaaacg tgttgctgtg ggctgcgacg atatgcccag accatcatga tcacacccgc   4920
gacaatcatc gggatggaaa gaatttgccc catgctgatg tactgcaccc aggcaccggt   4980
aaactgcgcg tcgggctggc ggaaaaactc aacaatgatg cgaaacgcgc cgtaaccaat   5040
caggaacaaa cctgagacag ctcccattgg gcgtggttta cgaatataca ggttgaggat   5100
aataaacagc accacacctt ccagcagcag ctcgtaaagc tgtgatgggt ggcgcggcag   5160
cacaccgtaa gtgtcgaaaa tggattgcca ctgcgggttg gtttgcagca gcaaaatatc   5220
ttctgtacgg gagccaggga acagcatggc aaacgggaag ttcgggtcaa cgcggcccca   5280
caattcaccg ttaataaagt tgcccagacg cccggcacca agaccaaacg gaatgagtgg   5340
tgcgataaaa tcagagacct ggaagaagga acgtttagta cggcgggcga agataatcat   5400
caccacgata acgccaatca ggccgccgtg gaaagacatg ccgccgtccc agacacggaa   5460
cagatacagc ggatcggcca taaactgcgg gaaattgtag aacagaacat aaccaatacg   5520
tcccccgagg aagacgccga ggaagcccgc atagagtaag ttttcaactt cattttggt   5580
ccagccgctg cccggacgat tcgcccgtcg tgttgccagc cacattgcaa aaatgaaacc   5640
caccagatac atcaggccgt accagtgaag cgccacgggt cctattgaga aaatgaccgg   5700
atcaaactcc ggaaaatgca gatagctact ggtcatctgt caccacaagt tcttgttatt   5760
tcgctgaaag agaacagcga ttgaaatgcg cgccgcaggt ttcaggcgct ccaaaggtgc   5820
gaataatagc acaaggggac ctggctggtt gccggatacc gttaaaagat atgtata      5877
```

<210> SEQ ID NO 35
<211> LENGTH: 455
<212> TYPE: PRT
<213> ORGANISM: Escherichia coli

<400> SEQUENCE: 35

```
Met Phe Gly Ile Ile Ile Ser Val Ile Val Leu Ile Thr Met Gly Tyr
1               5                   10                  15

Leu Ile Leu Lys Asn Tyr Lys Pro Gln Val Val Leu Ala Ala Ala Gly
            20                  25                  30

Ile Phe Leu Met Met Cys Gly Val Trp Leu Gly Phe Gly Gly Val Leu
        35                  40                  45

Asp Pro Thr Lys Ser Ser Gly Tyr Leu Ile Val Asp Ile Tyr Asn Glu
    50                  55                  60

Ile Leu Arg Met Leu Ser Asn Arg Ile Ala Gly Leu Gly Leu Ser Ile
65                  70                  75                  80

Met Ala Val Gly Gly Tyr Ala Arg Tyr Met Glu Arg Ile Gly Ala Ser
                85                  90                  95

Arg Ala Met Val Ser Leu Leu Ser Arg Pro Leu Lys Leu Ile Arg Ser
            100                 105                 110
```

```
Pro Tyr Ile Ile Leu Ser Ala Thr Tyr Val Ile Gly Gln Ile Met Ala
            115                 120                 125

Gln Phe Ile Thr Ser Ala Ser Gly Leu Gly Met Leu Leu Met Val Thr
        130                 135                 140

Leu Phe Pro Thr Leu Val Ser Leu Gly Val Ser Arg Leu Ser Ala Val
145                 150                 155                 160

Ala Val Ile Ala Thr Thr Met Ser Ile Glu Trp Gly Ile Leu Glu Thr
                165                 170                 175

Asn Ser Ile Phe Ala Ala Gln Val Ala Gly Met Lys Ile Ala Thr Tyr
            180                 185                 190

Phe Phe His Tyr Gln Leu Pro Val Ala Ser Cys Val Ile Ile Ser Val
        195                 200                 205

Ala Ile Ser His Phe Phe Val Gln Arg Ala Phe Asp Lys Lys Asp Lys
    210                 215                 220

Asn Ile Asn His Glu Gln Ala Glu Gln Lys Ala Leu Asp Asn Val Pro
225                 230                 235                 240

Pro Leu Tyr Tyr Ala Ile Leu Pro Val Met Pro Leu Ile Leu Met Leu
                245                 250                 255

Gly Ser Leu Phe Leu Ala His Val Gly Leu Met Gln Ser Glu Leu His
            260                 265                 270

Leu Val Val Met Leu Leu Ser Leu Thr Val Thr Met Phe Val Glu
        275                 280                 285

Phe Phe Arg Lys His Asn Leu Arg Glu Thr Met Asp Asp Val Gln Ala
        290                 295                 300

Phe Phe Asp Gly Met Gly Thr Gln Phe Ala Asn Val Val Thr Leu Val
305                 310                 315                 320

Val Ala Gly Glu Ile Phe Ala Lys Gly Leu Thr Thr Ile Gly Thr Val
                325                 330                 335

Asp Ala Val Ile Arg Gly Ala Glu His Ser Gly Leu Gly Gly Ile Gly
            340                 345                 350

Val Met Ile Ile Met Ala Leu Val Ile Ala Ile Cys Ala Ile Val Met
        355                 360                 365

Gly Ser Gly Asn Ala Pro Phe Met Ser Phe Ala Ser Leu Ile Pro Asn
    370                 375                 380

Ile Ala Ala Gly Leu His Val Pro Ala Val Val Met Ile Met Pro Met
385                 390                 395                 400

His Phe Ala Thr Thr Leu Ala Arg Ala Val Ser Pro Ile Thr Ala Val
                405                 410                 415

Val Val Val Thr Ser Gly Ile Ala Gly Val Ser Pro Phe Ala Val Val
            420                 425                 430

Lys Arg Thr Ala Ile Pro Met Ala Val Gly Phe Val Val Asn Met Ile
        435                 440                 445

Ala Thr Ile Thr Leu Phe Tyr
    450                 455

<210> SEQ ID NO 36
<211> LENGTH: 263
<212> TYPE: PRT
<213> ORGANISM: Escherichia coli

<400> SEQUENCE: 36

Met Gly Leu Met Asn Ala Phe Asp Ser Gln Thr Glu Asp Ser Pro
1               5                   10                  15

Ala Ile Gly Arg Asn Leu Arg Ser Arg Pro Leu Ala Arg Lys Lys Leu
            20                  25                  30
```

Ser Glu Met Val Glu Glu Leu Glu Gln Met Ile Arg Arg Arg Glu
        35                  40                  45

Phe Gly Glu Gly Glu Gln Leu Pro Ser Glu Arg Glu Leu Met Ala Phe
 50                  55                  60

Phe Asn Val Gly Arg Pro Ser Val Arg Glu Ala Leu Ala Ala Leu Lys
 65                  70                  75                  80

Arg Lys Gly Leu Val Gln Ile Asn Asn Gly Glu Arg Ala Arg Val Ser
                 85                  90                  95

Arg Pro Ser Ala Asp Thr Ile Ile Gly Glu Leu Ser Gly Met Ala Lys
                100                 105                 110

Asp Phe Leu Ser His Pro Gly Gly Ile Ala His Phe Glu Gln Leu Arg
            115                 120                 125

Leu Phe Phe Glu Ser Ser Leu Val Arg Tyr Ala Ala Glu His Ala Thr
        130                 135                 140

Asp Glu Gln Ile Asp Leu Leu Ala Lys Ala Leu Glu Ile Asn Ser Gln
145                 150                 155                 160

Ser Leu Asp Asn Asn Ala Ala Phe Ile Arg Ser Asp Val Asp Phe His
                165                 170                 175

Arg Val Leu Ala Glu Ile Pro Gly Asn Pro Ile Phe Met Ala Ile His
                180                 185                 190

Val Ala Leu Leu Asp Trp Leu Ile Ala Ala Arg Pro Thr Val Thr Asp
            195                 200                 205

Gln Ala Leu His Glu His Asn Asn Val Ser Tyr Gln Gln His Ile Ala
        210                 215                 220

Ile Val Asp Ala Ile Arg Arg His Asp Pro Asp Glu Ala Asp Arg Ala
225                 230                 235                 240

Leu Gln Ser His Leu Asn Ser Val Ser Ala Thr Trp His Ala Phe Gly
                245                 250                 255

Gln Thr Thr Asn Lys Lys Lys
                260

<210> SEQ ID NO 37
<211> LENGTH: 297
<212> TYPE: PRT
<213> ORGANISM: Escherichia coli

<400> SEQUENCE: 37

Met Ala Thr Asn Leu Arg Gly Val Met Ala Ala Leu Leu Thr Pro Phe
 1               5                  10                  15

Asp Gln Gln Gln Ala Leu Asp Lys Ala Ser Leu Arg Arg Leu Val Gln
                20                  25                  30

Phe Asn Ile Gln Gln Gly Ile Asp Gly Leu Tyr Val Gly Gly Ser Thr
            35                  40                  45

Gly Glu Ala Phe Val Gln Ser Leu Ser Glu Arg Glu Gln Val Leu Glu
 50                  55                  60

Ile Val Ala Glu Glu Ala Lys Gly Lys Ile Lys Leu Ile Ala His Val
 65                  70                  75                  80

Gly Cys Val Ser Thr Ala Glu Ser Gln Gln Leu Ala Ala Ser Ala Lys
                 85                  90                  95

Arg Tyr Gly Phe Asp Ala Val Ser Ala Val Thr Pro Phe Tyr Tyr Pro
                100                 105                 110

Phe Ser Phe Glu Glu His Cys Asp His Tyr Arg Ala Ile Ile Asp Ser
            115                 120                 125

Ala Asp Gly Leu Pro Met Val Val Tyr Asn Ile Pro Ala Leu Ser Gly

```
                     130                 135                 140
Val Lys Leu Thr Leu Asp Gln Ile Asn Thr Leu Val Thr Leu Pro Gly
145                 150                 155                 160

Val Gly Ala Leu Lys Gln Thr Ser Gly Asp Leu Tyr Gln Met Glu Gln
                165                 170                 175

Ile Arg Arg Glu His Pro Asp Leu Val Leu Tyr Asn Gly Tyr Asp Glu
                180                 185                 190

Ile Phe Ala Ser Gly Leu Leu Ala Gly Ala Asp Gly Gly Ile Gly Ser
                195                 200                 205

Thr Tyr Asn Ile Met Gly Trp Arg Tyr Gln Gly Ile Val Lys Ala Leu
                210                 215                 220

Lys Glu Gly Asp Ile Gln Thr Ala Gln Lys Leu Gln Thr Glu Cys Asn
225                 230                 235                 240

Lys Val Ile Asp Leu Leu Ile Lys Thr Gly Val Phe Arg Gly Leu Lys
                245                 250                 255

Thr Val Leu His Tyr Met Asp Val Val Ser Val Pro Leu Cys Arg Lys
                260                 265                 270

Pro Phe Gly Pro Val Asp Glu Lys Tyr Leu Pro Glu Leu Lys Ala Leu
                275                 280                 285

Ala Gln Gln Leu Met Gln Glu Arg Gly
                290                 295

<210> SEQ ID NO 38
<211> LENGTH: 496
<212> TYPE: PRT
<213> ORGANISM: Escherichia coli

<400> SEQUENCE: 38

Met Ser Thr Thr Thr Gln Asn Ile Pro Trp Tyr Arg His Leu Asn Arg
1               5                   10                  15

Ala Gln Trp Arg Ala Phe Ser Ala Ala Trp Leu Gly Tyr Leu Leu Asp
                20                  25                  30

Gly Phe Asp Phe Val Leu Ile Ala Leu Val Leu Thr Glu Val Gln Gly
            35                  40                  45

Glu Phe Gly Leu Thr Thr Val Gln Ala Ala Ser Leu Ile Ser Ala Ala
        50                  55                  60

Phe Ile Ser Arg Trp Phe Gly Gly Leu Met Leu Gly Ala Met Gly Asp
65                  70                  75                  80

Arg Tyr Gly Arg Arg Leu Ala Met Val Thr Ser Ile Val Leu Phe Ser
                85                  90                  95

Ala Gly Thr Leu Ala Cys Gly Phe Ala Pro Gly Tyr Ile Thr Met Phe
                100                 105                 110

Ile Ala Arg Leu Val Ile Gly Met Gly Met Ala Gly Glu Tyr Gly Ser
                115                 120                 125

Ser Ala Thr Tyr Val Ile Glu Ser Trp Pro Lys His Leu Arg Asn Lys
                130                 135                 140

Ala Ser Gly Phe Leu Ile Ser Gly Phe Ser Val Gly Ala Val Val Ala
145                 150                 155                 160

Ala Gln Val Tyr Ser Leu Val Val Pro Val Trp Gly Trp Arg Ala Leu
                165                 170                 175

Phe Phe Ile Gly Ile Leu Pro Ile Ile Phe Ala Leu Trp Leu Arg Lys
                180                 185                 190

Asn Ile Pro Glu Ala Glu Asp Trp Lys Glu Lys His Ala Gly Lys Ala
                195                 200                 205
```

Pro Val Arg Thr Met Val Asp Ile Leu Tyr Arg Gly Glu His Arg Ile
            210                 215                 220

Ala Asn Ile Val Met Thr Leu Ala Ala Ala Thr Ala Leu Trp Phe Cys
225                 230                 235                 240

Phe Ala Gly Asn Leu Gln Asn Ala Ala Ile Val Ala Val Leu Gly Leu
                245                 250                 255

Leu Cys Ala Ala Ile Phe Ile Ser Phe Met Val Gln Ser Ala Gly Lys
            260                 265                 270

Arg Trp Pro Thr Gly Val Met Leu Met Val Val Leu Phe Ala Phe
            275                 280                 285

Leu Tyr Ser Trp Pro Ile Gln Ala Leu Leu Pro Thr Tyr Leu Lys Thr
290                 295                 300

Asp Leu Ala Tyr Asn Pro His Thr Val Ala Asn Val Leu Phe Phe Ser
305                 310                 315                 320

Gly Phe Gly Ala Ala Val Gly Cys Cys Val Gly Gly Phe Leu Gly Asp
                325                 330                 335

Trp Leu Gly Thr Arg Lys Ala Tyr Val Cys Ser Leu Leu Ala Ser Gln
            340                 345                 350

Leu Leu Ile Ile Pro Val Phe Ala Ile Gly Gly Ala Asn Val Trp Val
            355                 360                 365

Leu Gly Leu Leu Leu Phe Phe Gln Gln Met Leu Gly Gln Gly Ile Ala
370                 375                 380

Gly Ile Leu Pro Lys Leu Ile Gly Gly Tyr Phe Asp Thr Asp Gln Arg
385                 390                 395                 400

Ala Ala Gly Leu Gly Phe Thr Tyr Asn Val Gly Ala Leu Gly Gly Ala
                405                 410                 415

Leu Ala Pro Ile Ile Gly Ala Leu Ile Ala Gln Arg Leu Asp Leu Gly
            420                 425                 430

Thr Ala Leu Ala Ser Leu Ser Phe Ser Leu Thr Phe Val Val Ile Leu
            435                 440                 445

Leu Ile Gly Leu Asp Met Pro Ser Arg Val Gln Arg Trp Leu Arg Pro
            450                 455                 460

Glu Ala Leu Arg Thr His Asp Ala Ile Asp Gly Lys Pro Phe Ser Gly
465                 470                 475                 480

Ala Val Pro Phe Gly Ser Ala Lys Asn Asp Leu Val Lys Thr Lys Ser
                485                 490                 495

<210> SEQ ID NO 39
<211> LENGTH: 229
<212> TYPE: PRT
<213> ORGANISM: Escherichia coli

<400> SEQUENCE: 39

Met Ser Leu Leu Ala Gln Leu Asp Gln Lys Ile Ala Ala Asn Gly Gly
1               5                   10                  15

Leu Ile Val Ser Cys Gln Pro Val Pro Asp Ser Pro Leu Asp Lys Pro
            20                  25                  30

Glu Ile Val Ala Ala Met Ala Leu Ala Ala Glu Gln Ala Gly Ala Val
        35                  40                  45

Ala Ile Arg Ile Glu Gly Val Ala Asn Leu Gln Ala Thr Arg Ala Val
    50                  55                  60

Val Ser Val Pro Ile Ile Gly Ile Val Lys Arg Asp Leu Glu Asp Ser
65                  70                  75                  80

Pro Val Arg Ile Thr Ala Tyr Ile Glu Asp Val Asp Ala Leu Ala Gln
                85                  90                  95

```
Ala Gly Ala Asp Ile Ala Ile Asp Gly Thr Asp Arg Pro Arg Pro
            100                 105                 110

Val Pro Val Glu Thr Leu Leu Ala Arg Ile His His His Gly Leu Leu
        115                 120                 125

Ala Met Thr Asp Cys Ser Thr Pro Glu Asp Gly Leu Ala Cys Gln Lys
    130                 135                 140

Leu Gly Ala Glu Ile Ile Gly Thr Thr Leu Ser Gly Tyr Thr Thr Pro
145                 150                 155                 160

Glu Thr Pro Glu Glu Pro Asp Leu Ala Leu Val Lys Thr Leu Ser Asp
                165                 170                 175

Ala Gly Cys Arg Val Ile Ala Glu Gly Arg Tyr Asn Thr Pro Ala Gln
            180                 185                 190

Ala Ala Asp Ala Met Arg His Gly Ala Trp Ala Val Thr Val Gly Ser
        195                 200                 205

Ala Ile Thr Arg Leu Glu His Ile Cys Gln Trp Tyr Asn Thr Ala Met
    210                 215                 220

Lys Lys Ala Val Leu
225

<210> SEQ ID NO 40
<211> LENGTH: 291
<212> TYPE: PRT
<213> ORGANISM: Escherichia coli

<400> SEQUENCE: 40

Met Thr Thr Leu Ala Ile Asp Ile Gly Gly Thr Lys Leu Ala Ala Ala
1               5                   10                  15

Leu Ile Gly Ala Asp Gly Gln Ile Arg Asp Arg Arg Glu Leu Pro Thr
            20                  25                  30

Pro Ala Ser Gln Thr Pro Glu Ala Leu Arg Asp Ala Leu Ser Ala Leu
        35                  40                  45

Val Ser Pro Leu Gln Ala His Ala Gln Arg Val Ala Ile Ala Ser Thr
    50                  55                  60

Gly Ile Ile Arg Asp Gly Ser Leu Leu Ala Leu Asn Pro His Asn Leu
65                  70                  75                  80

Gly Gly Leu Leu His Phe Pro Leu Val Lys Thr Leu Glu Gln Leu Thr
                85                  90                  95

Asn Leu Pro Thr Ile Ala Ile Asn Asp Ala Gln Ala Ala Ala Trp Ala
            100                 105                 110

Glu Phe Gln Ala Leu Asp Gly Asp Ile Thr Asp Met Val Phe Ile Thr
        115                 120                 125

Val Ser Thr Gly Val Gly Gly Gly Val Val Ser Gly Cys Lys Leu Leu
    130                 135                 140

Thr Gly Pro Gly Gly Leu Ala Gly His Ile Gly His Thr Leu Ala Asp
145                 150                 155                 160

Pro His Gly Pro Val Cys Gly Cys Gly Arg Thr Gly Cys Val Glu Ala
                165                 170                 175

Ile Ala Ser Gly Arg Gly Ile Ala Ala Ala Gln Gly Glu Leu Ala
            180                 185                 190

Gly Ala Asp Ala Lys Thr Ile Phe Thr Arg Ala Gly Gln Gly Asp Glu
        195                 200                 205

Gln Ala Gln Gln Leu Ile His Arg Ser Ala Arg Thr Leu Ala Arg Leu
    210                 215                 220

Ile Ala Asp Ile Lys Ala Thr Thr Asp Cys Gln Cys Val Val Val Gly
```

```
                    225                 230                 235                 240

Gly Ser Val Gly Leu Ala Glu Gly Tyr Leu Ala Leu Val Glu Thr Tyr
                245                 250                 255

Leu Ala Gln Glu Pro Ala Ala Phe His Val Asp Leu Leu Ala Ala His
            260                 265                 270

Tyr Arg His Asp Ala Gly Leu Leu Gly Ala Ala Leu Leu Ala Gln Gly
        275                 280                 285

Glu Lys Leu
    290

<210> SEQ ID NO 41
<211> LENGTH: 154
<212> TYPE: PRT
<213> ORGANISM: Escherichia coli

<400> SEQUENCE: 41

Met Met Met Gly Glu Val Gln Ser Leu Pro Ser Ala Gly Leu His Pro
1               5                   10                  15

Ala Leu Gln Asp Ala Leu Thr Leu Ala Leu Ala Ala Arg Pro Gln Glu
            20                  25                  30

Lys Ala Pro Gly Arg Tyr Glu Leu Gln Gly Asp Asn Ile Phe Met Asn
        35                  40                  45

Val Met Thr Phe Asn Thr Gln Ser Pro Val Glu Lys Lys Ala Glu Leu
    50                  55                  60

His Glu Gln Tyr Ile Asp Ile Gln Leu Leu Asn Gly Glu Glu Arg
65                  70                  75                  80

Ile Leu Phe Gly Met Ala Gly Thr Ala Arg Gln Cys Glu Glu Phe His
                85                  90                  95

His Glu Asp Asp Tyr Gln Leu Cys Ser Thr Ile Asp Asn Glu Gln Ala
            100                 105                 110

Ile Ile Leu Lys Pro Gly Met Phe Ala Val Phe Met Pro Gly Glu Pro
        115                 120                 125

His Lys Pro Gly Cys Val Val Gly Glu Pro Gly Glu Ile Lys Lys Val
    130                 135                 140

Val Val Lys Val Lys Ala Asp Leu Met Ala
145                 150

<210> SEQ ID NO 42
<211> LENGTH: 5861
<212> TYPE: DNA
<213> ORGANISM: Escherichia coli

<400> SEQUENCE: 42
gaacattgtt gaactccgtg tcaaaagaaa acggtcaatc ccataaacgg cagattgaaa      60
acaacgatgt tatattttt  gcaaggctat ttatggtgcg gatgtcgtgt ttttaattgt     120
aggtgaggtg atttttcatt aaaaaatatg cgcttatgat tatttttgtaa gaacacattc   180 ataatattca taatgctcgt gaatagtctt ataataatt  caaacgggat gtttttatct    240
gcgttacatt aatttttcgc aatagttaat tattccgtta attatggtaa tgatgaggca    300
caaagagaaa accctgccat tttcccctac tttcaatcct gtgataggat gtcactgatg    360
atgttaatca cactgaccct acagaatggg ccttatgaac gcatttgatt cgcaaaccga    420
agattcttca cctgcaattg gtcgcaactt gcgtagccgc ccgctggcgc gtaaaaaact    480
ctccgaaatg gtggaagaag agctggaaca tgatgatccgc cgtcgtgaat ttggcgaagg    540
tgaacaatta ccgtctgaac gcgaactgat ggcgttcttt aacgtcgggc gtccttcggt    600
```

-continued

```
gcgtgaagcg ctggcagcgt taaaacgcaa aggtctggtg caaataaaca acggcgaacg      660
cgctcgcgtc tcgcgtcctt ctgcggacac tatcatcggt gagctttccg gcatggcgaa      720
agatttcctt tctcatcccg gtgggattgc ccatttcgaa caattacgtc tgttctttga      780
atccagtctg gtgcgctatg cggctgaaca tgccaccgat gagcaaatcg atttgctggc      840
aaaagcactg gaaatcaaca gtcagtcgct ggataacaac gcggcattca ttcgttcaga      900
cgttgatttc caccgcgtgc tggcggagat ccccggtaac ccaatcttca tggcgatcca      960
cgttgccctg ctcgactggc ttattgccgc acgcccaacg gttaccgatc aggcactgca     1020
cgaacataac aacgttagtt atcaacagca tattgcgatc gttgatgcga tccgccgtca     1080
tgatcctgac gaagccgatc gtgcgttgca atcgcatctc aacagcgtct ctgctacctg     1140
gcacgctttc ggtcagacca ccaacaaaaa gaaataatgc cactttagtg aagcagatcg     1200
cattataagc tttctgtatg gggtgttgct taattgatct ggtataacag gtataaaggt     1260
atatcgttta tcagacaagc atcacttcag aggtatttat ggcaacgaat ttacgtggcg     1320
taatggctgc actcctgact cctttttgacc aacaacaagc actggataaa gcgagtctgc     1380
gtcgcctggt tcagttcaat attcagcagg gcatcgacgg tttatacgtg ggtggttcga     1440
ccggcgaggc ctttgtacaa agccttttccg agcgtgaaca ggtactggaa atcgtcgccg     1500
aagaggcgaa aggtaagatt aaactcatcg cccacgtcgg ttgcgtcagc accgccgaaa     1560
gccaacaact tgcggcatcg gctaaacgtt atggcttcga tgccgtctcc gccgtcacgc     1620
cgttctacta tccttttcagc tttgaagaac actgcgatca ctatcgggca attattgatt     1680
cggcggatgg tttgccgatg gtggtgtaca acattccagc cctgagtggg gtaaaactga     1740
ccctggatca gatcaacaca cttgttacat tgcctggcgt aggtgcgctg aaacagacct     1800
ctggcgatct ctatcagatg gagcagatcc gtcgtgaaca tcctgatctt gtgctctata     1860
acggttacga cgaaatcttc gcctctggtc tgctggcggg cgctgatggt ggtatcggca     1920
gtacctacaa catcatgggc tggcgctatc aggggatcgt taaggcgctg aaagaaggcg     1980
atatccagac cgcgcagaaa ctgcaaactg aatgcaataa agtcattgat ttactgatca     2040
aaacgggcgt attccgcggc ctgaaaactg tcctccatta tatggatgtc gtttctgtgc     2100
cgctgtgccg caaaccgttt ggaccggtag atgaaaaata tctgccagaa ctgaaggcgc     2160
tggcccagca gttgatgcaa gagcgcgggt gagttgtttc ccctcgctcg ccctaccgg     2220 gtgagggaa ataaacgcat ctgtacccta caattttcat accaaagcgt gtgggcatcg     2280 cccaccgcg gagactcaca atgagtacta caacccagaa tatcccgtgg tatcgccatc     2340
tcaaccgtgc acaatggcgc gcattttccg ctgcctggtt gggatatctg cttgacggtt     2400
ttgatttcgt ttaatcgcc ctggtactca ccgaagtaca aggtgaattc gggctgacga     2460
cggtgcaggc ggcaagtctg atctctgcag ccttttatctc tcgctggttc ggcggcctga     2520
tgctcggcgc tatgggtgac cgctacgggc gtcgtctggc aatggtcacc agcatcgttc     2580
tcttctcggc cgggacgctg gcctgcggct ttgcgccagg ctacatcacc atgtttatcg     2640
ctcgtctggt catcggcatg gggatggcgg gtgaatacgg ttccagcgcc acctatgtca     2700
ttgaaagctg gccaaaacat ctgcgtaaca agccagtgg ttttttgatt tcaggcttct     2760 ctgtggggc cgtcgttgcc gctcaggtct atagcctggt ggttccggtc tggggctggc     2820
gtgcgctgtt ctttatcggc attttgccaa tcatctttgc tctctggctg cgtaaaaaca     2880
tcccggaagc ggaagactgg aaagagaaac acgcaggtaa agcaccagta cgcacaatgg     2940
```

```
tggatattct ctaccgtggt gaacatcgca ttgccaatat cgtaatgaca ctggcggcgg    3000
ctactgcgct gtggttctgc ttcgccggta acctgcaaaa tgccgcgatc gtcgctgttc    3060
ttgggctgtt atgcgccgca atctttatca gctttatggt gcagagtgca ggcaaacgct    3120
ggccaacggg cgtaatgctg atggtggtcg tgttgtttgc tttcctctac tcatggccga    3180
ttcaggcgct gctgccaacg tatctgaaaa ccgatctggc ttataacccg catactgtag    3240
ccaatgtgct gttctttagt ggctttggcg cggcggtggg atgctgcgta ggtgcttcc     3300
tcggtgactg gctgggaacc cgcaaagcgt acgtttgtag cctgctggcc tcgcagctgc    3360
tgattattcc ggtatttgcg attggcggcg caaacgtctg ggtgctcggt ctgttactgt    3420
tcttccagca aatgcttgga caagggatcg ccgggatctt accaaaactg attggcggtt    3480
atttcgatac cgaccagcgt gcagcggcc tgggctttac ctacaacgtt ggcgcattgg     3540
gcggtgcact ggccccaatc atcggcgcgt tgatcgctca acgtctggat ctgggtactg    3600
cgctggcatc gctctcgttc agtctgacgt tcgtggtgat cctgctgatt gggctggata    3660
tgccttctcg cgttcagcgt tggttgcgcc cggaagcgtt gcgtactcat gacgctatcg    3720
acggtaaacc attcagcggt gccgtgccgt ttggcagcgc caaaaacgat ttagtcaaaa    3780
ccaaaagtta atcctgttgc ccggtctatg taccgggcct ttcgctaagg gaagatgtat    3840
gtcgttactt gcacaactgg atcaaaaaat cgctgctaac ggtggcctga ttgtctcctg    3900
ccagccggtt ccggacagcc cgctcgataa acccgaaatc gtcgccgcca tggcattagc    3960
ggcagaacag gcgggcgcgg ttgccattcg cattgaaggt gtggcaaatc tgcaagccac    4020
gcgtgcggtg gtgagcgtgc cgattattgg aattgtgaaa cgcgatctgg aggattctcc    4080
ggtacgcatc acggcctata ttgaagatgt tgatgcgctg gcgcaggcgg gcgcggacat    4140
tatcgccatt gacggcaccg accgcccgcg tccggtgcct gttgaaacgc tgctggcacg    4200
tattcaccat cacggtttac tggcgatgac cgactgctca acgccggaag acggcctggc    4260
atgccaaaag ctgggagccg aaattattgg cactacgctt tctggctata ccacgcctga    4320
aacgccagaa gagccggatc tggcgctggt gaaaacgttg agcgacgccg atgtcgggt     4380
gattgccgaa gggcgttaca acacgcctgc tcaggcggcg gatgcgatgc gccacggcgc    4440
gtgggcggtg acgtcggtt ctgcaatcac gcgtcttgag cacatttgtc agtggtacaa     4500
cacagcgatg aaaaaggcgg tgctatgacc acactggcga ttgatatcgg cggtactaaa    4560
cttgccgccg cgctgattgg cgctgacggg cagatccgcg atcgtcgtga acttcctacg    4620
ccagccagcc agacaccaga agccttgcgt gatgccttat ccgcattagt ctctccgttg    4680
caagctcatg cgcagcgggt tgccatcgct tcgaccggga taatccgtga cggcagcttg    4740
ctggcgctta atccgcataa tcttggtgga ttgctacact ttccgttagt caaaacgctg    4800
gaacaactta ccaatttgcc gaccattgcc attaacgacg cgcaggccgc agcatgggcg    4860
gagtttcagg cgctggatgg cgatataacc gatatggtct ttatcaccgt ttccaccggc    4920
gttggcggcg gtgtagtgag cggctgcaaa ctgcttaccg ccctggcgg tctgcggggg     4980
catatcgggc atacgcttgc cgatccacac ggcccagtct gcggctgtgg acgcacaggt    5040
tgcgtggaag cgattgcttc tggtcgcggc attcagcgg cagcgcaggg ggagttggct     5100
ggcgcggatg cgaaaactat tttcacgcgc gccgggcagg gtgacgagca ggcgcagcag    5160
ctgattcacc gctccgcacg tacgcttgca aggctgatcg ctgatattaa agccacaact    5220
gattgccagt gcgtggtggt cggtggcagc gttggtctgg cagaagggta tctgcgctg     5280
gtggaaacgt atctggcgca ggagccagcg gcatttcatg ttgatttact ggcggcgcat    5340
```

-continued

```
taccgccatg atgcaggttt acttggggct gcgctgttgg cccagggaga aaaattatga   5400
tgatgggtga agtacagtca ttaccgtctg ctgggttaca tcctgcgtta caggacgcgt   5460
taacgctggc attagctgcc agaccgcaag aaaaagcgcc gggtcgttac gaattacagg   5520
gcgacaatat ctttatgaat gtcatgacgt ttaacactca atcgcccgtc gagaaaaaag   5580
cggaattgca cgagcaatac attgatatcc agctgttatt aaacggtgag gaacggattc   5640
tgtttggcat ggcaggcact gcgcgtcagt gtgaagagtt ccaccatgag gatgattatc   5700
agctttgcag caccattgat aacgagcaag ccatcatctt aaaaccggga atgttcgccg   5760
tgtttatgcc aggtgaaccg cataaaccag gatgcgttgt cggcgagcct ggagagatta   5820
aaaaggttgt ggtgaaggtt aaggctgatt taatggctta a                       5861
```

<210> SEQ ID NO 43
<211> LENGTH: 264
<212> TYPE: PRT
<213> ORGANISM: Escherichia coli

<400> SEQUENCE: 43

```
Met Lys Gln Tyr Leu Glu Leu Met Gln Lys Val Leu Asp Glu Gly Thr
1               5                   10                  15

Gln Lys Asn Asp Arg Thr Gly Thr Gly Thr Leu Ser Ile Phe Gly His
                20                  25                  30

Gln Met Arg Phe Asn Leu Gln Asp Gly Phe Pro Leu Val Thr Thr Lys
            35                  40                  45

Arg Cys His Leu Arg Ser Ile Ile His Glu Leu Leu Trp Phe Leu Gln
        50                  55                  60

Gly Asp Thr Asn Ile Ala Tyr Leu His Glu Asn Asn Val Thr Ile Trp
65                  70                  75                  80

Asp Glu Trp Ala Asp Glu Asn Gly Asp Leu Gly Pro Val Tyr Gly Lys
                85                  90                  95

Gln Trp Arg Ala Trp Pro Thr Pro Asp Gly Arg His Ile Asp Gln Ile
            100                 105                 110

Thr Thr Val Leu Asn Gln Leu Lys Asn Asp Pro Asp Ser Arg Arg Ile
        115                 120                 125

Ile Val Ser Ala Trp Asn Val Gly Glu Leu Asp Lys Met Ala Leu Ala
130                 135                 140

Pro Cys His Ala Phe Phe Gln Phe Tyr Val Ala Asp Gly Lys Leu Ser
145                 150                 155                 160

Cys Gln Leu Tyr Gln Arg Ser Cys Asp Val Phe Leu Gly Leu Pro Phe
                165                 170                 175

Asn Ile Ala Ser Tyr Ala Leu Leu Val His Met Met Ala Gln Gln Cys
            180                 185                 190

Asp Leu Glu Val Gly Asp Phe Val Trp Thr Gly Gly Asp Thr His Leu
        195                 200                 205

Tyr Ser Asn His Met Asp Gln Thr His Leu Gln Leu Ser Arg Glu Pro
    210                 215                 220

Arg Pro Leu Pro Lys Leu Ile Ile Lys Arg Lys Pro Glu Ser Ile Phe
225                 230                 235                 240

Asp Tyr Arg Phe Glu Asp Phe Glu Ile Glu Gly Tyr Asp Pro His Pro
                245                 250                 255

Gly Ile Lys Ala Pro Val Ala Ile
            260
```

MICROORGANISMS AND METHODS FOR PRODUCING SIALYLATED AND N-ACETYLGLUCOSAMINE-CONTAINING OLIGOSACCHARIDES

RELATED APPLICATIONS

This application is a national stage application, filed under 35 U.S.C. §371, of International Application No. PCT/US2014/029804, filed on Mar. 14, 2014, which claims benefit of, and priority to, U.S. Ser. No. 61/782,999, filed on Mar. 14, 2013; the contents of which are hereby incorporated by reference in its entirety.

INCORPORATION-BY-REFERENCE OF SEQUENCE LISTING

The contents of the text file named "37847_512001WO_ST25.txt", which was created on Jun. 9, 2014, and is 144 KB in size, are hereby incorporated by reference in their entireties.

FIELD OF THE INVENTION

The invention provides compositions and methods for producing purified oligosaccharides, in particular certain N-acetylglucosamine-containing and/or sialylated oligosaccharides that are typically found in human milk.

BACKGROUND OF THE INVENTION

Human milk contains a diverse and abundant set of neutral and acidic oligosaccharides (human milk oligosaccharides, hMOS). Many of these molecules are not utilized directly by infants for nutrition, but they nevertheless serve critical roles in the establishment of a healthy gut microbiome, in the prevention of disease, and in immune function. Prior to the invention described herein, the ability to produce hMOS inexpensively at large scale was problematic. For example, hMOS production through chemical synthesis was limited by stereo-specificity issues, precursor availability, product impurities, and high overall cost. As such, there is a pressing need for new strategies to inexpensively manufacture large quantities of hMOS for a variety of commercial applications.

SUMMARY OF THE INVENTION

The invention described herein features efficient and economical methods for producing N-acetylglucosamine-containing and/or sialylated oligosaccharides.

The invention provides a method for producing an N-acetylglucosamine-containing oligosaccharide in a bacterium comprising the following steps: providing a bacterium that comprises an exogenous UDP-GlcNAc:Galα/β-R β 3-N-acetylglucosaminyltransferase and a functional lactose permease; and culturing the bacterium in the presence of lactose. The N-acetylglucosamine-containing oligosaccharide is then retrieved from the bacterium or from a culture supernatant of the bacterium.

The invention further provides a method for producing a sialylated oligosaccharide in a bacterium comprising the following steps: providing a bacterium that comprises an exogenous sialyl-transferase gene, a deficient sialic acid catabolic pathway, a sialic acid synthetic capability, and a functional lactose permease gene; and culturing the bacterium in the presence of lactose. The sialylated oligosaccharide is then retrieved from the bacterium or from a culture supernatant of the bacterium. Specifically, a sialic acid synthetic capability comprises expressing exogenous CMP-Neu5Ac synthetase, an exogenous sialic acid synthase, and an exogenous UDP-GlcNAc-2-epimerase, or a functional variant or fragment thereof.

In both methods for producing N-acetylglucosamine-containing and/or sialylated oligosaccharides, it is preferable that the bacterium further comprises the capability for increased UDP-GlcNAc production. By "increased production capability" is meant that the host bacterium produces greater than 10%, 20%, 50%, 100%, 2-fold, 5-fold, 10-fold, or more of a product than the native, endogenous bacterium. Preferably, the bacterium over-expresses a positive endogenous regulator of UDP-GlcNAc synthesis. For example, the bacterium overexpresses the nagC gene of *Escherichia coli*. Alternatively, the bacterium over-expresses the *Escherichia coli* glmS (L-glutamine:D-fructose-6-phosphate aminotransferase) gene, or alternatively, over-expresses the *Escherichia coli* glmY gene (a positive translational regulator of glmS), or, alternatively over-expresses the *Escherichia coli* glmZ gene (another positive translational regulator of glmS: glmY and glmZ are described in Reichenbach et al *Nucleic Acids Res* 36, 2570-80 (2008)). Alternatively, the bacterium over-expresses any combination of such approaches. For example, the bacterium over-expresses nagC and glmS. Alternatively, the bacterium over-expresses nagC and glmY. Alternatively, the bacterium over-expresses nagC and glmZ. The methods also further encompass over-expressing any functional variant or fragment of nagC, glmS, glmY and glmZ and any combination thereof. By "overexpression" is meant that the gene transcript or encoded gene product is 10%, 20%, 50%, 2-fold, 5-fold, 10-fold, or more than the level expressed or produced by the corresponding native, naturally-occurring, or endogenous gene.

The invention described herein details the manipulation of genes and pathways within bacteria such as the enterobacterium *Escherichia coli* K12 (*E. coli*) leading to high level synthesis of hMOS. Other strains of *E. coli* for suitable for use in the present invention include *E. coli* MG1655, *E. coli* W3110, *E. coli* DH5aE, *E. coli* B, *E. coli* C, and *E. coli* W. A variety of bacterial species are suitable for use in the oligosaccharide biosynthesis methods, for example *Erwinia herbicola (Pantoea agglomerans), Citrobacter freundii, Pantoea citrea, Pectobacterium carotovorum,* or *Xanthomonas campestris*. Bacteria of the genus *Bacillus* are suitable for use, including *Bacillus subtilis, Bacillus licheniformis, Bacillus coagulans, Bacillus thermophilus, Bacillus laterosporus, Bacillus megaterium, Bacillus mycoides, Bacillus pumilus, Bacillus lentus, Bacillus cereus,* and *Bacillus circulans*. Similarly, bacteria of the genera *Lactobacillus* and *Lactococcus* are modified using the methods of this invention, including but not limited to *Lactobacillus acidophilus, Lactobacillus salivarius, Lactobacillus plantarum, Lactobacillus helveticus, Lactobacillus delbrueckii, Lactobacillus rhamnosus, Lactobacillus bulgaricus, Lactobacillus crispatus, Lactobacillus gasseri, Lactobacillus casei, Lactobacillus reuteri, Lactobacillus jensenii,* and *Lactococcus lactis. Streptococcus thermophiles* and *Proprionibacterium freudenreichii* are also suitable bacterial species for the invention described herein. Also included as part of this invention are strains, modified as described here, from the genera *Enterococcus* (e.g., *Enterococcus faecium* and *Enterococcus thermophiles*), *Bacteroides* (e.g., *Bacteroides caccae, Bacteroides cellulosilyticus, Bacteroides dorei, Bacteroides eggerthii, Bacteroides finegoldii, Bacteroides* fragilis, Bacteroides nordii, Bacteroides ovatus, Bacteroides salyersiae, Bacteroides thetaiotaomicron, Bacteroides uniformis, Bacteroides vulgatus and Bacteroides xylanisolvens), Bifidobacterium (e.g., Bifidobacterium longum, Bifidobacterium infantis, and Bifidobacterium bifidum), Parabacteroides (e.g. Parabacteroides distasonis, Parabacteroides goldsteinii, Parabacteroides johnsonii and Parabacteroides merdae), Prevotella (e.g., Prevotella copri), Sporolactobacillus spp., Micromomospora spp., Micrococcus spp., Rhodococcus spp., and Pseudomonas (e.g., Pseudomonas fluorescens and Pseudomonas aeruginosa). Bacteria comprising the characteristics described herein are cultured in the presence of lactose, and an N-acetylglucosamine-containing or sialylated oligosaccharide is retrieved, either from the bacterium itself or from a culture supernatant of the bacterium. The N-acetylglucosamine-containing or sialylated oligosaccharide is purified for use in therapeutic or nutritional products, or the bacteria are used directly in such products.

The bacterium comprises a deleted or inactivated (i.e., non-functional) endogenous β-galactosidase gene. For example, the β-galactosidase gene comprises an E. coli lacZ gene (e.g., GenBank Accession Number V00296.1 (GI: 41901), incorporated herein by reference). The endogenous lacZ gene of the E. coli is deleted or functionally inactivated, but in such a way that expression of the downstream lactose permease (lacY) gene remains intact, i.e. a functional lactose permease gene is also present in the bacterium. By deleted is meant that a portion or the whole coding sequence is absent, such that no gene product is produced. An "inactivated" gene does not produce a gene product that functions as the native, naturally-occuring, or endogenous gene. For example, the functional activity of an inactivated β-galactosidase gene product is reduced to 10%, 20%, 50%, or 100%, 1-fold, 2-fold, 5-fold, or 10-fold less than the functional activity of the native, naturally-occurring, endogenous gene product.

The lactose permease gene is an endogenous lactose permease gene or an exogenous lactose permease gene. For example, the lactose permease gene comprises an E. coli lacY gene (e.g., GenBank Accession Number V00295.1 (GI:41897), incorporated herein by reference). Many bacteria possess the inherent ability to transport lactose from the growth medium into the cell, by utilizing a transport protein that is either a homolog of the E. coli lactose permease (e.g., as found in Bacillus licheniformis), or a transporter that is a member of the ubiquitous PTS sugar transport family (e.g., as found in Lactobacillus casei and Lactobacillus rhamnosus). For bacteria lacking an inherent ability to transport extracellular lactose into the cell cytoplasm, this ability is conferred by an exogenous lactose transporter gene (e.g., E. coli lacY) provided on recombinant DNA constructs, and supplied either on a plasmid expression vector or as exogenous genes integrated into the host chromosome.

For the production of N-acetylglucosamine-containing oligosaccharides, the bacterium comprises an exogenous UDP-GlcNAc:Galα/β-R β 3-N-acetylglucosaminyltransferase gene or a functional variant or fragment thereof. This exogenous UDP-GlcNAc:Galα/β-R β 3-N-acetylglucosaminyltransferase gene is obtained from any one of a number of sources, e.g., the LgtA gene described from N. meningitides (SEQ ID NO:16 Genbank protein Accession AAF42258.1, incorporated herein by reference) or N. gonorrhoeae (Genbank protein Accession ACF31229.1). Optionally, an additional exogenous glycosyltransferase gene is co-expressed in the bacterium comprising an exogenous UDP-GlcNAc: Galα/β-R β 3-N-acetylglucosaminyltransferase. For example, a β-1,4-galactosyltransferase gene is co-expressed with the UDP-GlcNAc:Galα/β-R β3-N-acetylglucosaminyltransferase gene. This exogenous β-1,4-galactosyltransferase gene is obtained from any one of a number of sources, e.g., that described from N. meningitidis, the LgtB gene (Genbank protein Accession AAF42257.1), or from H. pylori, the Lex2B gene (SEQ ID NO:17 Genbank protein Accession NP_207619.1, incorporated herein by reference). Optionally, the additional exogenous glycosyltransferase gene co-expressed in the bacterium comprising an exogenous UDP-GlcNAc:Galα/β-R β 3-N-acetylglucosaminyltransferase gene is a β-1,3-galactosyltransferase gene, e.g., that described from E. coli O55:H7, the WbgO gene (SEQ ID NO:18 Genbank protein Accession YP_003500090.1, incorporated herein by reference), or from H. pylori, the jhp0563 gene (Genbank protein Accession AEZ55696.1). Functional variants and fragments of any of the enzymes described above are also encompassed by the present invention.

In one embodiment, the N-acteylglucosamine-containing oligosaccharides produced by the methods described herein include Lacto-N-triose 2 (LNT2), Lacto-N-tetraose (LNT), Lacto-N-neotetraose (LNnT), Lacto-N-fucopentaose I (LNF I), Lacto-N-fucopentaose II (LNF II), Lacto-N-fucopentaose III (LNF III), Lacto-N-fucopentaose V (LNF V), Lacto-N-difucohexaose I (LDFH I), Lacto-N-difucohexaose II (LDFH II), and Lacto-N-neodifucohexaose II (LFNnDFH II).

For the production of sialyl-oligosaccharides, the bacterium comprises an exogenous sialyl-transferase gene. For example, the exogenous sialyl-transferase gene encodes α(2,3) sialyl-transferase or the exogenous sialyl-transferase gene encodes α(2,6) sialyl-transferase or the exogenous sialyl-transferase gene encodes α(2,8) sialyltransferase. The exogenous sialyl-transferase genes is obtained from any one of a number of sources, e.g., those described from N. meningitidis, N. gonorrhoeae, and from a number of organisms of the genus Photobacterium. Examples of α(2,8) sialyltransferases, useful for the production of polysialic acid for example, are found in Campylobacter jejuni (CstII: ADN52706) and Neisseria meningitides (or siaD: AAA20478).

The bacteria used herein to produce hMOS are genetically engineered to comprise an increased intracellular lactose pool (as compared to wild type) and to comprise UDP-GlcNAc:Galα/β-R β 3-N-acetylglucosaminyltransferase and/or sialyl-transferase activity. Optionally, they also comprise β-1,4-galactosyltransferase or β-1,3-galactosyltransferase activity, and/or α-1,2-, α-1,3- and/or α-1,4-fucosyltransferase activity. In some cases, the bacterium further comprises a functional, wild-type E. coli lacZ+ gene inserted into an endogenous gene, for example, the lon gene in E. coli or the thyA gene in E. coli. In this manner, the bacterium further comprises a mutation in a lon gene or a mutation in the thyA gene. In these cases, the endogenous lacZ gene of the E. coli is deleted or functionally inactivated, but in such a way that expression of the downstream lactose permease (lacY) gene remains intact. The organism so manipulated maintains the ability to transport lactose from the growth medium, and to develop an intracellular lactose pool for use as an acceptor sugar in oligosaccharide synthesis, while also maintaining a low level of intracellular beta-galactosidase activity useful for a variety of additional purposes. For example, the invention also includes: a) methods for phenotypic marking of a gene locus in a β-galactosidase negative host cell by utilizing a β-galactosidase (e.g., lacZ) gene insert engineered to produce a low but readily detectable level of β-galactosidase activity, b) methods for readily detecting lytic bacteriophage contamination in fermentation runs through release and detection of cytoplasmic β-galactosidase in the cell culture medium, and c) methods for depleting a bacterial culture of residual lactose at the end of production runs. a), b) and c) are each achieved by utilizing a functional β-galactosidase (e.g., lacZ) gene insert carefully engineered to direct the expression of a low, but detectable level of β-galactosidase activity in an otherwise β-galactosidase negative host cell. The bacterium optionally further comprises a mutation in a lacA gene. Preferably, the bacterium accumulates an increased intracellular lactose pool, and produces a low level of beta-galactosidase. An increased intracellular pool is wherein the concentration of lactose in the host bacterium at least 10%, 20%, 50%, 2-fold, 5-fold, or 10-fold higher than that of the native, naturally-occurring bacterium.

In one aspect, the human milk oligosaccharide produced by engineered bacteria comprising an exogenous nucleic acid molecule encoding an UDP-GlcNAc:Galα/β-R β 3-N-acetylglucosaminyltransferase and an exogenous nucleic acid encoding β-1,4-galactosyltransferase is lacto-N-neotetraose (LNnT). In another aspect, the human milk oligosaccharide produced by engineered bacteria comprising an exogenous nucleic acid molecule encoding a UDP-GlcNAc:Galα/β-R β 3-N-acetylglucosaminyltransferase and an exogenous nucleic acid encoding β-1,3-galactosyltransferase is lacto-N-tetraose (LNT).

Described herein are compositions comprising a bacterial cell that produces the human milk oligosaccharide LNnT (lacto-N-neotetraose), wherein the bacterial cell comprises an exogenous UDP-GlcNAc:Galα/β-R β 3-N-acetylglucosaminyltransferase and an exogenous nucleic acid encoding a β-1,4-galactosyltransferase. Preferably, the bacterial cell is *E. coli*. The exogenous UDP-GlcNAc:Galα/β-R β 3-N-acetylglucosaminyltransferase gene is obtained from any one of a number of sources, e.g., the LgtA gene described from *N. meningitides*. The exogenous β-1,4-galactosyltransferase gene is obtained from any one of a number of sources, e.g., that described from *N. meningitidis*, the LgtB gene, or from *H. pylori*, the jhp0765 gene.

Additionally, the bacterium preferably comprises increased production of UDP-GlcNAc. An exemplary means to achieve this is by over-expression of a positive endogenous regulator of UDP-GlcNAc synthesis, for example, overexpression of the nagC gene of *Escherichia coli*. In one aspect, this nagC over-expression is achieved by providing additional copies of the nagC gene on a plasmid vector or by integrating additional nagC gene copies into the host cell chromosome. Alternatively, over-expression is achieved by modulating the strength of the ribosome binding sequence directing nagC translation or by modulating the strength of the promoter directing nagC transcription. As further alternatives the intracellular UDP-GlcNAc pool may be enhanced by other means, for example by over-expressing the *Escherichia coli* glmS (L-glutamine:D-fructose-6-phosphate aminotransferase) gene, or alternatively by over-expressing the *Escherichia coli* glmY gene (a positive translational regulator of glmS), or alternatively by over-expressing the *Escherichia coli* glmZ gene (another positive translational regulator of glmS), or alternatively by simultaneously using a combination of approaches. In one preferred embodiment, for example, the nagC (SEQ ID NO:19 Genbank protein Accession BAA35319.1, incorporated herein by reference) and glmS (SEQ ID NO:20 Genbank protein Accession NP_418185.1, incorporated herein by reference) genes which encode the sequences provided herein are overexpressed simultaneously in the same host cell in order to increase the intracellular pool of UDP-GlcNAc. Other components of UDP-GlcNAc metabolism include: (GlcNAc-1-P) N-acetylglucosamine-1-phosphate; (GlcN-1-P) glucosamine-1-phosphate; (GlcN-6-P) glucosamine-6-phosphate; (GlcNAc-6-P) N-acetylglucosamine-6-phosphate; and (Fruc-6-P) Fructose-6-phosphate. Bacteria comprising the characteristics described herein are cultured in the presence of lactose, and lacto-N-neotetraose is retrieved, either from the bacterium itself (i.e., by lysis) or from a culture supernatant of the bacterium.

Also within the invention is an isolated *E. coli* bacterium as described above and characterized as comprising a deleted or inactivated endogenous β-galactosidase gene, an inactivated or deleted lacA gene, and a functional lactose permease (lacY) gene.

Also described herein are compositions comprising a bacterial cell that produces the human milk oligosaccharide 6'-SL (6'-sialyllactose), wherein the bacterial cell comprises an exogenous sialyl-transferase gene encoding α(2,6)sialyltransferase. Preferably, the bacterial cell is *E. coli*. The exogenous sialyl-transferase gene utilized for 6'-SL production is obtained from any one of a number of sources, e.g., those described from a number of organisms of the genus *Photobacterium*. In yet another aspect, the human milk oligosaccharide produced by engineered bacteria comprising an exogenous nucleic acid molecule encoding an α(2,3) sialyltransferase is 3'-SL (3'-sialyllactose). The exogenous sialyltransferase gene utilized for 3'-SL production is obtained from any one of a number of sources, e.g., those described from *N. meningitidis* and *N. gonorrhoeae*.

Additionally, the bacterium contains a deficient sialic acid catabolic pathway. By "sialic acid catabolic pathway" is meant a sequence of reactions, usually controlled and catalyzed by enzymes, which results in the degradation of sialic acid. An exemplary sialic acid catabolic pathway in *Escherichia coli* is described herein. In the sialic acid catabolic pathway described herein, sialic acid (Neu5Ac; N-acetylneuraminic acid) is degraded by the enzymes NanA (N-acetylneuraminic acid lyase) and NanK (N-acetylmannosamine kinase) and NanE (N-acetylmannosamine-6-phosphate epimerase), all encoded in the nanATEK-yhcH operon, and repressed by NanR (ecocyc.org/ECOLI). A deficient sialic acid catabolic pathway is engineered in *Escherichia coli* by way of a mutation in endogenous nanA (N-acetylneuraminate lyase) (e.g., GenBank Accession Number D00067.1 (GI:216588), incorporated herein by reference) and/or nanK (N-acetylmannosamine kinase) genes (e.g., GenBank Accession Number (amino acid) BAE77265.1 (GI:85676015), incorporated herein by reference), and/or nanE (N-acetylmannosamine-6-phosphate epimerase, GI: 947745, incorporated herein by reference). Optionally, the nanT (N-acetylneuraminate transporter) gene is also inactivated or mutated. Other intermediates of sialic acid metabolism include: (ManNAc-6-P) N-acetylmannosamine-6-phosphate; (GlcNAc-6-P) N-acetylglucosamine-6-phosphate; (GlcN-6-P) Glucosamine-6-phosphate; and (Fruc-6-P) Fructose-6-phosphate. In some preferred embodiments, nanA is mutated. In other preferred embodiments, nanA and nanK are mutated, while nanE remains functional. In another preferred embodiment, nanA and nanE are mutated, while nanK has not been mutated, inactivated or deleted. A mutation is one or more changes in the nucleic acid sequence coding the gene product of nanA, nanK, nanE, and/or nanT. For example, the mutation may be 1, 2, 5, 10, 25, 50 or 100 changes in the nucleic acid sequence. For example, the nanA, nanK, nanE, and/or nanT is mutated by a null mutation. Null mutations as described herein encompass amino acid substitutions, additions, deletions, or insertions that either cause a loss of function of the enzyme (i.e., reduced or no activity) or loss of the enzyme (i.e., no gene product). By deleted is meant that the coding region is removed in whole or in part such that no gene product is produced. By inactivated is meant that the coding sequence has been altered such that the resulting gene product is functionally inactive or encodes a gene product with less than 100%, 80%, 50%, or 20% of the activity of the native, naturally-occurring, endogenous gene product. A "not mutated" gene or protein does not differ from a native, naturally-occurring, or endogenous coding sequence by 1, 2, 5, 10, 20, 50, 100, 200 or 500 more codons, or to the corresponding encoded amino acid sequence.

Moreover, the bacterium (e.g., *E. coli*) also comprises a sialic acid synthetic capability. For example, the bacterium comprises a sialic acid synthetic capability through provision of an exogenous UDP-GlcNAc 2-epimerase (e.g., neuC of *Campylobacter jejuni* (SEQ ID NO: 13, GenBank AAK91727.1; GI:15193223, incorporated herein by reference) or equivalent (e.g. *E. coli* S88 neuC GenBank YP_002392936.1; GI: 218560023), a Neu5Ac synthase (e.g., neuB of *C. jejuni* (SEQ ID NO:14 AAK91726.1GenBank GI:15193222, incorporated herein by reference) or equivalent, (e.g. *Flavobacterium limnosediminis* sialic acid synthase, GenBank GI:559220424), and/or a CMP-Neu5Ac synthetase (e.g., neuA of *C. jejuni* (SEQ ID NO: 15 GenBank AAK91728.1; GI:15193224, incorporated herein by reference) or equivalent, (e.g. *Vibrio brasiliensis* CMP-sialic acid synthase, GenBank GI: 493937153). Functional variants and fragments are also disclosed herein.

Additionally, the bacterium comprising a sialic acid synthetic capability preferably increased production of UDP-GlcNAc. An exemplary means to achieve this is by overexpression of a positive endogenous regulator of UDP-GlcNAc synthesis, for example, simultaneous overexpression of the nagC and glmS genes of *Escherichia coli*. This nagC and glmS over-expression is achieved by providing additional copies of the nagC and glmS genes on a plasmid vector, or by integrating additional nagC and glmS gene copies into the host cell chromosome. Alternatively, over-expression is achieved by modulating the strength of the ribosome binding sequence directing nagC (described by Sleight et al, Nucleic Acids Res. May 2010; 38(8): 2624-2636) and/or glmS translation, or by modulating the strength of the promoter/s directing nagC and glmS transcription (Sleight et al, Nucleic Acids Res. May 2010; 38(8): 2624-2636)

Bacteria comprising the characteristics described herein are cultured in the presence of lactose, and, in the instance where cells comprise an α(2,6) sialyltransferase (e.g. *Photobacterium* spp JT-ISH-224 (SEQ ID NO:21 Genbank protein Accession BAF92026.1, incorporated herein by reference), 6'-sialyllactose is retrieved, either from the bacterium itself or from a culture supernatant of the bacterium. In the instance where cells comprise an α(2,3) sialyltransferase, (e.g. *Neisseria meningitidis* 1st (Genbank protein Accession NP273962.1) 3'-sialyllactose is recovered either from the bacterium itself (e.g., by lysis of the bacterium) or from a culture supernatant of the bacterium.

Also within the invention is an isolated *E. coli* bacterium as described above and characterized as comprising a deleted or inactivated endogenous β-galactosidase gene, an exogenous sialyl-transferase gene, a deficient sialic acid catabolic pathway, a sialic acid synthetic capability, a deleted lacA gene, and a functional lactose permease (lacY) gene.

A purified N-acetylglucosamine-containing or sialylated oligosaccharide produced by the methods described above is also within the invention. A purified oligosaccharide, e.g., 6'-SL, is one that is at least 90%, 95%, 98%, 99%, or 100% (w/w) of the desired oligosaccharide by weight. Purity is assessed by any known method, e.g., thin layer chromatography or other electrophoretic or chromatographic techniques known in the art. The invention includes a method of purifying an N-acetylglucosamine-containing or sialylated oligosaccharide produced by the genetically engineered bacteria described above, which method comprises separating the desired N-acetylglucosamine-containing or sialylated oligosaccharide (e.g., 6'-SL) from contaminants in a bacterial cell extract or lysate, or bacterial cell culture supernatant. Contaminants include bacterial DNA, protein and cell wall components, and yellow/brown sugar caramels sometimes formed in spontaneous chemical reactions in the culture medium.

The oligosaccharides are purified and used in a number of products for consumption by humans as well as animals, such as companion animals (dogs, cats) as well as livestock (bovine, equine, ovine, caprine, or porcine animals, as well as poultry). For example, a pharmaceutical composition comprising purified 6'-sialyllactose (6'-SL) and an excipient is suitable for oral administration. Large quantities of 6'-SL are produced in bacterial hosts, e.g., an *E. coli* bacterium comprising a heterologous sialyltransferase, e.g., a heterologous α(2,6)sialyltransferase. An *E. coli* bacterium comprising an enhanced cytoplasmic pool of each of the following: lactose and CMP-Neu5Ac, is useful in such production systems. In the case of lactose, endogenous *E. coli* metabolic pathways and genes are manipulated in ways that result in the generation of increased cytoplasmic concentrations of lactose, as compared to levels found in wild type *E. coli*. For example, the bacteria contain at least 10%, 20%, 50%, 2×, 5×, 10× or more of the levels in a corresponding wild type bacteria that lacks the genetic modifications described above. In the case of CMP-Neu5Ac, endogenous Neu5Ac catabolism genes are inactivated and exogenous CMP-Neu5Ac biosynthesis genes introduced into *E. coli* resulting in the generation of a cytoplasmic pool of CMP-Neu5Ac not found in the wild type bacterium.

A method of producing a pharmaceutical composition comprising a purified hMOS is carried out by culturing the bacterium described above, purifying the hMOS produced by the bacterium, and combining the hMOS with an excipient or carrier to yield a dietary supplement for oral administration. These compositions are useful in methods of preventing or treating enteric and/or respiratory diseases in infants and adults. Accordingly, the compositions are administered to a subject suffering from or at risk of developing such a disease using known methods of clinical therapy.

The invention also provides for increasing, in *E. coli*, the intracellular concentration of the nucleotide sugar uridine diphosphate N-acetylglucosamine (UDP-GlcNAc). This is achieved by over-expressing the bi-functional endogenous positive regulator of UDP-GlcNac synthesis and repressor of glucosamine and N-acetylglucosamine catabolism, nagC, simultaneously with the gene encoding L-glutamine:D-fructose-6-phosphate aminotransferase, glmS.

The invention also provides for increasing the intracellular concentration of lactose in *E. coli*, for cells grown in the presence of lactose, by using manipulations of endogenous *E. coli* genes involved in lactose import, export, and catabolism. In particular, described herein are methods of increasing intracellular lactose levels in *E. coli* genetically engineered to produce a human milk oligosaccharide by incorporating a lacA mutation into the genetically modified *E. coli*. The lacA mutation prevents the formation of intracellular acetyl-lactose, which not only removes this molecule as a contaminant from subsequent purifications, but also eliminates *E. coli*'s ability to export excess lactose from its cytoplasm, thus greatly facilitating purposeful manipulations of the *E. coli* intracellular lactose pool.

Also described herein are bacterial host cells with the ability to accumulate a intracellular lactose pool while simultaneously possessing low, functional levels of cytoplasmic β-galactosidase activity, for example as provided by the introduction of a functional recombinant *E. coli* lacZ gene, or by a β-galactosidase gene from any of a number of other organisms (e.g., the lac4 gene of *Kluyveromyces lactis* (e.g., GenBank Accession Number M84410.1 (GI:173304), incorporated herein by reference). Low, functional levels of cytoplasmic β-galactosidase include β-galactosidase activity levels of between 0.05 and 200 units, e.g., between 0.05 and 5 units, between 0.05 and 4 units, between 0.05 and 3 units, or between 0.05 and 2 units (for standard definition see: Miller J H, Laboratory CSH. Experiments in molecular genetics. Cold Spring Harbor Laboratory Cold Spring Harbor, N.Y.; 1972; incorporated herein by reference). This low level of cytoplasmic β-galactosidase activity, while not high enough to significantly diminish the intracellular lactose pool, is nevertheless very useful for tasks such as phenotypic marking of desirable genetic loci during construction of host cell backgrounds, for detection of cell lysis due to undesired bacteriophage contaminations in fermentation processes, for the facile removal of undesired residual lactose at the end of fermentations, or for in-process fermentation QC purposes (i.e. as a non-standard phenotype the provision of a weak lacZ phenotype aids in culture purity assessments).

Methods of purifying a N-acetylglucosamine-containing or sialylated oligosaccharide produced by the methods described herein are carried out by binding the oligosaccharide from a bacterial cell lysate or bacterial cell culture supernatant of the bacterium to a carbon column, and subsequently eluting it from the column. Purified N-acetylglucosamine-containing or sialylated oligosaccharides are produced by the methods described herein.

Optionally, the invention features a vector, e.g., a vector containing a nucleic acid. The vector can further include one or more regulatory elements, e.g., a heterologous promoter. The regulatory elements can be operably linked to a protein gene, fusion protein gene, or a series of genes linked in an operon in order to express the fusion protein. To maintain the plasmid vector stably within the cell a selectable marker is included within its sequence, such as an antibiotic resistance gene or a gene that complements a nutritional auxotrophy of the host bacterium. For example, in *E. coli*, a thymidine deficiency caused by a chromosomal defect in the thymidylate synthase gene (thyA) can be complemented by a plasmid borne wild type copy of the thyA (M. Belfort, G. F. Maley, F. Maley, *Proceedings of the National Academy of Sciences* 80, 1858 (1983)) gene. Alternatively an adenine deficiency caused by a chromosomal deficiency in the adenylosuccinate synthetase (purA) gene (S. A. Wolfe, J. M. Smith, *J Biol Chem* 263, 19147-53 (1988)) can be complemented by a plasmid borne wild type copy of purA. Two plasmid vectors may be utilized simultaneously within the same bacterial cell by employing separate selectable markers, for example one plasmid utilizing thyA selection and one utilizing purA selection, and by utilizing two compatible plasmid replicons, for example in *E. coli* two such compatible replicons comprise the ColE1 (pUC) replicon and the p15A (pACYC) replicon (R. E. Bird, *J Bacteriol* 145, 1305-9 (1981)). In yet another aspect, the invention comprises an isolated recombinant cell, e.g., a bacterial cell containing aforementioned nucleic acid molecule/s or vector/s. The nucleic acid sequences can be optionally integrated into the genome.

The invention provides a method of treating, preventing, or reducing the risk of infection in a subject comprising administering to said subject a composition comprising a human milk oligosaccharide, purified from a culture of a recombinant strain of the current invention, wherein the hMOS binds to a pathogen and wherein the subject is infected with or at risk of infection with the pathogen. In one aspect, the infection is caused by a Norwalk-like virus or *Campylobacter jejuni*. The subject is preferably a mammal in need of such treatment. The mammal is, e.g., any mammal, e.g., a human, a primate, a mouse, a rat, a dog, a cat, a cow, a horse, or a pig. In a preferred embodiment, the mammal is a human. For example, the compositions are formulated into animal feed (e.g., pellets, kibble, mash) or animal food supplements for companion animals, e.g., dogs or cats, as well as livestock or animals grown for food consumption, e.g., cattle, sheep, pigs, chickens, and goats. Preferably, the purified hMOS is formulated into a powder (e.g., infant formula powder or adult nutritional supplement powder, each of which is mixed with a liquid such as water or juice prior to consumption) or in the form of tablets, capsules or pastes or is incorporated as a component in dairy products such as milk, cream, cheese, yogurt or kefir, or as a component in any beverage, or combined in a preparation containing live microbial cultures intended to serve as probiotics, or in prebiotic preparations intended to enhance the growth of beneficial microorganisms either in vitro or in vivo. For example, the purified sugar (e.g., LNnT or 6'-SL) can be mixed with a *Bifidobacterium* or *Lactobacillus* in a probiotic nutritional composition. (i.e. *Bifidobacteria* are beneficial components of a normal human gut flora and are also known to utilize hMOS for growth.

All genes described herein also include a description of the corresponding encoded gene products. As such, the uses of exogenous genes as described herein encompass nucleic acids that encode the gene product sequences disclosed herein. The person skilled in the art could readily generate nucleic acid sequences that encode the protein sequences described herein and introduce such sequences into expression vectors to carry out the present invention.

The term "substantially pure" in reference to a given polypeptide, polynucleotide or oligosaccharide means that the polypeptide, polynucleotide or oligosaccharide is substantially free from other biological macromolecules. The substantially pure polypeptide, polynucleotide or oligosaccharide is at least 75% (e.g., at least 80, 85, 95, or 99%) pure by dry weight. Purity can be measured by any appropriate calibrated standard method, for example, by column chromatography, polyacrylamide gel electrophoresis, thin layer chromatography (TLC) or HPLC analysis.

Polynucleotides, polypeptides, and oligosaccharides of the invention are purified and/or isolated. Purified defines a degree of sterility that is safe for administration to a human subject, e.g., lacking infectious or toxic agents. Specifically, as used herein, an "isolated" or "purified" nucleic acid molecule, polynucleotide, polypeptide, protein or oligosaccharide, is substantially free of other cellular material, or culture medium when produced by recombinant techniques, or chemical precursors or other chemicals when chemically synthesized. For example, purified hMOS compositions are at least 60% by weight (dry weight) the compound of interest. Preferably, the preparation is at least 75%, more preferably at least 90%, and most preferably at least 99%, by weight the compound of interest. Purity is measured by any appropriate calibrated standard method, for example, by column chromatography, polyacrylamide gel electrophoresis, thin layer chromatography (TLC) or HPLC analysis. For example, a "purified protein" refers to a protein that has been separated from other proteins, lipids, and nucleic acids with which it is naturally associated. Preferably, the protein constitutes at least 10, 20, 50 70, 80, 90, 95, 99-100% by dry weight of the purified preparation.

By "isolated nucleic acid" is meant a nucleic acid that is free of the genes that flank it in the naturally-occurring genome of the organism from which the nucleic acid is derived. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones. For example, the isolated nucleic acid is a purified cDNA or RNA polynucleotide.

A "heterologous promoter", when operably linked to a nucleic acid sequence, refers to a promoter which is not naturally associated with the nucleic acid sequence.

The term "over-express" as used herein refers to gene transcript or encoded gene product is 10%, 20%, 50%, 2-fold, 5-fold, 10-fold, or more than the level expressed or produced by a native, naturally-occurring, or endogenous gene in a bacterium in which it naturally occurs. For example, the host bacterium described herein are engineered to over-express an exogenous gene transcript or encoded gene product of UDP-GlcNAc:Galα/β-R β3-N-acetylglucosaminyltransferase, nagC, glmS, glmY, glmZ, a sialyltransferase, a β-galactosyltransferase, an α-fucosyltransferase, CMP-Neu5Ac synthetase, a sialic acid synthase, or a UDP-GlcNAc 2-epimerase, i.e., a gene or gene product with a sequence corresponding to that of a bacterium other than the host bacterium.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible to a particular adverse condition, disorder, or disease, and thus relates to the prevention of the occurrence of symptoms and/or their underlying cause.

By the terms "effective amount" and "therapeutically effective amount" of a formulation or formulation component is meant a nontoxic but sufficient amount of the formulation or component to provide the desired effect.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

N-acetylmannosamine; (ΔnanK) mutated N-acetylmannosamine kinase; (nanE) wild-type N-acetylmannosamine-6-phosphate epimerase; (ManNAc-6-P) N-acetylmannosamine-6-phosphate; (GlcNAc-6-P) N-acetylglucosamine-6-phosphate; (GlcN-6-P) Glucosamine-6-phosphate; (Fruc-6-P) Fructose-6-phosphate; (neuA), CMP-N-acetylneuraminic acid synthetase; (CMP-Neu5Ac) CMP-N-acetylneuraminic acid; (neuB), N-acetylneuraminic acid synthase; (neuC) UDP-GlcNAc-2-epimerase; and (UDP-GlcNAc) uridine diphosphate N-acetylglucosamine.

Figure 4:
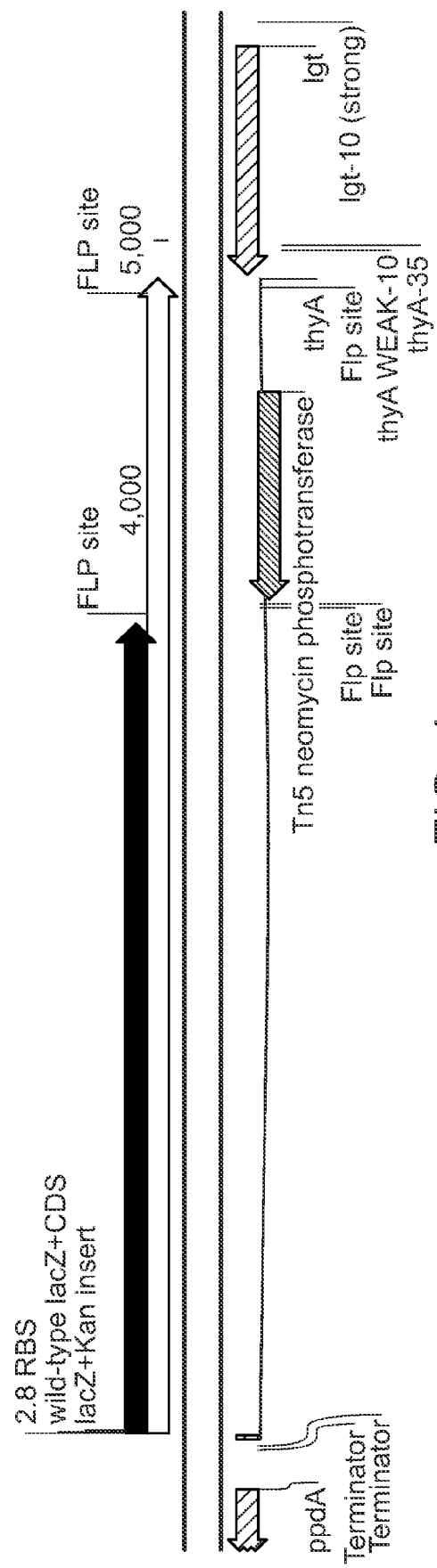

FIG. 4 is a schematic that illustrates the new configuration of genes engineered at the *Escherichia coli* thyA locus in strains used to produce N-acetylglucosamine-containing oligosaccharides.

Figure 5:
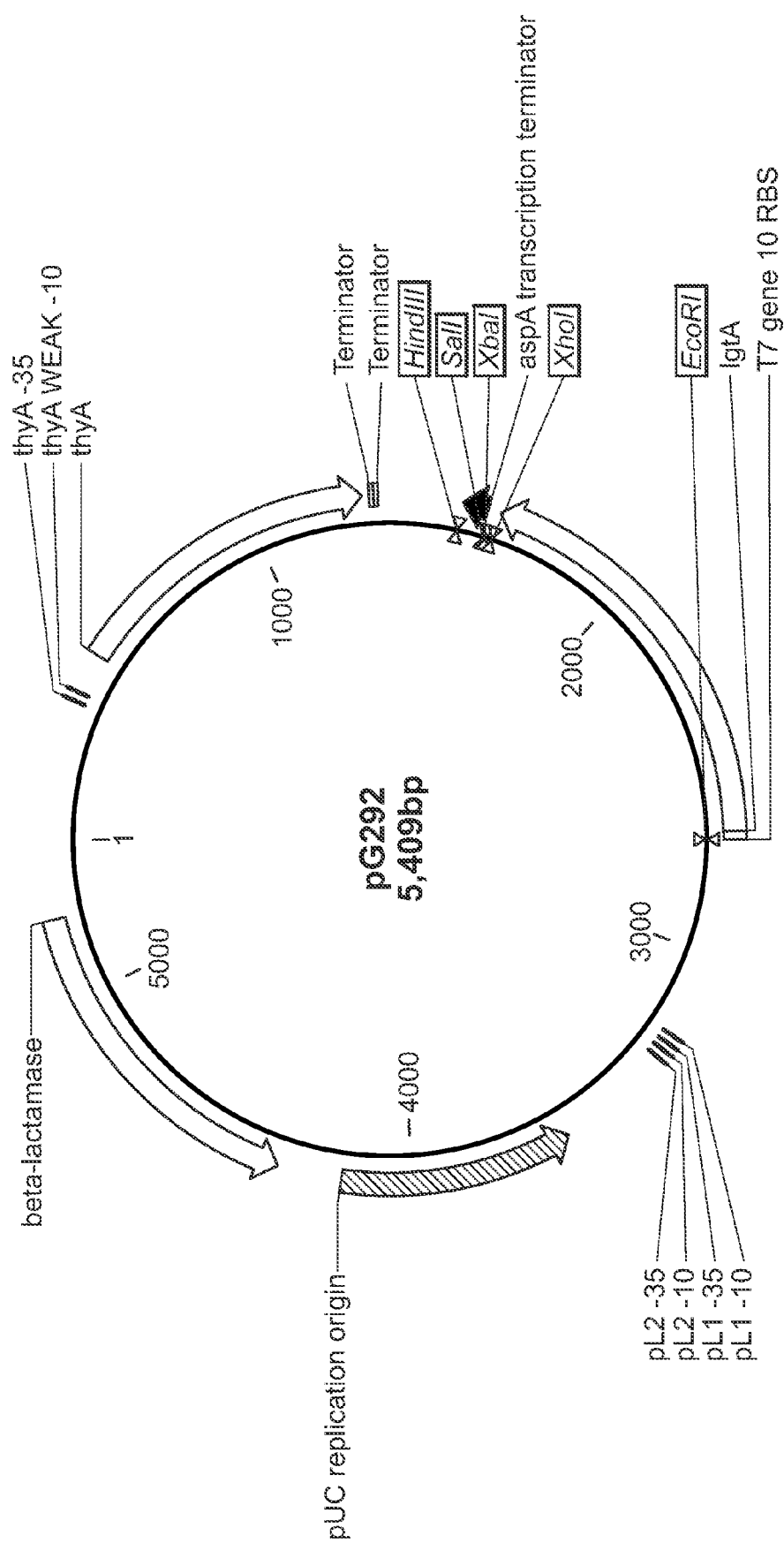

FIG. 5 is a plasmid map of pG292, which expresses the *N. meningitidis* β(1,3)-N-acetylglucosaminyltransferase gene lgtA.

Figure 6:
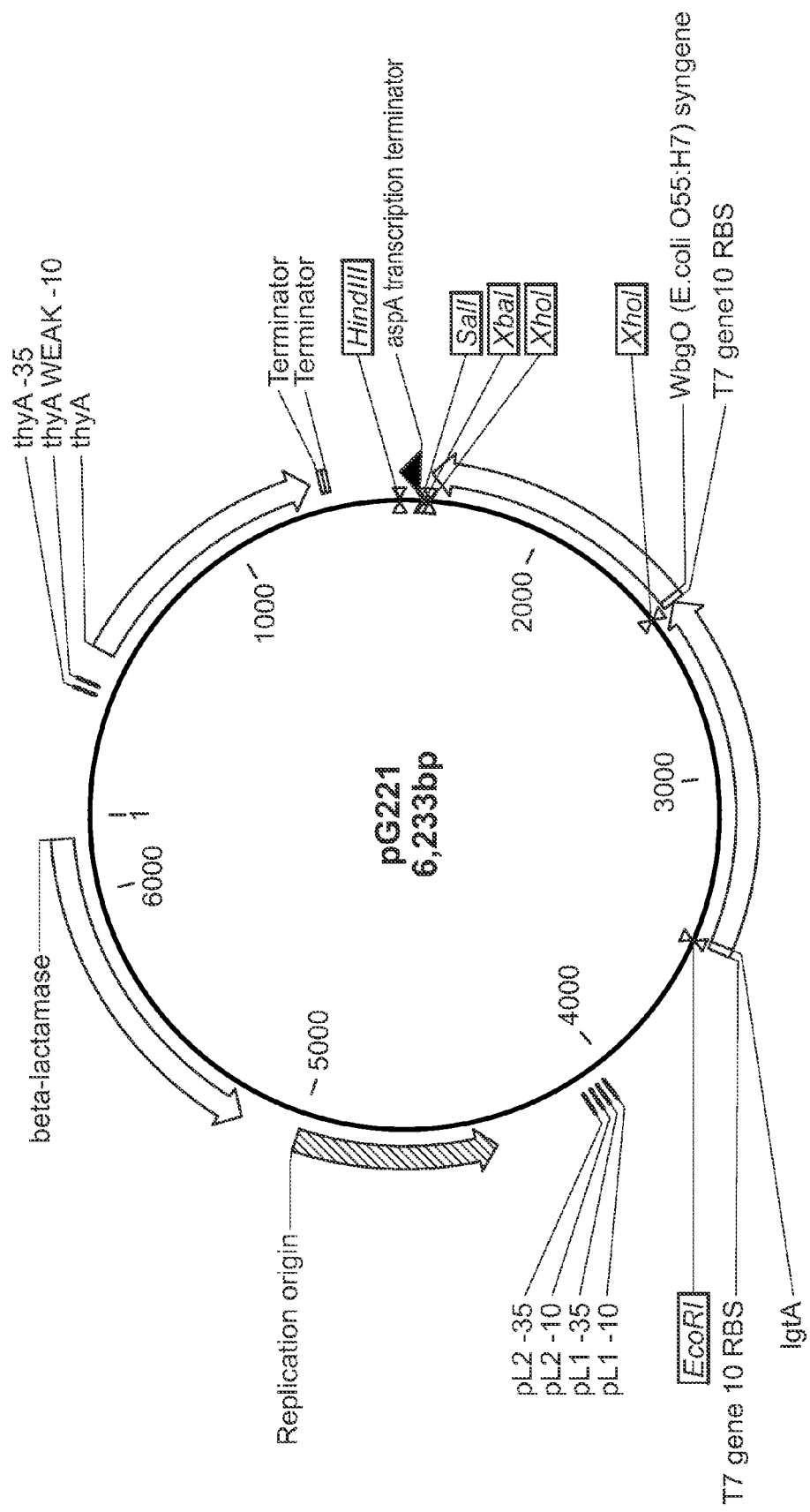

FIG. 6 is a plasmid map of pG221, which expresses, as an operon, the *N. meningitidis* β(1,3)-N-acetylglucosaminyltransferase gene lgtA and the *E. coli* O55:H7 wbgO β(1,3)-galactosyltransferase gene.

Figure 7:
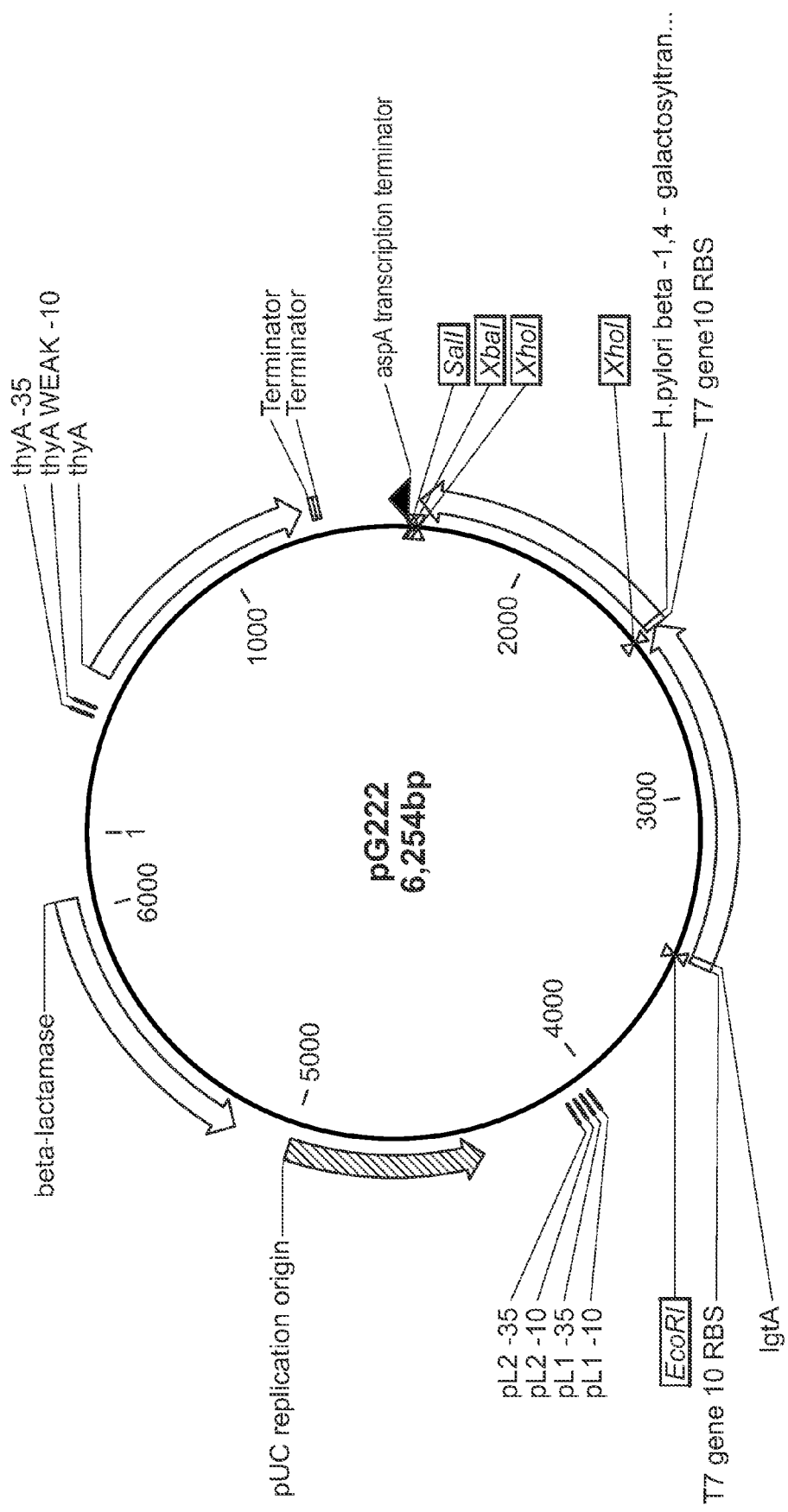

FIG. 7 is a plasmid map of pG222, which expresses, as an operon, the *N. meningitidis* β(1,3)-N-acetylglucosaminyltransferase gene lgtA and the *H. pylori* 4GalT (jhp0765) β(1,4)-galactosyltransferase gene.

Figure 8:
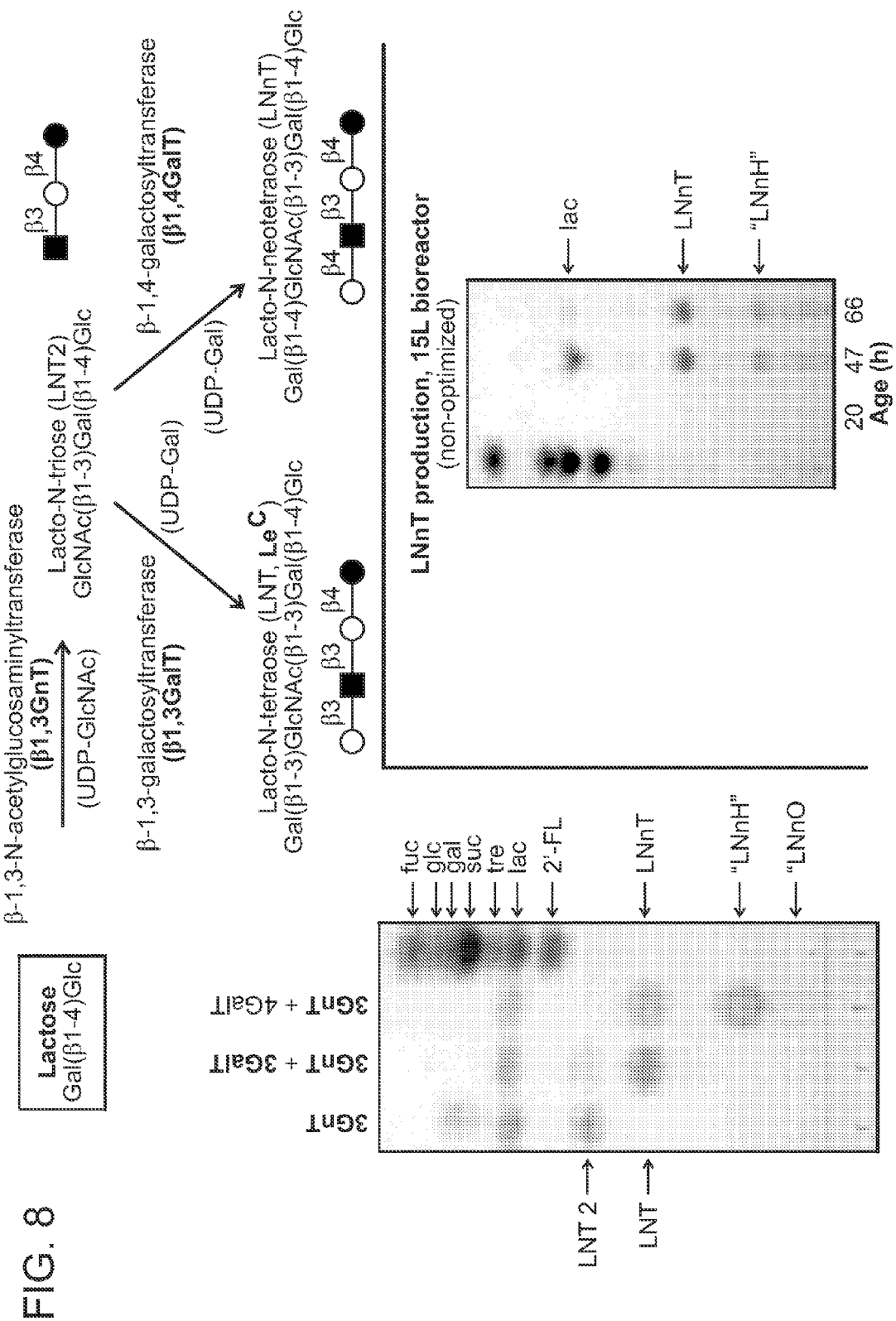

FIG. 8 illustrates schematically the enzymatic reactions necessary to produce from lactose, via the intermediate trisaccharide lacto-N-triose 2 (LNT2), the two human milk oligosaccharides: Lacto-N-tetraose (LNT) and Lacto-N-neotetraose (LNnT). A thin layer chromatogram (on left) is presented of culture medium samples taken from small scale *E. coli* cultures and demonstrating synthesis of LNT2, LNT and LNnT. A second thin layer chromatogram (on right) is presented of culture medium samples taken from a 15 L *E. coli* bioreactor culture-demonstrating synthesis of LNnT.

Figure 9:
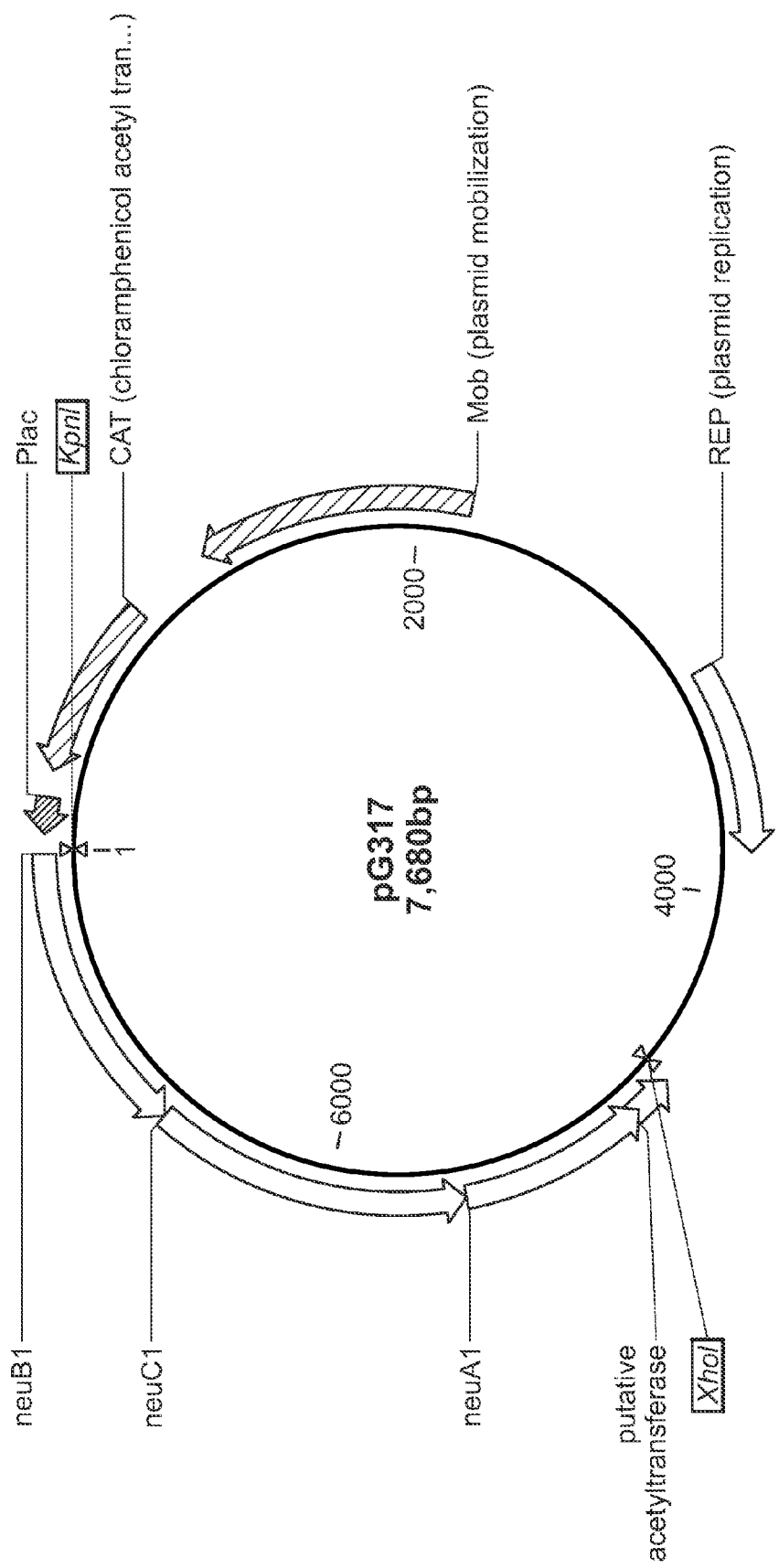

FIG. 9 is a plasmid map of pG317, a low-copy vector which expresses as an operon, under the control of the *E. coli* lac promoter, the *Campylobacter jejuni* ATCC43438 neuB, neuC and neuA genes, encoding N-acetylneuraminate synthase, UDP-N-acetylglucosamine 2-epimerase, and N-acetylneuraminate cytidylyltransferase, respectively.

Figure 10:
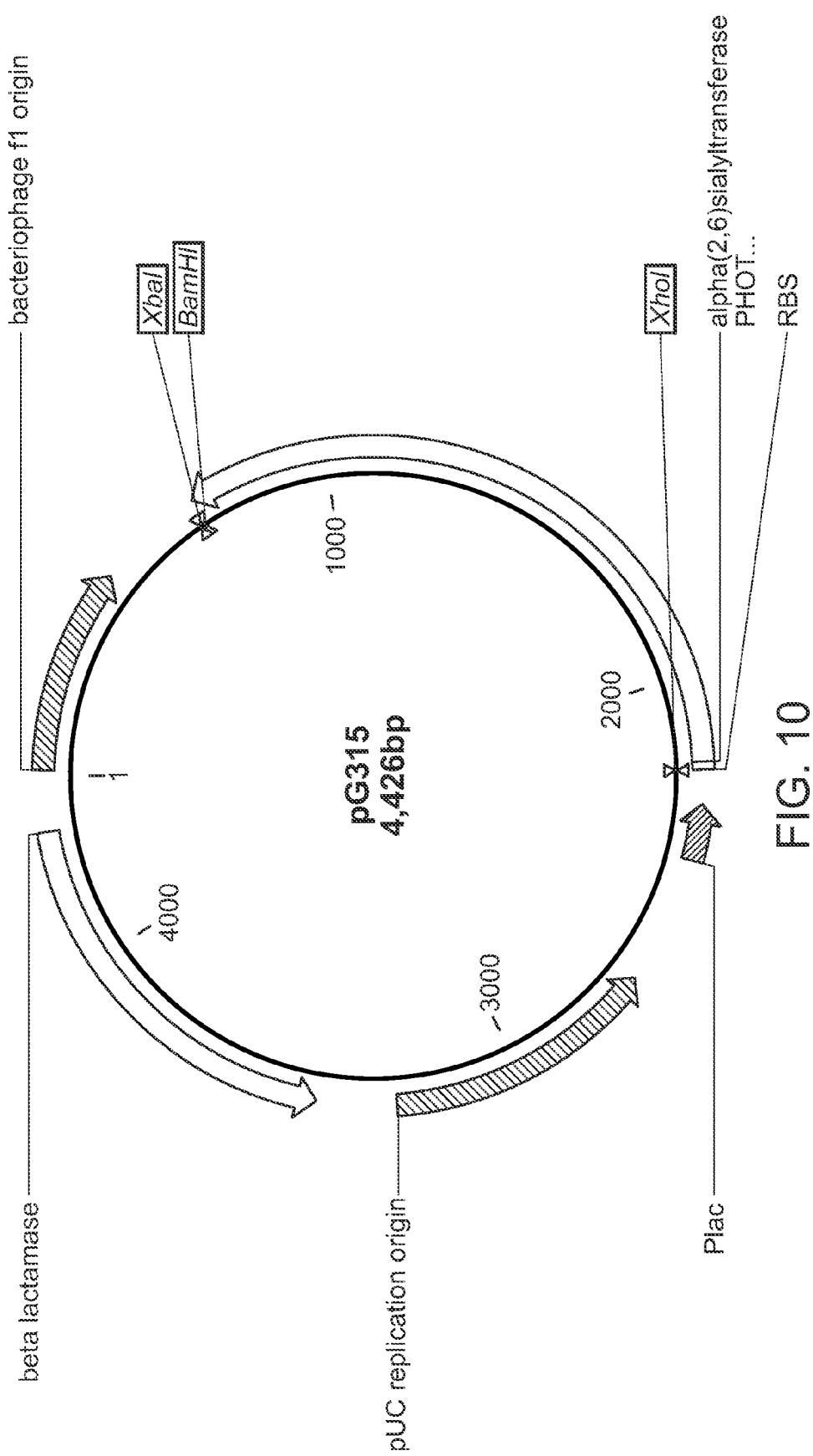

FIG. 10 is a plasmid map of pG315, a multi-copy vector which expresses a gene encoding an α(2,6) sialyltransferase from *Photobacterium* spp JT-ISH-224, under the control of the *E. coli* lac promoter.

Figure 11:
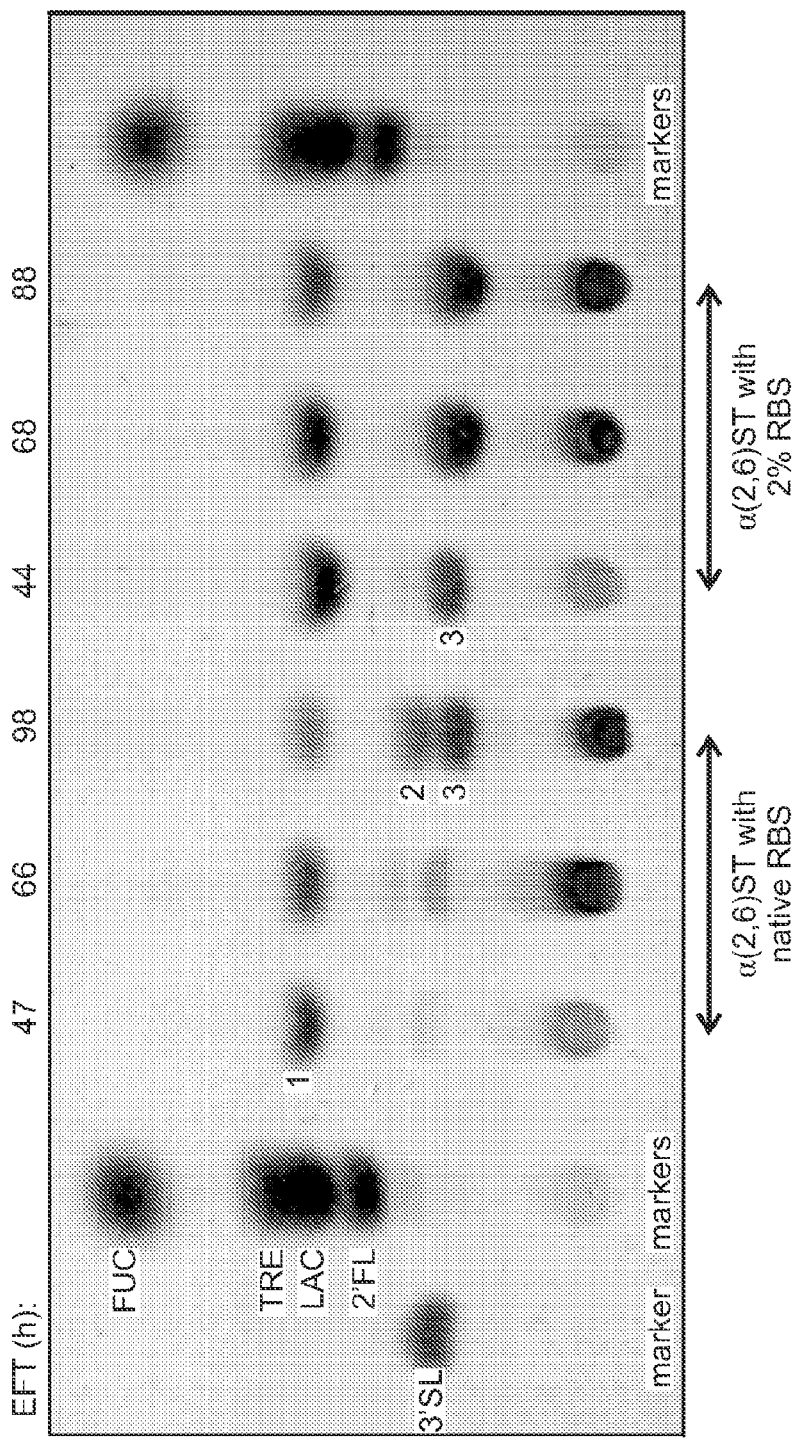

FIG. 11 is a photograph of a thin layer chromatogram showing 6'-SL in culture medium produced by *E. coli* strain E547 (ΔnanRATEK), containing plasmids expressing a bacterial α(2,3)sialyltransferase and neuA, neuB and neuC. FIG. 11 also shows a TLC analysis of culture supernatants from two fermentations producing 6'-sialyllactose (6'-SL). Samples to the left of the figure are taken from a fermentation of an *E. coli* strain containing pG315 (carrying a strong RBS in front of the α(2,6)sialyltransferase gene in the vector). Samples on the right of the figure are taken from a fermentation of an *E. coli* strain containing a close variant of pG315 that carries a weaker RBS in front of the α(2,6) sialyltransferase gene.

Figure 12:
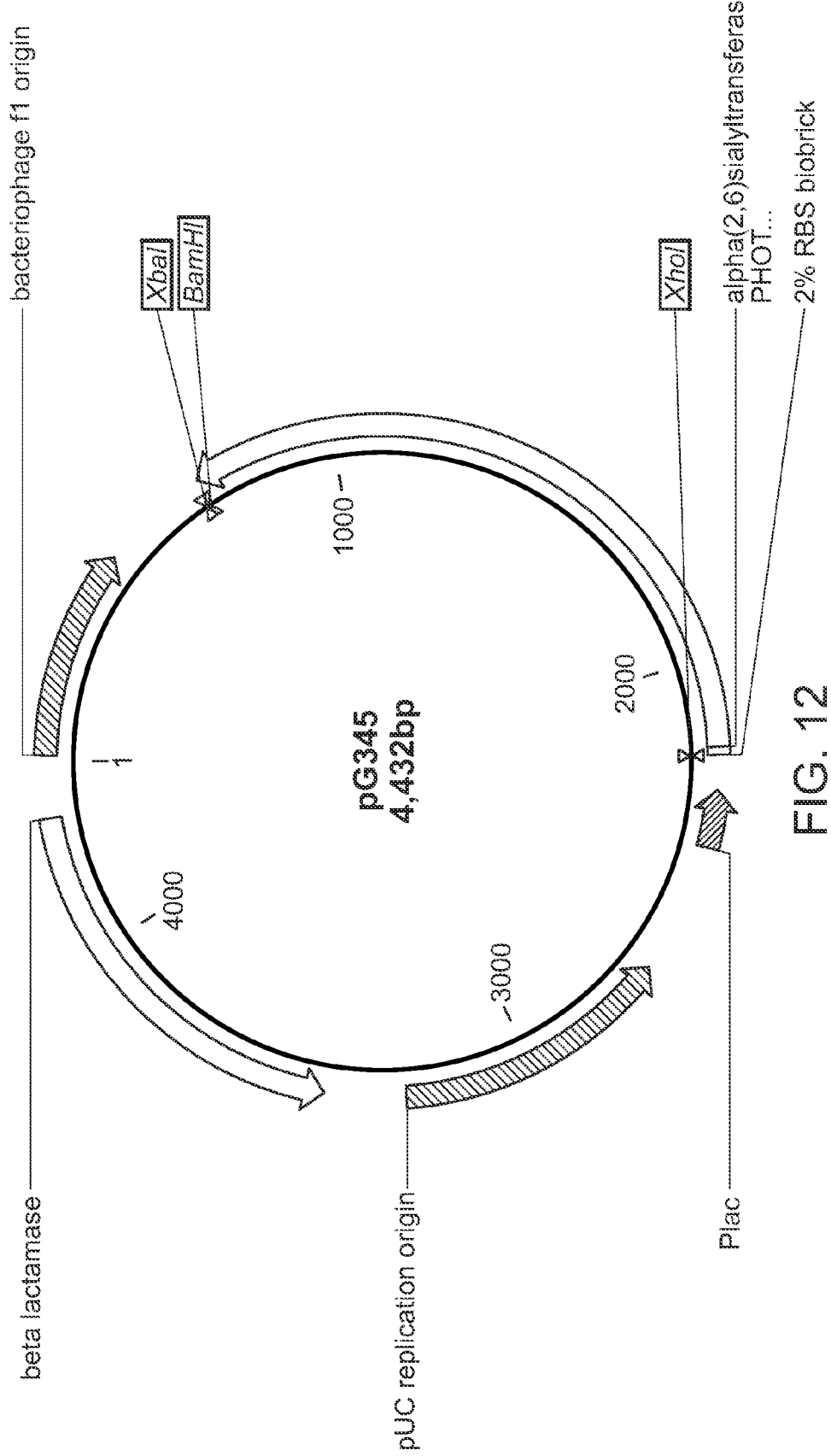

FIG. 12 is a plasmid map of pG345, a multi-copy vector which expresses a gene encoding an α(2,6) sialyltransferase from *Photobacterium* spp JT-ISH-224, under the control of a weaker ribosomal binding site (SEQ ID NO:8) and the *E. coli* lac promoter.

Figure 13:
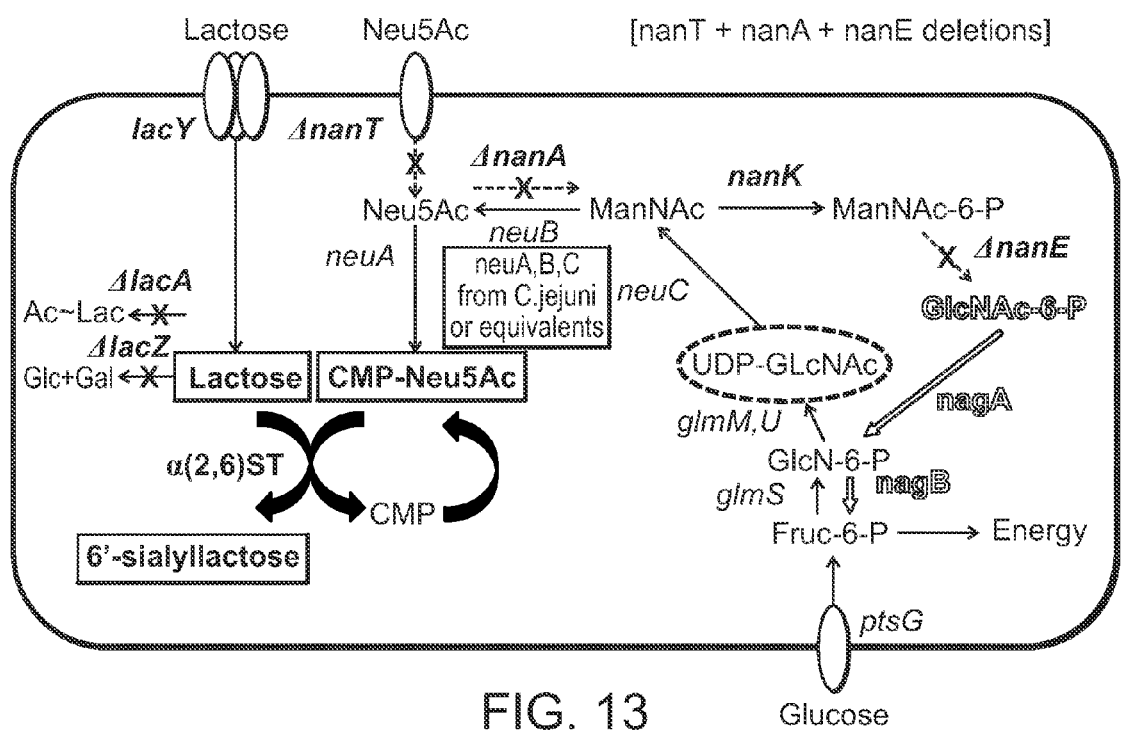

FIG. 13 is a schematic demonstrating metabolic pathways and a second example (utilizing nanT, nanA and nanE deletions) of the changes introduced into them to engineer 6'-sialyllactose (6'-SL) synthesis in *E. coli*. Abbreviations include: (Neu5Ac) N-acetylneuraminic acid, sialic acid; (ΔnanT) mutated N-acetylneuraminic acid transporter; (ΔnanA) mutated N-acetylneuraminic acid lyase; (ManNAc) N-acetylmannosamine; (nanK) wild-type N-acetylmannosamine kinase; (ΔnanE) mutated N-acetylmannosamine-6-phosphate epimerase; (ManNAc-6-P) N-acetylmannosamine-6-phosphate; (GlcNAc-6-P) N-acetylglucosamine-6-phosphate; (GlcN-6-P) Glucosamine-6-phosphate; (Fruc-6-P) Fructose-6-phosphate; (neuA), CMP-N-acetylneuraminic acid synthetase; (CMP-Neu5Ac) CMP-N-acetylneuraminic acid; (neuB), N-acetylneuraminic acid synthase; (neuC) UDP-GlcNAc-2-epimerase; and (UDP-GlcNAc) uridine diphosphate N-acetylglucosamine.

Figure 14:
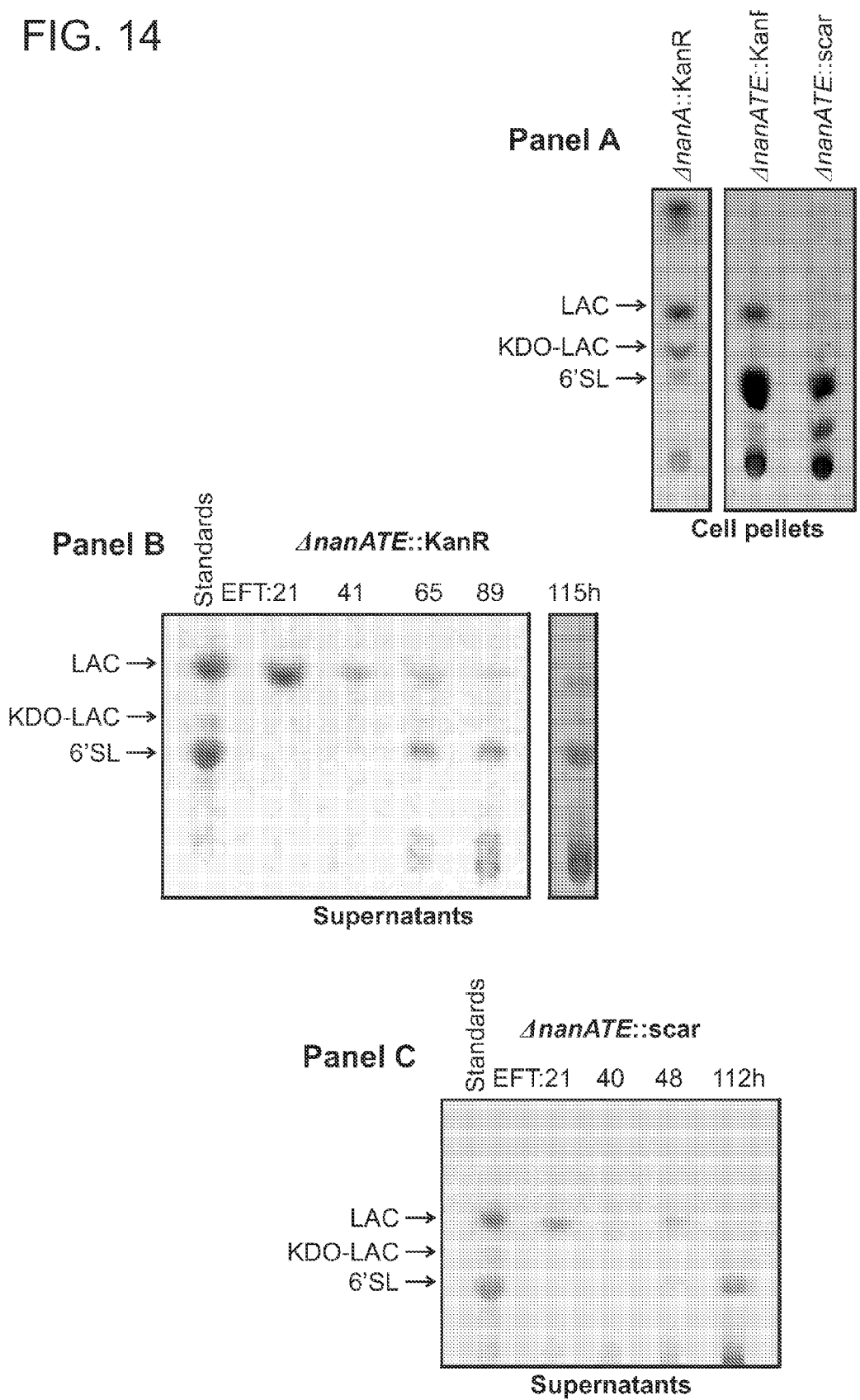
Figure 15:
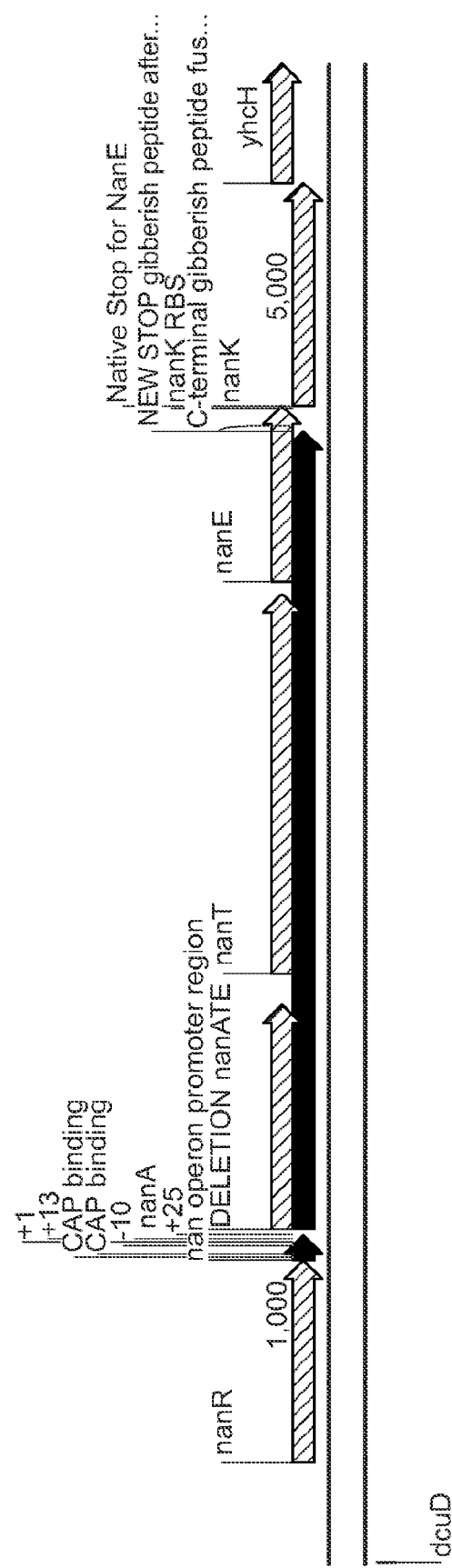

FIG. 14 illustrates the TLC analysis of cell pellets and or supernatants from a three pilot scale fermentation experiments using three *E. coli* strains carrying various combinations of nan mutations FIG. 15 is a schematic illustrating the location of the gene deletion made within the *E. coli* nan operon to generate the [nanR+, nanA, nanT, nanE, nanK+] mutant locus of strains E1017 and E1018.

Figure 16:
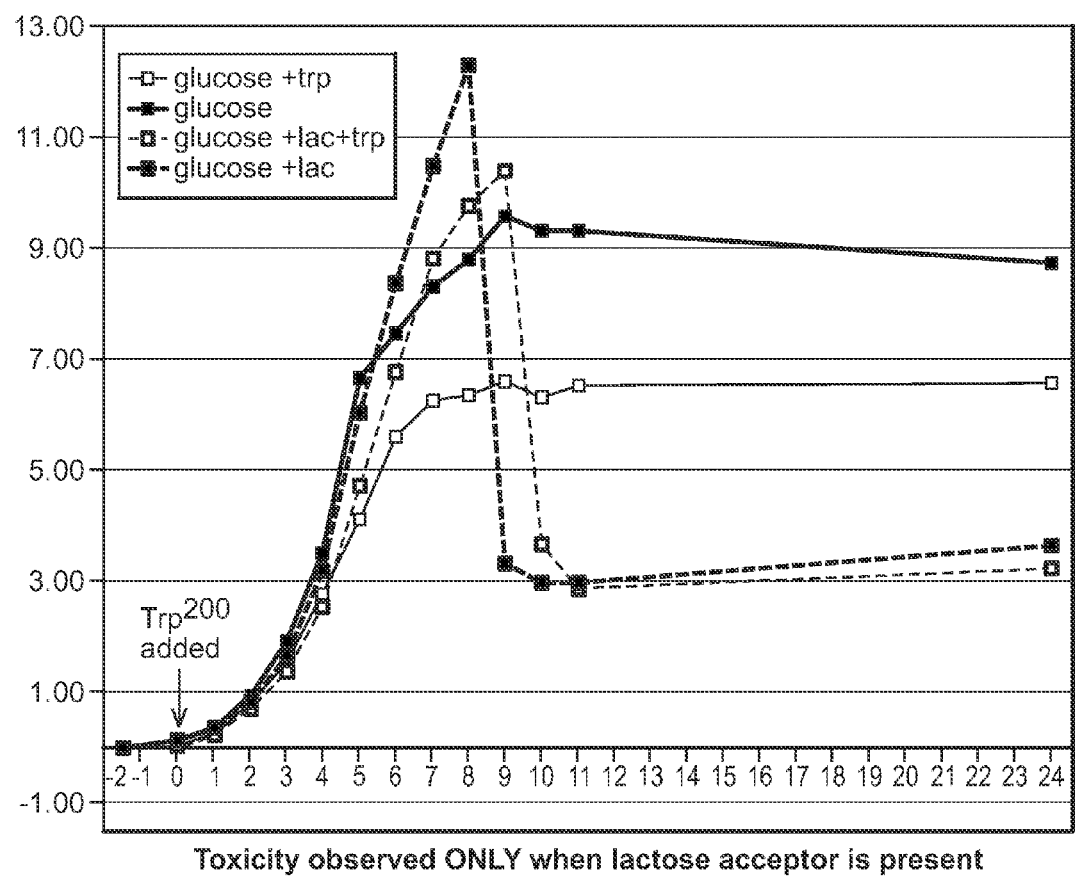

FIG. 16 is a cell density growth curve plot of four cultures of E680 transformed with pG292, induced or un-induced by tryptophan addition, and in the presence or absence of lactose in the growth medium. Abundant cell lysis is seen in the lactose-containing cultures.

Figure 17:
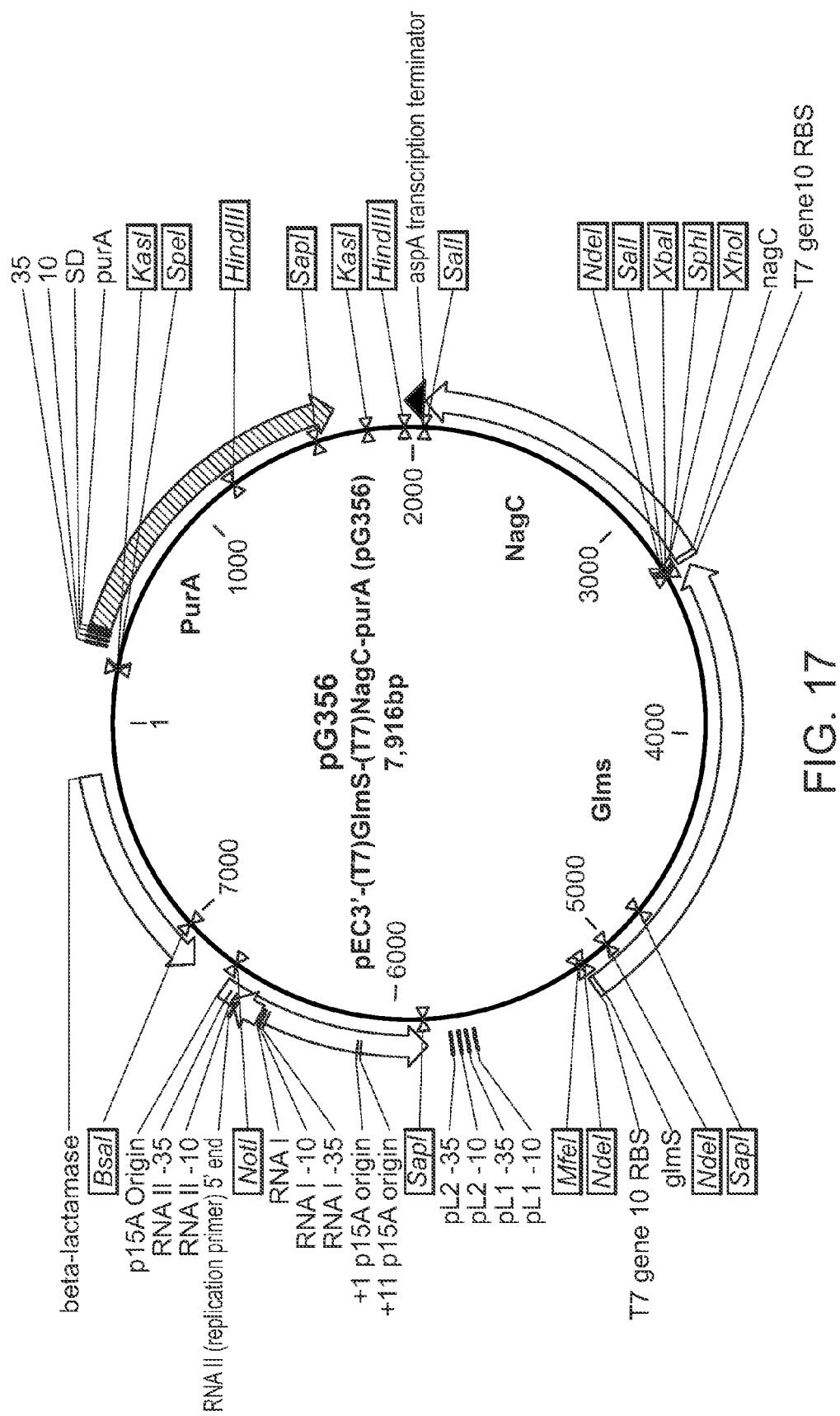

FIG. 17 is a plasmid map of pG356, which expresses, as an operon, the *E. coli* glmS and nagC genes. pG356 carries a p15A replication origin and both ampC and purA selectable markers.

Figure 18:
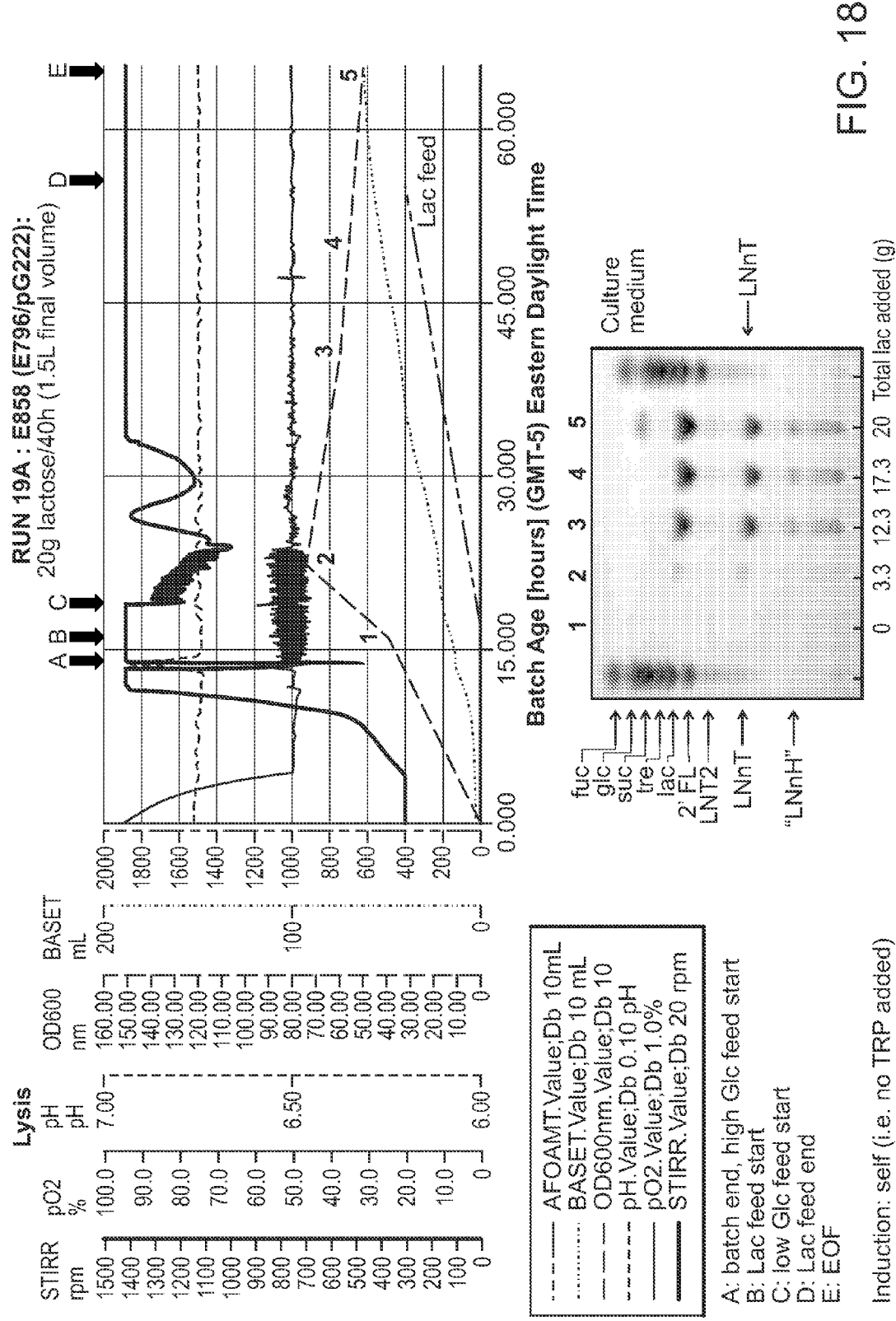

FIG. 18 is a fementation parameter trace and TLC culture supernatant analysis (for LNnT production) of a 1.5 L bioreactor culture of E796 transformed with pG222.

Figure 19:
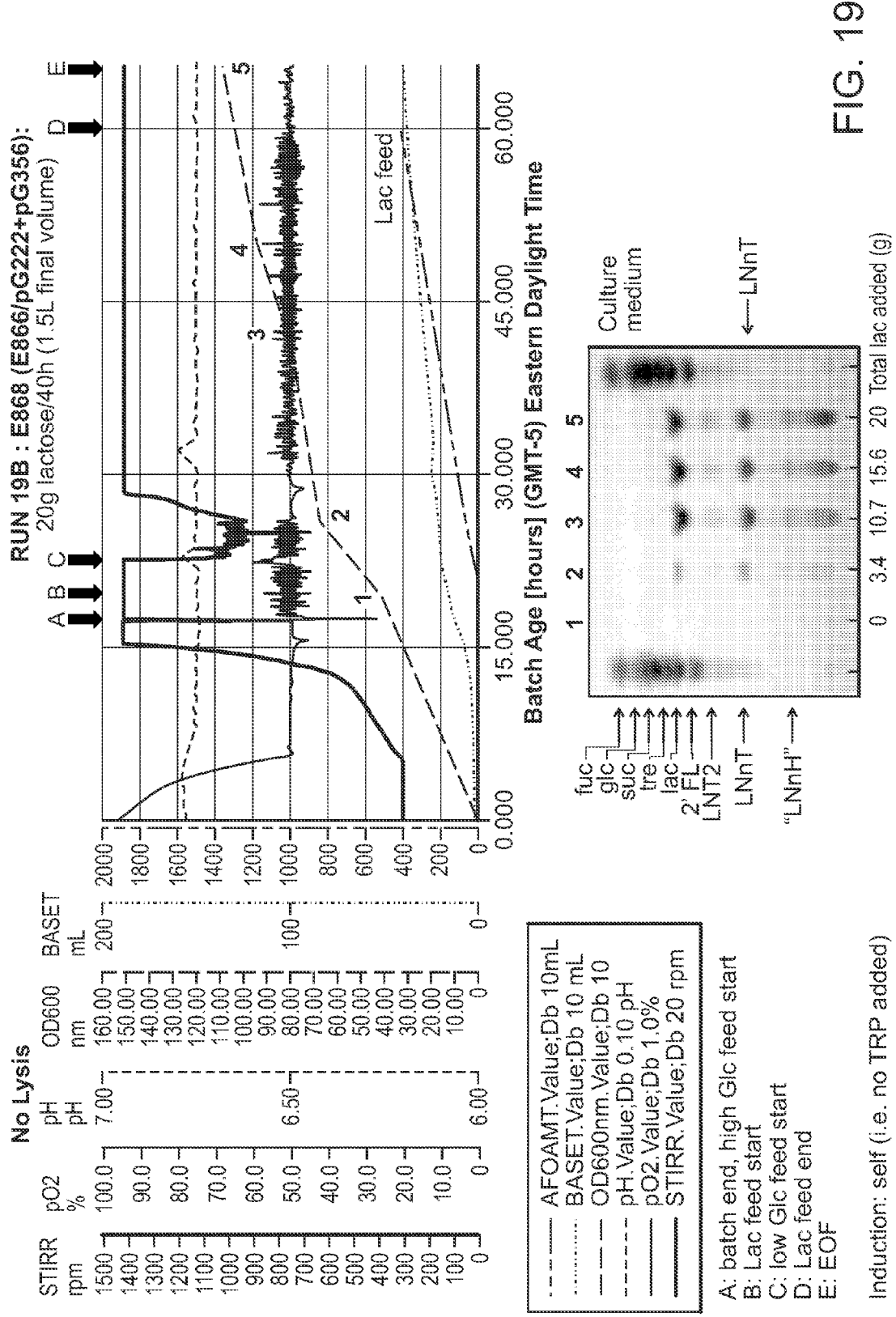

FIG. 19 is a fementation parameter trace and TLC culture supernatant analysis (for LNnT production) of a 1.5 L bioreactor culture of E866 transformed with both pG222 and pG356.

DETAILED DESCRIPTION OF THE INVENTION

Described herein are genetic constructs and methods for production of N-acetylglucosamine-containing human milk oligosaccharides (hMOS) and sialyloligosaccharides. In order to make both N-acetylglucosamine-containing and sialyl-containing hMOS, one needs to tap into the cellular UDP-GlcNAc pool. Doing so can be challenging, since UDP-GlcNAc is an essential metabolite for bacteria (used to make the cell wall). The constructs, compositions, and methods of the invention overcome difficulties of the past by enhancing the UDP-GlcNAc pool, a strategy that represents an advantage in the production of both classes of hMOS. Other distinctions over earlier approaches represent improvements and/or confer advantages over those earlier strategies.

hMOS

Human milk glycans, which comprise both oligosaccharides (hMOS) and their glycoconjugates, play significant roles in the protection and development of human infants, and in particular the infant gastrointestinal (GI) tract. Milk oligosaccharides found in various mammals differ greatly, and their composition in humans is unique (Hamosh M., 2001 Pediatr Clin North Am, 48:69-86; Newburg D. S., 2001 Adv Exp Med Biol, 501:3-10). Moreover, glycan levels in human milk change throughout lactation and also vary widely among individuals (Morrow A. L. et al., 2004 J Pediatr, 145:297-303; Chaturvedi P et al., 2001 Glycobiology, 11:365-372). Previously, a full exploration of the roles of hMOS was limited by the inability to adequately characterize and measure these compounds. In recent years sensitive and reproducible quantitative methods for the analysis of both neutral and acidic hMOS have been developed (Erney, R., Hilty, M., Pickering, L., Ruiz-Palacios, G., and Prieto, P. (2001) *Adv Exp Med Biol* 501, 285-297. Bao, Y., and Newburg, D. S. (2008) *Electrophoresis* 29, 2508-2515). Approximately 200 distinct oligosaccharides have been identified in human milk, and combinations of a small number of simple epitopes are responsible for this diversity (Newburg D. S., 1999 Curr_Med Chem, 6:117-127; Ninonuevo M. et al., 2006 J Agric Food Chem, 54:7471-74801). hMOS are composed of 5 monosaccharides: D-glucose (Glc), D-galactose (Gal), N-acetylglucosamine (GlcNAc), L-fucose (Fuc), and sialic acid (N-acetyl neuraminic acid, Neu5Ac, NANA). hMOS are usually divided into two groups according to their chemical structures: neutral compounds containing Glc, Gal, GlcNAc, and Fuc, linked to a lactose (Galβ1-4Glc) core, and acidic compounds including the same sugars, and often the same core structures, plus NANA (Charlwood J. et al., 1999 Anal_Biochem, 273:261-277; Martín-Sosa et al., 2003 J Dairy Sci, 86:52-59; Parkkinen J. and Finne J., 1987 Methods Enzymol, 138:289-300; Shen Z. et al., 2001 J Chromatogr A, 921:315-321). Approximately 70-80% of oligosaccharides in human milk are fucosylated. A smaller proportion of the oligosaccharides in human milk are sialylated, or are both fucosylated and sialylated.

Interestingly, hMOS as a class, survive transit through the intestine of infants very efficiently, a function of their being poorly transported across the gut wall and of their resistance to digestion by human gut enzymes (Chaturvedi, P., Warren, C. D., Buescher, C. R., Pickering, L. K. & Newburg, D. S. Adv Exp Med Biol 501, 315-323 (2001)). One consequence of this survival in the gut is that hMOS are able to function as prebiotics, i.e. they are available to serve as an abundant carbon source for the growth of resident gut commensal microorganisms (Ward, R. E., Niñonuevo, M., Mills, D. A., Lebrilla, C. B., and German, J. B. (2007) *Mol Nutr Food Res* 51, 1398-1405). Recently, there is burgeoning interest in the role of diet and dietary prebiotic agents in determining the composition of the gut microflora, and in understanding the linkage between the gut microflora and human health (Roberfroid, M., Gibson, G. R., Hoyles, L., McCartney, A. L., Rastall, R., Rowland, I., Wolvers, D., Watzl, B., Szajewska, H., Stahl, B., Guarner, F., Respondek, F., Whelan, K., Coxam, V., Davicco, M. J., Léotoing, L., Wittrant, Y., Delzenne, N. M., Cani, P. D., Neyrinck, A. M., and Meheust, A. (2010) *Br J Nutr* 104 Suppl 2, S1-63).

A number of human milk glycans possess structural homology to cell receptors for enteropathogens, and serve roles in pathogen defense by acting as molecular receptor "decoys". For example, pathogenic strains of *Campylobacter* bind specifically to glycans in human milk containing the H-2 epitope, i.e., 2'-fucosyl-N-acetyllactosamine or 2'-fucosyllactose (2'-FL); *Campylobacter* binding and infectivity are inhibited by 2'-FL and other glycans containing this H-2 epitope (Ruiz-Palacios, G. M., Cervantes, L. E., Ramos, P., Chavez-Munguia, B., and Newburg, D. S. (2003) *J Biol Chem* 278, 14112-14120). Similarly, some diarrheagenic *E. coli* pathogens are strongly inhibited in vivo by hMOS containing 2'-linked fucose moieties. Several major strains of human caliciviruses, especially the noroviruses, also bind to 2'-linked fucosylated glycans, and this binding is inhibited by human milk 2'-linked fucosylated glycans. Consumption of human milk that has high levels of these 2'-linked fucosyloligosaccharides has been associated with lower risk of norovirus, *Campylobacter*, ST of *E. coli*-associated diarrhea, and moderate-to-severe diarrhea of all causes in a Mexican cohort of breastfeeding children (Newburg D. S. et al., 2004 Glycobiology, 14:253-263; Newburg D. S. et al., 1998 Lancet, 351:1160-1164). Several pathogens are also known to utilize sialylated glycans as their host receptors, such as influenza (Couceiro, J. N., Paulson, J. C. & Baum, L. G. Virus Res 29, 155-165 (1993)), parainfluenza (Amonsen, M., Smith, D. F., Cummings, R. D. & Air, G. M. J Virol 81, 8341-8345 (2007), and rotoviruses (Kuhlenschmidt, T. B., Hanafin, W. P., Gelberg, H. B. & Kuhlenschmidt, M. S. Adv Exp Med Biol 473, 309-317 (1999)). The sialyl-Lewis X epitope is used by *Helicobacter pylori* (Mandavi, J., Sondén, B., Hurtig, M., Olfat, F. O., et al. Science 297, 573-578 (2002)), *Pseudomonas aeruginosa* (Scharfman, A., Delmotte, P., Beau, J., Lamblin, G., et al. Glycoconj J 17, 735-740 (2000)), and some strains of noroviruses (Rydell, G. E., Nilsson, J., Rodriguez-Diaz, J., Ruvoën-Clouet, N., et al. Glycobiology 19, 309-320 (2009)).

The nucleotide sugar uridine diphosphate N-acetylglucosamine (UDP-GlcNAc) is a key metabolic intermediate in bacteria, where it is involved in the synthesis and maintenance of the cell envelope. In all known bacterial classes, UDP-GlcNAc is used to make peptidoglycan (murein); a polymer comprising the bacterial cell wall whose structural integrity is absolutely essential for growth and survival. In addition, gram-negative bacteria use UDP-GlcNAc for the synthesis of lipid A, an important component of the outer cell membrane. Thus, for bacteria, the ability to maintain an adequate intracellular pool of UDP-GlcNAc is critical.

Figure 1:
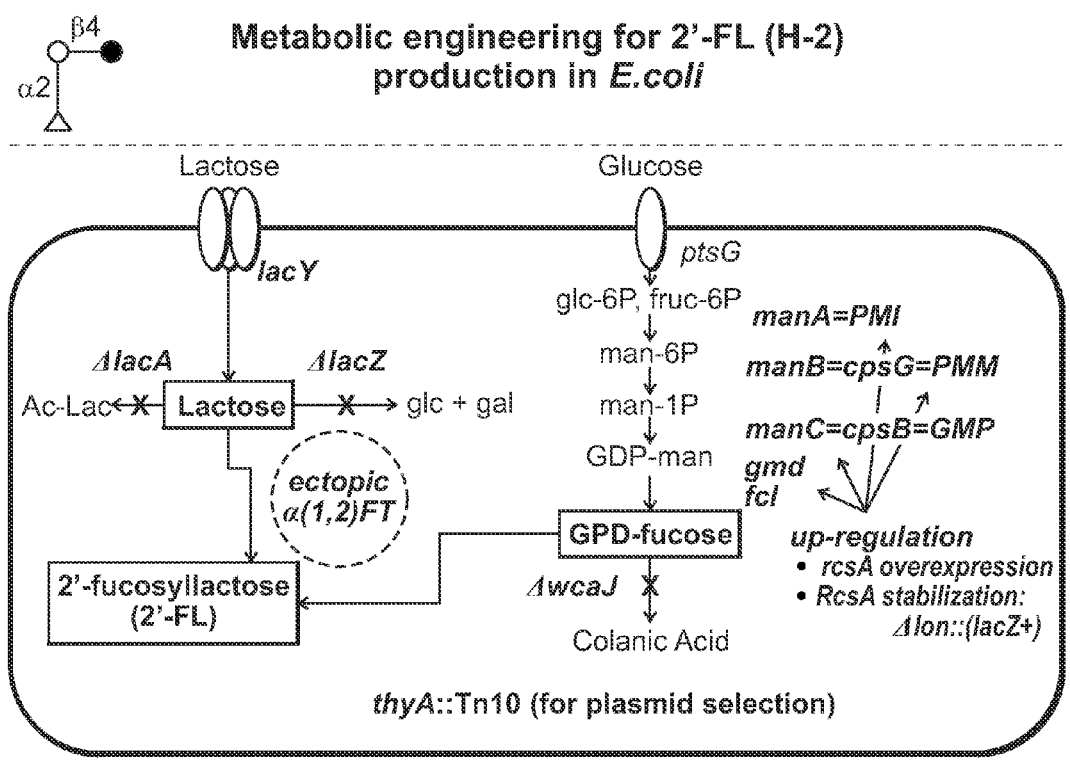
FIG. 1 is a schematic demonstrating metabolic pathways and the changes introduced into them to engineer 2'-fucosyllactose (2'-FL) synthesis in *Escherichia coli* (*E. coli*). Specifically, the lactose synthesis pathway and the GDP-fucose synthesis pathway are illustrated. In the GDP-fucose synthesis pathway: manA=phosphomannose isomerase (PMI), manB=phosphomannomutase (PMM), manC=mannose-1-phosphate guanylyltransferase (GMP), gmd=GDP-mannose-4,6-dehydratase, fcl=GDP-fucose synthase (GFS), and ΔwcaJ=mutated UDP-glucose lipid carrier transferase.

Biosynthesis of certain human milk oligosaccharides (hMOS) has been achieved in engineered strains of the bacterium, *Escherichia coli* K12. As described herein, simple fucosylated hMOS, e.g. 2'-fucosyllactose (2'-FL), 3-fucosyllactose (3-FL), and lactodifucotetraose (LDFT), are produced efficiently by live *E. coli* through artificially enhancing existing intracellular pools of GDP-fucose (the nucleotide sugar donor) and lactose (the accepting sugar), and by then using these enhanced pools as substrates for heterologous recombinant fucosyltransferases (FIG. 1). Since neither the lactose nor GDP-fucose pools are essential for *E. coli* survival, biosynthesis of simple fucosylated hMOS is achieved at good yields without negative consequences on the host bacterium's growth or viability. However, to synthesize more complex hMOS in *E. coli*, use of the critical bacterial UDP-GlcNAc pool is required, with consequent potential impacts on cell viability.

Figure 2:
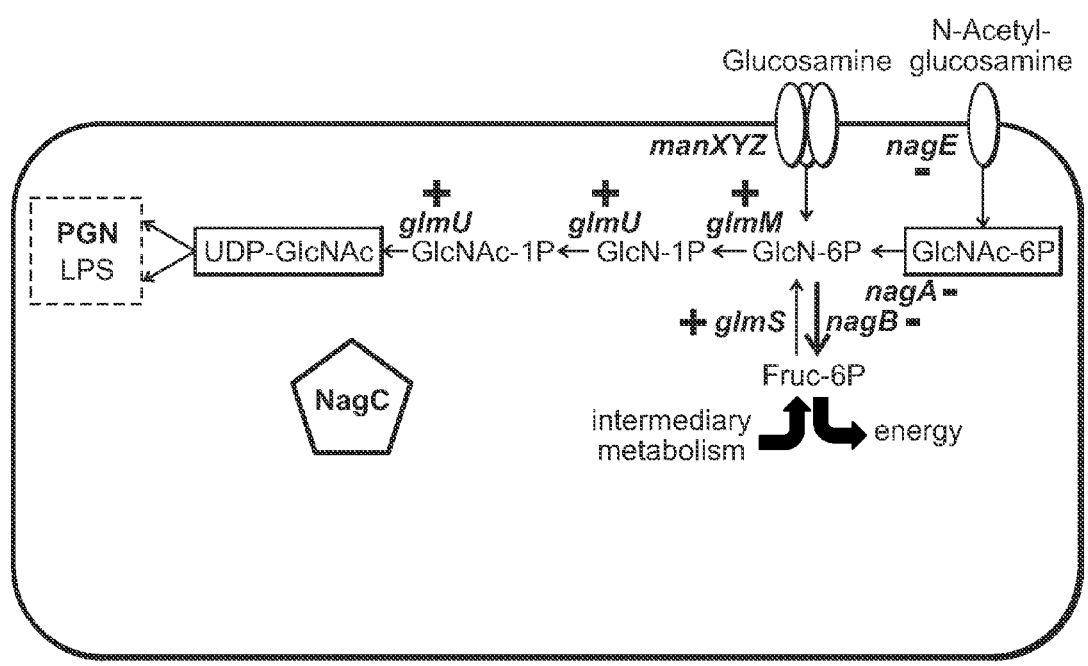
FIG. 2 is a schematic demonstrating metabolic pathways involved in the synthesis of UDP-GlcNAc (uridine diphosphate N-acetylglucosamine) and catabolism of glucosamine and N-acetylglucosamine in *E. coli*. In the schematic: (GlcNAc-1-P) N-acetylglucosamine-1-phosphate; (GlcN-1-P) glucosamine-1-phosphate; (GlcN-6-P) glucosamine-6-phosphate; (GlcNAc-6-P) N-acetylglucosamine-6-phosphate; and (Fruc-6-P) Fructose-6-phosphate; glmS (L-glutamine:D-fructose-6-phosphate aminotransferase), glmM (phosphoglucosamine mutase), glmU (fused N-acetyl glucosamine-1-phosphate uridyltransferase and glucosamine-1-phosphate acetyl transferase), nagC (bifunctional transcriptional activator/repressor protein), nagA (N-acetylglucosamine-6-phosphate deacetylase) and nagB (glucosamine-6-phosphate deaminase), nagE (N-acetylglucosamine transporter] and manXYZ [glucosamine transporter).

The UDP-GlcNAc pool in *E. coli* is produced through the combined action of three glm genes, glmS (L-glutamine:D-fructose-6-phosphate aminotransferase), glmM (phosphoglucosamine mutase), and the bifunctional glmU (fused N-acetyl glucosamine-1-phosphate uridyltransferase and glucosamine-1-phosphate acetyl transferase) (FIG. 2). These three genes direct a steady flow of carbon to UDP-GlcNAc, a flow that originates with fructose-6-phosphate (an abundant molecule of central energy metabolism). Expression of the glm genes is under positive control by the transcriptional activator protein, NagC.

When *E. coli* encounters glucosamine or N-acetyl-glucosamine in its environment, these molecules are each transported into the cell via specific membrane transport proteins and are used either to supplement the flow of carbon to the UDP-GlcNAc pool, or alternatively they are consumed to generate energy, under the action of nag operon gene products (i.e. nagA [N-acetylglucosamine-6-phosphate deacetylase] and nagB [glucosamine-6-phosphate deaminase]). In contrast to the glm genes, expression of nagA and nagB are under negative transcriptional control, but by the same regulatory protein as the glm genes, i.e. NagC. NagC is thus bi-functional, able to activate UDP-GlcNAc synthesis, while at the same time repressing the degradation of glucosamine-6-phosphate and N-acetylglucosamine-6-phosphate.

The binding of NagC to specific regulatory DNA sequences (operators), whether such binding results in gene activation or repression, is sensitive to fluctuations in the cytoplasmic level of the small-molecule inducer and metabolite, GlcNAc-6-phosphate. Intracellular concentrations of GlcNAc-6-phosphate increase when N-acetylglucosamine is available as a carbon source in the environment, and thus under these conditions the expression of the glm genes (essential to maintain the vital UDP-GlcNAc pool) would decrease, unless a compensatory mechanism is brought into play. E. coli maintains a baseline level of UDP-GlcNAc synthesis through continuous expression of nagC directed by two constitutive promoters, located within the upstream nagA gene. This constitutive level of nagC expression is supplemented approximately threefold under conditions where the degradative nag operon is induced, and by this means E. coli ensures an adequate level of glm gene expression under all conditions, even when N-acetylglucosamine is being utilized as a carbon source.

Figure 3:
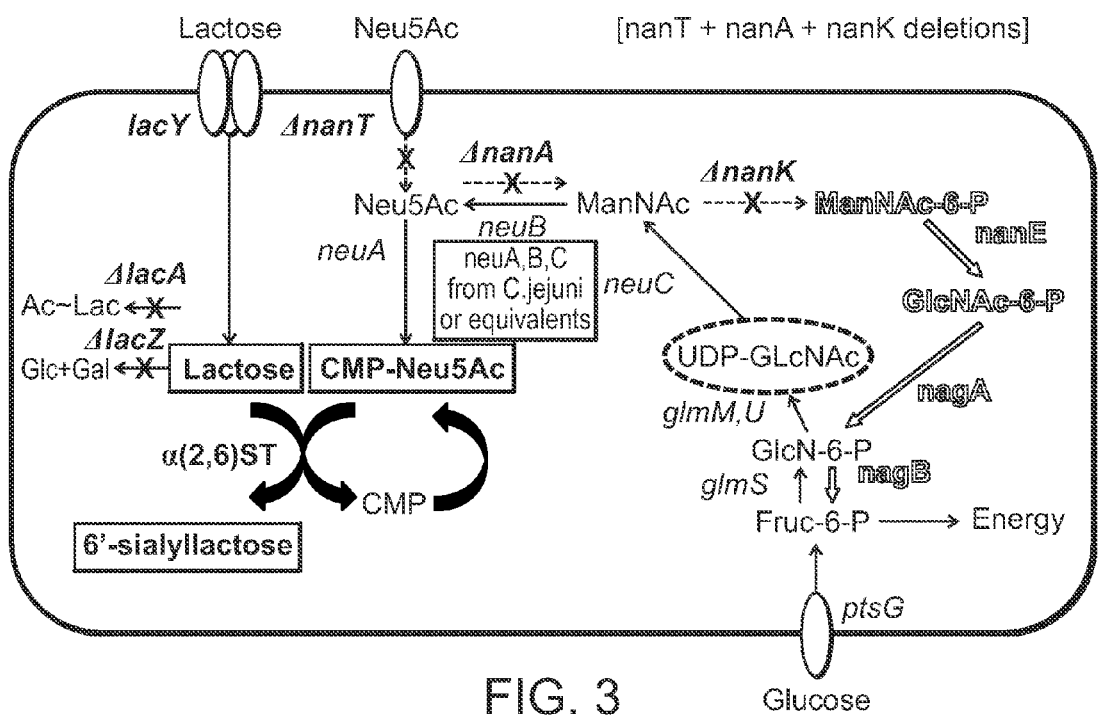
FIG. 3 is a schematic demonstrating metabolic pathways and one example (utilizing nanT, nanA and nanK deletions) of the changes introduced into them to engineer 6'-sialyllactose (6'-SL) synthesis in *E. coli*. Abbreviations include: (Neu5Ac) N-acetylneuraminic acid, sialic acid; (ΔnanT) mutated N-acetylneuraminic acid transporter; (ΔnanA) mutated N-acetylneuraminic acid lyase; (ManNAc)

Many hMOS incorporate GlcNAc into their structures directly, and many also incorporate sialic acid, a sugar whose synthesis involves consumption of UDP-GlcNAc (FIG. 3, FIG. 13). Thus, synthesis of many types of hMOS in engineered E. coli carries the significant risk of reduced product yield and compromised cell viability resulting from depletion of the bacterium's UDP-GlcNAc pool. One way to address this problem during engineered synthesis of GlcNAc- or sialic acid-containing hMOS is to boost the UDP-GlcNAc pool through simultaneous over-expression of nagC, or preferably by simultaneous over-expression of both nagC and glmS.

While studies suggest that human milk glycans could be used as prebiotics and as antimicrobial anti-adhesion agents, the difficulty and expense of producing adequate quantities of these agents of a quality suitable for human consumption has limited their full-scale testing and perceived utility. What has been needed is a suitable method for producing the appropriate glycans in sufficient quantities at reasonable cost. Prior to the invention described herein, there were attempts to use several distinct synthetic approaches for glycan synthesis. Novel chemical approaches can synthesize oligosaccharides (Flowers, H. M. Methods Enzymol 50, 93-121 (1978); Seeberger, P. H. Chem Commun (Camb) 1115-1121 (2003)), but reactants for these methods are expensive and potentially toxic (Koeller, K. M. & Wong, C. H. Chem Rev 100, 4465-4494 (2000)). Enzymes expressed from engineered organisms (Albermann, C., Piepersberg, W. & Wehmeier, U. F. Carbohydr Res 334, 97-103 (2001); Bettler, E., Samain, E., Chazalet, V., Bosso, C., et al. Glycoconj J 16, 205-212 (1999); Johnson, K. F. Glycoconj J 16, 141-146 (1999); Palcic, M. M. Curr Opin Biotechnol 10, 616-624 (1999); Wymer, N. & Toone, E. J. Curr Opin Chem Biol 4, 110-119 (2000)) provide a precise and efficient synthesis (Palcic, M. M. Curr Opin Biotechnol 10, 616-624 (1999)); Crout, D. H. & Vic, G. Curr Opin Chem Biol 2, 98-111 (1998)), but the high cost of the reactants, especially the sugar nucleotides, limits their utility for low-cost, large-scale production. Microbes have been genetically engineered to express the glycosyltransferases needed to synthesize oligosaccharides from the bacteria's innate pool of nucleotide sugars (Endo, T., Koizumi, S., Tabata, K., Kakita, S. & Ozaki, A. Carbohydr Res 330, 439-443 (2001); Endo, T., Koizumi, S., Tabata, K. & Ozaki, A. Appl Microbiol Biotechnol 53, 257-261 (2000); Endo, T. & Koizumi, S. Curr Opin Struct Biol 10, 536-541 (2000); Endo, T., Koizumi, S., Tabata, K., Kakita, S. & Ozaki, A. Carbohydr Res 316, 179-183 (1999); Koizumi, S., Endo, T., Tabata, K. & Ozaki, A. Nat Biotechnol 16, 847-850 (1998)). However, low overall product yields and high process complexity have limited the commercial utility of these approaches.

Prior to the invention described herein, which enables the inexpensive production of large quantities of neutral and acidic hMOS, it had not been possible to fully investigate the ability of this class of molecule to inhibit pathogen binding, or indeed to explore their full range of potential additional functions.

Prior to the invention described herein, chemical syntheses of hMOS were possible, but were limited by stereo-specificity issues, precursor availability, product impurities, and high overall cost (Flowers, H. M. Methods Enzymol 50, 93-121 (1978); Seeberger, P. H. Chem Commun (Camb) 1115-1121 (2003); Koeller, K. M. & Wong, C. H. Chem Rev 100, 4465-4494 (2000)). Also, prior to the invention described herein, in vitro enzymatic syntheses were also possible, but were limited by a requirement for expensive nucleotide-sugar precursors. The invention overcomes the shortcomings of these previous attempts by providing new strategies to inexpensively manufacture large quantities of human milk oligosaccharides for use as dietary supplements. The invention described herein makes use of an engineered bacterium E. coli (or other bacteria) engineered to produce sialylated oligosaccharides in commercially viable levels, for example the methods described herein enable the production of 3'-SL at >50 g/L in bioreactors.

Variants and Functional Fragments

The present invention features introducing exogenous genes into bacterium to manipulate the pathways to increase UDP-GlcNAc pools, to produce sialylated oligosaccharides and to produce N-acetylglucosamine-containing oligosaccharides. In any of the methods described herein, the genes or gene products may be variants or functional fragments thereof.

A variant of any of genes or gene products disclosed herein may have 50%, 55%, 60%, 65%, 70%, 75%, 80%, 85%, 90%, 95%, 96%, 97%, 98%, or 99% sequence identity to the nucleic acid or amino acid sequences described herein. The term "% identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. For example, % identity is relative to the entire length of the coding regions of the sequences being compared, or the length of a particular fragment or functional domain thereof.

Variants as disclosed herein also include homolog, orthologs, or paralogs of the genes or gene products described herein that retain the same biological function as the genes or gene products specified herein. These variants can be used interchangeably with the genes recited in these methods. Such variants may demonstrate a percentage of homology or identity, for example, 50%, 55%, 60%, 65%, 70%, 75%, 80%, 85%, 90%, 95%, 96%, 97%, 98%, or 99% identity conserved domains important for biological function, preferably in a functional domain, e.g. catalytic domain.

For sequence comparison, one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Percent identity is determined using BLAST and PSI-BLAST (Altschul et al., 1990, J Mol Biol 215:3, 403-410; Altschul et al., 1997, Nucleic Acids Res 25:17, 3389-402). For the PSI-BLAST search, the following exemplary parameters are employed: (1) Expect threshold was 10; (2) Gap cost was Existence:11 and Extension:1; (3) The Matrix employed was BLOSUM62; (4) The filter for low complexity regions was "on".

Changes can be introduced by mutation into the nucleic acid sequence or amino acid sequence of any of the genes or gene products described herein, leading to changes in the amino acid sequence of the encoded protein or enzyme, without altering the functional ability of the protein or enzyme. For example, nucleotide substitutions leading to amino acid substitutions at "non-essential" amino acid residues can be made in the sequence of any of sequences expressly disclosed herein. A "non-essential" amino acid residue is a residue at a position in the sequence that can be altered from the wild-type sequence of the polypeptide without altering the biological activity, whereas an "essential" amino acid residue is a residue at a position that is required for biological activity. For example, amino acid residues that are conserved among members of a family of proteins are not likely to be amenable to mutation. Other amino acid residues, however, (e.g., those that are poorly conserved among members of the protein family) may not be as essential for activity and thus are more likely to be amenable to alteration. Thus, another aspect of the invention pertains to nucleic acid molecules encoding the proteins or enzymes disclosed herein that contain changes in amino acid residues relative to the amino acid sequences disclosed herein that are not essential for activity.

An isolated nucleic acid molecule encoding a protein homologous to any of the genes described herein can be created by introducing one or more nucleotide substitutions, additions or deletions into the corresponding nucleotide sequence, such that one or more amino acid substitutions, additions or deletions are introduced into the encoded protein.

Mutations can be introduced into a nucleic acid sequence such that the encoded amino acid sequence is altered by standard techniques, such as site-directed mutagenesis and PCR-mediated mutagenesis. Preferably, conservative amino acid substitutions are made at one or more predicted nonessential amino acid residues. A "conservative amino acid substitution" is one in which the amino acid residue is replaced with an amino acid residue having a similar side chain. Families of amino acid residues having similar side chains have been defined in the art. Certain amino acids have side chains with more than one classifiable characteristic. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, tryptophan, cysteine), nonpolar side chains (e.g., alanine, valine, leucine, isoleucine, proline, phenylalanine, methionine, tyrosine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a given polypeptide is replaced with another amino acid residue from the same side chain family. Alternatively, in another embodiment, mutations can be introduced randomly along all or part of a given coding sequence, such as by saturation mutagenesis, and the resultant mutants can be screened for given polypeptide biological activity to identify mutants that retain activity. Conversely, the invention also provides for variants with mutations that enhance or increase the endogenous biological activity. Following mutagenesis of the nucleic acid sequence, the encoded protein can be expressed by any recombinant technology known in the art and the activity of the protein can be determined. An increase, decrease, or elimination of a given biological activity of the variants disclosed herein can be readily measured by the ordinary person skilled in the art, i.e., by measuring the capability for mediating oligossacharide modification, synthesis, or degradation (via detection of the products).

The present invention also provides for functional fragments of the genes or gene products described herein. A fragment, in the case of these sequences and all others provided herein, is defined as a part of the whole that is less than the whole. Moreover, a fragment ranges in size from a single nucleotide or amino acid within a polynucleotide or polypeptide sequence to one fewer nucleotide or amino acid than the entire polynucleotide or polypeptide sequence. Finally, a fragment is defined as any portion of a complete polynucleotide or polypeptide sequence that is intermediate between the extremes defined above.

For example, fragments of any of the proteins or enzymes disclosed herein or encoded by any of the genes disclosed herein can be 10 to 20 amino acids, 10 to 30 amino acids, 10 to 40 amino acids, 10 to 50 amino acids, 10 to 60 amino acids, 10 to 70 amino acids, 10 to 80 amino acids, 10 to 90 amino acids, 10 to 100 amino acids, 50 to 100 amino acids, 75 to 125 amino acids, 100 to 150 amino acids, 150 to 200 amino acids, 200 to 250 amino acids, 250 to 300 amino acids, 300 to 350 amino acids, 350 to 400 amino acids, 400 to 450 amino acids, or 450 to 500 amino acids. The fragments encompassed in the present invention comprise fragments that retain functional fragments. As such, the fragments preferably retain the catalytic domains that are required or are important for functional activity. Fragments can be determined or generated by using the sequence information herein, and the fragments can be tested for functional activity using standard methods known in the art. For example, the encoded protein can be expressed by any recombinant technology known in the art and the activity of the protein can be determined. The biological function of said fragment can be measured by measuring ability to synthesize or modify a substrate oligosaccharide, or conversely, to catabolize an oligosaccharide substrate.

EXAMPLE 1

Engineering of *E. coli* to Generate Host Strains for the Production of N-acetylglucosamine-Containing Human Milk Oligosaccharides The *E. coli* K12 prototroph, W3110, was chosen as the parent background for hMOS biosynthesis. This strain had previously been modified at the ampC locus by the introduction of a tryptophan-inducible $P_{trpB}$-cI+ repressor construct (McCoy, J. & Lavallie, E. Current protocols in molecular biology/edited by Frederick M. Ausubel et al., (2001)), enabling economical production of recombinant proteins from the phage λ $P_L$ promoter (Sanger, F., Coulson, A. R., Hong, G. F., Hill, D. F. & Petersen, G. B. J Mol Biol 162, 729-773 (1982)) through induction with millimolar concentrations of tryptophan (Mieschendahl, M., Petri, T. & Hänggi, U. Nature Biotechnology 4, 802-808 (1986)). The strain GI724, an *E. coli* W3110 derivative containing the tryptophan-inducible $P_{trpB}$-cI+ repressor construct in ampC, was used at the basis for further *E. coli* strain manipulations Biosynthesis of hMOS requires the generation of an enhanced cellular pool of lactose. This enhancement was achieved in strain GI724 through several manipulations of the chromosome using λ, Red recombineering (Court, D. L., Sawitzke, J. A. & Thomason, L. C. Annu Rev Genet 36, 361-388 (2002)) and generalized P1 phage transduction (Thomason, L. C., Costantino, N. & Court, D. L. Mol Biol Chapter 1, Unit 1.17 (2007)). The ability of the *E. coli* host strain to accumulate intracellular lactose was first engineered by simultaneous deletion of the endogenous β-galactosidase gene (lacZ) and the lactose operon repressor gene (lacI). During construction of this deletion, the lacIq promoter was placed immediately upstream of the lactose permease gene, lacY. The modified strain thus maintains its ability to transport lactose from the culture medium (via LacY), but is deleted for the wild-type copy of the lacZ (β-galactosidase) gene responsible for lactose catabolism. An intracellular lactose pool is therefore created when the modified strain is cultured in the presence of exogenous lactose.

An additional modification useful for increasing the cytoplasmic pool of free lactose (and hence the final yield of hMOS) is the incorporation of a lacA mutation. LacA is a lactose acetyltransferase that is only active when high levels of lactose accumulate in the *E. coli* cytoplasm. High intracellular osmolarity (e.g., caused by a high intracellular lactose pool) can inhibit bacterial growth, and *E. coli* has evolved a mechanism for protecting itself from high intra cellular osmolarity caused by lactose by "tagging" excess intracellular lactose with an acetyl group using LacA, and then actively expelling the acetyl-lactose from the cell (Danchin, A. Bioessays 31, 769-773 (2009)). Production of acetyl-lactose in *E. coli* engineered to produce human milk oligosaccharides is therefore undesirable: it reduces overall yield. Moreover, acetyl-lactose is a side product that complicates oligosaccharide purification schemes. The incorporation of a lacA mutation resolves these problems, as carrying a deletion of the lacA gene renders the bacterium incapable of synthesizing acetyl-lactose.

A thyA (thymidylate synthase) mutation was introduced by almost entirely deleting the thyA gene and replacing it by an inserted functional, wild-type, but promoter-less *E. coli* lacZ+ gene carrying the 2.8 ribosome binding site (SEQ ID NO: 10) (ΔthyA::(2.8RBS lacZ+,kan')). λ Red recombineering was used to perform the construction. FIG. 4 illustrates the new configuration of genes thus engineered at the thyA locus. The complete DNA sequence of the region, with annotations in GenBank format is disclosed herein. Genomic DNA sequence surrounding the lacZ+ insertion into the thyA region is set forth in SEQ ID NO: 1.

The thyA defect can be complemented in trans by supplying a wild-type thyA gene on a multicopy plasmid (Belfort, M., Maley, G. F. & Maley, F. Proceedings of the National Academy of Sciences 80, 1858 (1983)). This complementation is used herein as a means of plasmid maintenance (eliminating the need for a more conventional antibiotic selection scheme to maintain plasmid copy number).

The genotype of strain E680 is given below. E680 incorporates all the changes discussed above and is a host strain suitable for the production of N-acetylglucosamine-containing oligosaccharides.

F'402 proA+B+, PlacIq-lacY, Δ(lacI-lacZ) 158, ΔlacA398/araC, Δgpt-mhpC, ΔthyA::(2.8RBS lacZ+, KAN), rpoS+, rph+, ampC::(Ptrp T7g10 RBS-λcI+, CAT)

E796 is a strain similar to E680 and carries a thyA (thymidylate synthase) mutation, introduced by almost entirely deleting the thyA gene and replacing it by an inserted functional, wild-type, but promoter-less *E. coli* lacZ+ gene but carrying the 0.8 ribosome binding site (SEQ ID NO: 11) [ΔthyA::(0.8RBS lacZ+, KAN)]. The genotype of strain E796 is given below. E796 incorporates all the changes discussed above and is a host strain suitable for the production of N-acetylglucosamine-containing oligosaccharides.

F'402 proA+B+, PlacIq-lacY, Δ(lacI-lacZ) 158, ΔlacA398/araC, Δgpt-mhpC, ΔthyA::(2.8RBS lacZ+, KAN), rpoS+, rph+, ampC::(Ptrp T7g10 RBS-λcI+, CAT)

E866 is a strain similar to E796 and is useful for dual plasmid selection. E866 also carries a thyA (thymidylate synthase) mutation, introduced by almost entirely deleting the thyA gene and replacing it by an inserted functional, wild-type, but promoter-less *E. coli* lacZ+ gene and carrying the 0.8 ribosome binding site (SEQ ID NO: 11) [ΔthyA::(0.8RBS lacZ+)]. In addition to the thyA deletion E866 also carries a deletion of the purA gene. The genotype of strain E866 is given below. E866 incorporates all the changes discussed above and is a host strain suitable for the production of N-acetylglucosamine-containing oligosaccharides.

F'402 proA+B+, PlacIq-lacY, Δ(lacI-lacZ) 158, ΔlacA398/araC, Δgpt-mhpC, ΔthyA::(0.8RBS lacZ+), rpoS+, rph+, ampC::(Ptrp T7g10 RBS-λcI+, CAT), ΔpurA727::KAN

EXAMPLE 2

Production of N-acetylglucosamine-containing Human Milk Oligosaccharides in *E. coli*: Lacto-N-tetraose (LNT) and Lacto-N-neotetraose (LNnT)

The first step in the synthesis (from a lactose precursor) of both Lacto-N-tetraose (LNT) and Lacto-N-neotetraose (LNnT) is the addition of a β(1,3)N-acetylglucosamine residue to lactose, utilizing a heterologous β(1,3)-N-acetylglucosaminyltransferase to form Lacto-N-triose 2 (LNT2). The plasmid pG292 (ColE1, thyA+, bla+, $P_L$-lgtA) (SEQ ID NO: 2, FIG. 5) carries the lgtA β(1,3)-N-acetylglucosaminyltransferase gene of *N. meningitidis* and can direct the production of LNT2 in *E. coli* strain E680 under appropriate culture conditions. pG221 (ColE1, thyA+, bla+, $P_L$-lgtA-wbgO) (SEQ ID NO: 3, FIG. 6) is a derivative of pG292 that carries (arranged as an operon) both the lgtA β(1,3)-N-acetylglucosaminyltransferase gene of *N. meningitidis* and the wbgO β(1,3)-galactosyltransferase gene of *E. coli* O55: H7. pG221 directs the production of LNT in *E. coli* strain E680 under appropriate culture conditions. pG222 (ColE1, thyA+, bla+, $P_L$—lgtA-4GalT) (SEQ ID NO: 4, FIG. 7) is a derivative of pG292 that carries (arranged as an operon) both the lgtA β(1,3)-N-acetylglucosaminyltransferase gene of *N. meningitidis* and the 4GalT (jhp0765) β(1,4)-galactosyltransferase gene of *H. pylori*. pG222 directs the production of LNnT in *E. coli* strain E680 under appropriate culture conditions.

The addition of tryptophan to the lactose-containing growth medium of cultures of any one of the E680-derivative strains transformed with plasmids pG292, pG221 or pG222 leads, for each particular E680/plasmid combination, to activation of the host *E. coli* tryptophan utilization repressor TrpR, subsequent repression of $P_{trpB}$, and a consequent decrease in cytoplasmic cI levels, which results in a de-repression of $P_L$, expression of lgtA, lgtA+wbgO, or IgtA+4GalT respectively, and production of LNT2, LNT, or LNnT respectively.

For LNT2, LNT, or LNnT production in small scale laboratory cultures (<100 ml), strains were grown at 30° C. in a selective medium lacking both thymidine and tryptophan to early exponential phase (e.g., M9 salts, 0.5% glucose, 0.4% casaminoacids). Lactose was then added to a final concentration of 0.5 or 1%, along with tryptophan (200 µM final) to induce expression of the respective glycosyltransferases, driven from the $P_L$ promoter. At the end of the induction period (~24 h), TLC analysis was performed on aliquots of cell-free culture medium. FIG. 8 illustrates schematically the enzymatic reactions necessary to produce from lactose, via the intermediate trisaccharide lacto-N-triose 2 (LNT2), the two human milk oligosaccharides; Lacto-N-tetraose (LNT) and Lacto-N-neotetraose (LNnT). A thin layer chromatogram (on left) is presented of culture medium samples taken from small scale *E. coli* cultures and demonstrating synthesis of LNT2, LNT, and LNnT (utilizing induced, lactose-containing cultures of E680 transformed with pG292, pG221 or pG222 respectively). A second thin layer chromatogram (on right) is presented of culture medium samples taken from an *E. coli* E680/pG222 15 L bioreactor culture and demonstrating synthesis of LNnT (as well as the higher molecular weight hMOS, Lacto-N-neohexaose, LNnH).

Although the above results clearly demonstrate how it is possible to synthesize GlcNAc-containing oligosaccharides (i.e. LNT2, LNT and LNnT) in engineered *E. coli*, FIG. 14 illustrates a serious problem faced when attempting to use the *E. coli* UDP-GlcNAc pool during such syntheses. In FIG. 14 four separate cultures of E680, transformed with pG292, were grown in the presence and absence of lactose, and with LgtA expression both induced and uninduced by tryptophan addition. It can clearly be seen that massive cell lysis occurs in the cultures where lactose is present—i.e. in those cultures where LgtA draws down the cellular UDP-GlcNAc pool by adding GlcNAc to lactose (and making LNT2). In so doing, UDP-GlcNAc is diverted from cell wall biosynthesis towards hMOS biosynthesis, and cell lysis results. This lysis can be monitored readily not only by the precipitous drop in culture density as seen in the figure, but also by the appearance of DNA in the culture medium.

EXAMPLE 3

Boosting the Cellular UDP-GlcNAc Pool Prevents Cell Lysis During the Biosynthesis of LNnT in Engineered *E. coli*

To examine the impact of enhancing the *E. coli* cellular UDP-GlcNAc pool during synthesis of N-acetylglucosamine-containing hMOS the p15A replicon plasmid pG356 was constructed (FIG. 19 and SEQ ID NO:12). pG356 carries a p15A replicon (compatible with ColE1 replicons), purA and ampC selectable markers, and a synthetic operon (under control of the pL promoter) carrying the *E. coli* glmS (encoding L-glutamine:D-fructose-6-phosphate aminotransferase) and nagC (encoding the bi-functional transcriptional activator/repressor of glm and nag operons) genes. When pL is active in strains carrying the plasmid pG356, the UDP-GlcNAc pool increases. Strain E796 (see example 1) was transformed with pG222 (FIG. 7), and strain E866 (see example 1) was transformed with both pG222 (FIG. 7) and pG356 (FIG. 19). (Strains E796 and E866 are isogenic save for the purA mutation found in E866 that is used for pG356 plasmid retention). Identical 1.5 L fermentation runs were performed on each of the transformed strains. Optical density of the cultures and LNnT biosynthesis was followed, along with standard fermentation parameters. As can be seen in FIG. 18, the E796/pG222 culture produced LNnT, but lysed when the cell density reached 75 OD600, and achieved a final cell density at end-of-fermentation of only 50 OD600. In contrast (FIG. 19) with the E866/pG222+pG356 culture (where expression of the glmS and bagC genes enhance the intracellular UDP-GlcNAc pool) LNnT was also produced, but with no cell lysis observed. In this culture end-of-fermentation cell density reached 108 OD600—more than twice the density achieved for E796/pG222.

EXAMPLE 4

Production of 6'-sialyllactose (6'-SL) by Engineered *E. coli* (ΔnanRATEK)

For the production of 6' sialyllactose, *Escherichia coli* GI724 (ATCC55151) was engineered with a set of mutations that cause cytoplasmic accumulation of non-acetylated lactose precursor and prevent the degradation of N-acetyl-5-neuraminic acid (FIG. 3). In particular, the lacZ (β-galactosidase) and lacA (lactose acetyl transferase) genes from the lac operon were deleted, leaving the LacIq repressor and the LacY permease fully functional. The LacY permease can be driven by weak (e.g. lac8) or strong (e.g. Ptac) promoters. The entire nan operon (nanRATEK; structural and regulatory genes involved in neuraminic acid degradation) was deleted in this example. *E. coli* genome manipulations were achieved using a combination of standard molecular genetics techniques, specifically lambda-Red recombineering, allele exchanges with positive selection suicide vectors, and P1 transductions (FIG. 3). The host genotype of strain E781, suitable for production of sialylated hMOS, is presented below:

ampC::(Ptrp-λcI+), lacIq lacPL8, ΔnanRATEK471, ΔlacZ690, ΔlacA 745

To produce 6'-sialyllactose, the cellular UDP-GlcNAc pool must be converted into the sugar-nucleotide activated precursor, CMP-NeuAc, which in turn can function as a donor molecule for a sugar acceptor (i.e. lactose) in a sialyltransferase-catalyzed reaction (FIG. 3). To this purpose, three genes from *Campylobacter jejuni* ATCC43438, encoding i) UDP-N-acetylglucosamine 2-epimerase (NeuC), ii) N-acetylneuraminate synthase (NeuB), and iii) N-Acetylneuraminate cytidylyltransferase (NeuA), were constitutively co-expressed in the engineered *E. coli* strain described above, along with a gene encoding an α(2,6) sialyltransferase from *Photobacterium* spp JT-ISH-224 (SEQ ID NO:21 Genbank protein Accession BAF92026, incorporated herein by reference). The neu genes were expressed from a low copy number plasmid vector (pG317, FIG. 9, SEQ ID NO: 5) carrying a constitutive lac promoter (pBBR1 ori, cat+, Plac), while the α(2,6)sialyltransferase gene was expressed from a high copy number plasmid vector (pG315, FIG. 10, SEQ ID NO: 6) carrying a constitutive lac promoter (ColE1 ori, bla+, Plac). To prevent the synthesis of side-products, the relative expression for the α(2,6)sialyltransferase gene compared to the neu genes is modulated by engineering differing ribosomal binding sites (RBS) providing various degrees of translational efficiency upstream of the α(2,6)sialyltransferase gene. Engineered strains were grown to high density in pilot scale fermentors using a batch to fed-batch strategy. FIG. 11 is a TLC analysis of culture supernatants from two such fermentations, with samples to the left of the figure being taken from a fermentation of a strain containing pG315 (and thus carrying the RBS presented in SEQ ID NO: 7 in front of the α(2,6) sialyltransferase gene in the vector). Samples on the right of the figure are taken from a fermentation of a strain containing a close variant of pG315 (pG345, FIG. 12, SEQ ID NO:9, carrying the weaker RBS presented in SEQ ID NO: 8 in front of the α(2,6)sialyltransferase gene and replacing the RBS presented in SEQ ID NO: 7). In both cases, the lactose precursor was added at a cell density of 50 $OD_{600}$ and efficient conversion to final products was achieved within 48 hours from the lactose addition. The final yield of 6'SL was increased when utilizing the plasmid with the weaker RBS upstream of the α(2,6)sialyltransferase gene, and moreover the level of KDO-lactose side product is very significantly decreased using this weaker RBS. The identity of the 6'-SL purified using activated carbon column chromatography was confirmed by ESI mass spectrometry and NMR.

EXAMPLE 5

Production of 6'-sialyllactose (6'-SL) by engineered *E. coli.* (ΔnanA, ΔnanATE)

For the production of 6' sialyllactose, *Escherichia coli* GI724 (ATCC55151) was engineered with a set of mutations that cause cytoplasmic accumulation of non-acetylated lactose precursor and prevent the degradation of N-acetyl-5-neuraminic acid (FIG. 13). In particular, the lacZ (β-galactosidase) and lacA (lactose acetyl transferase) genes from the lac operon were deleted, leaving the LacIq repressor and the LacY permease fully functional. The LacY permease can be driven by weak (e.g. lac8) or strong (e.g. Ptac) promoters. While the entire nan operon (nanRATEK; structural and regulatory genes involved in neuraminic acid degradation) can be deleted to abolish neuraminic acid catabolism as in Example 4, lesser deletions encompassing just the nanA, or nanA, nanT and nanE, or nanA and nanE genes, are also suitable. In all the instances where the nanE gene was mutated, the last 104 bp of the nanE gene were left intact to allow for undisturbed transcription/translation of downstream nanK, although other lengths of residual nanE sequence are possible. *E. coli* genome manipulations were achieved using a combination of standard molecular genetics techniques, specifically lambda-Red recombineering, allele exchanges with positive selection suicide vectors, and P1 transductions (FIG. 13). The host genotypes of strains E971, E1017 and E1018, suitable for production of sialylated hMOS with various yield and purity, are presented below:

ampC::(Ptrp-λcI+), lacIq lacPL8, ΔnanA:: kanR, ΔlacZ690, ΔlacA::scar, ampC::(Ptrp-λcI+), lacIq lacPL8, ΔnanATE::kanR::nanK+, ΔlacZ690, ΔlacA:: scar and ampC::(Ptrp-λcI+), lacIq lacPL8, ΔnanATE::scar::nanK+, ΔlacZ690, ΔlacA:: scar respectively To produce 6'-sialyllactose, the cellular UDP-GlcNAc pool must be converted into the sugar-nucleotide activated precursor, CMP-NeuAc, which in turn can function as a donor molecule for a sugar acceptor (i.e. lactose) in a sialyltransferase-catalyzed reaction (FIG. 13). To this purpose, three genes from *Campylobacter jejuni* ATCC43438, encoding i) UDP-N-acetylglucosamine 2-epimerase (NeuC), ii) N-acetylneuraminate synthase (NeuB), and iii) N-Acetylneuraminate cytidylyltransferase (NeuA), were constitutively co-expressed in the engineered *E. coli* strain described above, along with a gene encoding an α(2,6) sialyltransferase from *Photobacterium* spp JT-ISH-224. The neu genes were expressed from a low copy number plasmid vector (pG317, FIG. 9, SEQ ID NO: 5) carrying a constitutive lac promoter (pBBR1 ori, cat+, Plac), while the α(2,6)sialyltransferase gene was expressed from the weak RBS of SEQ ID NO: 8 in a high copy number plasmid vector (pG345, FIG. 12, SEQ ID NO: 9) carrying a constitutive lac promoter (ColE1 ori, bla+, Plac). Engineered strains were grown to high density in pilot scale fermentors using a batch to fed-batch strategy. FIG. 14 is a TLC analysis of culture pellets or supernatants from three such fermentations. Panel A shows production and accumulation of 6'SL in the cells of three genetic backgrounds (only the relevant nan mutations are shown for strains E971, E1017 and E1018), Panel B and C show production and accumulation of 6'SL in the extracellular milieu (supernatants) in strains E971, E1017 and E1018 (only the relevant nan mutations are shown) with estimated maximum volumetric yields of 15 g per liter of supernatant. In all cases, the lactose precursor was added at a cell density of 40 $OD_{600}$ and steady state conversion to final products was achieved within approximately 90 hours from the lactose addition (EFT is elapsed fermentation time).

The various sequences presented herein are recited below.

SEQ ID NO: 1
>E680_thyA::2.8RBS_lacZ *Escherichia coli* str.

```
GCAGCGGAACTCACAAGGCACCATAACGTCCCCTCCCTGATAACGCTGATACTGTGGTCG

CGGTTATGCCAGTTGGCATCTTCACGTAAATAGAGCAAATAGTCCCGCGCCTGGCTGGCG

GTTTGCCATAGCCGTTGCGACTGCTGCCAGTATTGCCAGCCATAGAGTCCACTTGCGCTT

AGCATGACCAAAATCAGCATCGCGACCAGCGTTTCAATCAGCGTATAACCACGTTGTGTT

TTCATGCCGGCAGTATGGAGCGAGGAGAAAAAAAGACGAGGGCCAGTTTCTATTTCTTCG

GCGCATCTTCCGGACTATTTACGCCGTTGCAGGACGTTGCAAAATTTCGGGAAGGCGTCT

CGAAGAATTTAACGGAGGGTAAAAAAACCGACGCACACTGGCGTCGGCTCTGGCAGGATG
```

-continued

```
TTTCGTAATTAGATAGCCACCGGCGCTTTattaaacctactATGACCATGATTACGGATT
CACTGGCCGTCGTTTTACAACGTCGTGACTGGGAAAACCCTGGCGTTACCCAACTTAATC
GCCTTGCAGCACATCCCCCTTTCGCCAGCTGGCGTAATAGCGAAGAGGCCCGCACCGATC
GCCCTTCCCAACAGTTGCGCAGCCTGAATGGCGAATGGCGCTTTGCCTGGTTTCCGGCAC
CAGAAGCGGTGCCGGAAAGCTGGCTGGAGTGCGATCTTCCTGAGGCCGATACTGTCGTCG
TCCCCTCAAACTGGCAGATGCACGGTTACGATGCGCCCATCTACACCAACGTGACCTATC
CCATTACGGTCAATCCGCCGTTTGTTCCCACGGAGAATCCGACGGGTTGTTACTCGCTCA
CATTTAATGTTGATGAAAGCTGGCTACAGGAAGGCCAGACGCGAATTATTTTTGATGGCG
TTAACTCGGCGTTTCATCTGTGGTGCAACGGGCGCTGGGTCGGTTACGGCCAGGACAGTC
GTTTGCCGTCTGAATTTGACCTGAGCGCATTTTTACGCGCCGGAGAAAACCGCCTCGCGG
TGATGGTGCTGCGCTGGAGTGACGGCAGTTATCTGGAAGATCAGGATATGTGGCGGATGA
GCGGCATTTTCCGTGACGTCTCGTTGCTGCATAAACCGACTACACAAATCAGCGATTTCC
ATGTTGCCACTCGCTTTAATGATGATTTCAGCCGCGCTGTACTGGAGGCTGAAGTTCAGA
TGTGCGGCGAGTTGCGTGACTACCTACGGGTAACAGTTTCTTTATGGCAGGGTGAAACGC
AGGTCGCCAGCGGCACCGCGCCTTTCGGCGGTGAAATTATCGATGAGCGTGGTGGTTATG
CCGATCGCGTCACACTACGTCTGAACGTCGAAAACCCGAAACTGTGGAGCGCCGAAATCC
CGAATCTCTATCGTGCGGTGGTTGAACTGCACACCGCCGACGGCACGCTGATTGAAGCAG
AAGCCTGCGATGTCGGTTTCCGCGAGGTGCGGATTGAAAATGGTCTGCTGCTGCTGAACG
GCAAGCCGTTGCTGATTCGAGGCGTTAACCGTCACGAGCATCATCCTCTGCATGGTCAGG
TCATGGATGAGCAGACGATGGTGCAGGATATCCTGCTGATGAAGCAGAACAACTTTAACG
CCGTGCGCTGTTCGCATTATCCGAACCATCCGCTGTGGTACACGCTGTGCGACCGCTACG
GCCTGTATGTGGTGGATGAAGCCAATATTGAAACCCACGGCATGGTGCCAATGAATCGTC
TGACCGATGATCCGCGCTGGCTACCGGCGATGAGCGAACGCGTAACGCGAATGGTGCAGC
GCGATCGTAATCACCCGAGTGTGATCATCTGGTCGCTGGGGAATGAATCAGGCCACGGCG
CTAATCACGACGCGCTGTATCGCTGGATCAAATCTGTCGATCCTTCCCGCCCGGTGCAGT
ATGAAGGCGGCGGAGCCGACACCACGGCCACCGATATTATTTGCCCGATGTACGCGCGCG
TGGATGAAGACCAGCCCTTCCCGGCTGTGCCGAAATGGTCCATCAAAAAATGGCTTTCGC
TACCTGGAGAGACGCGCCCGCTGATCCTTTGCGAATACGCCCACGCGATGGGTAACAGTC
TTGGCGGTTTCGCTAAATACTGGCAGGCGTTTCGTCAGTATCCCCGTTTACAGGGCGGCT
TCGTCTGGGACTGGGTGGATCAGTCGCTGATTAAATATGATGAAAACGGCAACCCGTGGT
CGGCTTACGGCGGTGATTTTGGCGATACGCCGAACGATCGCCAGTTCTGTATGAACGGTC
TGGTCTTTGCCGACCGCACGCCGCATCCAGCGCTGACGGAAGCAAAACACCAGCAGCAGT
TTTTCCAGTTCCGTTTATCCGGGCAAACCATCGAAGTGACCAGCGAATACCTGTTCCGTC
ATAGCGATAACGAGCTCCTGCACTGGATGGTGGCGCTGGATGGTAAGCCGCTGGCAAGCG
GTGAAGTGCCTCTGGATGTCGCTCCACAAGGTAAACAGTTGATTGAACTGCCTGAACTAC
CGCAGCCGGAGAGCGCCGGGCAACTCTGGCTCACAGTACGCGTAGTGCAACCGAACGCGA
CCGCATGGTCAGAAGCCGGGCACATCAGCGCCTGGCAGCAGTGGCGTCTGGCGGAAAACC
TCAGTGTGACGCTCCCCGCCGCGTCCCACGCCATCCCGCATCTGACCACCAGCGAAATGG
ATTTTTGCATCGAGCTGGGTAATAAGCGTTGGCAATTTAACCGCCAGTCAGGCTTTCTTT
CACAGATGTGGATTGGCGATAAAAAACAACTGtTGACGCCGCTGCGCGATCAGTTCACCC
```

-continued

```
GTGCACCGCTGGATAACGACATTGGCGTAAGTGAAGCGACCCGCATTGACCCTAACGCCT

GGGTCGAACGCTGGAAGGCGGCGGGCCATTACCAGGCCGAAGCAGCGTTGTTGCAGTGCA

CGGCAGATACACTTGCTGATGCGGTGCTGATTACGACCGCTCACGCGTGGCAGCATCAGG

GGAAAACCTTATTTATCAGCCGGAAAACCTACCGGATTGATGGTAGTGGTCAAATGGCGA

TTACCGTTGATGTTGAAGTGGCGAGCGATACACCGCATCCGGCGCGGATTGGCCTGAACT

GCCAGCTGGCGCAGGTAGCAGAGCGGGTAAACTGGCTCGGATTAGGGCCGCAAGAAAACT

ATCCCGACCGCCTTACTGCCGCCTGTTTTGACCGCTGGGATCTGCCATTGTCAGACATGT

ATACCCCGTACGTCTTCCCGAGCGAAAACGGTCTGCGCTGCGGGACGCGCGAATTGAATT

ATGGCCCACACCAGTGGCGCGGCGACTTCCAGTTCAACATCAGCCGCTACAGTCAACAGC

AACTGATGGAAACCAGCCATCGCCATCTGCTGCACGCGGAAGAAGGCACATGGCTGAATA

TCGACGGTTTCCATATGGGGATTGGTGGCGACGACTCCTGGAGCCCGTCAGTATCGGCGG

AATTCCAGCTGAGCGCCGGTCGCTACCATTACCAGTTGGTCTGGTGTCAAAAATAAGCGG

CCGCtTTATGTAGGCTGGAGCTGCTTCGAAGTTCCTATACTTTCTAGAGAATAGGAACTT

CGGAATAGGAACTTCAAGATCCCCTTATTAGAAGAACTCGTCAAGAAGGCGATAGAAGGC

GATGCGCTGCGAATCGGGAGCGGCGATACCGTAAAGCACGAGGAAGCGGTCAGCCCATTC

GCCGCCAAGCTCTTCAGCAATATCACGGGTAGCCAACGCTATGTCCTGATAGCGGTCCGC

CACACCCAGCCGGCCACAGTCGATGAATCCtGAAAAGCGGCCATTTTCCACCATGATATT

CGGCAAGCAGGCATCGCCATGGGTCACGACGAGATCCTCGCCGTCGGGCATGCGCGCCTT

GAGCCTGGCGAACAGTTCGGCTGGCGCGAGCCCCTGATGCTCTTCGTCCAGATCATCCTG

ATCGACAAGACCGGCTTCCATCCGAGTACGTGCTCGCTCGATGCGATGTTTCGCTTGGTG

GTCGAATGGGCAGGTAGCCGGATCAAGCGTATGCAGCCGCCGCATTGCATCAGCCATGAT

GGATACTTTCTCGGCAGGAGCAAGGTGAGATGACAGGAGATCCTGCCCCGGCACTTCGCC

CAATAGCAGCCAGTCCCTTCCCGCTTCAGTGACAACGTCGAGCACAGCTGCGCAAGGAAC

GCCCGTCGTGGCCAGCCACGATAGCCGCGCTGCCTCGTCCTGCAGTTCATTCAGGGCACC

GGACAGGTCGGTCTTGACAAAAAGAACCGGGCGCCCCTGCGCTGACAGCCGGAACACGGC

GGCATCAGAGCAGCCGATTGTCTGTTGTGCCCAGTCATAGCCGAATAGCCTCTCCACCCA

AGCGGCCGGAGAACCTGCGTGCAATCCATCTTGTTCAATCATGCGAAACGATCCTCATCC

TGTCTCTTGATCAGATCTTGATCCCCTGCGCCATCAGATCCTTGGCGGCAAGAAAGCCAT

CCAGTTTACTTTGCAGGGCTTCCCAACCTTACCAGAGGGCGCCCCAGCTGGCAATTCCGG

TTCGCTTGCTGTCCATAAAACCGCCCAGTCTAGCTATCGCCATGTAAGCCCACTGCAAGC

TACCTGCTTTCTCTTTGCGCTTGCGTTTTCCCTTGTCCAGATAGCCCAGTAGCTGACATT

CATCCGGGGTCAGCACCGTTTCTGCGGACTGGCTTTCTACGTGTTCCGCTTCCTTTAGCA

GCCCTTGCGCCCTGAGTGCTTGCGGCAGCGTGAGCTTCAAAAGCGCTCTGAAGTTCCTAT

ACTTTCTAGAGAATAGGAACTTCGAACTGCAGGTCGACGGATCCCCGGAATCATGGTTCC

TCAGGAAACGTGTTGCTGTGGGCTGCGACGATATGCCCAGACCATCATGATCACACCCGC

GACAATCATCGGGATGGAAAGAATTTGCCCCATGCTGATGTACTGCACCCAGGCACCGGT

AAACTGCGCGTCGGGCTGGCGGAAAAACTCAACAATGATGCGAAACGCGCCGTAACCAAT

CAGGAACAAACCTGAGACAGCTCCCATTGGGCGTGGTTTACGAATATACAGGTTGAGGAT

AATAAACAGCACCACACCTTCCAGCAGCAGCTCGTAAAGCTGTGATGGGTGGCGCGGCAG

CACACCGTAAGTGTCGAAAATGGATTGCCACTGCGGGTTGGTTTGCAGCAGCAAAATATC

TTCTGTACGGGAGCCAGGGAACAGCATGGCAAACGGGAAGTTCGGGTCAACGCGGCCCCA
```

```
CAATTCACCGTTAATAAAGTTGCCCAGACGCCCGGCACCAAGACCAAACGGAATGAGTGG

TGCGATAAAATCAGAGACCTGGAAGAAGGAACGTTTAGTACGGCGGGCGAAGATAATCAT

CACCACGATAACGCCAATCAGGCCGCCGTGGAAAGACATGCCGCCGTCCCAGACACGGAA

CAGATACAGCGGATCGGCCATAAACTGCGGGAAATTGTAGAACAGAACATAACCAATACG

TCCCCCGAGGAAGACGCCGAGGAAGCCCGCATAGAGTAAGTTTTCAACTTCATTTTTGGT

CCAGCCGCTGCCCGGACGATTCGCCCGTCGTGTTGCCAGCCACATTGCAAAAATGAAACC

CACCAGATACATCAGGCCGTACCAGTGAAGCGCCACGGGTCCTATTGAGAAAATGACCGG

ATCAAACTCCGGAAAATGCAGATAGCTACTGGTCATCTGTCACCACAAGTTCTTGTTATT

TCGCTGAAAGAGAACAGCGATTGAAATGCGCGCCGCAGGTTTCAGGCGCTCCAAAGGTGC

GAATAATAGCACAAGGGGACCTGGCTGGTTGCCGGATACCGTTAAAAGATATGTATA
```

SEQ ID NO: 2
>pG292, complete sequence.
```
TCGCGCGTTTCGGTGATGACGGTGAAAACCTCTGACACATGCAGCTCCCGGAGACGGTCA

CAGCTTGTCTGTAAGCGGATGCCGGGAGCAGACAAGCCCGTCAGGGCGCGTCAGCGGGTG

TTGGCGGGTGTCGGGGCTGGCTTAACTATGCGGCATCAGAGCAGATTGTACTGAGAGTGC

ACCATATATGCGGTGTGAAATACCGCACAGATGCGTAAGGAGAAAATACCGCATCAggcg ccTCCTCAACCTGTATATTCGTAAACCACGCCCAATGGGAGCTGTCTCAGGTTTGTTCCT

GATTGGTTACGGCGCGTTTCGCATCATTGTTGAGTTTTTCCGCCAGCCCGACGCGCAGTT

TACCGGTGCCTGGGTGCAGTACATCAGCATGGGGCAAATTCTTTCCATCCCGATGATTGT

CGCGGGTGTGATCATGATGGTCTGGGCATATCGTCGCAGCCCACAGCAACACGTTTCCTG

AGGAACCATGAAACAGTATTTAGAACTGATGCAAAAAGTGCTCGACGAAGGCACACAGAA

AAACGACCGTACCGGAACCGGAACGCTTTCCATTTTTGGTCATCAGATGCGTTTTAACCT

GCAAGATGGATTCCCGCTGGTGACAACTAAACGTTGCCACCTGCGTTCCATCATCCATGA

ACTGCTGTGGTTTCTGCAGGGCGACACTAACATTGCTTATCTACACGAAAACAATGTCAC

CATCTGGGACGAATGGGCCGATGAAAACGGCGACCTCGGGCAGTGTATGGTAAACAGTG

GCGCGCCTGGCCAACGCCAGATGGTCGTCATATTGACCAGATCACTACGGTACTGAACCA

GCTGAAAAACGACCCGGATTCGCGCCGCATTATTGTTTCAGCGTGGAACGTAGGCGAACT

GGATAAAATGGCGCTGGCACCGTGCCATGCATTCTTCCAGTTCTATGTGGCAGACGGCAA

ACTCTCTTGCCAGCTTTATCAGCGCTCCTGTGACGTCTTCCTCGGCCTGCCGTTCAACAT

TGCCAGCTACGCGTTATTGGTGCATATGATGGCGCAGCAGTGCGATCTGGAAGTGGGTGA

TTTTGTCTGGACCGGTGGCGACACGCATCTGTACAGCAACCATATGGATCAAACTCATCT

GCAATTAAGCCGCGAACCGCGTCCGCTGCCGAAGTTGATTATCAAACGTAAACCCGAATC

CATCTTCGACTACCGTTTCGAAGACTTTGAGATTGAAGGCTACGATCCGCATCCGGGCAT

TAAAGCGCCGGTGGCTATCTAATTACGAAACATCCTGCCAGAGCCGACGCCAGTGTGCGT

CGGTTTTTTTACCCTCCGTTAAATTCTTCGAGACGCCTTCCCGAAggcgccATTCGCCAT

TCAGGCTGCGCAACTGTTGGGAAGGGCGATCGGTGCGGGCCTCTTCGCTATTACGCCAGC

TGGCGAAAGGGGGATGTGCTGCAAGGCGATTAAGTTGGGTAACGCCAGGGTTTTCCCAGT

CACGACGTTGTAAAACGACGGCCAGTGCCAAGCTTACTGCTCACAAGAAAAAAGGCACGT

CATCTGACGTGCCTTTTTTATTTGTACTACCCTGTACGATTACTGCAGGTCGACTCTAGA

TGCATGCTCGAGTCAACGGTTTTTCAGCAATCGGTGCAAAATGCCGAAGTATTGCCTCAA

GGTAAACAGCCGCCGCATCCTGCCGTCTGCCGCAAAATCCAGCCACGCGCCGGCGGGCAG
```

-continued

```
CGTGTCCGTCCGTTTGAAGCATTGGTACAAAAACCGGCGGGCGCGTTCAAAATCTTCTTC

CGGCAAATGTTTCTCCAGCAATTCATACGCTACTGCTTTTATTTGGCGGTATTCAAGGCT

GTCGAACCGGGTTTTAAAACCCATAGACTGCAAAAAATCGTTTCTGGCGGTTTTTTGGAT

GCCTTGCGCGATTTCGTGTTGGCGGATGCTGTATTTGGATGAAACCTGATTGGCGTGAAG

GCGGTATTTGACCAAGGCTTCGGGATAATAAGCCAGCCTGCCCAATTTGCTGACATCGTA

CCAAAATTGGTAATCTTCCGCCCAATCCCGCTCGGTGTTGTAACGCAAACCGCCGTCAAT

GACGCTGCGCCTCATAATCATCGTGTTGTTGTGTATGGGGTTGCCGAAAGGGAAAAAGTC

GGCAATGTCTTCGTGTCGGGTCGGTTTTTTCCAAATTTTGCCGTGTTCGTGGTGCCGCGC

CAGCCGGTTGCCGTCCTTTTCTTCCGACAAAACTTCCAGCCACGCACCCATCGCGATGAT

GCTGCGGTCTTTTTCCATCTCACCCACGATTTTCTCAATCCAGTCGGGGCGGCAATATC

GTCTGCATCGGTGCGCGCAATATATTCCCCCCCCCCCCCCGACTTTGCCAATTCATCCAG

CCCGATGTTTAAAGAGGGAATCAGACCGGAATTGCGCGGCTGCGCGAGGATGCGGATGCG

GCCGTCCTGTTCTTGGAAACGCTGGGCAATGGCAAGCGTACCGTCCGTCGAGCCGTCATC

GACAATCAAAATATCCAAGTTGCGCCAAGTTTGATTCACGACGGCGGCTAATGATTGGGC

GAAATATTTTTCTACGTTGTAGGCGCAAATCAATACGCTGACTAAAGGCTGCAATTTATT

CTCCCGATAGGCACGATGCCGTCTGAAGGCTTCAGACGGCATATGtatatctccttcttg aaTTCTAACAATTGATTGAATGTATGCAAATAAATGCATACACCATAGGTGTGGTTTAAT

TTGATGCCCTTTTTCAGGGCTGGAATGTGTAAGAGCGGGGTTATTTATGCTGTTGTTTTT

TTGTTACTCGGGAAGGGCTTTACCTCTTCCGCATAAACGCTTCCATCAGCGTTTATAGTT

AAAAAAATCTTTCGGAACTGGTTTTGCGCTTACCCCAACCAACAGGGGATTTGCTGCTTT

CCATTGAGCCTGTTTCTCTGCGCGACGTTCGCGGCGGCGTGTTTGTGCATCCATCTGGAT

TCTCCTGTCAGTTAGCTTTGGTGGTGTGTGGCAGTTGTAGTCCTGAACGAAAACCCCCCG

CGATTGGCACATTGGCAGCTAATCCGGAATCGCACTTACGGCCAATGCTTCGTTTCGTAT

CACACACCCCAAAGCCTTCTGCTTTGAATGCTGCCCTTCTTCAGGGCTTAATTTTTAAGA

GCGTCACCTTCATGGTGGTCAGTGCGTCCTGCTGATGTGCTCAGTATCACCGCCAGTGGT

ATTTATGTCAACACCGCCAGAGATAATTTATCACCGCAGATGGTTATCTGTATGTTTTTT

ATATGAATTTATTTTTTGCAGGGGGGCATTGTTTGGTAGGTGAGAGATCAATTCTGCATT

AATGAATCGGCCAACGCGCGGGGAGAGGCGGTTTGCGTATTGGGCGCTCTTCCGCTTCCT

CGCTCACTGACTCGCTGCGCTCGGTCGTTCGGCTGCGGCGAGCGGTATCAGCTCACTCAA

AGGCGGTAATACGGTTATCCACAGAATCAGGGGATAACGCAGGAAAGAACATGTGAGCAA

AAGGCCAGCAAAAGGCCAGGAACCGTAAAAAGGCCGCGTTGCTGGCGTTTTTCCATAGGC

TCCGCCCCCCTGACGAGCATCACAAAAATCGACGCTCAAGTCAGAGGTGGCGAAACCCGA

CAGGACTATAAAGATACCAGGCGTTTCCCCCTGGAAGCTCCCTCGTGCGCTCTCCTGTTC

CGACCCTGCCGCTTACCGGATACCTGTCCGCCTTTCTCCCTTCGGGAAGCGTGGCGCTTT

CTCATAGCTCACGCTGTAGGTATCTCAGTTCGGTGTAGGTCGTTCGCTCCAAGCTGGGCT

GTGTGCACGAACCCCCCGTTCAGCCCGACCGCTGCGCCTTATCCGGTAACTATCGTCTTG

AGTCCAACCCGGTAAGACACGACTTATCGCCACTGGCAGCAGCCACTGGTAACAGGATTA

GCAGAGCGAGGTATGTAGGCGGTGCTACAGAGTTCTTGAAGTGGTGGCCTAACTACGGCT

ACACTAGAAGGACAGTATTTGGTATCTGCGCTCTGCTGAAGCCAGTTACCTTCGGAAAAA

GAGTTGGTAGCTCTTGATCCGGCAAACAAACCACCGCTGGTAGCGGTGGTTTTTTTGTTT

GCAAGCAGCAGATTACGCGCAGAAAAAAAGGATCTCAAGAAGATCCTTTGATCTTTTCTA
```

-continued

```
CGGGGTCTGACGCTCAGTGGAACGAAAACTCACGTTAAGGGATTTTGGTCATGAGATTAT

CAAAAAGGATCTTCACCTAGATCCTTTTAAATTAAAAATGAAGTTTTAAATCAATCTAAA

GTATATATGAGTAAACTTGGTCTGACAGTTACCAATGCTTAATCAGTGAGGCACCTATCT

CAGCGATCTGTCTATTTCGTTCATCCATAGTTGCCTGACTCCCCGTCGTGTAGATAACTA

CGATACGGGAGGGCTTACCATCTGGCCCCAGTGCTGCAATGATACCGCGAGACCCACGCT

CACCGGCTCCAGATTTATCAGCAATAAACCAGCCAGCCGGAAGGGCCGAGCGCAGAAGTG

GTCCTGCAACTTTATCCGCCTCCATCCAGTCTATTAATTGTTGCCGGGAAGCTAGAGTAA

GTAGTTCGCCAGTTAATAGTTTGCGCAACGTTGTTGCCATTGCTACAGGCATCGTGGTGT

CACGCTCGTCGTTTGGTATGGCTTCATTCAGCTCCGGTTCCCAACGATCAAGGCGAGTTA

CATGATCCCCCATGTTGTGCAAAAAAGCGGTTAGCTCCTTCGGTCCTCCGATCGTTGTCA

GAAGTAAGTTGGCCGCAGTGTTATCACTCATGGTTATGGCAGCACTGCATAATTCTCTTA

CTGTCATGCCATCCGTAAGATGCTTTTCTGTGACTGGTGAGTACTCAACCAAGTCATTCT

GAGAATAGTGTATGCGGCGACCGAGTTGCTCTTGCCCGGCGTCAATACGGGATAATACCG

CGCCACATAGCAGAACTTTAAAAGTGCTCATCATTGGAAAACGTTCTTCGGGGCGAAAAC

TCTCAAGGATCTTACCGCTGTTGAGATCCAGTTCGATGTAACCCACTCGTGCACCCAACT

GATCTTCAGCATCTTTTACTTTCACCAGCGTTTCTGGGTGAGCAAAAACAGGAAGGCAAA

ATGCCGCAAAAAAGGGAATAAGGGCGACACGGAAATGTTGAATACTCATACTCTTCCTTT

TTCAATATTATTGAAGCATTTATCAGGGTTATTGTCTCATGAGCGGATACATATTTGAAT

GTATTTAGAAAAATAAACAAATAGGGGTTCCGCGCACATTTCCCCGAAAAGTGCCACCTG

ACGTCTAAGAAACCATTATTATCATGACATTAACCTATAAAAATAGGCGTATCACGAGGC

CCTTTCGTC
```

```
                                             SEQ ID NO: 3
>pG221, complete sequence.
TCGCGCGTTTCGGTGATGACGGTGAAAACCTCTGACACATGCAGCTCCCGGAGACGGTCA

CAGCTTGTCTGTAAGCGGATGCCGGGAGCAGACAAGCCCGTCAGGGCGCGTCAGCGGGTG

TTGGCGGGTGTCGGGGCTGGCTTAACTATGCGGCATCAGAGCAGATTGTACTGAGAGTGC

ACCATATATGCGGTGTGAAATACCGCACAGATGCGTAAGGAGAAAATACCGCATCAggcg ccTCCTCAACCTGTATATTCGTAAACCACGCCCAATGGGAGCTGTCTCAGGTTTGTTCCT

GATTGGTTACGGCGCGTTTCGCATCATTGTTGAGTTTTTCCGCCAGCCCGACGCGCAGTT

TACCGGTGCCTGGGTGCAGTACATCAGCATGGGGCAAATTCTTTCCATCCCGATGATTGT

CGCGGGTGTGATCATGATGGTCTGGGCATATCGTCGCAGCCCACAGCAACACGTTTCCTG

AGGAACCATGAAACAGTATTTAGAACTGATGCAAAAAGTGCTCGACGAAGGCACACAGAA

AAACGACCGTACCGGAACCGGAACGCTTTCCATTTTTGGTCATCAGATGCGTTTTAACCT

GCAAGATGGATTCCCGCTGGTGACAACTAAACGTTGCCACCTGCGTTCCATCATCCATGA

ACTGCTGTGGTTTCTGCAGGGCGACACTAACATTGCTTATCTACACGAAAACAATGTCAC

CATCTGGGACGAATGGGCCGATGAAAACGGCGACCTCGGGCCAGTGTATGGTAAACAGTG

GCGCGCCTGGCCAACGCCAGATGGTCGTCATATTGACCAGATCACTACGGTACTGAACCA

GCTGAAAAACGACCCGGATTCGCGCCGCATTATTGTTTCAGCGTGGAACGTAGGCGAACT

GGATAAAATGGCGCTGGCACCGTGCCATGCATTCTTCCAGTTCTATGTGGCAGACGGCAA

ACTCTCTTGCCAGCTTTATCAGCGCTCCTGTGACGTCTTCCTCGGCCTGCCGTTCAACAT

TGCCAGCTACGCGTTATTGGTGCATATGATGGCGCAGCAGTGCGATCTGGAAGTGGGTGA
```

-continued

```
TTTTGTCTGGACCGGTGGCGACACGCATCTGTACAGCAACCATATGGATCAAACTCATCT

GCAATTAAGCCGCGAACCGCGTCCGCTGCCGAAGTTGATTATCAAACGTAAACCCGAATC

CATCTTCGACTACCGTTTCGAAGACTTTGAGATTGAAGGCTACGATCCGCATCCGGGCAT

TAAAGCGCCGGTGGCTATCTAATTACGAAACATCCTGCCAGAGCCGACGCCAGTGTGCGT

CGGTTTTTTTACCCTCCGTTAAATTCTTCGAGACGCCTTCCCGAAggcgccATTCGCCAT

TCAGGCTGCGCAACTGTTGGGAAGGGCGATCGGTGCGGGCCTCTTCGCTATTACGCCAGC

TGGCGAAAGGGGATGTGCTGCAAGGCGATTAAGTTGGGTAACGCCAGGGTTTTCCCAGT

CACGACGTTGTAAAACGACGGCCAGTGCCAAGCTTACTGCTCACAAGAAAAAAGGCACGT

CATCTGACGTGCCTTTTTATTTGTACTACCCTGTACGATTACTGCAGGTCGACTCTAGA

TGCATGCTCGAGTTATTATTTAATATATTTACAATAGATGAAGGACGCAATCGTACGGAT

ACCGCCGAACAGGTAGTTAATGTTACCGGTCAGGAAGAAGCACTTCATTTTGATAACCAG

GTCGTTAACCATCACCATGTACAGGTTTTTTTTTGCGGTAGACTGACCTTCGTGCAGGCG

GTAGTAGAACAGGTATTCCGGCAGGTTTTGGAACTTGATTTTTGCCAGGCTCAGACGGTT

CCACAGCTCGTAATCTTCGGAGTAGTTAGAAAACATATAACCACCGATGCTCGCGATGAC

TTTTTTACGAAACATTACGCTCGGGTGAACAATACAACACTTATACGGCAGGTTTTTAAC

GATGTCCAGGTTCTCTTCCGGCAGTTTGGTCTTGTTGATTTCACGACCTTTGTCGTCAAT

AAAGATTGCGTTGGTACCCACAACATCTACGTACGGATTGTTCTTCAGGAAGTCAACCTG

TTTAGTAAAACGGTCCGGGTGAGAGATGTCGTCAGAGTCCATACGGGCAATAAATTCGCC

GTTGCTCAGGTCGATCGCTTTGTTCAGGGAGTACGGCAGGTAAGCGATGTTAGTGCGGAT

CAGTTTGATTTTGTCGTTAACTTTGTGTTTCAGTTCGTTATAGAAGTCGTCAGTGCAGCA

GTTCGCAACGATGATGATTTCGAAGCTGCTGAAGGTCTGAGACAGGATGCTGTTGATCGC

TTCGTCCAGAAAAGGGTTTTTCTTGTTAACAGGCAGGATAACGCTCACAACCGGGTGGGT

AGATTCCGCGGATTCCGCTTCATCGATGATCATATGTATATCTCCTTCTTCTCGAGTCAA

CGGTTTTTCAGCAATCGGTGCAAAATGCCGAAGTATTGCCTCAAGGTAAACAGCCGCCGC

ATCCTGCCGTCTGCCGCAAAATCCAGCCACGCGCCGGCGGGCAGCGTGTCCGTCCGTTTG

AAGCATTGGTACAAAAACCGGCGGGCGCGTTCAAAATCTTCTTCCGGCAAATGTTTCTCC

AGCAATTCATACGCTACTGCTTTTATTTGGCGGTATTCAAGGCTGTCGAACCGGGTTTTA

AAACCCATAGACTGCAAAAAATCGTTTCTGGCGGTTTTTTGGATGCCTTGCGCGATTTCG

TGTTGGCGGATGCTGTATTTGGATGAAACCTGATTGGCGTGAAGGCGGTATTTGACCAAG

GCTTCGGGATAATAAGCCAGCCTGCCCAATTTGCTGACATCGTACCAAAATTGGTAATCT

TCCGCCCAATCCCGCTCGGTGTTGTAACGCAAACCGCCGTCAATGACGCTGCGCCTCATA

ATCATCGTGTTGTTGTGTATGGGGTTGCCGAAAGGGAAAAAGTCGGCAATGTCTTCGTGT

CGGGTCGGTTTTTTCCAAATTTTGCCGTGTTCGTGGTGCCGCGCCAGCCGGTTGCCGTCC

TTTTCTTCCGACAAAACTTCCAGCCACGCACCCATCGCGATGATGCTGCGGTCTTTTTCC

ATCTCACCCACGATTTTCTCAATCCAGTCGGGGCGGCAATATCGTCTGCATCGGTGCGC

GCAATATATTCCCCCCCCCCCCCCGACTTTGCCAATTCATCCAGCCCGATGTTTAAAGAG

GGAATCAGACCGGAATTGCGCGGCTGCGCGAGGATGCGGATGCGGCCGTCCTGTTCTTGG

AAACGCTGGGCAATGGCAAGCGTACCGTCCGTCGAGCCGTCATCGACAATCAAAATATCC

AAGTTGCGCCAAGTTTGATTCACGACGGCGGCTAATGATTGGGCGAAATATTTTTCTACG

TTGTAGGCGCAAATCAATACGCTGACTAAAGGCTGCAATTTATTCTCCCGATAGGCACGA

TGCCGTCTGAAGGCTTCAGACGGCATATGtatatctccttcttgaaTTCTAACAATTGAT
```

```
TGAATGTATGCAAATAAATGCATACACCATAGGTGTGGTTTAATTTGATGCCCTTTTTCA

GGGCTGGAATGTGTAAGAGCGGGGTTATTTATGCTGTTGTTTTTTGTTACTCGGGAAGG

GCTTTACCTCTTCCGCATAAACGCTTCCATCAGCGTTTATAGTTAAAAAAATCTTTCGGA

ACTGGTTTTGCGCTTACCCCAACCAACAGGGGATTTGCTGCTTTCCATTGAGCCTGTTTC

TCTGCGCGACGTTCGCGGCGGCGTGTTTGTGCATCCATCTGGATTCTCCTGTCAGTTAGC

TTTGGTGGTGTGTGGCAGTTGTAGTCCTGAACGAAAACCCCCCGCGATTGGCACATTGGC

AGCTAATCCGGAATCGCACTTACGGCCAATGCTTCGTTTCGTATCACACACCCCAAAGCC

TTCTGCTTTGAATGCTGCCCTTCTTCAGGGCTTAATTTTTAAGAGCGTCACCTTCATGGT

GGTCAGTGCGTCCTGCTGATGTGCTCAGTATCACCGCCAGTGGTATTTATGTCAACACCG

CCAGAGATAATTTATCACCGCAGATGGTTATCTGTATGTTTTTTATATGAATTTATTTTT

TGCAGGGGGCATTGTTTGGTAGGTGAGAGATCAATTCTGCATTAATGAATCGGCCAACG

CGCGGGGAGAGGCGGTTTGCGTATTGGGCGCTCTTCCGCTTCCTCGCTCACTGACTCGCT

GCGCTCGGTCGTTCGGCTGCGGCGAGCGGTATCAGCTCACTCAAAGGCGGTAATACGGTT

ATCCACAGAATCAGGGGATAACGCAGGAAAGAACATGTGAGCAAAAGGCCAGCAAAAGGC

CAGGAACCGTAAAAAGGCCGCGTTGCTGGCGTTTTTCCATAGGCTCCGCCCCCCTGACGA

GCATCACAAAAATCGACGCTCAAGTCAGAGGTGGCGAAACCCGACAGGACTATAAAGATA

CCAGGCGTTTCCCCCTGGAAGCTCCCTCGTGCGCTCTCCTGTTCCGACCCTGCCGCTTAC

CGGATACCTGTCCGCCTTTCTCCCTTCGGGAAGCGTGGCGCTTTCTCATAGCTCACGCTG

TAGGTATCTCAGTTCGGTGTAGGTCGTTCGCTCCAAGCTGGGCTGTGTGCACGAACCCCC

CGTTCAGCCCGACCGCTGCGCCTTATCCGGTAACTATCGTCTTGAGTCCAACCCGGTAAG

ACACGACTTATCGCCACTGGCAGCAGCCACTGGTAACAGGATTAGCAGAGCGAGGTATGT

AGGCGGTGCTACAGAGTTCTTGAAGTGGTGGCCTAACTACGGCTACACTAGAAGGACAGT

ATTTGGTATCTGCGCTCTGCTGAAGCCAGTTACCTTCGGAAAAAGAGTTGGTAGCTCTTG

ATCCGGCAAACAAACCACCGCTGGTAGCGGTGGTTTTTTTGTTTGCAAGCAGCAGATTAC

GCGCAGAAAAAAAGGATCTCAAGAAGATCCTTTGATCTTTTCTACGGGGTCTGACGCTCA

GTGGAACGAAAACTCACGTTAAGGGATTTTGGTCATGAGATTATCAAAAAGGATCTTCAC

CTAGATCCTTTTAAATTAAAAATGAAGTTTTAAATCAATCTAAAGTATATATGAGTAAAC

TTGGTCTGACAGTTACCAATGCTTAATCAGTGAGGCACCTATCTCAGCGATCTGTCTATT

TCGTTCATCCATAGTTGCCTGACTCCCCGTCGTGTAGATAACTACGATACGGGAGGGCTT

ACCATCTGGCCCCAGTGCTGCAATGATACCGCGAGACCCACGCTCACCGGCTCCAGATTT

ATCAGCAATAAACCAGCCAGCCGGAAGGGCCGAGCGCAGAAGTGGTCCTGCAACTTTATC

CGCCTCCATCCAGTCTATTAATTGTTGCCGGGAAGCTAGAGTAAGTAGTTCGCCAGTTAA

TAGTTTGCGCAACGTTGTTGCCATTGCTACAGGCATCGTGGTGTCACGCTCGTCGTTTGG

TATGGCTTCATTCAGCTCCGGTTCCCAACGATCAAGGCGAGTTACATGATCCCCCATGTT

GTGCAAAAAAGCGGTTAGCTCCTTCGGTCCTCCGATCGTTGTCAGAAGTAAGTTGGCCGC

AGTGTTATCACTCATGGTTATGGCAGCACTGCATAATTCTCTTACTGTCATGCCATCCGT

AAGATGCTTTTCTGTGACTGGTGAGTACTCAACCAAGTCATTCTGAGAATAGTGTATGCG

GCGACCGAGTTGCTCTTGCCCGGCGTCAATACGGGATAATACCGCGCCACATAGCAGAAC

TTTAAAAGTGCTCATCATTGGAAAACGTTCTTCGGGGCGAAAACTCTCAAGGATCTTACC

GCTGTTGAGATCCAGTTCGATGTAACCCACTCGTGCACCCAACTGATCTTCAGCATCTTT
```

-continued

```
TACTTTCACCAGCGTTTCTGGGTGAGCAAAAACAGGAAGGCAAAATGCCGCAAAAAGGG
AATAAGGGCGACACGGAAATGTTGAATACTCATACTCTTCCTTTTTCAATATTATTGAAG
CATTTATCAGGGTTATTGTCTCATGAGCGGATACATATTTGAATGTATTTAGAAAAATAA
ACAAATAGGGGTTCCGCGCACATTTCCCCGAAAAGTGCCACCTGACGTCTAAGAAACCAT
TATTATCATGACATTAACCTATAAAAATAGGCGTATCACGAGGCCCTTTCGTC
```

SEQ ID NO: 4
>pG222, complete sequence.
```
TCGCGCGTTTCGGTGATGACGGTGAAAACCTCTGACACATGCAGCTCCCGGAGACGGTCA
CAGCTTGTCTGTAAGCGGATGCCGGGAGCAGACAAGCCCGTCAGGGCGCGTCAGCGGGTG
TTGGCGGGTGTCGGGGCTGGCTTAACTATGCGGCATCAGAGCAGATTGTACTGAGAGTGC
ACCATATATGCGGTGTGAAATACCGCACAGATGCGTAAGGAGAAAATACCGCATCAggcg
ccTCCTCAACCTGTATATTCGTAAACCACGCCCAATGGGAGCTGTCTCAGGTTTGTTCCT
GATTGGTTACGGCGCGTTTCGCATCATTGTTGAGTTTTTCCGCCAGCCCGACGCGCAGTT
TACCGGTGCCTGGGTGCAGTACATCAGCATGGGGCAAATTCTTTCCATCCCGATGATTGT
CGCGGGTGTGATCATGATGGTCTGGGCATATCGTCGCAGCCCACAGCAACACGTTTCCTG
AGGAACCATGAAACAGTATTTAGAACTGATGCAAAAAGTGCTCGACGAAGGCACACAGAA
AAACGACCGTACCGGAACCGGAACGCTTTCCATTTTTGGTCATCAGATGCGTTTTAACCT
GCAAGATGGATTCCCGCTGGTGACAACTAAACGTTGCCACCTGCGTTCCATCATCCATGA
ACTGCTGTGGTTTCTGCAGGGCGACACTAACATTGCTTATCTACACGAAAACAATGTCAC
CATCTGGGACGAATGGGCCGATGAAAACGGCGACCTCGGGCCAGTGTATGGTAAACAGTG
GCGCGCCTGGCCAACGCCAGATGGTCGTCATATTGACCAGATCACTACGGTACTGAACCA
GCTGAAAAACGACCCGGATTCGCGCCGCATTATTGTTTCAGCGTGGAACGTAGGCGAACT
GGATAAAATGGCGCTGGCACCGTGCCATGCATTCTTCCAGTTCTATGTGGCAGACGGCAA
ACTCTCTTGCCAGCTTTATCAGCGCTCCTGTGACGTCTTCCTCGGCCTGCCGTTCAACAT
TGCCAGCTACGCGTTATTGGTGCATATGATGGCGCAGCAGTGCGATCTGGAAGTGGGTGA
TTTTGTCTGGACCGGTGGCGACACGCATCTGTACAGCAACCATATGGATCAAACTCATCT
GCAATTAAGCCGCGAACCGCGTCCGCTGCCGAAGTTGATTATCAAACGTAAACCCGAATC
CATCTTCGACTACCGTTTCGAAGACTTTGAGATTGAAGGCTACGATCCGCATCCGGGCAT
TAAAGCGCCGGTGGCTATCTAATTACGAAACATCCTGCCAGAGCCGACGCCAGTGTGCGT
CGGTTTTTTTACCCTCCGTTAAATTCTTCGAGACGCCTTCCCGAAggcgccATTCGCCAT
TCAGGCTGCGCAACTGTTGGGAAGGGCGATCGGTGCGGGCCTCTTCGCTATTACGCCAGC
TGGCGAAAGGGGGATGTGCTGCAAGGCGATTAAGTTGGGTAACGCCAGGGTTTTCCCAGT
CACGACGTTGTAAAACGACGGCCAGTGCCAAGCTTACTGCTCACAAGAAAAAAGGCACGT
CATCTGACGTGCCTTTTTATTTGTACTACCCTGTACGATTACTGCAGGTCGACTCTAGA
TGCATGctcgagTTATACAAACTGCCAATATTTCAAATATTTAAAATGGAGTTCTCTCAT
TAAGGCGATTTTAGGGCTATAAGGTTCTTCTTTTCGTGCTATCGTAGAGATTTGCTCATC
ATCAGCGATCACAAAAGGTTGTAACACCAGATTTTTCACGCCATGGATAAAAGTAGCGTC
CATTATCGTATCCACAGGAACAACCCATTTTCGGCTGCATTTCAAAAAAACTTTGGCAAT
CTTAGGCGTGATCACATAGCCTTGAGTCCCCACCCCTTCGCTATAAGCTTTAATGATCCC
CACACGCTCTTGTATCTCGTGGTTTTTATGGCTCAATGGCTCACTTTTTACACTGGCATC
ATACAATAAATGCATCAAGCGGATATAGCCTAACTCTTGGATGTGTTTTTCTAAAAAATC
CAAGCCCTCTTTAAAATCCTCTTTCAAGGTTATATCGTCTTCTAAAATACAGATCGCTTC
```

-continued

```
ATTGAGTTCTATGCATTTTTCCCACAAGGAATAATGACTCGCATAGCACCCAAGCTCCCC
CAAGCTCATAAACTTCGCATGGTATTTTAAAGCGTAATAAAACTTAGAAACCTCACTGAT
GAGATTGGTTGTAATCCCCATGTCTTTGATGTTTTGCGTGATGAAATAAGGGTGTAAATG
CTTTTTCACTAAGGGGTGCAACCCGCCTTCAAAAGTTTTAGAATAAATCGCATCAAAAAT
TTGCGCTTGGTGGTGGGTGGCATTGATGCTATTGAGTAAAGTTGTGGTGTCTCTAAAAAC
TAAACCAAATGTATCGCACACTTTTTGATTTAAAGAAATGGCAAAAACACGCAtATGtat
atctccttcttCTCGAGTCAACGGTTTTTCAGCAATCGGTGCAAAATGCCGAAGTATTGC
CTCAAGGTAAACAGCCGCCGCATCCTGCCGTCTGCCGCAAAATCCAGCCACGCGCCGGCG
GGCAGCGTGTCCGTCCGTTTGAAGCATTGGTACAAAAACCGGCGGGCGCGTTCAAAATCT
TCTTCCGGCAAATGTTTCTCCAGCAATTCATACGCTACTGCTTTTATTTGGCGGTATTCA
AGGCTGTCGAACCGGGTTTTAAAACCCATAGACTGCAAAAAATCGTTTCTGGCGGTTTTT
TGGATGCCTTGCGCGATTTCGTGTTGGCGGATGCTGTATTTGGATGAAACCTGATTGGCG
TGAAGGCGGTATTTGACCAAGGCTTCGGGATAATAAGCCAGCCTGCCCAATTTGCTGACA
TCGTACCAAAATTGGTAATCTTCCGCCCAATCCCGCTCGGTGTTGTAACGCAAACCGCCG
TCAATGACGCTGCGCCTCATAATCATCGTGTTGTTGTGTATGGGGTTGCCGAAAGGGAAA
AAGTCGGCAATGTCTTCGTGTCGGGTCGGTTTTTTCCAAATTTTGCCGTGTTCGTGGTGC
CGCGCCAGCCGGTTGCCGTCCTTTTCTTCCGACAAAACTTCCAGCCACGCACCCATCGCG
ATGATGCTGCGGTCTTTTTCCATCTCACCCACGATTTTCTCAATCCAGTCGGGGCGGCA
ATATCGTCTGCATCGGTGCGCGCAATATATTCCCCCCCCCCCCCCGACTTTGCCAATTCA
TCCAGCCCGATGTTTAAAGAGGGAATCAGACCGGAATTGCGCGGCTGCGCGAGGATGCGG
ATGCGGCCGTCCTGTTCTTGGAAACGCTGGGCAATGGCAAGCGTACCGTCCGTCGAGCCG
TCATCGACAATCAAAATATCCAAGTTGCGCCAAGTTTGATTCACGACGGCGGCTAATGAT
TGGGCGAAATATTTTTCTACGTTGTAGGCGCAAATCAATACGCTGACTAAAGGCTGCAAT
TTATTCTCCCGATAGGCACGATGCCGTCTGAAGGCTTCAGACGGCATATGtatatctcct
tcttgaaTTCTAACAATTGATTGAATGTATGCAAATAAATGCATACACCATAGGTGTGGT
TTAATTTGATGCCCTTTTTCAGGGCTGGAATGTGTAAGAGCGGGGTTATTTATGCTGTTG
TTTTTTTGTTACTCGGGAAGGGCTTTACCTCTTCCGCATAAACGCTTCCATCAGCGTTTA
TAGTTAAAAAAATCTTTCGGAACTGGTTTTGCGCTTACCCCAACCAACAGGGGATTTGCT
GCTTTCCATTGAGCCTGTTTCTCTGCGCGACGTTCGCGGCGGCGTGTTTGTGCATCCATC
TGGATTCTCCTGTCAGTTAGCTTTGGTGGTGTGTGGCAGTTGTAGTCCTGAACGAAAACC
CCCCGCGATTGGCACATTGGCAGCTAATCCGGAATCGCACTTACGGCCAATGCTTCGTTT
CGTATCACACACCCCAAAGCCTTCTGCTTTGAATGCTGCCCTTCTTCAGGGCTTAATTTT
TAAGAGCGTCACCTTCATGGTGGTCAGTGCGTCCTGCTGATGTGCTCAGTATCACCGCCA
GTGGTATTTATGTCAACACCGCCAGAGATAATTTATCACCGCAGATGGTTATCTGTATGT
TTTTTATATGAATTTATTTTTTGCAGGGGGGCATTGTTTGGTAGGTGAGAGATCAATTCT
GCATTAATGAATCGGCCAACGCGCGGGGAGAGGCGGTTTGCGTATTGGGCGCTCTTCCGC
TTCCTCGCTCACTGACTCGCTGCGCTCGGTCGTTCGGCTGCGGCGAGCGGTATCAGCTCA
CTCAAAGGCGGTAATACGGTTATCCACAGAATCAGGGGATAACGCAGGAAAGAACATGTG
AGCAAAAGGCCAGCAAAAGGCCAGGAACCGTAAAAAGGCCGCGTTGCTGGCGTTTTTCCA
TAGGCTCCGCCCCCCTGACGAGCATCACAAAAATCGACGCTCAAGTCAGAGGTGGCGAAA
```

-continued

```
CCCGACAGGACTATAAAGATACCAGGCGTTTCCCCCTGGAAGCTCCCTCGTGCGCTCTCC

TGTTCCGACCCTGCCGCTTACCGGATACCTGTCCGCCTTTCTCCCTTCGGGAAGCGTGGC

GCTTTCTCATAGCTCACGCTGTAGGTATCTCAGTTCGGTGTAGGTCGTTCGCTCCAAGCT

GGGCTGTGTGCACGAACCCCCCGTTCAGCCCGACCGCTGCGCCTTATCCGGTAACTATCG

TCTTGAGTCCAACCCGGTAAGACACGACTTATCGCCACTGGCAGCAGCCACTGGTAACAG

GATTAGCAGAGCGAGGTATGTAGGCGGTGCTACAGAGTTCTTGAAGTGGTGGCCTAACTA

CGGCTACACTAGAAGGACAGTATTTGGTATCTGCGCTCTGCTGAAGCCAGTTACCTTCGG

AAAAAGAGTTGGTAGCTCTTGATCCGGCAAACAAACCACCGCTGGTAGCGGTGGTTTTTT

TGTTTGCAAGCAGCAGATTACGCGCAGAAAAAAAGGATCTCAAGAAGATCCTTTGATCTT

TTCTACGGGGTCTGACGCTCAGTGGAACGAAAACTCACGTTAAGGGATTTTGGTCATGAG

ATTATCAAAAAGGATCTTCACCTAGATCCTTTTAAATTAAAAATGAAGTTTTAAATCAAT

CTAAAGTATATATGAGTAAACTTGGTCTGACAGTTACCAATGCTTAATCAGTGAGGCACC

TATCTCAGCGATCTGTCTATTTCGTTCATCCATAGTTGCCTGACTCCCCGTCGTGTAGAT

AACTACGATACGGGAGGGCTTACCATCTGGCCCCAGTGCTGCAATGATACCGCGAGACCC

ACGCTCACCGGCTCCAGATTTATCAGCAATAAACCAGCCAGCCGGAAGGGCCGAGCGCAG

AAGTGGTCCTGCAACTTTATCCGCCTCCATCCAGTCTATTAATTGTTGCCGGGAAGCTAG

AGTAAGTAGTTCGCCAGTTAATAGTTTGCGCAACGTTGTTGCCATTGCTACAGGCATCGT

GGTGTCACGCTCGTCGTTTGGTATGGCTTCATTCAGCTCCGGTTCCCAACGATCAAGGCG

AGTTACATGATCCCCCATGTTGTGCAAAAAAGCGGTTAGCTCCTTCGGTCCTCCGATCGT

TGTCAGAAGTAAGTTGGCCGCAGTGTTATCACTCATGGTTATGGCAGCACTGCATAATTC

TCTTACTGTCATGCCATCCGTAAGATGCTTTTCTGTGACTGGTGAGTACTCAACCAAGTC

ATTCTGAGAATAGTGTATGCGGCGACCGAGTTGCTCTTGCCCGGCGTCAATACGGGATAA

TACCGCGCCACATAGCAGAACTTTAAAAGTGCTCATCATTGGAAAACGTTCTTCGGGGCG

AAAACTCTCAAGGATCTTACCGCTGTTGAGATCCAGTTCGATGTAACCCACTCGTGCACC

CAACTGATCTTCAGCATCTTTTACTTTCACCAGCGTTTCTGGGTGAGCAAAAACAGGAAG

GCAAAATGCCGCAAAAAAGGGAATAAGGGCGACACGGAAATGTTGAATACTCATACTCTT

CCTTTTTCAATATTATTGAAGCATTTATCAGGGTTATTGTCTCATGAGCGGATACATATT

TGAATGTATTTAGAAAAATAAACAAATAGGGGTTCCGCGCACATTTCCCCGAAAAGTGCC

ACCTGACGTCTAAGAAACCATTATTATCATGACATTAACCTATAAAAATAGGCGTATCAC

GAGGCCCTTTCGTC

SEQ ID NO: 5
>pG317, complete sequence.
GTACCCAGCTTTTGTTCCCTTTAGTGAGGGTTAATTGCGCGCTTGGCGTAATCATGGTCA

TAGCTGTTTCCTGTGTGAAATTGTTATCCGCTCACAATTCCACACAACATACGAGCCGGA

AGCATAAAGTGTAAAGCCTGGGGTGCCTAATGAGTGAGCTAACTCACATTAATTGCGTTG

CGCTCACTGCCCGCTTTCCAGTCGGGAAACCTGTCGTGCCAGCTGCATTAATGAATCGGC

CAACGCGCGGGGAGAGGCGGTTTGCGTATTGGGCGCATGCATAAAAACTGTTGTAATTCA

TTAAGCATTCTGCCGACATGGAAGCCATCACAAACGGCATGATGAACCTGAATCGCCAGC

GGCATCAGCACCTTGTCGCCTTGCGTATAATATTTGCCCATGGTGAAAACGGGGGCGAAG

AAGTTGTCCATATTGGCCACGTTTAAATCAAAACTGGTGAAACTCACCCAGGGATTGGCT

GAGACGAAAAACATATTCTCAATAAACCCTTTAGGGAAATAGGCCAGGTTTTCACCGTAA

CACGCCACATCTTGCGAATATATGTGTAGAAACTGCCGGAAATCGTCGTGGTATTCACTC
```

```
CAGAGCGATGAAAACGTTTCAGTTTGCTCATGGAAAACGGTGTAACAAGGGTGAACACTA

TCCCATATCACCAGCTCACCGTCTTTCATTGCCATACGGAATTCCGGATGAGCATTCATC

AGGCGGGCAAGAATGTGAATAAAGGCCGGATAAAACTTGTGCTTATTTTTCTTTACGGTC

TTTAAAAAGGCCGTAATATCCAGCTGAACGGTCTGGTTATAGGTACATTGAGCAACTGAC

TGAAATGCCTCAAAATGTTCTTTACGATGCCATTGGGATATATCAACGGTGGTATATCCA

GTGATTTTTTTCTCCATTTTAGCTTCCTTAGCTCCTGAAAATCTCGATAACTCAAAAAAT

ACGCCCGGTAGTGATCTTATTTCATTATGGTGAAAGTTGGAACCTCTTACGTGCCGATCA

ACGTCTCATTTTCGCCAAAAGTTGGCCCAGGGCTTCCCGGTATCAACAGGGACACCAGGA

TTTATTTATTCTGCGAAGTGATCTTCCGTCACAGGTATTTATTCGAAGACGAAAGGGCCT

CGTGATACGCCTATTTTTATAGGTTAATGTCATGATAATAATGGTTTCTTAGACGTCAGG

TGGCACTTTTCGGGGAAATGTGCGCGCCCGCGTTCCTGCTGGCGCTGGGCCTGTTTCTGG

CGCTGGACTTCCCGCTGTTCCGTCAGCAGCTTTTCGCCCACGGCCTTGATGATCGCGGCG

GCCTTGGCCTGCATATCCCGATTCAACGGCCCCAGGGCGTCCAGAACGGGCTTCAGGCGC

TCCCGAAGGTCTCGGGCCGTCTCTTGGGCTTGATCGGCCTTCTTGCGCATCTCACGCGCT

CCTGCGGCGGCCTGTAGGGCAGGCTCATACCCCTGCCGAACCGCTTTTGTCAGCCGGTCG

GCCACGGCTTCCGGCGTCTCAACGCGCTTTGAGATTCCCAGCTTTTCGGCCAATCCCTGC

GGTGCATAGGCGCGTGGCTCGACCGCTTGCGGGCTGATGGTGACGTGGCCCACTGGTGGC

CGCTCCAGGGCCTCGTAGAACGCCTGAATGCGCGTGTGACGTGCCTTGCTGCCCTCGATG

CCCCGTTGCAGCCCTAGATCGGCCACAGCGGCCGCAAACGTGGTCTGGTCGCGGGTCATC

TGCGCTTTGTTGCCGATGAACTCCTTGGCCGACAGCCTGCCGTCCTGCGTCAGCGGCACC

ACGAACGCGGTCATGTGCGGGCTGGTTTCGTCACGGTGGATGCTGGCCGTCACGATGCGA

TCCGCCCCGTACTTGTCCGCCAGCCACTTGTGCGCCTTCTCGAAGAACGCCGCCTGCTGT

TCTTGGCTGGCCGACTTCCACCATTCCGGGCTGGCCGTCATGACGTACTCGACCGCCAAC

ACAGCGTCCTTGCGCCGCTTCTCTGGCAGCAACTCGCGCAGTCGGCCCATCGCTTCATCG

GTGCTGCTGGCCGCCCAGTGCTCGTTCTCTGGCGTCCTGCTGGCGTCAGCGTTGGGCGTC

TCGCGCTCGCGGTAGGCGTGCTTGAGACTGGCCGCCACGTTGCCCATTTTCGCCAGCTTC

TTGCATCGCATGATCGCGTATGCCGCCATGCCTGCCCCTCCCTTTTGGTGTCCAACCGGC

TCGACGGGGCAGCGCAAGGCGGTGCCTCCGGCGGGCCACTCAATGCTTGAGTATACTCA

CTAGACTTTGCTTCGCAAAGTCGTGACCGCCTACGGCGGCTGCGGCGCCCTACGGGCTTG

CTCTCCGGGCTTCGCCCTGCGCGGTCGCTGCGCTCCCTTGCCAGCCCGTGGATATGTGGA

CGATGGCCGCGAGCGGCCACCGGCTGGCTCGCTTCGCTCGGCCCGTGGACAACCCTGCTG

GACAAGCTGATGGACAGGCTGCGCCTGCCCACGAGCTTGACCACAGGGATTGCCCACCGG

CTACCCAGCCTTCGACCACATACCCACCGGCTCCAACTGCGCGGCCTGCGGCCTTGCCCC

ATCAATTTTTTTAATTTTCTCTGGGGAAAAGCCTCCGGCCTGCGGCCTGCGCGCTTCGCT

TGCCGGTTGGACACCAAGTGGAAGGCGGGTCAAGGCTCGCGCAGCGACCGCGCAGCGGCT

TGGCCTTGACGCGCCTGGAACGACCCAAGCCTATGCGAGTGGGGCAGTCGAAGGCGAAG

CCCGCCCGCCTGCCCCCCGAGCCTCACGGCGGCGAGTGCGGGGGTTCCAAGGGGCAGCG

CCACCTTGGGCAAGGCCGAAGGCCGCGCAGTCGATCAACAAGCCCCGGAGGGGCCACTTT

TTGCCGGAGGGGGAGCCGCGCCGAAGGCGTGGGGGAACCCCGCAGGGGTGCCCTTCTTTG

GGCACCAAAGAACTAGATATAGGGCGAAATGCGAAAGACTTAAAAATCAACAACTTAAAA
```

-continued

```
AAGGGGGGTACGCAACAGCTCATTGCGGCACCCCCCGCAATAGCTCATTGCGTAGGTTAA
AGAAAATCTGTAATTGACTGCCACTTTTACGCAACGCATAATTGTTGTCGCGCTGCCGAA
AAGTTGCAGCTGATTGCGCATGGTGCCGCAACCGTGCGGCACCCTACCGCATGGAGATAA
GCATGGCCACGCAGTCCAGAGAAATCGGCATTCAAGCCAAGAACAAGCCCGGTCACTGGG
TGCAAACGGAACGCAAAGCGCATGAGGCGTGGGCCGGGCTTATTGCGAGGAAACCCACGG
CGGCAATGCTGCTGCATCACCTCGTGGCGCAGATGGGCCACCAGAACGCCGTGGTGGTCA
GCCAGAAGACACTTTCCAAGCTCATCGGACGTTCTTTGCGGACGGTCCAATACGCAGTCA
AGGACTTGGTGGCCGAGCGCTGGATCTCCGTCGTGAAGCTCAACGGCCCCGGCACCGTGT
CGGCCTACGTGGTCAATGACCGCGTGGCGTGGGGCCAGCCCCGCGACCAGTTGCGCCTGT
CGGTGTTCAGTGCCGCCGTGGTGGTTGATCACGACGACCAGGACGAATCGCTGTTGGGGC
ATGGCGACCTGCGCCGCATCCCGACCCTGTATCCGGGCGAGCAGCAACTACCGACCGGCC
CCGGCGAGGAGCCGCCCAGCCAGCCCGGCATTCCGGGCATGGAACCAGACCTGCCAGCCT
TGACCGAAACGGAGGAATGGGAACGGCGCGGGCAGCAGCGCCTGCCGATGCCCGATGAGC
CGTGTTTTCTGGACGATGGCGAGCCGTTGGAGCCGCCGACACGGGTCACGCTGCCGCGCC
GGTAGCACTTGGGTTGCGCAGCAACCCGTAAGTGCGCTGTTCCAGACTATCGGCTGTAGC
CGCCTCGCCGCCCTATACCTTGTCTGCCTCCCCGCGTTGCGTCGCGGTGCATGGAGCCGG
GCCACCTCGACCTGAATGGAAGCCGGCGGCACCTCGCTAACGGATTCACCGTTTTTATCA
GGCTCTGGGAGGCAGAATAAATGATCATATCGTCAATTATTACCTCCACGGGGAGAGCCT
GAGCAAACTGGCCTCAGGCATTTGAGAAGCACACGGTCACACTGCTTCCGGTAGTCAATA
AACCGGTAAACCAGCAATAGACATAAGCGGCTATTTAACGACCCTGCCCTGAACCGACGA
CCGGGTCGAATTTGCTTTCGAATTTCTGCCATTCATCCGCTTATTATCACTTATTCAGGC
GTAGCACCAGGCGTTTAAGGGCACCAATAACTGCCTTAAAAAAATTACGCCCCGCCCTGC
CACTCATCGCAGTCGGCCTATTGGTTAAAAAATGAGCTGATTTAACAAAAATTTAACGCG
AATTTTAACAAAATATTAACGCTTACAATTTCCATTCGCCATTCAGGCTGCGCAACTGTT
GGGAAGGGCGATCGGTGCGGGCCTCTTCGCTATTACGCCAGCTGGCGAAAGGGGGATGTG
CTGCAAGGCGATTAAGTTGGGTAACGCCAGGGTTTTCCCAGTCACGACGTTGTAAAACGA
CGGCCAGTGAGCGCGCGTAATACGACTCACTATAGGGCGAATTGGAGCTCCACCGCGGTG
GCGGCCGCTCTAGAACTAGTGGATCCCCCGGGCTGCAGGAATTCGATATCAAGCTTATCG
ATACCGTCGACCTCGAGTTAAGTCTCTAATCGATTGTTTTCCAATGGAATGGTTATAAAA
TCTTTGGTTTTTAGTCTTGAAAATCTTCTAGGATTTTCTATGTAAGTTTTTGTATAAATA
TTATATTGCTTTAATAAATTTAATATATTTTTATTGCATTTTAAGGTTATTTTTTCCATA
TCTGTTCAACCTTTTTTAAATCCTCCAAACAGTCAATATCTAAACTTGAGCTTTCGTCCA
TTAAAAAATGCTTGGTTTTGCTTTGTAAAAAGCTAGGATTGTTTAAAAATTCTTTTATCT
TTAAAATATAAATTGCACCATTGCTCATATAAGTTTTAGGCAATTTTTGCCTTGGCATAA
AAGGATATTCATCATTACAAATCCCTGCTAAATCGCCACAATCATTACAAACAAAGGCTT
TTAGAATTTTATTATCACATTCGCTTACGCTAATTAGGGCATTTGCATTGCTATTTTTAT
AAAGATTAAAAGCTTCATTAATATGAATATTTGTTCTTAGCGGTGAAGTGGGTTGTAAAA
AAACTACATCTTCATAATCTTTATAAAATTTTAGAGCATGTAACAGCACTTTATCGCTTG
TGGTATCATCTTGTGCAAGGCTAATTGGGCGTTTTAAAATATCAACATTTTGACTTTTTG
CATAATTTAAAATTTCATCACTATCACTGCTTACAACAACTTTACTAATGCTTTTAGCAT
TTAGTGCAGCTTTGATCGTGTAGTAAATTAAAGGTTTATTGTTTAATAAAACCAAATTTT
```

-continued

```
TATTTTTAATACCCTTTGAGCCACCACGAGCAGGGATTATTGCTAAGCTCATTTTATATC
CTTAAAAACTTTTTGTGTGCTGAGTTTAAAAAAATCTCCGCTTTGTAAATATTCAAAAAA
TAATTTTGAGCTATCTAAAATCTCTAACTTAGCGCTAAATAAATCTTGTTTTTTATGAAT
AGTGTTAATAGCTTTTAGTATTTCATCACTATTTGCATTAACTTTTAGTGTATTTTCATT
GCCAAGTCTTCCATTTTGTCTTGAGCCAACTAAAATCCCTGCTGTTTTTAAGTATAAGGC
CTCTTTTAAAATACAACTTGAATTACCTATTATAAAATCAGCATTTTTTAACAAAGTTAT
AAAATACTCAAATCTAAGCGATGGAAAAAGCTTAAATCTAGGGTTATTTTTAAACTCTTC
ATAGCTTTGCAAGATTAATTCAAAACCTAAATCATTATTTGGATAAATAACAATATAATT
TTTATTACTTTGTATCAGTGCTTTTACTAAATTGTCTGCTTGATTTTTAATGCTAGTAAT
TTCAGTTGTAACAGGATGAAACATAAGCAAAGCGTAGTTTTCATAATTTATATCATAATA
TTTTTTTGCTTCGCTAAGTGAAATTTTATTATCGTTTAAAAGTTCTAAATCAGGCGAACC
TATGATAAAAATAGATTTTTCATCTTCTCCAAGCTGCATTAAACGCCTTTTTGCAAACTC
ATCATTTACTAAATGAATATGAGCTAGTTTTGATATAGCGTGGCGTAAGCTATCGTCAAT
AGTTCCTGAAATCTCTCCGCCTTCAATATGCGCTACTAAGATATTATTTAATGCTCCAAC
AATAGCTGCTGCTAAAGGCTCAATTCTATCTCCATGTACTACGATTAAATCAGGTTTTAG
CTCATTTGCATACCTTGAAAATCCATCAATTGTAGTAGCTAAAGCCTTATCAGTTTGATA
ATATTTATCATAATTTATAAATTCATAAATATTTTAAAGCCATTTTTATAAAGTTCTTT
AACTGTATAGCCAAAATTTTTACTTAAGTGCATTCCTGTTGCAAAGATGTAAAGTTCAAA
TTCGCTTGAGTTTTGCACCCTGTACATTAAAGATTTAATCTTAGAATAATCAGCCCTAGA
GCCTGTTATAAAAAGGATTTTTTTCACGCAAAATCCTCATAGCTTAACTGAGCATCATTT
TCTATATCTCTTAATGCTTTTTTGCCTAAAATATTTTCAAATTCAGCCGCACTAATTCCA
CCAAGTCCAGGTCTTTTAACCCAAATATTATCCATAGATAAAACTTCGCCTTTTTTAATA
TCTTTAATGCTAACTACACTTGCAAAGGCAAAATCAATTGTAACTTGTTCTTGTTTAGCC
GCTTTTTTACTTTCATTATTTCCTCTTATTATAGCCATTTGCTCACTTTGTATAATTAGC
TCTTTTAAAGCCTTTGTATCCATAGAACAAACTATATCAGGGCCACTTCTATGCATACTA
TCAGTAAAATGTCTTTCAAGCACACAAGCTCCAAGTACAACTGCACCTAAACACGCAAGA
TTATCTGTTGTGTGGTCGCTTAAGCCTACCATACAAGAAAATTCTTTTTTTAACTCAAGC
ATAGCGTTTAATCTTACAAGATTATGCGGGGTTGGGTAAAGATTGGTCGTGTGCATTAAA
ACAAAAGGAATTTCATTGTCTAATAAGATTTTTACAGTTGGTTTTATACTTTCAATACTA
TTCATTCCTGTGCTAACTATCATAGGCTTTTTAAAGGCTGCTATGTGTTTAATAAGCGGA
TAATTATTACACTCACCTGAACCAATCTTAAAAGCACTAACTCCCATATCTTCTAAGCGG
TTCGCACCTGCACGAGAAAAAGGTGTGCTAAGATAAACAAGACCTAATTTTTCTGTGTAT
TCTTTAAGTGCTAGCTCATCTTTATAATCCAAAGCACATTTTTGCATAATCTCATAAATG
CTTATTTTTGCATTACCAGGAATTACTTTTTTAGCGGCCTTACTCATCTCATCTTCAACA
ATATGAGTTTGATGCTTTATAATCTTAGCACCTGCGCTAAAGGCTGCATCTACCATAATT
TTAGCTAGTTCTAAACTGCCATTATGATTAATGCCTATTTCAGGTACGACTAAGGGTGCT
TTTTCTTCACTTATGATTATATTTTGTATTTTTATTTCTTTCATTTATTTTCCTCCTTAG
```

SEQ ID NO: 6
>pG315, complete sequence
```
CTAAATTGTAAGCGTTAATATTTTGTTAAAATTCGCGTTAAATTTTTGTTAAATCAGCTC
ATTTTTTAACCAATAGGCCGAAATCGGCAAAATCCCTTATAAATCAAAAGAATAGACCGA
```

-continued

```
GATAGGGTTGAGTGTTGTTCCAGTTTGGAACAAGAGTCCACTATTAAAGAACGTGGACTC

CAACGTCAAAGGGCGAAAAACCGTCTATCAGGGCGATGGCCCACTACGTGAACCATCACC

CTAATCAAGTTTTTTGGGGTCGAGGTGCCGTAAAGCACTAAATCGGAACCCTAAAGGGAG

CCCCCGATTTAGAGCTTGACGGGAAAGCCGGCGAACGTGGCGAGAAAGGAAGGGAAGAA

AGCGAAAGGAGCGGGCGCTAGGGCGCTGGCAAGTGTAGCGGTCACGCTGCGCGTAACCAC

CACACCCGCCGCGCTTAATGCGCCGCTACAGGGCGCGTCCCATTCGCCATTCAGGCTGCG

CAACTGTTGGGAAGGGCGATCGGTGCGGGCCTCTTCGCTATTACGCCAGCTGGCGAAAGG

GGGATGTGCTGCAAGGCGATTAAGTTGGGTAACGCCAGGGTTTTCCCAGTCACGACGTTG

TAAAACGACGGCCAGTGAGCGCGCGTAATACGACTCACTATAGGGCGAATTGGAGCTCCA

CCGCGGTGGCGGCCGCTCTAGAACTAGTGGATCCCTAGACTGCAATACAAACACCTGTTT

CACAATTTGGCAGATCAGCCCAAAAAAGTACATTCTCTTCTTTTACAATACCTAGTTTTA

TCATTACTTGAACTAAAGGACTTCTCAAAGCAGTTTCACGATCAGTTATAGTTTCTGTCG

ATGTAAAAACTATAAATTTAATTTTTTCAGCTGGTATCGTGAAATATAAAGAGCTCGCTA

TACCAGCAACTGCATCAGGAAGCATATCTGTCATCATCAAAACTTCAAATGATATTTTTG

ATGGAATATCAACCATTGAAGGATAGTTTTGCATTATTAATGTATTAATGATACCGCCAC

CAGGGTGACCTTTGAAGAACAAATCATAACTATTGCCTAAATAATGTGGGCTCGATTCAT

TAATTGCATTATTAATGACATTAATTTGTTGTTTCGCATAATACTCTCTTTCATGGTTAC

CAGCCCATACAGTCGTACCTGTAAACACAAAGTTTGGTAAATTAGATGAATTATATTCAT

TTTGTAATTTTTGTTTGTCAAAATTAACAATCGATAAGAATAATTCTTGTTGTTTGCTAT

TGAATTTTTTGAAACCATCCCATTGCATTTGCTTTAAACTATCACCAATATAGTCTCGTA

ACTCATGTAATGATGGTTCTAAAGTTAAATAATCTTTTCTTAAAAAATGGTAGTTAGCTG

GATATAGTTTTTGCCAGTTATAAACAGATGATGTTCCTGTATTTGAAGTGTCTTCATTGA

TACCATTAATGACATCCTCAAGATAATCTTTACCAATTTTTAAATTATCTGTTTTATTTA

ATGTATCTCTCCAGTTATATAAATTTACATATTCTGCTGAACCATCATCATATAAATCTA

TATTTGTTACCGTAACGTTATTAAACGAATTTAATTCTTTTAGTATTGGCACTAAATTAT

CAAATGAATGAGCAGTGTTAGAGCTAAGTTTAACATTCAATCTATGCTTTGTTTGTGCTT

GCTTAACAATTTCTTGTACTAAGTCAGCTGGTGTATGGTTATTTATCAATGCAAACGATG

TAATATTTAACTCTTTCATTTGCTCATCAGTCGGAACTATTCTCCCCCAAGCTATATATC

TTTGTGCTGTAGGATTTTCTTCTTCCGATTTAATAATATCCATTAGCTGCTGAAGAGTTG

GAAGAGATGCATGATCAACATAAACCTCTAAAGATGGAGCCACTACGTTTAATGTTACTT

TTGTTATATATTTTTCACCTTTATTACTAACACCATTAAAATCAAAGCAGTACTTTTCAT

CGTCATCTAATCGTGGCGCCACTACAGATAATGATATTGACTCTTTATTTTGTTCTGTTA

ATAGTTGTTGCGTACCACAAGTTTGTACCCAAGAGTGTTTTGTAAAAGAGATGTTTGATT

GATTAATTGGCTCTAAATTAACATACTCCTCATCAATAATAGTTTTATTAATATCATTTT

TAATAATAGATTGTGTATTTTCTTCTGACATggtctgtttcctcCTCGAGGGGGGCCCG

GTACCCAGCTTTTGTTCCCTTTAGTGAGGGTTAATTGCGCGCTTGGCGTAATCATGGTCA

TAGCTGTTTCCTGTGTGAAATTGTTATCCGCTCACAATTCCACACAACATACGAGCCGGA

AGCATAAAGTGTAAAGCCTGGGGTGCCTAATGAGTGAGCTAACTCACATTAATTGCGTTG

CGCTCACTGCCCGCTTTCCAGTCGGGAAACCTGTCGTGCCAGCTGCATTAATGAATCGGC

CAACGCGCGGGGAGAGGCGGTTTGCGTATTGGGCGCTCTTCCGCTTCCTCGCTCACTGAC

TCGCTGCGCTCGGTCGTTCGGCTGCGGCGAGCGGTATCAGCTCACTCAAAGGCGGTAATA
```

-continued

```
CGGTTATCCACAGAATCAGGGGATAACGCAGGAAAGAACATGTGAGCAAAAGGCCAGCAA

AAGGCCAGGAACCGTAAAAAGGCCGCGTTGCTGGCGTTTTTCCATAGGCTCCGCCCCCCT

GACGAGCATCACAAAAATCGACGCTCAAGTCAGAGGTGGCGAAACCCGACAGGACTATAA

AGATACCAGGCGTTTCCCCCTGGAAGCTCCCTCGTGCGCTCTCCTGTTCCGACCCTGCCG

CTTACCGGATACCTGTCCGCCTTTCTCCCTTCGGGAAGCGTGGCGCTTTCTCATAGCTCA

CGCTGTAGGTATCTCAGTTCGGTGTAGGTCGTTCGCTCCAAGCTGGGCTGTGTGCACGAA

CCCCCCGTTCAGCCCGACCGCTGCGCCTTATCCGGTAACTATCGTCTTGAGTCCAACCCG

GTAAGACACGACTTATCGCCACTGGCAGCAGCCACTGGTAACAGGATTAGCAGAGCGAGG

TATGTAGGCGGTGCTACAGAGTTCTTGAAGTGGTGGCCTAACTACGGCTACACTAGAAGG

ACAGTATTTGGTATCTGCGCTCTGCTGAAGCCAGTTACCTTCGGAAAAAGAGTTGGTAGC

TCTTGATCCGGCAAACAAACCACCGCTGGTAGCGGTGGTTTTTTTGTTTGCAAGCAGCAG

ATTACGCGCAGAAAAAAAGGATCTCAAGAAGATCCTTTGATCTTTTCTACGGGGTCTGAC

GCTCAGTGGAACGAAAACTCACGTTAAGGGATTTTGGTCATGAGATTATCAAAAAGGATC

TTCACCTAGATCCTTTTAAATTAAAAATGAAGTTTTAAATCAATCTAAAGTATATATGAG

TAAACTTGGTCTGACAGTTACCAATGCTTAATCAGTGAGGCACCTATCTCAGCGATCTGT

CTATTTCGTTCATCCATAGTTGCCTGACTCCCCGTCGTGTAGATAACTACGATACGGGAG

GGCTTACCATCTGGCCCCAGTGCTGCAATGATACCGCGAGACCCACGCTCACCGGCTCCA

GATTTATCAGCAATAAACCAGCCAGCCGGAAGGGCCGAGCGCAGAAGTGGTCCTGCAACT

TTATCCGCCTCCATCCAGTCTATTAATTGTTGCCGGGAAGCTAGAGTAAGTAGTTCGCCA

GTTAATAGTTTGCGCAACGTTGTTGCCATTGCTACAGGCATCGTGGTGTCACGCTCGTCG

TTTGGTATGGCTTCATTCAGCTCCGGTTCCCAACGATCAAGGCGAGTTACATGATCCCCC

ATGTTGTGCAAAAAAGCGGTTAGCTCCTTCGGTCCTCCGATCGTTGTCAGAAGTAAGTTG

GCCGCAGTGTTATCACTCATGGTTATGGCAGCACTGCATAATTCTCTTACTGTCATGCCA

TCCGTAAGATGCTTTTCTGTGACTGGTGAGTACTCAACCAAGTCATTCTGAGAATAGTGT

ATGCGGCGACCGAGTTGCTCTTGCCCGGCGTCAATACGGGATAATACCGCGCCACATAGC

AGAACTTTAAAAGTGCTCATCATTGGAAAACGTTCTTCGGGGCGAAAACTCTCAAGGATC

TTACCGCTGTTGAGATCCAGTTCGATGTAACCCACTCGTGCACCCAACTGATCTTCAGCA

TCTTTTACTTTCACCAGCGTTTCTGGGTGAGCAAAAACAGGAAGGCAAAATGCCGCAAAA

AAGGGAATAAGGGCGACACGGAAATGTTGAATACTCATACTCTTCCTTTTTCAATATTAT

TGAAGCATTTATCAGGGTTATTGTCTCATGAGCGGATACATATTTGAATGTATTTAGAAA

AATAAACAAATAGGGGTTCCGCGCACATTTCCCCGAAAAGTGCCAC
```

SEQ ID NO: 7
```
CTCGAGgaggaaacagaccATG
```

SEQ ID NO: 8
```
CTCGAGgaaagaggggacaaactagATG
```

SEQ ID NO: 9
>pG345, complete sequence
```
CTAAATTGTAAGCGTTAATATTTTGTTAAAATTCGCGTTAAATTTTTGTTAAATCAGCTC

ATTTTTTAACCAATAGGCCGAAATCGGCAAAATCCCTTATAAATCAAAAGAATAGACCGA

GATAGGGTTGAGTGTTGTTCCAGTTTGGAACAAGAGTCCACTATTAAAGAACGTGGACTC

CAACGTCAAAGGGCGAAAAACCGTCTATCAGGGCGATGGCCCACTACGTGAACCATCACC

CTAATCAAGTTTTTTGGGGTCGAGGTGCCGTAAAGCACTAAATCGGAACCCTAAAGGGAG
```

-continued

```
CCCCCGATTTAGAGCTTGACGGGGAAAGCCGGCGAACGTGGCGAGAAAGGAAGGGAAGAA

AGCGAAAGGAGCGGGCGCTAGGGCGCTGGCAAGTGTAGCGGTCACGCTGCGCGTAACCAC

CACACCCGCCGCGCTTAATGCGCCGCTACAGGGCGCGTCCCATTCGCCATTCAGGCTGCG

CAACTGTTGGGAAGGGCGATCGGTGCGGGCCTCTTCGCTATTACGCCAGCTGGCGAAAGG

GGGATGTGCTGCAAGGCGATTAAGTTGGGTAACGCCAGGGTTTTCCCAGTCACGACGTTG

TAAAACGACGGCCAGTGAGCGCGCGTAATACGACTCACTATAGGGCGAATTGGAGCTCCA

CCGCGGTGGCGGCCGCTCTAGAACTAGTGGATCCCTAGACTGCAATACAAACACCTGTTT

CACAATTTGGCAGATCAGCCCAAAAAAGTACATTCTCTTCTTTTACAATACCTAGTTTTA

TCATTACTTGAACTAAAGGACTTCTCAAAGCAGTTTCACGATCAGTTATAGTTTCTGTCG

ATGTAAAAACTATAAATTTAATTTTTTCAGCTGGTATCGTGAAATATAAAGAGCTCGCTA

TACCAGCAACTGCATCAGGAAGCATATCTGTCATCATCAAAACTTCAAATGATATTTTTG

ATGGAATATCAACCATTGAAGGATAGTTTTGCATTATTAATGTATTAATGATACCGCCAC

CAGGGTGACCTTTGAAGAACAAATCATAACTATTGCCTAAATAATGTGGGCTCGATTCAT

TAATTGCATTATTAATGACATTAATTTGTTGTTTCGCATAATACTCTCTTTCATGGTTAC

CAGCCCATACAGTCGTACCTGTAAACACAAAGTTTGGTAAATTAGATGAATTATATTCAT

TTTGTAATTTTTGTTTGTCAAAATTAACAATCGATAAGAATAATTCTTGTTGTTTGCTAT

TGAATTTTTTGAAACCATCCCATTGCATTTGCTTTAAACTATCACCAATATAGTCTCGTA

ACTCATGTAATGATGGTTCTAAAGTTAAATAATCTTTTCTTAAAAAATGGTAGTTAGCTG

GATATAGTTTTTGCCAGTTATAAACAGATGATGTTCCTGTATTTGAAGTGTCTTCATTGA

TACCATTAATGACATCCTCAAGATAATCTTTACCAATTTTTAAATTATCTGTTTTATTTA

ATGTATCTCTCCAGTTATATAAATTTACATATTCTGCTGAACCATCATCATATAAATCTA

TATTTGTTACCGTAACGTTATTAAACGAATTTAATTCTTTTAGTATTGGCACTAAATTAT

CAAATGAATGAGCAGTGTTAGAGCTAAGTTTAACATTCAATCTATGCTTTGTTTGTGCTT

GCTTAACAATTTCTTGTACTAAGTCAGCTGGTGTATGGTTATTTATCAATGCAAACGATG

TAATATTTAACTCTTTCATTTGCTCATCAGTCGGAACTATTCTCCCCCAAGCTATATATC

TTTGTGCTGTAGGATTTTCTTCTTCCGATTTAATAATATCCATTAGCTGCTGAAGAGTTG

GAAGAGATGCATGATCAACATAAACCTCTAAAGATGGAGCCACTACGTTTAATGTTACTT

TTGTTATATATTTTTCACCTTTATTACTAACACCATTAAAATCAAAGCAGTACTTTTCAT

CGTCATCTAATCGTGGCGCCACTACAGATAATGATATTGACTCTTTATTTTGTTCTGTTA

ATAGTTGTTGCGTACCACAAGTTTGTACCCAAGAGTGTTTTGTAAAAGAGATGTTTGATT

GATTAATTGGCTCTAAATTAACATACTCCTCATCAATAATAGTTTTATTAATATCATTTT

TAATAATAGATTGTGTATTTTCTTCTGACATctagtttgtccctctttcCTCGAGGGGG

GGCCCGGTACCCAGCTTTTGTTCCCTTTAGTGAGGGTTAATTGCGCGCTTGGCGTAATCA

TGGTCATAGCTGTTTCCTGTGTGAAATTGTTATCCGCTCACAATTCCACACAACATACGA

GCCGGAAGCATAAAGTGTAAAGCCTGGGGTGCCTAATGAGTGAGCTAACTCACATTAATT

GCGTTGCGCTCACTGCCCGCTTTCCAGTCGGGAAACCTGTCGTGCCAGCTGCATTAATGA

ATCGGCCAACGCGCGGGGAGAGGCGGTTTGCGTATTGGGCGCTCTTCCGCTTCCTCGCTC

ACTGACTCGCTGCGCTCGGTCGTTCGGCTGCGGCGAGCGGTATCAGCTCACTCAAAGGCG

GTAATACGGTTATCCACAGAATCAGGGGATAACGCAGGAAAGAACATGTGAGCAAAAGGC

CAGCAAAAGGCCAGGAACCGTAAAAAGGCCGCGTTGCTGGCGTTTTTCCATAGGCTCCGC

CCCCCTGACGAGCATCACAAAAATCGACGCTCAAGTCAGAGGTGGCGAAACCCGACAGGA
```

```
CTATAAAGATACCAGGCGTTTCCCCCTGGAAGCTCCCTCGTGCGCTCTCCTGTTCCGACC

CTGCCGCTTACCGGATACCTGTCCGCCTTTCTCCCTTCGGGAAGCGTGGCGCTTTCTCAT

AGCTCACGCTGTAGGTATCTCAGTTCGGTGTAGGTCGTTCGCTCCAAGCTGGGCTGTGTG

CACGAACCCCCCGTTCAGCCCGACCGCTGCGCCTTATCCGGTAACTATCGTCTTGAGTCC

AACCCGGTAAGACACGACTTATCGCCACTGGCAGCAGCCACTGGTAACAGGATTAGCAGA

GCGAGGTATGTAGGCGGTGCTACAGAGTTCTTGAAGTGGTGGCCTAACTACGGCTACACT

AGAAGGACAGTATTTGGTATCTGCGCTCTGCTGAAGCCAGTTACCTTCGGAAAAAGAGTT

GGTAGCTCTTGATCCGGCAAACAAACCACCGCTGGTAGCGGTGGTTTTTTTGTTTGCAAG

CAGCAGATTACGCGCAGAAAAAAAGGATCTCAAGAAGATCCTTTGATCTTTTCTACGGGG

TCTGACGCTCAGTGGAACGAAAACTCACGTTAAGGGATTTTGGTCATGAGATTATCAAAA

AGGATCTTCACCTAGATCCTTTTAAATTAAAAATGAAGTTTTAAATCAATCTAAAGTATA

TATGAGTAAACTTGGTCTGACAGTTACCAATGCTTAATCAGTGAGGCACCTATCTCAGCG

ATCTGTCTATTTCGTTCATCCATAGTTGCCTGACTCCCCGTCGTGTAGATAACTACGATA

CGGGAGGGCTTACCATCTGGCCCCAGTGCTGCAATGATACCGCGAGACCCACGCTCACCG

GCTCCAGATTTATCAGCAATAAACCAGCCAGCCGGAAGGGCCGAGCGCAGAAGTGGTCCT

GCAACTTTATCCGCCTCCATCCAGTCTATTAATTGTTGCCGGGAAGCTAGAGTAAGTAGT

TCGCCAGTTAATAGTTTGCGCAACGTTGTTGCCATTGCTACAGGCATCGTGGTGTCACGC

TCGTCGTTTGGTATGGCTTCATTCAGCTCCGGTTCCCAACGATCAAGGCGAGTTACATGA

TCCCCCATGTTGTGCAAAAAAGCGGTTAGCTCCTTCGGTCCTCCGATCGTTGTCAGAAGT

AAGTTGGCCGCAGTGTTATCACTCATGGTTATGGCAGCACTGCATAATTCTCTTACTGTC

ATGCCATCCGTAAGATGCTTTTCTGTGACTGGTGAGTACTCAACCAAGTCATTCTGAGAA

TAGTGTATGCGGCGACCGAGTTGCTCTTGCCCGGCGTCAATACGGGATAATACCGCGCCA

CATAGCAGAACTTTAAAAGTGCTCATCATTGGAAAACGTTCTTCGGGGCGAAAACTCTCA

AGGATCTTACCGCTGTTGAGATCCAGTTCGATGTAACCCACTCGTGCACCCAACTGATCT

TCAGCATCTTTTACTTTCACCAGCGTTTCTGGGTGAGCAAAAACAGGAAGGCAAAATGCC

GCAAAAAAGGGAATAAGGGCGACACGGAAATGTTGAATACTCATACTCTTCCTTTTTCAA

TATTATTGAAGCATTTATCAGGGTTATTGTCTCATGAGCGGATACATATTTGAATGTATT

TAGAAAAATAAACAAATAGGGGTTCCGCGCACATTTCCCCGAAAAGTGCCAC
```

```
                                         SEQ ID NO: 10
CTTTattaaacctactATG
```

```
                                         SEQ ID NO: 11
CTTTcttcaacctactATG
```

```
                                         SEQ ID NO: 12
>pEC3'-(T7)GlmS-(T7)NagC-purA_(pG356)
TCGCGCGTTTCGGTGATGACGGTGAAAACCTCTGACACATGCAGCTCCCGGAGACGGTCA

CAGCTTGTCTGTAAGCGGATGCCGGGAGCAGACAAGCCCGTCAGGGCGCGTCAGCGGGTG

TTGGCGGGTGTCGGGGCTGGCTTAACTATGCGGCATCAGAGCAGATTGTACTGAGAGTGC

ACCATATATGCGGTGTGAAATACCGCACAGATGCGTAAGGAGAAAATACCGCATCAGGCG

CCactagtGTTGAGGAAAACGATTGGCTGAACAAAAAACAGACTGATCGAGGTCATTTTT

GAGTGCAAAAGTGCTGTAACTCTGAAAAAGCGATGGTAGAATCCATTTTTAAGCAAACG

GTGATTTTGAAAAATGGGTAACAACGTCGTCGTACTGGGCACCCAATGGGGTGACGAAGG
```

-continued

```
TAAAGGTAAGATCGTCGATCTTCTGACTGAACGGGCTAAATATGTTGTACGCTACCAGGG

CGGTCACAACGCAGGCCATACTCTCGTAATCAACGGTGAAAAAACCGTTCTCCATCTTAT

TCCATCAGGTATTCTCCGCGAGAATGTAACCAGCATCATCGGTAACGGTGTTGTGCTGTC

TCCGGCCGCGCTGATGAAAGAGATGAAAGAACTGGAAGACCGTGGCATCCCCGTTCGTGA

GCGTCTGCTGCTGTCTGAAGCATGTCCGCTGATCCTTGATTATCACGTTGCGCTGGATAA

CGCGCGTGAGAAAGCGCGTGGCGCGAAAGCGATCGGCACCACCGGTCGTGGTATCGGGCC

TGCTTATGAAGATAAAGTAGCACGTCGCGGTCTGCGTGTTGGCGACCTTTTCGACAAAGA

AACCTTCGCTGAAAAACTGAAAGAAGTGATGGAATATCACAACTTCCAGTTGGTTAACTA

CTACAAAGCTGAAGCGGTTGATTACCAGAAAGTTCTGGATGATACGATGGCTGTTGCCGA

CATCCTGACTTCTATGGTGGTTGACGTTTCTGACCTGCTCGACCAGGCGCGTCAGCGTGG

CGATTTCGTCATGTTTGAAGGTGCGCAGGGTACGCTGCTGGATATCGACCACGGTACTTA

TCCGTACGTAACTTCTTCCAACACCACTGCTGGTGGCGTGGCGACCGGTTCCGGCCTGGG

CCCGCGTTATGTTGATTACGTTCTGGGTATCCTCAAAGCTTACTCCACTCGTGTAGGTGC

AGGTCCGTTCCCGACCGAACTGTTTGATGAAACTGGCGAGTTCCTCTGCAAGCAGGGTAA

CGAATTCGGCGCAACTACGGGGCGTCGTCGTCGTACCGGCTGGCTGGACACCGTTGCCGT

TCGTCGTGCGGTACAGCTGAACTCCCTGTCTGGCTTCTGCCTGACTAAACTGGACGTTCT

GGATGGCCTGAAAGAGGTTAAACTCTGCGTGGCTTACCGTATGCCGGATGGTCGCGAAGT

GACTACCACTCCGCTGGCAGCTGACGACTGGAAAGGTGTAGAGCCGATTTACGAAACCAT

GCCGGGCTGGTCTGAATCCACCTTCGGCGTGAAAGATCGTAGCGGCCTGCCGCAGGCGGC

GCTGAACTATATCAAGCGTATTGAAGAGCTGACTGGTGTGCCGATCGATATCATCTCTAC

CGGTCCGGATCGTACTGAAACCATGATTCTGCGCGACCCGTTCGACGCGTAATTCTGGTA

CGCCTGGCAGATATTTTGCCTGCCGGGCGAACAGTGTGATACATTGCTGTGTCGGGTAAG

CCATTACGCTATCCGACACAGTGTTAAATCCTCGCTTTTTTCCTTCCCCagatctGGCGC

CATTCGCCATTCAGGCTGCGCAACTGTTGGGAAGGGCGATCGGTGCGGGCCTCTTCGCTA

TTACGCCAGCTGGCGAAAGGGGGATGTGCTGCAAGGCGATTAAGTTGGGTAACGCCAGGG

TTTTCCCAGTCACGACGTTGTAAAACGACGGCCAGTGCCAAGCTTACTGCTCACAAGAAA

AAAGGCACGTCATCTGACGTGCCTTTTTTATTTGTACTACCCTGTACGATTACTGCAGGT

CGACTTAATTTTCCAGCAAATGCTGGAGCAAAATACCGTTGAGCATGGCGCGTTTTACCA

GCGCAAAAGCGCCGATTGCCGAGCGGTGATCCAGCTCAGAACGTACCACCGGCAGATTAG

TGCGAAACGCCTTCAGCGCCTGGGTATTAATGCAGCTTTCAATAGCAGGGAGCAGCACTT

TATCGGCTTCGGTGATTTCACCGGCAATAACAATTTTTTGCGGATTAAATAAGTTGATAG

CAATGGCGATGGTTTTACCCAGATGACGACCGACATACTCAATTACTTCCGACGCCAGAC

TATCGCCTTTGTTCGCGGCTTTGCAGATAGTTTTGATGGTGCAGTCGTCCAGCGGCACGC

GGCTCTGGTAGCCCTGCTTTAACAGATTCAACACCCGTTGTTCAATGGCAGCGTTGGCAG

CGATAGTTTCCAGGCAGCCAAAGTTGCCGCAGTGGCAGCGTTCACCCAGCGGTTCGACCT

GAATATGGCCAATTTCACCGACGTTGCCGTTGCGGCCAATAAAAATGCGCCCGTTAGAGA

TAATCCCGGCCCCGGTTCCGCGATGGACACGCACCAGAATGGAGTCTTCGCAATCCTGAC

TTGCACCGAAGTAGTGCTCCGCCAGCGCCAGACTACGGATATCGTGACCAACGAAACAGG

TCACTTTAAAACGTTCTTCCAGAGCTTCTACCAGCCCCCAGTTTTCTACCTGAATATGCG

GCATGTAATGAATTTTGCCGCTGTCCGGGTCAACAAGCCCTGGCAGGATCACCGAAATCG
```

-continued

```
CGATCAGCTCGCGCAGTTTGCGCTGGTAGCTATCAATAAACTGAGCAATGGCATTCAACA
GGGCATGTTCCAGCGTTTGCTGGGTACGTTCCGGCAGCGGGTAATGTTCTTCTGCCAGCA
CTTTGCTGCTGAGATCAAACAGAGTGATGGTGGCGTCATGACGACCAAGCCGTACGCCGA
TTGCGTGGAAATTGCGGGTTTCGGTGACGATGGAGATAGCGCGGCGGCCCCCGGTGGAGG
CCTGCTGATCAACTTCTTTGATCAGCCCGCGTTCGATAAGCTGACGCGTAATTTTGGTTA
CGCTGGCGGGGGCAAGCTGGCTTTGCTCGGCAATCTGAATCCGCGAGATTGGCCCGTACT
GGTCAATCAGGCGATAAACCGCCGCGCTGTTAAGCTGTTTTACGAGATCAACATTACCTA
TCTGAGCTTGTCCGCCTGGTGTCATATGTATATCTCCTTCTTgtcgacTCTAGATGCATG
CTCGAGATTACTCAACCGTAACCGATTTTGCCAGGTTACGCGGCTGGTCAACGTCGGTGC
CTTTGATCAGCGCGACATGGTAAGCCAGCAGCTGCAGCGGAACGGTGTAGAAGATCGGTG
CAATCACCTCTTCCACATGCGGCATCTCGATGATGTGCATGTTATCGCTACTTACAAAAC
CCGCATCCTGATCGGCGAAGACATACAACTGACCGCCACGCGCGCGAACTTCTTCAATGT
TGGATTTCAGTTTTTCCAGCAATTCGTTGTTCGGTGCAACAACAATAACCGGCATATCGG
CATCAATTAGCGCCAGCGGACCGTGTTTCAGTTCGCCAGCAGCGTAGGCTTCAGCGTGAA
TGTAAGAGATCTCTTTCAACTTCAATGCGCCTTCCAGCGCGATTGGGTACTGATCGCCAC
GGCCCAGGAACAGCGCGTGATGTTTGTCAGAGAAATCTTCTGCCAGCGCTTCAATGCGTT
TGTCCTGAGACAGCATCTGCTCAATACGGCTCGGCAGCGCCTGCAGACCATGCACGATGT
CATGTTCAATGGAGGCATCCAGACCTTTCAGGCGAGACAGCTTCGCCACCAGCATCAACA
GCACAGTTAACTGAGTGGTGAATGCTTTAGTGGATGCCACGCCGATTTCTGTACCCGCGT
TGGTCATTAGCGCCAGATCGGATTCGCGCACCAGAGAAGAACCCGGAACGTTACAGATTG
CCAGTGAACCAAGGTAACCCAGCTCTTTCGACAGACGCAGGCCAGCCAGGGTATCCGCGG
TTTCGCCAGACTGTGACAAGGTGATCATCAGGCTGTTACGACGCACGGCAGATTTGCGAT
AGCGGAATTCAGAGGCGATTTCGACGTCGCACGGAATACCTGCTAGCGATTCAAACCAGT
AGCGGGAAACCATACCGGAGTTATAAGAAGTACCACAGGCGAGGATCTGAATATGCTCAA
CCTTCGACAGCAGTTCGTCGGCGTTCGGTCCCAGCTCGCTTAAATCAACCTGACCGTGGC
TGATGCGTCCGGTAAGGGTGTTTTTGATCGCGTTCGGCTGTTCGTAGATCTCTTTCTGCA
TGTAGTGACGGTAAATGCCTTTATCGCCCGCGTCATATTGCAGATTGGATTCGATATCCT
GACGTTTTACTTCCGCGCCAGTTTTATCGAAGATGTTTACCGAACGGCGAGTGATTTCCG
CAATATCGCCCTCTTCAAGGAAGATAAAGCGACGGGTCACCGGCAACAGCGCCAGCTGGT
CAGAAGCGATAAAGTTTTCGCCCATCCCCAGGCCAATCACCAGCGGACTACCAGAACGTG
CCGCCAGCAGGGTATCCGGGTGACGGGAGTCCATGATCACTGTACCGTACGCACCACGCA
GCTGCGGGATAGCACGCAGAACGGCCTCACGCAGAGTCCCGCCTTGTTTCAGCTCCCAGT
TCACCAGATGGGCAATCACTTCGGTGTCGGTTTCAGAAACGAAGGTATAGCCACGCGCTT
TTAGCTCTTCACGCAGCGGTTCATGGTTTTCGATGATGCCGTTATGCACCACCACAATGT
GTTCAGAAACATGCGGATGCGCATTCACTTCTGAAGGTTCACCGTGGGTCGCCCAGCGAG
TGTGAGCAATACCAGTGCCGCCATGCAGAGGATGTTCTTCCGCTGCCTGTGCCAGCATCT
GGACTTTACCGAGGCGACGCAGGCGGGTCATATGACCTTCTGCATCAACAACGGCCAGAC
CGGCAGAGTCATATCCGCGGTATTCCAGACGACGTAAACCTTCAAGAAGGATTTCTGCTA
CATCACGTTGCGCGATCGCGCCAACAATTCCACACATATGtatatctccttcttgaaTTC
TAACAATTGATTGAATGTATGCAAATAAATGCATACACCATAGGTGTGGTTTAATTTGAT
GCCCTTTTTCAGGGCTGGAATGTGTAAGAGCGGGGTTATTTATGCTGTTGTTTTTTTGTT
```

-continued

```
ACTCGGGAAGGGCTTTACCTCTTCCGCATAAACGCTTCCATCAGCGTTTATAGTTAAAAA
AATCTTTCGGAACTGGTTTTGCGCTTACCCCAACCAACAGGGGATTTGCTGCTTTCCATT
GAGCCTGTTTCTCTGCGCGACGTTCGCGGCGGCGTGTTTGTGCATCCATCTGGATTCTCC
TGTCAGTTAGCTTTGGTGGTGTGTGGCAGTTGTAGTCCTGAACGAAAACCCCCCGCGATT
GGCACATTGGCAGCTAATCCGGAATCGCACTTACGGCCAATGCTTCGTTTCGTATCACAC
ACCCCAAAGCCTTCTGCTTTGAATGCTGCCCTTCTTCAGGGCTTAATTTTTAAGAGCGTC
ACCTTCATGGTGGTCAGTGCGTCCTGCTGATGTGCTCAGTATCACCGCCAGTGGTATTTA
TGTCAACACCGCCAGAGATAATTTATCACCGCAGATGGTTATCTGTATGTTTTTTATATG
AATTTATTTTTTGCAGGGGGGCATTGTTTGGTAGGTGAGAGATCAATTCTGCATTAATGA
ATCGGCCAACGCGCGGGGAGAGGCGGTTTGCGTATTGGGCGCTCTTCCGCTGCTAGCGGA
GTGTATACTGGCTTACTATGTTGGCACTGATGAGGGTGTCAGTGAAGTGCTTCATGTGGC
AGGAGAAAAAAGGCTGCACCGGTGCGTCAGCAGAATATGTGATACAGGATATATTCCGCT
TCCTCGCTCACTGACTCGCTACGCTCGGTCGTTCGACTGCGGCGAGCGGAAATGGCTTAC
GAACGGGCGGAGATTTCCTGGAAGATGCCAGGAAGATACTTAACAGGGAAGTGAGAGGG
CCGCGGCAAAGCCGTTTTTCCATAGGCTCCGCCCCCCTGACAAGCATCACGAAATCTGAC
GCTCAAATCAGTGGTGGCGAAACCCGACAGGACTATAAAGATACCAGGCGTTTCCCCCTG
GCGGCTCCCTCGTGCGCTCTCCTGTTCCTGCCTTTCGGTTTACCGGTGTCATTCCGCTGT
TATGGCCGCGTTTGTCTCATTCCACGCCTGACACTCAGTTCCGGGTAGGCAGTTCGCTCC
AAGCTGGACTGTATGCACGAACCCCCCGTTCAGTCCGACCGCTGCGCCTTATCCGGTAAC
TATCGTCTTGAGTCCAACCCGGAAAGACATGCAAAAGCACCACTGGCAGCAGCCACTGGT
AATTGATTTAGAGGAGTTAGTCTTGAAGTCATGCGCCGGTTAAGGCTAAACTGAAAGGAC
AAGTTTTGGTGACTGCGCTCCTCCAAGCCAGTTACCTCGGTTCAAAGAGTTGGTAGCTCA
GAGAACCTTCGAAAAACCGCCCTGCAAGGCGGTTTTTTCGTTTTCAGAGCAAGAGATTAC
GCGCAGACCAAAACGATCTCAAGAAGATCATCTTATTAATCAGATAAAATATTTCTAGGC
ggccgcGAACGAAAACTCACGTTAAGGGATTTTGGTCATGAGATTATCAAAAAGGATCTT
CACCTAGATCCTTTTAAATTAAAAATGAAGTTTTAAATCAATCTAAAGTATATATGAGTA
AACTTGGTCTGACAGTTACCAATGCTTAATCAGTGAGGCACCTATCTCAGCGATCTGTCT
ATTTCGTTCATCCATAGTTGCCTGACTCCCCGTCGTGTAGATAACTACGATACGGGAGGG
CTTACCATCTGGCCCCAGTGCTGCAATGATACCGCGAGACCCACGCTCACCGGCTCCAGA
TTTATCAGCAATAAACCAGCCAGCCGGAAGGGCCGAGCGCAGAAGTGGTCCTGCAACTTT
ATCCGCCTCCATCCAGTCTATTAATTGTTGCCGGGAAGCTAGAGTAAGTAGTTCGCCAGT
TAATAGTTTGCGCAACGTTGTTGCCATTGCTACAGGCATCGTGGTGTCACGCTCGTCGTT
TGGTATGGCTTCATTCAGCTCCGGTTCCCAACGATCAAGGCGAGTTACATGATCCCCCAT
GTTGTGCAAAAAAGCGGTTAGCTCCTTCGGTCCTCCGATCGTTGTCAGAAGTAAGTTGGC
CGCAGTGTTATCACTCATGGTTATGGCAGCACTGCATAATTCTCTTACTGTCATGCCATC
CGTAAGATGCTTTTCTGTGACTGGTGAGTACTCAACCAAGTCATTCTGAGAATAGTGTAT
GCGGCGACCGAGTTGCTCTTGCCCGGCGTCAATACGGGATAATACCGCGCCACATAGCAG
AACTTTAAAAGTGCTCATCATTGGAAAACGTTCTTCGGGGCGAAAACTCTCAAGGATCTT
ACCGCTGTTGAGATCCAGTTCGATGTAACCCACTCGTGCACCCAACTGATCTTCAGCATC
```

```
TTTTACTTTCACCAGCGTTTCTGGGTGAGCAAAAACAGGAAGGCAAAATGCCGCAAAAA

GGGAATAAGGGCGACACGGAAATGTTGAATACTCATACTCTTCCTTTTTCAATATTATTG

AAGCATTTATCAGGGTTATTGTCTCATGAGCGGATACATATTTGAATGTATTTAGAAAAA

TAAACAAATAGGGGTTCCGCGCACATTTCCCCGAAAAGTGCCACCTGACGTCTAAGAAAC

CATTATTATCATGACATTAACCTATAAAAATAGGCGTATCACGAGGCCCTTTCGTC
```

SEQ ID NO: 13
```
>neuC_N-acetylglucosamine-6-phosphate-2-
epimerase_GI_15193223_in_pG317
MKKILFITGSRADYSKIKSLMYRVQNSSEFELYIFATGMHLSKNFGYTVKELYKNGFKNI

YEFINYDKYYQTDKALATTIDGFSRYANELKPDLIVVHGDRIEPLAAAIVGALNNILVAH

IEGGEISGTIDDSLRHAISKLAHIHLVNDEFAKRRLMQLGEDEKSIFIIGSPDLELLNDN

KISLSEAKKYYDINYENYALLMFHPVTTEITSIKNQADNLVKALIQSNKNYIVIYPNNDL

GFELILQSYEEFKNNPRFKLFPSLRFEYFITLLKNADFIIGNSSCILKEALYLKTAGILV

GSRQNGRLGNENTLKVNANSDEILKAINTIHKKQDLFSAKLEILDSSKLFFEYLQSGDFF

KLSTQKVFKDIK
```

SEQ ID NO: 14
```
>neuB_sialic_acid_synthase_GI_15193222_in_pG317
MKEIKIQNIIISEEKAPLVVPEIGINHNGSLELAKIMVDAAFSAGAKIIKHQTHIVEDEM

SKAAKKVIPGNAKISIYEIMQKCALDYKDELALKEYTEKLGLVYLSTPFSRAGANRLEDM

GVSAFKIGSGECNNYPLIKHIAAFKKPMIVSTGMNSIESIKPTVKILLDNEIPFVLMHTT

NLYPTPHNLVRLNAMLELKKEFSCMVGLSDHTTDNLACLGAVVLGACVLERHFTDSMHRS

GPDIVCSMDTKALKELIIQSEQMAIIRGNNESKKAAKQEQVTIDFAFASVVSIKDIKKGE

VLSMDNIWVKRPGLGGISAAEFENILGKKALRDIENDAQLSYEDFA
```

SEQ ID NO: 15
```
>neuA_CMP-Neu5Ac_synthase_GI_15193224_in_pG317
MSLAIIPARGGSKGIKNKNLVLLNNKPLIYYTIKAALNAKSISKVVVSSDSDEILNYAKS

QNVDILKRPISLAQDDTTSDKVLLHALKFYKDYEDVVFLQPTSPLRTNIHINEAFNLYKN

SNANALISVSECDNKILKAFVCNDCGDLAGICNDEYPFMPRQKLPKTYMSNGAIYILKIK

EFLNNPSFLQSKTKHFLMDESSSLDIDCLEDLKKVEQIWKK
```

SEQ ID NO: 16
```
>AAF42258 lacto-N-neotetraose biosynthesis glycosyl
transferase LgtA [Neisseria meningitidis MC58].
MPSEAFRRHRAYRENKLQPLVSVLICAYNVEKYFAQSLAAVVNQTWRNLDILIVDDGSTD

GTLAIAQRFQEQDGRIRILAQPRNSGLIPSLNIGLDELAKSGGGGEYIARTDADDIAAPD

WIEKIVGEMEKDRSIIAMGAWLEVLSEEKDGNRLARHHEHGKIWKKPTRHEDIADFFPFG

NPIHNNTMIMRRSVIDGGLRYNTERDWAEDYQFWYDVSKLGRLAYYPEALVKYRLHANQV

SSKYSIRQHEIAQGIQKTARNDFLQSMGFKTRFDSLEYRQIKAVAYELLEKHLPEEDFER

ARRFLYQCFKRTDTLPAGAWLDFAADGRMRRLFTLRQYFGILHRLLKNR
```

SEQ ID NO: 17
```
>NP_207619 lipooligosaccharide 5G8 epitope
biosynthesis-associated protein Lex2B
[Helicobacter pylori 26695].
MRVFAISLNQKVCDTFGLVFRDTTTLLNSINATHHQAQIFDAIYSKTFEGGLHPLVKKHL

HPYFITQNIKDMGITTNLISEVSKFYYALKYHAKFMSLGELGCYASHYSLWEKCIELNEA

ICILEDDITLKEDFKEGLDFLEKHIQELGYIRLMHLLYDASVKSEPLSHKNHEIQERVGI

IKAYSEGVGTQGYVITPKIAKVFLKCSRKWVPVDTIMDATFIHGVKNLVLQPFVIADDE

QISTIARKEEPYSPKIALMRELHFKYLKYWQFV
```

-continued

SEQ ID NO: 18
[E.coli_WbgO_YP_003500090 putative glycosyl
transferase WbgO [Escherichia coli O55:H7
str. CB9615].
MIIDEAESAESTHPVVSVILPVNKKNPFLDEAINSILSQTFSSFEIIIVANCCTDDFYNE

LKHKVNDKIKLIRTNIAYLPYSLNKAIDLSNGEFIARMDSDDISHPDRFTKQVDFLKNNP

YVDVVGTNAIFIDDKGREINKTKLPEENLDIVKNLPYKCCIVHPSVMFRKKVIASIGGYM

FSNYSEDYELWNRLSLAKIKFQNLPEYLFYYRLHEGQSTAKKNLYMVMVNDLVIKMKCFF

LTGNINYLFGGIRTIASFIYCKYIK

SEQ ID NO: 19
>BAA35319 DNA-binding transcriptional dual regulator
nagC [Escherichia coli str. K-12 substr. W3110].
MTPGGQAQIGNVDLVKQLNSAAVYRLIDQYGPISRIQIAEQSQLAPASVTKITRQLIERG

LIKEVDQQASTGGRRAISIVTETRNFHAIGVRLGRHDATITLFDLSSKVLAEEHYPLPER

TQQTLEHALLNAIAQFIDSYQRKLRELIAISVILPGLVDPDSGKIHYMPHIQVENWGLVE

ALEERFKVTCFVGHDIRSLALAEHYFGASQDCEDSILVRVHRGTGAGIISNGRIFIGRNG

NVGEIGHIQVEPLGERCHCGNFGCLETIAANAAIEQRVLNLLKQGYQSRVPLDDCTIKTI

CKAANKGDSLASEVIEYVGRHLGKTIAIAINLFNPQKIVIAGEITEADKVLLPAIESCIN

TQALKAFRTNLPVVRSELDHRSAIGAFALVKRAMLNGILLQHLLEN

SEQ ID NO: 20
>NP_418185 L-glutamine:D-fructose-6-phosphate
aminotransferase glmS [Escherichia coli str.
K-12 substr. MG1655].
MCGIVGAIAQRDVAEILLEGLRRLEYRGYDSAGLAVVDAEGHMTRLRRLGKVQMLAQAAE

EHPLHGGTGIAHTRWATHGEPSEVNAHPHVSEHIVVVHNGIIENHEPLREELKARGYTFV

SETDTEVIAHLVNWELKQGGTLREAVLRAIPQLRGAYGTVIMDSRHPDTLLAARSGSPLV

IGLGMGENFIASDQLALLPVTRRFIFLEEGDIAEITRRSVNIFDKTGAEVKRQDIESNLQ

YDAGDKGIYRHYMQKEIYEQPNAIKNTLTGRISHGQVDLSELGPNADELLSKVEHIQILA

CGTSYNSGMVSRYWFESLAGIPCDVEIASEFRYRKSAVRRNSLMITLSQSGETADTLAGL

RLSKELGYLGSLAICNVPGSSLVRESDLALMTNAGTEIGVASTKAFTTQLTVLLMLVAKL

SRLKGLDASIEHDIVHGLQALPSRIEQMLSQDKRIEALAEDFSDKHHALFLGRGDQYPIA

LEGALKLKEISYIHAEAYAAGELKHGPLALIDADMPVIVVAPNNELLEKLKSNIEEVRAR

GGQLYVFADQDAGFVSSDNMHIIEMPHVEEVIAPIFYTVPLQLLAYHVALIKGTDVDQPR

NLAKSVTVE

SEQ ID NO: 21
>BAF92026 beta-galactoside alpha-2,6-sialyltransferase
[Photobacterium sp. JT-ISH-224].
MKNFLLLTLILLTACNNSEENTQSIIKNDINKTIIDEEYVNLEPINQSNISFTKHSWVQT

CGTQQLLTEQNKESISLSVVAPRLDDDEKYCFDFNGVSNKGEKYITKVTLNVVAPSLEVY

VDHASLPTLQQLMDIIKSEEENPTAQRYIAWGRIVPTDEQMKELNITSFALINNHTPADL

VQEIVKQAQTKHRLNVKLSSNTAHSFDNLVPILKELNSFNNVTVTNIDLYDDGSAEYVNL

YNWRDTLNKTDNLKIGKDYLEDVINGINEDTSNTGTSSVYNWQKLYPANYHFLRKDYLTL

EPSLHELRDYIGDSLKQMQWDGFKKFNSKQQELFLSIVNFDKQKLQNEYNSSNLPNFVFT

GTTVWAGNHEREYYAKQQINVINNAINESSPHYLGNSYDLFFKGHPGGGIINTLIMQNYP

SMVDIPSKISFEVLMMTDMLPDAVAGIASSLYFTIPAEKIKFIVFTSTETITDRETALRS

PLVQVMIKLGIVKEENVLFWADLPNCETGVCIAV

Provided below is the DNA sequence in Genbank format of the new configuration of genes engineered at the *Escherichia coli* thyA locus in strains used to produce N-acetylglucosamine-containing oligosaccharides.

```
LOCUS       E680_thyA::2.8RBS_lacZ 5877 bp DNA linear BCT
            04 MAR. 2013
DEFINITION  Escherichia coli str. K-12 substr. MG1655, complete genome.
ACCESSION   NC_000913
VERSION     NC_000913.2 GI:49175990
KEYWORDS    .
SOURCE      Escherichia coli str. K-12 substr. MG1655 (unknown)
ORGANISM    Escherichia coli str. K-12 substr. MG1655
            Bacteria; Proteobacteria; Gammaproteobacteria;
            Enterobacteriales;
            Enterobacteriaceae; Escherichia.
REFERENCE   1 (bases 1 to 4639675)
AUTHORS     Riley,M., Abe,T., Arnaud,M.B., Berlyn,M.K., Blattner,F.R.,
            Chaudhuri,R.R., Glasner,J.D., Horiuchi,T., Keseler,I.M.,
            Kosuge,T.,
            Mori,H., Perna,N.T., Plunkett,G. III, Rudd,K.E., Serres,M.H.,
            Thomas,G.H., Thomson,N.R., Wishart,D. and Wanner,B.L.
TITLE       Escherichia coli K-12: a cooperatively developed annotation
            snapshot--2005
JOURNAL     Nucleic Acids Res. 34 (1), 1-9 (2006)
PUBMED      16397293
REMARK      Publication Status: Online-Only
REFERENCE   2 (bases 1 to 4639675)
AUTHORS     Blattner,F.R., Plunkett,G. III, Bloch,C.A., Perna,N.T.,
            Burland,V.,
            Riley,M., Collado-Vides,J., Glasner,J.D., Rode,C.K.,
            Mayhew,G.F.,
            Gregor,J., Davis,N.W., Kirkpatrick,H.A., Goeden,M.A.,
            Rose,D.J.,
            Mau,B. and Shao,Y.
TITLE       The complete genome sequence of Escherichia coli K-12
JOURNAL     Science 277 (5331), 1453-1474 (1997)
PUBMED      9278503
REFERENCE   3 (bases 1 to 4639675)
AUTHORS     Arnaud,M., Berlyn,M.K.B., Blattner,F.R., Galperin,M.Y.,
            Glasner,J.D., Horiuchi,T., Kosuge,T., Mori,H., Perna,N.T.,
            Plunkett,G. III, Riley,M., Rudd,K.E., Serres,M.H., Thomas,G.H.
            and
            Wanner,B.L.
TITLE       Workshop on Annotation of Escherichia coli K-12
JOURNAL     Unpublished
REMARK      Woods Hole, Mass., on 14-18 Nov. 2003 (sequence
            corrections)
REFERENCE   4 (bases 1 to 4639675)
AUTHORS     Glasner,J.D., Perna,N.T., Plunkett,G. III, Anderson,B.D.,
            Bockhorst,J., Hu,J.C., Riley,M., Rudd,K.E. and Serres,M.H.
TITLE       ASAP: Escherichia coli K-12 strain MG1655 version m56
JOURNAL     Unpublished
REMARK      ASAP download 10 June 2004 (annotation updates)
REFERENCE   5 (bases 1 to 4639675)
```

-continued

```
AUTHORS     Hayashi,K., Morooka,N., Mori,H. and Horiuchi,T.
TITLE       A more accurate sequence comparison between genomes of
            Escherichia
            coli K12 W3110 and MG1655 strains
JOURNAL     Unpublished
REMARK      GenBank accessions AG613214 to AG613378 (sequence corrections)
REFERENCE   6  (bases 1 to 4639675)
AUTHORS     Perna, N. T.
TITLE       Escherichia coli K-12 MG1655 yqiK-rfaE intergenic region,
            genomic
            sequence correction
JOURNAL     Unpublished
REMARK      GenBank accession AY605712 (sequence corrections)
REFERENCE   7  (bases 1 to 4639675)
AUTHORS     Rudd,K.E.
TITLE       A manual approach to accurate translation start site
            annotation: an
            E. coli K-12 case study
JOURNAL     Unpublished
REFERENCE   8  (bases 1 to 4639675)
CONSRTM     NCBI Genome Project
TITLE       Direct Submission
JOURNAL     Submitted (04-MAR-2013) National Center for Biotechnology
            Information, NIH, Bethesda, MD 20894, USA
REFERENCE   9  (bases 1 to 4639675)
AUTHORS     Rudd,K.E.
TITLE       Direct Submission
JOURNAL     Submitted (06-FEB-2013) Department of Biochemistry and
            Molecular
            Biology, University of Miami Miller School of Medicine, 118
            GautierBldg., Miami, FL 33136, USA
REMARK      Sequence update by submitter
REFERENCE   10 (bases 1 to 4639675)
AUTHORS     Rudd,K.E.
TITLE       Direct Submission
JOURNAL     Submitted (24-APR-2007) Department of Biochemistry and
            Molecular
            Biology, University of Miami Miller School of Medicine, 118
            Gautier Bldg., Miami, FL 33136, USA
REMARK      Annotation update from ecogene.org as a multi-database
            collaboration
REFERENCE   11 (bases 1 to 4639675)
AUTHORS     Plunkett,G. III.
TITLE       Direct Submission
JOURNAL     Submitted (07-FEB-2006) Laboratory of Genetics, University of
            Wisconsin, 425G Henry Mall, Madison, WI 53706-1580, USA
REMARK      Protein updates by submitter
REFERENCE   12 (bases 1 to 4639675)
```

| | |
|---|---|
| AUTHORS | Plunkett,G. III. |
| TITLE | Direct Submission |
| JOURNAL | Submitted (10-JUN-2004) Laboratory of Genetics, University of Wisconsin, 425G Henry Mall, Madison, WI 53706-1580, USA |
| REMARK | Sequence update by submitter |
| REFERENCE | 13 (bases 1 to 4639675) |
| AUTHORS | Plunkett,G. III. |
| TITLE | Direct Submission |
| JOURNAL | Submitted (13-OCT-1998) Laboratory of Genetics, University of Wisconsin, 425G Henry Mall, Madison, WI 53706-1580, USA |
| REFERENCE | 14 (bases 1 to 4639675) |
| AUTHORS | Blattner,F.R. and Plunkett,G. III. |
| TITLE | Direct Submission |
| JOURNAL | Submitted (02-SEP-1997) Laboratory of Genetics, University of Wisconsin, 425G Henry Mall, Madison, WI 53706-1580, USA |
| REFERENCE | 15 (bases 1 to 4639675) |
| AUTHORS | Blattner,F.R. and Plunkett,G. III. |
| TITLE | Direct Submission |
| JOURNAL | Submitted (16-JAN-1997) Laboratory of Genetics, University of Wisconsin, 425G Henry Mall, Madison, WI 53706-1580, USA |
| COMMENT | PROVISIONAL REFSEQ: This record has not yet been subject to final<br>NCBI review. The reference sequence is identical to U00096.<br>On Jun 24, 2004 this sequence version replaced gi:16127994.<br>Current U00096 annotation updates are derived from EcoGene ecogene.org. Suggestions for updates can be sent to Dr.<br>Kenneth Rudd (krudd@miami.edu). These updates are being generated<br>from a collaboration that also includes ASAP/ERIC,the Coli Genetic<br>Stock Center, EcoliHub, EcoCyc, RegulonDB and UniProtKB/Swiss-Prot. |
| COMPLETENESS: | full length. |
| FEATURES | Location/Qualifiers |
| gene | complement(<1..245)<br>/gene="ppdA"<br>/locus_tag="b2826"<br>/gene_synonym="ECK2822; JW2794"<br>/db_xref="EcoGene:EG12081"<br>/db_xref="GeneID:945393" |
| CDS | complement(<1..245)<br>/gene="ppdA"<br>/locus_tag="b2826"<br>/gene_synonym="ECK2822; JW2794"<br>/function="putative enzyme; Not classified"<br>/GO_component="GO:0009289 - pilus"<br>/GO_process="GO:0009101 - glycoprotein biosynthetic process"<br>/note="prepilin peptidase dependent protein A"<br>/codon_start=1<br>/transl_table=11<br>/product="hypothetical protein"<br>/protein_id="NP_417303.1"<br>/db_xref="GI:16130730"<br>/db_xref="ASAP:ABE-0009266"<br>/db_xref="UniProtKB/Swiss-Prot:P33554"<br>/db_xref="EcoGene:EG12081"<br>/db_xref="GeneID:945393" |

(SEQ ID NO: 22)
/translation="MKTQRGYTLIETLVAMLILVMLSASGLYGWQYWQQSQRLWQTAS

QARDYLLYLREDANWHNRDHSISVIREGTLWCLVSSAAGANTCHGSSPLVFVPRWPEV

EMSDLTPSLAFFGLRNTAWAGHIRFKNSTGEWWLVVSPWGRLRLCQQGETEGCL"

| | |
|---|---|
| source | join(<1..449,4852..+225877)<br>/organism="*Escherichia coli* str.K-12 substr. MG1655"<br>/mol_type="genomic DNA"<br>/strain="K-12"<br>/sub_strain="MG1655"<br>/db_xref="taxon:511145" |
| primer | 346..366<br>/note=cagtcagtcaggcgccTTCGGGAAGGCGTCTCGAAGA (SEQ ID NO: 23)<br>/label=0268-THYA-R |
| misc_feature | complement(388..394)<br>/feature_type="Hairpin loop"<br>/label=Terminator |
| primer | 400..449<br>/note=GGCGTCGGCTCTGGCAGGATGTTTCGTAATTAGATAGCCACCGGCGCTTTag<br>GaaacctactATGACCATGATTACGGATTCAC (SEQ ID NO: 24)<br>/label="50bp thyA 3 prime homology" |
| primer | 400..483<br>/note=GGCGTCGGCTCTGGCAGGATGTTTCGTAATTAGATAGCCACCGGCGCTTTat<br>taaacctactATGACCATGATTACGGATTCAC (SEQ ID NO: 25)<br>/label=1389-thyAKANlacZ-R-2-8 |
| primer | 400..483<br>/note=GGCGTCGGCTCTGGCAGGATGTTTCGTAATTAGATAGCCACCGGCGCTTTCt<br>tCaacctactATGACCATGATTACGGATTCAC (SEQ ID NO: 26)<br>/label=1516-thyAKANlacZ-R-0-8 |
| primer | 400..483<br>/note=GGCGTCGGCTCTGGCAGGATGTTTCGTAATTAGATAGCCACCGGCGCTTTag<br>GaaacctactATGACCATGATTACGGATTCAC (SEQ ID NO: 27)<br>/label="1041-thyAKANlacZ-R (4-8)" |
| misc_feature | complement(401..407)<br>/feature_type="Hairpin loop"<br>/label=Terminator |
| primer | 405..472<br>/note=CGGCTCTGGCAGGATGTTTCGTAATTAGATAGCCACCGGCGCTTTaTTaaac<br>ctactATGACCATGAT (SEQ ID NO: 28)<br>/label=1394-2/8-F |
| gene | complement(join(429..449,4852..4854))<br>/gene="thyA" |
| CDS | complement(join(429..449,4852..4854))<br>/gene="thyA"<br>/note="ECK2823:JW2795:b2827"<br>/codon_start=1<br>/transl_table=11<br>/product="thymidylate synthetase"<br>/protein_id="BAE76896.1"<br>/db_xref="GI:85675643" |

(SEQ ID NO: 43)
/translation="MKQYLELMQKVLDEGTQKNDRTGTGTLSIFGHQMRFNLQDGFPL

VTTKRCHLRSIIHELLWFLQGDTNIAYLHENNVTIWDEWADENGDLGPVYGKQWRAWP

TPDGRHIDQITTVLNQLKNDPDSRRIIVSAWNVGELDKMALAPCHAFFQFYVADGKLS

CQLYQRSCDVFLGLPFNIASYALLVHMMAQQCDLEVGDFVWTGGDTHLYSNHMDQTHL

QLSREPRPLPKLIIKRKPESIFDYRFEDFEIEGYDPHPGIKAPVAI"

| | |
|---|---|
| RBS | 450..461<br>/label="2.8 RBS" |

```
source          450..3536
                /organism="Escherichia coli W3110"
                /mol_type="genomic DNA"
                /strain="K-12"
                /sub_strain="W3110"
                /db_xref="taxon:316407"
                /note="synonym: Escherichia coli str. K12 substr.
                W3110"
misc_feature    450..4851
                /feature_type=Insertion
                /note="originates from KanR-lacZRBS (E403)"
                /label=Insert
misc_feature    449"450
                /feature type="RBS variation site"
                /label="C in 0/8"
misc_feature    450..453
                /feature_type="RBS variation site"
                /label="CTTC in 0/8"
misc_feature    451..452
                /feature_type="RBS variation site"
                /label="GG in 4/8"
misc_feature    451..452
                /feature_type="RBS variation site"
                /label="TT in 2/8"
CDS             462..3536
                /gene="lacZ"
                /note="ECK0341:JW0335:b0344"
                /codon_start=1
                /transl_table=11
                /product="beta-D-galactosidase"
                /protein_id="BAE76126.1"
                /db_xref="GI:85674486"
```

(SEQ ID NO: 29)

/translation="MTMITDSLAVVLQRRDWENPGVTQLNRLAAHPPFASWRNSEEAR

TDRPSQQLRSLNGEWRFAWFPAPEAVPESWLECDLPEADTVVVPSNWQMHGYDAPIYT

NVTYPITVNPPFVPTENPTGCYSLTFNVDESWLQEGQTRIIFDGVNSAFHLWCNGRWV

GYGQDSRLPSEFDLSAFLRAGENRLAVMVLRWSDGSYLEDQDMWRMSGIFRDVSLLHK

PTTQISDFHVATRFNDDFSRAVLEAEVQMCGELRDYLRVTVSLWQGETQVASGTAPFG

GEIIDERGGYADRVTLRLNVENPKLWSAEIPNLYRAVVELHTADGTLIEAEACDVGFR

EVRIENGLLLLNGKPLLIRGVNRHEHHPLHGQVMDEQTMVQDILLMKQNNFNAVRCSH

YPNHPLWYTLCDRYGLYVVDEANIETHGMVPMNRLTDDPRWLPAMSERVTRMVQRDRN

HPSVIIWSLGNESGHGANHDALYRWIKSVDPSRPVQYEGGGADTTATDIICPMYARVD

EDQPFPAVPKWSIKKWLSLPGETRPLILCEYAHAMGNSLGGFAKYWQAFRQYPRLQGG

FVWDWVDQSLIKYDENGNPWSAYGGDFGDTPNDRQFCMNGLVFADRTPHPALTEAKHQ

QQFFQFRLSGQTIEVTSEYLFRHSDNELLHWMVALDGKPLASGEVPLDVAPQGKQLIE

LPELPQPESAGQLWLTVRVVQPNATAWSEAGHISAWQQWRLAENLSVTLPAASHAIPH

LTTSEMDFCIELGNKRWQFNRQSGFLSQMWIGDKKQLLTPLRDQFTRAPLDNDIGVSE

ATRIDPNAWVERWKAAGHYQAEAALLQCTADTLADAVLITTAHAWQHQGKTLFISRKT

YRIDGSGQMAITVDVEVASDTPHPARIGLNCQLAQVAERVNWLGLGPQENYPDRLTAA

CFDRWDLPLSDMYTPYVFPSENGLRCGTRELNYGPHQWRGDFQFNISRYSQQQLMETS

HRHLLHAEEGTWLNIDGFHMGIGGDDSWSPSVSAEFQLSAGRYHYQLVWCQK"

```
                /label="wild-type lacZ+CDS"
primer          complement(1325..1345)
                /note=TTCAGACGTAGTGTGACGCGA
                /label=1042-thyAlacZcheck
```

```
primer          2754..2776
                /note=TTTCTTTCACAGATGTGGATTGG
                /label="1395-mid lacZ-F"

primer          complement(2779..2801)
                /note=CGGCGTCAGCAGTTGTTTTTTAT
                /label="1396-mid lacZ-R"

mutation        2793
                /label="C in MG1655 lacZ (silent change)"

scar            complement(3549..3567)
                /label="KD13 downstream scar sequence"

source          3549..4851
                /organism="Template plasmid pKD13"
                /mol_type="genomic DNA"
                /db_xref="taxon:170493"

primer          3549..3568
                /label="0339 Plw-P2b"

repeat unit     3568..3579
                /label="FLP site"

misc_feature    complement(3568..3601)
                /feature type="FRT site"
                /label="34bp FRT site"

note            complement(3568..4789)
                /label="excised region upon pCP20 introduction"

repeat unit     complement(3590..3601)
                /label="Flp site"

misc_feature    complement(3602..3615)
                /feature type="FRT site"
                /note="natural FRT site"
                /label="upstream FRT site"

repeat_unit     complement(3604..3615)
                /label="Flp site"

misc_feature    complement(3628..4422)
                /feature type="CDS (KAN resistance)"
                /note="kanamycin resistance"
                /codon_start=1
                /transl_table=11
                /product="Tn5 neomycin phosphotransferase"
                /protein_id="AAL02037.1"
                /db_xref="GI:15554336"
```
(SEQ ID NO: 30)
```
/translation="MIEQDGLHAGSPAAWVERLFGYDWAQQTIGCSDAAVFRLSAQGR

PVLFVKTDLSGALNELQDEAARLSWLATTGVPCAAVLDVVTEAGRDWLLLGEVPGQDL

LSSHLAPAEKVSIMADAMRRLHTLDPATCPFDHQAKHRIERARTRMEAGLVDQDDLDE

EHQGLAPAELFARLKARMPDGEDLVVTHGDACLPNIMVENGRFSGFIDCGRLGVADRY

QDIALATRDIAEELGGEWADRFLVLYGIAAPDSQRIAFYRLLDEFF"

primer          complement(3677..3696)
                /label="0389 KD13 K4"

primer_bind     3791..3810
                /label="common priming site kt"

primer          3791..3810
                /label="0344 Wanner Kt primer"

mutation        3811
                /label="A in wt (silent change)"

primer          complement(4242..4261)
                /label="0343 Wanner K2 primer"

primer_bind     4261..4280
                /label="common priming site k2"
```

```
                                                     -continued primer_bind      4352..4371
                 /label="common priming site k1"

primer           4352..4371
                 /label="0342 Wanner K1 primer"

repeat_unit      4790..4801
                 /label="FLP site"

scar             complement(4790..4851)
                 /label="KD13 upstream scar"

misc_feature     complement(4790..4823)
                 /feature_type="FRT site"
                 /label="34bp FRT site"

repeat_unit      complement(4812..4823)
                 /label="Flp site"

primer           complement(4832..4851)
                 /label="0338 P4w-P1b"

primer           complement(4832..4901)
                 /note=TCTGGGCATATCGTCGCAGCCCACAGCAACACGTTTCCTGAGGAACCATGAT
                 TCCGGGGATCCGTCGACC (SEQ ID NO: 31)
                 /label=1040-thyAKANlacZ-F Site             complement(4858..4863)
                 /site_type="binding site"
                 /label="thyA RBS"

gene             complement(4861..5736)
                 /gene="lgt"

CDS              complement(4861..5736)
                 /gene="lgt"
                 /note="ECK2824:JW2796:b2828"
                 /codon_start=1
                 /transl_table=11
                 /product="phosphatidylglycerol-prolipoprotein
                 diacylglyceryl transferase"
                 /protein_id="BAE76897.1"
                 /db_xref="GI:85675644"
                                                                  (SEQ ID NO: 32)
/translation="MTSSYLHFPEFDPVIFSIGPVALHWYGLMYLVGFIFAMWLATRR
ANRPGSGWTKNEVENLLYAGFLGVFLGGRIGYVLFYNFPQFMADPLYLFRVWDGGMSF
HGGLIGVIVVMIIFARRTKRSFFQVSDFIAPLIPFGLGAGRLGNFINGELWGRVDPNF
PFAMLFPGSRTEDILLLQTNPQWQSIFDTYGVLPRHPSQLYELLLEGVVLFIILNLYI
RKPRPMGAVSGLFLIGYGAFRIIVEFFRQPDAQFTGAWVQYISMGQILSIPMIVAGVI
MMVWAYRRSPQQHVS"

promoter         complement(4957..4962)
                 /label="thyA WEAK -10"

promoter         complement(4978..4983)
                 /label="thyA -35"

primer           complement(5076..5099)
                 /note=cagtcagtcaggcgccTCCTCAACCTGTATATTCGTAAAC
                 (SEQ ID NO: 33)
                 /label=0267-THYA-F Site             complement(5739..5744)
                 /site_type="binding site"
                 /label="lgt RBS"

promoter         complement(5823..5828)
                 /label="lgt -10 (strong)"

ORIGIN
                                                              (SEQ ID NO: 34)
     1           GCAGCGGAAC TCACAAGGCA CCATAACGTC CCCTCCCTGA TAACGCTGAT ACTGTGGTCG
    61           CGGTTATGCC AGTTGGCATC TTCACGTAAA TAGAGCAAAT AGTCCCGCGC CTGGCTGGCG
```

-continued

```
 121        GTTTGCCATA GCCGTTGCGA CTGCTGCCAG TATTGCCAGC CATAGAGTCC ACTTGCGCTT
 181        AGCATGACCA AAATCAGCAT CGCGACCAGC GTTTCAATCA GCGTATAACC ACGTTGTGTT
 241        TTCATGCCGG CAGTATGGAG CGAGGAGAAA AAAAGACGAG GGCCAGTTTC TATTTCTTCG
 301        GCGCATCTTC CGGACTATTT ACGCCGTTGC AGGACGTTGA AAAATTTCGG GAAGGCGTCT
 361        CGAAGAATTT AACGGAGGGT AAAAAAACCG ACGCACACTG GCGTCGGCTC TGGCAGGATG
 421        TTTCGTAATT AGATAGCCAC CGGCGCTTTa ttaaacctac tATGACCATG ATTACGGATT
 481        CACTGGCCGT CGTTTTACAA CGTCGTGACT GGGAAAACCC TGGCGTTACC CAACTTAATC
 541        GCCTTGCAGC ACATCCCCCT TTCGCCAGCT GGCGTAATAG CGAAGAGGCC CGCACCGATC
 601        GCCCTTCCCA ACAGTTGCGC AGCCTGAATG GCGAATGGCG CTTTGCCTGG TTTCCGGCAC
 661        CAGAAGCGGT GCCGGAAAGC TGGCTGGAGT GCGATCTTCC TGAGGCCGAT ACTGTCGTCG
 721        TCCCCTCAAA CTGGCAGATG CACGGTTACG ATGCGCCCAT CTACACCAAC GTGACCTATC
 781        CCATTACGGT CAATCCGCCG TTTGTTCCCA CGGAGAATCC GACGGGTTGT TACTCGCTCA
 841        CATTTAATGT TGATGAAAGC TGGCTACAGG AAGGCCAGAC GCGAATTATT TTTGATGGCG
 901        TTAACTCGGC GTTTCATCTG TGGTGCAACG GGCGCTGGGT CGGTTACGGC CAGGACAGTC
 961        GTTTGCCGTC TGAATTTGAC CTGAGCGCAT TTTTACGCGC CGGAGAAAAC CGCCTCGCGG
1021        TGATGGTGCT GCGCTGGAGT GACGGCAGTT ATCTGGAAGA TCAGGATATG TGGCGGATGA
1081        GCGGCATTTT CCGTGACGTC TCGTTGCTGC ATAAACCGAC TACACAAATC AGCGATTTCC
1141        ATGTTGCCAC TCGCTTTAAT GATGATTTCA GCCGCGCTGT ACTGGAGGCT GAAGTTCAGA
1201        TGTGCGGCGA GTTGCGTGAC TACCTACGGG TAACAGTTTC TTTATGGCAG GGTGAAACGC
1261        AGGTCGCCAG CGGCACCGCG CCTTTCGGCG GTGAAATTAT CGATGAGCGT GGTGGTTATG
1321        CCGATCGCGT CACACTACGT CTGAACGTCG AAAACCCGAA ACTGTGGAGC GCCGAAATCC
1381        CGAATCTCTA TCGTGCGGTG GTTGAACTGC ACACCGCCGA CGGCACGCTG ATTGAAGCAG
1441        AAGCCTGCGA TGTCGGTTTC GCGAGGTGC GGATTGAAAA TGGTCTGCTG CTGCTGAACG
1501        GCAAGCCGTT GCTGATTCGA GGCGTTAACC GTCACGAGCA TCATCCTCTG CATGGTCAGG
1561        TCATGGATGA GCAGACGATG GTGCAGGATA TCCTGCTGAT GAAGCAGAAC AACTTTAACG
1621        CCGTGCGCTG TTCGCATTAT CCGAACCATC CGCTGTGGTA CACGCTGTGC GACCGCTACG
1681        GCCTGTATGT GGTGGATGAA GCCAATATTG AAACCCACGG CATGGTGCCA ATGAATCGTC
1741        TGACCGATGA TCCGCGCTGG CTACCGGCGA TGAGCGAACG CGTAACGCGA ATGGTGCAGC
1801        GCGATCGTAA TCACCCGAGT GTGATCATCT GGTCGCTGGG GAATGAATCA GGCCACGGCG
1861        CTAATCACGA CGCGCTGTAT CGCTGGATCA AATCTGTCGA TCCTTCCCGC CCGGTGCAGT
1921        ATGAAGGCGC CGGAGCCGAC ACCACGGCCA CCGATATTAT TTGCCCGATG TACGCGCGCG
1981        TGGATGAAGA CCAGCCCTTC CCGGCTGTGC CGAAATGGTC CATCAAAAAA TGGCTTTCGC
2041        TACCTGGAGA GACGCGCCCG CTGATCCTTT GCGAATACGC CCACGCGATG GGTAACAGTC
2101        TTGGCGGTTT CGCTAAATAC TGGCAGGCGT TTCGTCAGTA TCCCCGTTTA CAGGGCGGCT
2161        TCGTCTGGGA CTGGGTGGAT CAGTCGCTGA TTAAATATGA TGAAAACGGC AACCCGTGGT
2221        CGGCTTACGG CGGTGATTTT GGCGATACGC CGAACGATCG CCAGTTCTGT ATGAACGGTC
2281        TGGTCTTTGC CGACCGCACG CCGCATCCAG CGCTGACGGA AGCAAAACAC CAGCAGCAGT
2341        TTTTCCAGTT CCGTTTATCC GGGCAAACCA TCGAAGTGAC CAGCGAATAC CTGTTCCGTC
2401        ATAGCGATAA CGAGCTCCTG CACTGGATGG TGGCGCTGGA TGGTAAGCCG CTGGCAAGCG
2461        GTGAAGTGCC TCTGGATGTC GCTCCACAAG GTAAACAGTT GATTGAACTG CCTGAACTAC
```

-continued

```
2521  CGCAGCCGGA GAGCGCCGGG CAACTCTGGC TCACAGTACG CGTAGTGCAA CCGAACGCGA
2581  CCGCATGGTC AGAAGCCGGG CACATCAGCG CCTGGCAGCA GTGGCGTCTG GCGGAAAACC
2641  TCAGTGTGAC GCTCCCCGCC GCGTCCCACG CCATCCCGCA TCTGACCACC AGCGAAATGG
2701  ATTTTTGCAT CGAGCTGGGT AATAAGCGTT GGCAATTTAA CCGCCAGTCA GGCTTTCTTT
2761  CACAGATGTG GATTGGCGAT AAAAACAAC TGtTGACGCC GCTGCGCGAT CAGTTCACCC
2821  GTGCACCGCT GGATAACGAC ATTGGCGTAA GTGAAGCGAC CCGCATTGAC CCTAACGCCT
2881  GGGTCGAACG CTGGAAGGCG GCGGGCCATT ACCAGGCCGA AGCAGCGTTG TTGCAGTGCA
2941  CGGCAGATAC ACTTGCTGAT GCGGTGCTGA TTACGACCGC TCACGCGTGG CAGCATCAGG
3001  GGAAAACCTT ATTTATCAGC CGGAAAACCT ACCGGATTGA TGGTAGTGGT CAAATGGCGA
3061  TTACCGTTGA TGTTGAAGTG GCGAGCGATA CACCGCATCC GGCGCGGATT GGCCTGAACT
3121  GCCAGCTGGC GCAGGTAGCA GAGCGGGTAA ACTGGCTCGG ATTAGGGCCG CAAGAAAACT
3181  ATCCCGACCG CCTTACTGCC GCCTGTTTTG ACCGCTGGGA TCTGCCATTG TCAGACATGT
3241  ATACCCCGTA CGTCTTCCCG AGCGAAAACG GTCTGCGCTG CGGGACGCGC GAATTGAATT
3301  ATGGCCCACA CCAGTGGCGC GGCGACTTCC AGTTCAACAT CAGCCGCTAC AGTCAACAGC
3361  AACTGATGGA AACCAGCCAT CGCCATCTGC TGCACGCGGA AGAAGGCACA TGGCTGAATA
3421  TCGACGGTTT CCATATGGGG ATTGGTGGCG ACGACTCCTG GAGCCCGTCA GTATCGGCGG
3481  AATTCCAGCT GAGCGCCGGT CGCTACCATT ACCAGTTGGT CTGGTGTCAA AAATAAGCGG
3541  CCGCtTTATG TAGGCTGGAG CTGCTTCGAA GTTCCTATAC TTTCTAGAGA ATAGGAACTT
3601  CGGAATAGGA ACTTCAAGAT CCCCTTATTA GAAGAACTCG TCAAGAAGGC GATAGAAGGC
3661  GATGCGCTGC GAATCGGGAG CGGCGATACC GTAAAGCACG AGGAAGCGGT CAGCCCATTC
3721  GCCGCCAAGC TCTTCAGCAA TATCACGGGT AGCCAACGCT ATGTCCTGAT AGCGGTCCGC
3781  CACACCCAGC CGGCCACAGT CGATGAATCC tGAAAAGCGG CCATTTTCCA CCATGATATT
3841  CGGCAAGCAG GCATCGCCAT GGGTCACGAC GAGATCCTCG CCGTCGGGCA TGCGCGCCTT
3901  GAGCCTGGCG AACAGTTCGG CTGGCGCGAG CCCCTGATGC TCTTCGTCCA GATCATCCTG
3961  ATCGACAAGA CCGGCTTCCA TCCGAGTACG TGCTCGCTCG ATGCGATGTT TCGCTTGGTG
4021  GTCGAATGGG CAGGTAGCCG GATCAAGCGT ATGCAGCCGC CGCATTGCAT CAGCCATGAT
4081  GGATACTTTC TCGGCAGGAG CAAGGTGAGA TGACAGGAGA TCCTGCCCCG GCACTTCGCC
4141  CAATAGCAGC CAGTCCCTTC CCGCTTCAGT GACAACGTCG AGCACAGCTG CGCAAGGAAC
4201  GCCCGTCGTG GCCAGCCACG ATAGCCGCGC TGCCTCGTCC TGCAGTTCAT TCAGGGCACC
4261  GGACAGGTCG GTCTTGACAA AAAGAACCGG GCGCCCCTGC GCTGACAGCC GGAACACGGC
4321  GGCATCAGAG CAGCCGATTG TCTGTTGTGC CCAGTCATAG CCGAATAGCC TCTCCACCCA
4381  AGCGGCCGGA GAACCTGCGT GCAATCCATC TTGTTCAATC ATGCGAAACG ATCCTCATCC
4441  TGTCTCTTGA TCAGATCTTG ATCCCCTGCG CCATCAGATC CTTGGCGGCA AGAAAGCCAT
4501  CCAGTTTACT TTGCAGGGCT TCCCAACCTT ACCAGAGGGC GCCCCAGCTG GCAATTCCGG
4561  TTCGCTTGCT GTCCATAAAA CCGCCCAGTC TAGCTATCGC CATGTAAGCC CACTGCAAGC
4621  TACCTGCTTT CTCTTTGCGC TTGCGTTTTC CCTTGTCCAG ATAGCCCAGT AGCTGACATT
4681  CATCCGGGGT CAGCACCGTT TCTGCGGACT GGCTTTCTAC GTGTTCCGCT TCCTTTAGCA
4741  GCCCTTGCGC CCTGAGTGCT TGCGGCAGCG TGAGCTTCAA AAGCGCTCTG AAGTTCCTAT
4801  ACTTTCTAGA GAATAGGAAC TTCGAACTGC AGGTCGACGG ATCCCCGGAA TCATGGTTCC
4861  TCAGGAAACG TGTTGCTGTG GGCTGCGACG ATATGCCCAG ACCATCATGA TCACACCCGC
4921  GACAATCATC GGGATGGAAA GAATTTGCCC CATGCTGATG TACTGCACCC AGGCACCGGT
```

-continued

```
4981        AAACTGCGCG TCGGGCTGGC GGAAAAACTC AACAATGATG CGAAACGCGC CGTAACCAAT
5041        CAGGAACAAA CCTGAGACAG CTCCCATTGG GCGTGGTTTA CGAATATACA GGTTGAGGAT
5101        AATAAACAGC ACCACACCTT CCAGCAGCAG CTCGTAAAGC TGTGATGGGT GGCGCGGCAG
5161        CACACCGTAA GTGTCGAAAA TGGATTGCCA CTGCGGGTTG GTTTGCAGCA GCAAAATATC
5221        TTCTGTACGG GAGCCAGGGA ACAGCATGGC AAACGGAAG TTCGGGTCAA CGCGGCCCCA
5281        CAATTCACCG TTAATAAAGT TGCCCAGACG CCCGGCACCA AGACCAAACG GAATGAGTGG
5341        TGCGATAAAA TCAGAGACCT GGAAGAAGGA ACGTTTAGTA CGGCGGGCGA AGATAATCAT
5401        CACCACGATA ACGCCAATCA GGCCGCCGTG GAAAGACATG CCGCCGTCCC AGACACGGAA
5461        CAGATACAGC GGATCGGCCA TAAACTGCGG GAAATTGTAG AACAGAACAT AACCAATACG
5521        TCCCCCGAGG AAGACGCCGA GGAAGCCCGC ATAGAGTAAG TTTTCAACTT CATTTTTGGT
5581        CCAGCCGCTG CCCGGACGAT TCGCCCGTCG TGTTGCCAGC CACATTGCAA AAATGAAACC
5641        CACCAGATAC ATCAGGCCGT ACCAGTGAAG CGCCACGGGT CCTATTGAGA AAATGACCGG
5701        ATCAAACTCC GGAAAATGCA GATAGCTACT GGTCATCTGT CACCACAAGT TCTTGTTATT
5761        TCGCTGAAAG AGAACAGCGA TTGAAATGCG CGCCGCAGGT TTCAGGCGCT CCAAAGGTGC
5821        GAATAATAGC ACAAGGGGAC CTGGCTGGTT GCCGGATACC GTTAAAAGAT ATGTATA
//
```

Provided below is the DNA sequence in Genbank format of the configuration of genes at the *Escherichia coli* nan locus, and the details of the deletion endpoints found in engineered strains E1017 and E1018.

```
LOCUS         W3110_nanRATEKyhcH_region 5861 bp DNA linear BCT
              19FEB. 2009

DEFINITION    Escherichia coli str. K-12 substr. W3110 strain K-12.

ACCESSION     AC_000091

VERSION       AC_000091.1 GI:89106884

KEYWORDS      .

SOURCE        Escherichia coli str. K-12 substr. W3110 (unknown)

ORGANISM      Escherichia coli str. K-12 substr. W3110
              Bacteria; Proteobacteria; Gammaproteobacteria;
              Enterobacteriales;
              Enterobacteriaceae; Escherichia.

REFERENCE     1

AUTHORS       Riley,M., Abe,T., Arnaud,M.B., Berlyn,M.K., Blattner,F.R.,
              Chaudhuri,R.R., Glasner,J.D., Horiuchi,T., Keseler,I.M.,
              Kosuge,T.,
              Mori,H., Perna,N.T., Plunkett,G. III, Rudd,K.E., Serres,M.H.,
              Thomas,G.H., Thomson,N.R., Wishart,D. and Wanner,B.L.

TITLE         Escherichia coli K-12: a cooperatively developed annotation
              snapshot--2005

JOURNAL       Nucleic Acids Res. 34 (1), 1-9 (2006)

PUBMED        16397293

REMARK        Publication Status: Online-Only

REFERENCE     2 (bases 1 to 4646332)

AUTHORS       Hayashi,K., Morooka,N., Yamamoto,Y., Fujita,K., Isono,K.,
              Choi, S., Ohtsubo,E., Baba,T., Wanner,B.L., Mori,H. and
              Horiuchi,T.
```

| | |
|---|---|
| | -continued |
| TITLE | Highly accurate genome sequences of *Escherichia coli* K-12 strains<br>MG1655 and W3110 |
| JOURNAL | Mol. Syst. Biol. 2, 2006 (2006) |
| PUBMED | 16738553 |
| REFERENCE | 3 |
| AUTHORS | Yamamoto,Y., Aiba,H., Baba,T., Hayashi,K., Inada,T., Isono,K., Itoh,T., Kimura,S., Kitagawa,M., Makino,K., Miki,T., Mitsuhashi,N., Mizobuchi,K., Mori,H., Nakade,S., Nakamura,Y., Nashimoto,H., Oshima,T., Oyama,S., Saito,N., Sampei,G., Satoh,Y., Sivasundaram,S., Tagami,H., Takahashi,H., Takeda,J., Takemoto,K., Uehara,K., Wada,C., Yamagata,S. and Horiuchi,T. |
| TITLE | Construction of a contiguous 874-kb sequence of the *Escherichia*<br>*coli*-K12 genome corresponding to 50.0-68.8 min on the linkage map<br>and analysis of its sequence features |
| JOURNAL | DNA Res. 4 (2), 91-113 (1997) |
| PUBMED | 9205837 |
| REFERENCE | 4 |
| AUTHORS | Itoh,T., Aiba,H., Baba,T., Hayashi,K., Inada,T., Isono,K., Kasai,H., Kimura,S., Kitakawa,M., Kitagawa,M., Makino,K., Miki,T., Mizobuchi,K., Mori,H., Mori,T., Motomura,K., Nakade,S., Nakamura,Y., Nashimoto,H., Nishio,Y., Oshima,T., Saito,N., Sampei,G., Seki,Y., Sivasundaram,S., Tagami,H., Takeda,J., Takemoto,K., Wada,C., Yamamoto,Y. and Horiuchi,T. |
| TITLE | A 460-kb DNA sequence of the *Escherichia coli* K-12 genome corresponding to the 40.1-50.0 min region on the linkage map |
| JOURNAL | DNA Res. 3 (6), 379-392 (1996) |
| PUBMED | 9097040 |
| REFERENCE | 5 |
| AUTHORS | Aiba,H., Baba,T., Hayashi,K., Inada,T., Isono,K., Itoh,T., Kasai,H., Kashimoto,K., Kimura,S., Kitakawa,M., Kitagawa,M., Makino,K., Miki,T., Mizobuchi,K., Mori,H., Mori,T., Motomura,K., Nakade,S., Nakamura,Y., Nashimoto,H., Nishio,Y., Oshima,T., Saito,N., Sampei,G., Seki,Y., Sivasundaram,S., Tagami,H., Takeda,J., Takemoto,K., Takeuchi,Y., Wada,C., Yamamoto,Y. and Horiuchi,T. |
| TITLE | A 570-kb DNA sequence of the *Escherichia coli* K-12 genome corresponding to the 28.0-40.1 min region on the linkage map |
| JOURNAL | DNA Res. 3 (6), 363-377 (1996) |
| PUBMED | 9097039 |
| REFERENCE | 6 |
| AUTHORS | Arn,E.A. and Abelson,J.N. |
| TITLE | The 2'-5' RNA ligase of *Escherichia coli* Purification, cloning,<br>and genomic disruption |
| JOURNAL | J. Biol. Chem. 271 (49), 31145-31153 (1996) |
| PUBMED | 8940112 |
| REFERENCE | 7 |
| AUTHORS | Oshima,T., Aiba,H., Baba,T., Fujita,K., Hayashi,K., Honjo,A., Ikemoto,K., Inada,T., Itoh,T., Kajihara,M., Kanai,K., |

| | -continued |
|---|---|
| | Kashimoto,K., Kimura,S., Kitagawa,M., Makino,K., Masuda,S., Miki,T., Mizobuchi,K., Mori,H., Motomura,K., Nakamura,Y., Nashimoto,H., Nishio,Y., Saito,N., Sampei,G., Seki,Y., Tagami,H., Takemoto,K., Wada,C., Yamamoto,Y., Yano,M. and Horiuchi,T. |
| TITLE | A 718-kb DNA sequence of the *Escherichia coli* K-12 genome corresponding to the 12.7-28.0 min region on the linkage map |
| JOURNAL | DNA Res. 3 (3), 137-155 (1996) |
| PUBMED | 8905232 |
| REFERENCE | 8 |
| AUTHORS | Fujita,N., Mori,H., Yura,T. and Ishihama,A. |
| TITLE | Systematic sequencing of the *Escherichia coli* genome: analysis of the 2.4-4.1 min (110,917-193,643 bp) region |
| JOURNAL | Nucleic Acids Res. 22 (9), 1637-1639 (1994) |
| PUBMED | 8202364 |
| REFERENCE | 9 |
| AUTHORS | Janosi,L., Shimizu,I. and Kaji,A. |
| TITLE | Ribosome recycling factor (ribosome releasing factor) is essential for bacterial growth |
| JOURNAL | Proc. Natl. Acad. Sci. U.S.A. 91 (10), 4249-4253 (1994) |
| PUBMED | 8183897 |
| REFERENCE | 10 |
| AUTHORS | Allikmets,R., Gerrard,B., Court,D. and Dean,M. |
| TITLE | Cloning and organization of the abc and mdl genes of *Escherichia coli*: relationship to eukaryotic multidrug resistance |
| JOURNAL | Gene 136 (1-2), 231-236 (1993) |
| PUBMED | 7904973 |
| REFERENCE | 11 |
| AUTHORS | van Heeswijk,W.C., Rabenberg,M., Westerhoff,H.V. and Kahn,D. |
| TITLE | The genes of the glutamine synthetase adenylylation cascade are not regulated by nitrogen in *Escherichia coli* |
| JOURNAL | Mol. Microbiol. 9 (3), 443-457 (1993) |
| PUBMED | 8412694 |
| REFERENCE | 12 |
| AUTHORS | Zhao,S., Sandt,C.H., Feulner,G., Vlazny,D.A., Gray,J.A. and Hill,C.W. |
| TITLE | Rhs elements of *Escherichia coli* K-12: complex composites of shared and unique components that have different evolutionary histories |
| JOURNAL | J. Bacteriol. 175 (10), 2799-2808 (1993) |
| PUBMED | 8387990 |
| REFERENCE | 13 |
| AUTHORS | Yamada,M., Asaoka,S., Saier,M.H. Jr. and Yamada,Y. |

| | |
|---|---|
| TITLE | Characterization of the gcd gene from *Escherichia coli* K-12 W3110 and regulation of its expression |
| JOURNAL | J. Bacteriol. 175 (2), 568-571 (1993) |
| PUBMED | 8419307 |
| REFERENCE | 14 |
| AUTHORS | Cormack,R.S. and Mackie,G.A. |
| TITLE | Structural requirements for the processing of *Escherichia coli* ribosomal RNA by RNase E in vitro |
| JOURNAL | J. Mol. Biol. 228 (4), 1078-1090 (1992) |
| PUBMED | 1474579 |
| REFERENCE | 15 |
| AUTHORS | Gervais,F.G. and Drapeau,G.R. |
| TITLE | Identification, cloning, and characterization of rcsF, a new regulator gene for exopolysaccharide synthesis that suppresses the division mutation ftsZ84 in *Escherichia coli* K-12 |
| JOURNAL | J. Bacteriol. 174 (24), 8016-8022 (1992) |
| PUBMED | 1459951 |
| REFERENCE | 16 |
| AUTHORS | Yamanaka,K., Ogura,T., Niki,H. and Hiraga,S. |
| TITLE | Identification and characterization of the smbA gene, a suppressor of the mukB null mutant of *Escherichia coli* |
| JOURNAL | J. Bacteriol. 174 (23), 7517-7526 (1992) |
| PUBMED | 1447125 |
| REFERENCE | 17 |
| AUTHORS | Condon,C., Philips,J., Fu,Z.Y., Squires,C. and Squires,C.L. |
| TITLE | Comparison of the expression of the seven ribosomal RNA operons in *Escherichia coli* |
| JOURNAL | EMBO J. 11 (11), 4175-4185 (1992) |
| PUBMED | 1396599 |
| REFERENCE | 18 |
| AUTHORS | Arnqvist,A., Olsen,A., Pfeifer,J., Russell,D.G. and Normark,S. |
| TITLE | The Crl protein activates cryptic genes for curli formation and fibronectin binding in *Escherichia coli* HB101 |
| JOURNAL | Mol. Microbiol. 6 (17), 2443-2452 (1992) |
| PUBMED | 1357528 |
| REFERENCE | 19 |
| AUTHORS | Talarico,T.L., Ray,P.H., Dev,I.K., Merrill,B.M. and Dallas,W.S. |
| TITLE | Cloning, sequence analysis, and overexpression of *Escherichia coli* folK, the gene coding for 7,8-dihydro-6-hydroxymethylpterin-pyrophosphokinase |
| JOURNAL | J. Bacteriol. 174 (18), 5971-5977 (1992) |

-continued

| | |
|---|---|
| PUBMED | 1325970 |
| REFERENCE | 20 |
| AUTHORS | Li,S.J. and Cronan,J.E. Jr. |
| TITLE | The genes encoding the two carboxyltransferase subunits of *Escherichia coli* acetyl-CoA carboxylase |
| JOURNAL | J. Biol. Chem. 267 (24), 16841-16847 (1992) |
| PUBMED | 1355089 |
| REFERENCE | 21 |
| AUTHORS | Yura,T., Mori,H., Nagai,H., Nagata,T., Ishihama,A., Fujita,N., Isono,K., Mizobuchi,K. and Nakata,A. |
| TITLE | Systematic sequencing of the *Escherichia coli* genome: analysis of the 0-2.4 min region |
| JOURNAL | Nucleic Acids Res. 20 (13), 3305-3308 (1992) |
| PUBMED | 1630901 |
| REFERENCE | 22 |
| AUTHORS | Ghosh,S.K., Biswas,S.K., Paul,K. and Das,J. |
| TITLE | Nucleotide and deduced amino acid sequence of the recA gene of Vibrio cholerae |
| JOURNAL | Nucleic Acids Res. 20 (2), 372 (1992) |
| PUBMED | 1741267 |
| REFERENCE | 23 |
| AUTHORS | Smallshaw,J.E. and Kelln,R.A. |
| TITLE | Cloning, nucleotide sequence and expression of the *Escherichia coli* K-12 pyrH gene encoding UMP kinase |
| JOURNAL | Genetics (Life Sci. Adv.) 11, 59-65 (1992) |
| REFERENCE | 24 |
| AUTHORS | O'Neill,G.P., Grygorczyk,R., Adam,M. and Ford-Hutchinson,A.W. |
| TITLE | The nucleotide sequence of a voltage-gated chloride channel from the electric organ of Torpedo californica |
| JOURNAL | Biochim. Biophys. Acta 1129 (1), 131-134 (1991) |
| PUBMED | 1721838 |
| REFERENCE | 25 |
| AUTHORS | Kajie,S., Ideta,R., Yamato,I. and Anraku,Y. |
| TITLE | Molecular cloning and DNA sequence of dniR, a gene affecting anaerobic expression of the *Escherichia coli* hexaheme nitrite reductase |
| JOURNAL | FEMS Microbiol. Lett. 67 (2), 205-211 (1991) |
| PUBMED | 1663890 |
| REFERENCE | 26 |
| AUTHORS | Hershfield,M.S., Chaffee,S., Koro-Johnson,L., Mary,A., Smith,A.A. and Short,S.A. |
| TITLE | Use of site-directed mutagenesis to enhance the epitope-shielding effect of covalent modification of proteins with polyethylene glycol |

| | | |
|---|---|---|
| JOURNAL | Proc. Natl. Acad. Sci. U.S.A. 88 (16), 7185-7189 (1991) | |
| PUBMED | 1714590 | |
| REFERENCE | 27 | |
| AUTHORS | Shimizu,I. and Kaji,A. | |
| TITLE | Identification of the promoter region of the ribosome-releasing<br>factor cistron (frr) | |
| JOURNAL | J. Bacteriol. 173 (16), 5181-5187 (1991) | |
| PUBMED | 1860827 | |
| REFERENCE | 28 | |
| AUTHORS | Poulsen,L.K., Refn,A., Molin,S. and Andersson,P. | |
| TITLE | The gef gene from *Escherichia coli* is regulated at the level of<br>translation | |
| JOURNAL | Mol. Microbiol. 5 (7), 1639-1648 (1991) | |
| PUBMED | 1943701 | |
| REFERENCE | 29 | |
| AUTHORS | Poulsen,L.K., Refn,A., Molin,S. and Andersson,P. | |
| TITLE | Topographic analysis of the toxic Gef protein from *Escherichia coli* | |
| JOURNAL | Mol. Microbiol. 5 (7), 1627-1637 (1991) | |
| PUBMED | 1943700 | |
| REFERENCE | 30 | |
| AUTHORS | Kawamukai,M., Utsumi,R., Takeda,K., Higashi,A., Matsuda,H., Choi,Y.L. and Komano,T. | |
| TITLE | Nucleotide sequence and characterization of the sfsl gene: sfsl is<br>Involved in CRP*-dependent mal gene expression in *Escherichia coli* | |
| JOURNAL | J. Bacteriol. 173 (8), 2644-2648 (1991) | |
| PUBMED | 2013578 | |
| REFERENCE | 31 | |
| AUTHORS | Hulton,C.S., Higgins,C.F. and Sharp,P.M. | |
| TITLE | ERIC sequences: a novel family of repetitive elements in the<br>genomes of *Escherichia coli*, *Salmonella typhimurium* and other<br>enterobacteria | |
| JOURNAL | Mol. Microbiol. 5 (4), 825-834 (1991) | |
| PUBMED | 1713281 | |
| REFERENCE | 32 | |
| AUTHORS | Munro,A.W., Ritchie,G.Y., Lamb,A.J., Douglas,R.M. and Booth,I.R. | |
| TITLE | The cloning and DNA sequence of the gene for the<br>glutathione-regulated potassium-efflux system KefC of<br>*Escherichia coli* | |
| JOURNAL | Mol. Microbiol. 5 (3), 607-616 (1991) | |
| PUBMED | 2046548 | |
| REFERENCE | 33 | |

-continued

| | |
|---|---|
| AUTHORS | Arigoni,F., Kaminski,P.A., Hennecke,H. and Elmerich,C. |
| TITLE | Nucleotide sequence of the fixABC region of Azorhizobium caulinodans ORS571: similarity of the fixB product with eukaryotic flavoproteins, characterization of fixX, and identification of nifW |
| JOURNAL | Mol. Gen. Genet. 225 (3), 514-520 (1991) |
| PUBMED | 1850088 |
| REFERENCE | 34 |
| AUTHORS | Mattick,J.S., Anderson,B.J., Cox,P.T., Dalrymple,B.P., Bills,M.M., Hobbs,M. and Egerton,J.R. |
| TITLE | Gene sequences and comparison of the fimbrial subunits representative of Bacteroides nodosus serotypes A to I: class I and class II strains |
| JOURNAL | Mol. Microbiol. 5 (3), 561-573 (1991) |
| PUBMED | 1675419 |
| REFERENCE | 35 |
| AUTHORS | Company,M., Arenas,J. and Abelson,J. |
| TITLE | Requirement of the RNA helicase-like protein PRP22 for release of messenger RNA from spliceosomes |
| JOURNAL | Nature 349 (6309), 487-493 (1991) |
| PUBMED | 1992352 |
| REFERENCE | 36 |
| AUTHORS | Umeda,M. and Ohtsubo,E. |
| TITLE | Four types of IS1 with differences in nucleotide sequence reside in the *Escherichia coli* K-12 chromosome |
| JOURNAL | Gene 98 (1), 1-5 (1991) |
| PUBMED | 1849492 |
| REFERENCE | 37 |
| AUTHORS | Hirvas,L., Koski,P. and Vaara,M. |
| TITLE | The ompH gene of *Yersinia enterocolitica*: cloning, sequencing, expression, and comparison with known enterobacterial ompH sequences |
| JOURNAL | J. Bacteriol. 173 (3), 1223-1229 (1991) |
| PUBMED | 1991717 |
| REFERENCE | 38 |
| AUTHORS | Bouvier,J. and Stragier,P. |
| TITLE | Nucleotide sequence of the lsp-dapB interval in *Escherichia coli* |
| JOURNAL | Nucleic Acids Res. 19 (1), 180 (1991) |
| PUBMED | 2011499 |
| REFERENCE | 39 |
| AUTHORS | Dicker,I.B. and Seetharam,S. |
| TITLE | Cloning and nucleotide sequence of the firA gene and the firA200(Ts) allele from *Escherichia coli* |

| | |
|---|---|
| JOURNAL | J. Bacteriol. 173 (1), 334-344 (1991) |
| PUBMED | 1987124 |
| REFERENCE | 40 |
| AUTHORS | Grimm,B., Bull,A. and Breu,V. |
| TITLE | Structural genes of glutamate 1-semialdehyde aminotransferase for porphyrin synthesis in a cyanobacterium and *Escherichia coli* |
| JOURNAL | Mol. Gen. Genet. 225 (1), 1-10 (1991) |
| PUBMED | 1900346 |
| REFERENCE | 41 |
| AUTHORS | Allen,B.L., Gerlach,G.F. and Clegg,S. |
| TITLE | Nucleotide sequence and functions of mrk determinants necessary for expression of type 3 fimbriae in *Klebsiella pneumoniae* |
| JOURNAL | J. Bacteriol. 173 (2), 916-920 (1991) |
| PUBMED | 1670938 |
| REFERENCE | 42 |
| AUTHORS | Chen,H., Lawrence,C.B., Bryan,S.K. and Moses,R.E. |
| TITLE | Aphidicolin inhibits DNA polymerase II of *Escherichia coli*, an alpha-like DNA polymerase |
| JOURNAL | Nucleic Acids Res. 18 (23), 7185-7186 (1990) |
| PUBMED | 2124684 |
| REFERENCE | 43 |
| AUTHORS | Mallonee,D.H., White,W.B. and Hylemon,P.B. |
| TITLE | Cloning and sequencing of a bile acid-inducible operon from *Eubacterium sp.* strain VPI 12708 |
| JOURNAL | J. Bacteriol. 172 (12), 7011-7019 (1990) |
| PUBMED | 2254270 |
| REFERENCE | 44 |
| AUTHORS | Young,C., Collins-Emerson,J.M., Terzaghi,E.A. and Scott,D.B. |
| TITLE | Nucleotide sequence of Rhizobium loti nodI |
| JOURNAL | Nucleic Acids Res. 18 (22), 6691 (1990) |
| PUBMED | 2251131 |
| REFERENCE | 45 |
| AUTHORS | Chen,H., Sun,Y., Stark,T., Beattie,W. and Moses,R.E. |
| TITLE | Nucleotide sequence and deletion analysis of the polB gene of *Escherichia coli* |
| JOURNAL | DNA Cell Biol. 9 (9), 631-635 (1990) |
| PUBMED | 2261080 |
| REFERENCE | 46 |
| AUTHORS | Eriani,G., Delarue,M., Poch,O., Gangloff,J. and Moras,D. |
| TITLE | Partition of tRNA synthetases into two classes based on mutually exclusive sets of sequence motifs |
| JOURNAL | Nature 347 (6289), 203-206 (1990) |

-continued

| | |
|---|---|
| PUBMED | 2203971 |
| REFERENCE | 47 |
| AUTHORS | Showalter,R.E. and Silverman,M.R. |
| TITLE | Nucleotide sequence of a gene, hpt, for hypoxanthine phosphoribosyltransferase from *Vibrio harveyi* |
| JOURNAL | Nucleic Acids Res. 18 (15), 4621 (1990) |
| PUBMED | 2388850 |
| REFERENCE | 48 |
| AUTHORS | Martin-Verstraete,I., Debarbouille,M., Klier,A. and Rapoport,G. |
| TITLE | Levanase operon of *Bacillus subtilis* includes a fructose-specific phosphotransferase system regulating the expression of the operon |
| JOURNAL | J. Mol. Biol. 214 (3), 657-671 (1990) |
| PUBMED | 2117666 |
| REFERENCE | 49 |
| AUTHORS | Henrich,B., Monnerjahn,U. and Plapp,R. |
| TITLE | Peptidase D gene (pepD) of *Escherichia coli* K-12: nucleotide sequence, transcript mapping, and comparison with other peptidase genes |
| JOURNAL | J. Bacteriol. 172 (8), 4641-4651 (1990) |
| PUBMED | 1695895 |
| REFERENCE | 50 |
| AUTHORS | Nunn,D., Bergman,S. and Lory,S. |
| TITLE | Products of three accessory genes, pilB, pilC, and pilD, are required for biogenesis of *Pseudomonas aeruginosa pili* |
| JOURNAL | J. Bacteriol. 172 (6), 2911-2919 (1990) |
| PUBMED | 1971619 |
| REFERENCE | 51 |
| AUTHORS | Rosenthal,E.R. and Calvo,J.M. |
| TITLE | The nucleotide sequence of leuC from *Salmonella typhimurium* |
| JOURNAL | Nucleic Acids Res. 18 (10), 3072 (1990) |
| PUBMED | 2190189 |
| REFERENCE | 52 |
| AUTHORS | Kang,P.J. and Craig,E.A. |
| TITLE | Identification and characterization of a new *Escherichia coli* gene that is a dosage-dependent suppressor of a dnaK deletion mutation |
| JOURNAL | J. Bacteriol. 172 (4), 2055-2064 (1990) |
| PUBMED | 2180916 |
| REFERENCE | 53 |
| AUTHORS | Wurgler,S.M. and Richardson,C.C. |

| | |
|---|---|
| TITLE | Structure and regulation of the gene for dGTP triphosphohydrolase from *Escherichia coli* |
| JOURNAL | Proc. Natl. Acad. Sci. U.S.A. 87 (7), 2740-2744 (1990) |
| PUBMED | 2157212 |
| REFERENCE | 54 |
| AUTHORS | Schaaff,I., Hohmann,S. and Zimmermann,F.K. |
| TITLE | Molecular analysis of the structural gene for yeast transaldolase |
| JOURNAL | Eur. J. Biochem. 188 (3), 597-603 (1990) |
| PUBMED | 2185015 |
| REFERENCE | 55 |
| AUTHORS | Ricca,E. and Calvo,J.M. |
| TITLE | The nucleotide sequence of leuA from *Salmonella typhimurium* |
| JOURNAL | Nucleic Acids Res. 18 (5), 1290 (1990) |
| PUBMED | 2181403 |
| REFERENCE | 56 |
| AUTHORS | Honore,N. and Cole,S.T. |
| TITLE | Nucleotide sequence of the aroP gene encoding the general aromatic amino acid transport protein of *Escherichia coli* K-12: homology with yeast transport proteins |
| JOURNAL | Nucleic Acids Res. 18 (3), 653 (1990) |
| PUBMED | 2408019 |
| REFERENCE | 57 |
| AUTHORS | Angerer,A., Gaisser,S. and Braun,V. |
| TITLE | Nucleotide sequences of the sfuA, sfuB, and sfuC genes of *Serratia marcescens* suggest a periplasmic-binding-protein-dependent iron transport mechanism |
| JOURNAL | J. Bacteriol. 172 (2), 572-578 (1990) |
| PUBMED | 2404942 |
| REFERENCE | 58 |
| AUTHORS | Surin,B.P., Watson,J.M., Hamilton,W.D., Economou,A. and Downie, J.A. |
| TITLE | Molecular characterization of the nodulation gene, nodT, from two biovars of *Rhizobium leguminosarum* |
| JOURNAL | Mol. Microbiol. 4 (2), 245-252 (1990) |
| PUBMED | 2338917 |
| REFERENCE | 59 |
| AUTHORS | Zhou,Z. and Syvanen,M. |
| TITLE | Identification and sequence of the drpA gene from *Escherichia coli* |
| JOURNAL | J. Bacteriol. 172 (1), 281-286 (1990) |
| PUBMED | 1688424 |

| | |
|---|---|
| REFERENCE | 60 |
| AUTHORS | Roncero,M.I., Jepsen,L.P., Stroman,P. and van Heeswijck,R. |
| TITLE | Characterization of a leuA gene and an ARS element from *Mucor circinelloides* |
| JOURNAL | Gene 84 (2), 335-343 (1989) |
| PUBMED | 2693214 |
| REFERENCE | 61 |
| AUTHORS | Ichikawa,S. and Kaji,A. |
| TITLE | Molecular cloning and expression of ribosome releasing factor |
| JOURNAL | J. Biol. Chem. 264 (33), 20054-20059 (1989) |
| PUBMED | 2684966 |
| REFERENCE | 62 |
| AUTHORS | Minami-Ishii,N., Taketani,S., Osumi,T. and Hashimoto,T. |
| TITLE | Molecular cloning and sequence analysis of the cDNA for rat mitochondrial enoyl-CoA hydratase. Structural and evolutionary relationships linked to the bifunctional enzyme of the peroxisomal beta-oxidation system |
| JOURNAL | Eur. J. Biochem. 185 (1), 73-78 (1989) |
| PUBMED | 2806264 |
| REFERENCE | 63 |
| AUTHORS | Matsubara,Y., Indo,Y., Naito,E., Ozasa,H., Glassberg,R., Vockley,J., Ikeda,Y., Kraus,J. and Tanaka,K. |
| TITLE | Molecular cloning and nucleotide sequence of cDNAs encoding the precursors of rat long chain acyl-coenzyme A, short chain acyl-coenzyme A, and isovaleryl-coenzyme A dehydrogenases. Sequence homology of four enzymes of the acyl-CoA dehydrogenase family |
| JOURNAL | J. Biol. Chem. 264 (27), 16321-16331 (1989) |
| PUBMED | 2777793 |
| REFERENCE | 64 |
| AUTHORS | Roa,B.B., Connolly,D.M. and Winkler,M.E. |
| TITLE | Overlap between pdxA and ksgA in the complex pdxA-ksgA-apaG-apaH operon of *Escherichia coli* K-12 |
| JOURNAL | J. Bacteriol. 171 (9), 4767-4777 (1989) |
| PUBMED | 2670894 |
| REFERENCE | 65 |
| AUTHORS | Lindquist,S., Galleni,M., Lindberg,F. and Normark,S. |
| TITLE | Signalling proteins in enterobacterial AmpC beta-lactamase regulation |
| JOURNAL | Mol. Microbiol. 3 (8), 1091-1102 (1989) |
| PUBMED | 2691840 |
| REFERENCE | 66 |
| AUTHORS | Xie,Q.W., Tabor,C.W. and Tabor,H. |
| TITLE | Spermidine biosynthesis in *Escherichia coli*: promoter and termination regions of the speED operon |

| | |
|---|---|
| JOURNAL | J. Bacteriol. 171 (8), 4457-4465 (1989) |
| PUBMED | 2666401 |
| REFERENCE | 67 |
| AUTHORS | Sato,S., Nakada,Y. and Shiratsuchi,A. |
| TITLE | IS421, a new insertion sequence in Escherichia coli |
| JOURNAL | FEBS Lett. 249 (1), 21-26 (1989) |
| PUBMED | 2542093 |
| REFERENCE | 68 |
| AUTHORS | Liu,J.D. and Parkinson,J.S. |
| TITLE | Genetics and sequence analysis of the pcnB locus, an *Escherichia coli* gene involved in plasmid copy number control |
| JOURNAL | J. Bacteriol. 171 (3), 1254-1261 (1989) |
| PUBMED | 2537812 |
| REFERENCE | 69 |
| AUTHORS | Henrich,B., Schroeder,U., Frank,R.W. and Plapp,R. |
| TITLE | Accurate mapping of the *Escherichia coli* pepD gene by sequence analysis of its 5' flanking region |
| JOURNAL | Mol. Gen. Genet. 215 (3), 369-373 (1989) |
| PUBMED | 2651887 |
| REFERENCE | 70 |
| AUTHORS | Lipinska,B., Sharma,S. and Georgopoulos,C. |
| TITLE | Sequence analysis and regulation of the htrA gene of *Escherichia coli*: a sigma 32-independent mechanism of heat-inducible transcription |
| JOURNAL | Nucleic Acids Res. 16 (21), 10053-10067 (1988) |
| PUBMED | 3057437 |
| REFERENCE | 71 |
| AUTHORS | Sung,Y.C. and Fuchs,J.A. |
| TITLE | Characterization of the cyn operon in *Escherichia coli* K12 |
| JOURNAL | J. Biol. Chem. 263 (29), 14769-14775 (1988) |
| PUBMED | 3049588 |
| REFERENCE | 72 |
| AUTHORS | Lozoya,E., Hoffmann,H., Douglas,C., Schulz,W., Scheel,D. and Hahlbrock,K. |
| TITLE | Primary structures and catalytic properties of isoenzymes encoded by the two 4-coumarate: CoA ligase genes in parsley |
| JOURNAL | Eur. J. Biochem. 176 (3), 661-667 (1988) |
| PUBMED | 3169018 |
| REFERENCE | 73 |
| AUTHORS | Andrews,S.C. and Guest,J.R. |
| TITLE | Nucleotide sequence of the gene encoding the GMP reductase of *Escherichia coli* K12 |

-continued

| | |
|---|---|
| JOURNAL | Biochem. J. 255 (1), 35-43 (1988) |
| PUBMED | 2904262 |
| REFERENCE | 74 |
| AUTHORS | Jaiswal,A.K., McBride,O.W., Adesnik,M. and Nebert,D.W. |
| TITLE | Human dioxin-inducible cytosolic NAD(P)H:menadione oxidoreductase.<br>cDNA sequence and localization of gene to chromosome 16 |
| JOURNAL | J. Biol. Chem. 263 (27), 13572-13578 (1988) |
| PUBMED | 2843525 |
| REFERENCE | 75 |
| AUTHORS | Karpel,R., Olami,Y., Taglicht,D., Schuldiner,S. and Padan,E. |
| TITLE | Sequencing of the gene ant which affects the Na+/H+ antiporter activity in *Escherichia coli* |
| JOURNAL | J. Biol. Chem. 263 (21), 10408-10414 (1988) |
| PUBMED | 2839489 |
| REFERENCE | 76 |
| AUTHORS | Mellano,M.A. and Cooksey,D.A. |
| TITLE | Nucleotide sequence and organization of copper resistance genes<br>from *Pseudomonas syringae* pv. tomato |
| JOURNAL | J. Bacteriol. 170 (6), 2879-2883 (1988) |
| PUBMED | 3372485 |
| REFERENCE | 77 |
| AUTHORS | Coleman,J. and Raetz,C.R. |
| TITLE | First committed step of lipid A biosynthesis in *Escherichia coli*:<br>sequence of the 1pxA gene |
| JOURNAL | J. Bacteriol. 170 (3), 1268-1274 (1988) |
| PUBMED | 3277952 |
| REFERENCE | 78 |
| AUTHORS | Gebhard,W., Schreitmuller,T., Hochstrasser,K. and Wachter,E. |
| TITLE | Complementary DNA and derived amino acid sequence of the precursor<br>of one of the three protein components of the inter-alpha-trypsin<br>Inhibitor complex |
| JOURNAL | FEBS Lett. 229 (1), 63-67 (1988) |
| PUBMED | 2450046 |
| REFERENCE | 79 |
| AUTHORS | Tomasiewicz,H.G. and McHenry,C.S. |
| TITLE | Sequence analysis of the *Escherichia coli* dnaE gene |
| JOURNAL | J. Bacteriol. 169 (12), 5735-5744 (1987) |
| PUBMED | 3316192 |
| REFERENCE | 80 |
| AUTHORS | Crowell,D.N., Reznikoff,W.S. and Raetz,C.R. |
| TITLE | Nucleotide sequence of the *Escherichia coli* gene for lipid A disaccharide synthase |

| | |
|---|---|
| JOURNAL | J. Bacteriol. 169 (12), 5727-5734 (1987) |
| PUBMED | 2824445 |
| REFERENCE | 81 |
| AUTHORS | Tabor,C.W. and Tabor,H. |
| TITLE | The speEspeD operon of *Escherichia coli*. Formation and processing of a proenzyme form of S-adenosylmethionine decarboxylase |
| JOURNAL | J. Biol. Chem. 262 (33), 16037-16040 (1987) |
| PUBMED | 3316212 |
| REFERENCE | 82 |
| AUTHORS | Nonet,M.L., Marvel,C.C. and Tolan,D.R. |
| TITLE | The hisT-purF region of the *Escherichia coli* K-12 chromosome. Identification of additional genes of the hisT and purF operons |
| JOURNAL | J. Biol. Chem. 262 (25), 12209-12217 (1987) |
| PUBMED | 3040734 |
| REFERENCE | 83 |
| AUTHORS | Coulton,J.W., Mason,P. and Allatt,D.D. |
| TITLE | fhuC and fhuD genes for iron (III)-ferrichrome transport into *Escherichia coli* K-12 |
| JOURNAL | J. Bacteriol. 169 (8), 3844-3849 (1987) |
| PUBMED | 3301821 |
| REFERENCE | 84 |
| AUTHORS | Horiuchi,T., Nagasawa,T., Takano,K. and Sekiguchi,M. |
| TITLE | A newly discovered tRNA(1Asp) gene (aspV) of *Escherichia coli* K12 |
| JOURNAL | Mol. Gen. Genet. 206 (2), 356-357 (1987) |
| PUBMED | 3295485 |
| REFERENCE | 85 |
| AUTHORS | Ben-Bassat,A., Bauer,K., Chang,S.Y., Myambo,K., Boosman,A. and Chang, S. |
| TITLE | Processing of the initiation methionine from proteins: properties of the *Escherichia coli* methionine aminopeptidase and its gene structure |
| JOURNAL | J. Bacteriol. 169 (2), 751-757 (1987) |
| PUBMED | 3027045 |
| REFERENCE | 86 |
| AUTHORS | Gronger,P., Manian,S.S., Reilander,H., O'Connell,M., Priefer,U.B. and Puhler,A. |
| TITLE | Organization and partial sequence of a DNA region of the Rhizobium leguminosarum symbiotic plasmid pRL6JI containing the genes fixABC, nifA, nifB and a novel open reading frame |
| JOURNAL | Nucleic Acids Res. 15 (1), 31-49 (1987) |
| PUBMED | 3029674 |

-continued

| | |
|---|---|
| REFERENCE | 87 |
| AUTHORS | Richardson,K.K., Richardson,F.C., Crosby,R.M., Swenberg,J.A. and Skopek,T.R. |
| TITLE | DNA base changes and alkylation following in vivo exposure of *Escherichia coli* to N-methyl-N-nitrosourea or N-ethyl-N-nitrosourea |
| JOURNAL | Proc. Natl. Acad. Sci. U.S.A. 84 (2), 344-348 (1987) |
| PUBMED | 3540961 |
| REFERENCE | 88 |
| AUTHORS | Chye,M.L. and Pittard,J. |
| TITLE | Transcription control of the aroP gene in *Escherichia coli* K-12: analysis of operator mutants |
| JOURNAL | J. Bacteriol. 169 (1), 386-393 (1987) |
| PUBMED | 3025182 |
| REFERENCE | 89 |
| AUTHORS | Blanchin-Roland, S., Blanquet,S., Schmitter,J.M. and Fayat,G. |
| TITLE | The gene for *Escherichia coli* diadenosine tetraphosphatase is located immediately clockwise to folA and forms an operon with ksgA |
| JOURNAL | Mol. Gen. Genet. 205 (3), 515-522 (1986) |
| PUBMED | 3031429 |
| REFERENCE | 90 |
| AUTHORS | Takano,K., Nakabeppu,Y., Maki,H., Horiuchi,T. and Sekiguchi,M. |
| TITLE | Structure and function of dnaQ and mutD mutators of *Escherichia coli* |
| JOURNAL | Mol. Gen. Genet. 205 (1), 9-13 (1986) |
| PUBMED | 3540531 |
| REFERENCE | 91 |
| AUTHORS | Mackie,G.A. |
| TITLE | Structure of the DNA distal to the gene for ribosomal protein S20 in *Escherichia coli* K12: presence of a strong terminator and an IS1 element |
| JOURNAL | Nucleic Acids Res. 14 (17), 6965-6981 (1986) |
| PUBMED | 2429258 |
| REFERENCE | 92 |
| AUTHORS | Koster,W. and Braun,V. |
| TITLE | Iron hydroxamate transport of *Escherichia coli*: nucleotide sequence of the fhuB gene and identification of the protein |
| JOURNAL | Mol. Gen. Genet. 204 (3), 435-442 (1986) |
| PUBMED | 3020380 |
| REFERENCE | 93 |
| AUTHORS | Breton,R., Sanfacon,H., Papayannopoulos,I., Biemann,K. and Lapointe, J. |

| | -continued |
|---|---|
| TITLE | Glutamyl-tRNA synthetase of *Escherichia coli*. Isolation and primary structure of the gltX gene and homology with other aminoacyl-tRNA synthetases |
| JOURNAL | J. Biol. Chem. 261 (23), 10610-10617 (1986) |
| PUBMED | 3015933 |
| REFERENCE | 94 |
| AUTHORS | Birnbaum,M.J., Haspel,H.C. and Rosen,O.M. |
| TITLE | Cloning and characterization of a cDNA encoding the rat brain glucose-transporter protein |
| JOURNAL | Proc. Natl. Acad. Sol. U.S.A. 83 (16), 5784-5788 (1986) |
| PUBMED | 3016720 |
| REFERENCE | 95 |
| AUTHORS | Cox,E.C. and Horner,D.L. |
| TITLE | DNA sequence and coding properties of mutD(dnaQ) a dominant *Escherichia coli* mutator gene |
| JOURNAL | J. Mol. Biol. 190 (1), 113-117 (1986) |
| PUBMED | 3023634 |
| REFERENCE | 96 |
| AUTHORS | Ohki,M., Tamura,F., Nishimura,S. and Uchida,H. |
| TITLE | Nucleotide sequence of the *Escherichia coli* dnaJ gene and purification of the gene product |
| JOURNAL | J. Biol. Chem. 261 (4), 1778-1781 (1986) |
| PUBMED | 3003084 |
| REFERENCE | 97 |
| AUTHORS | Coulton,J.W., Mason,P., Cameron,D.R., Carmel,G., Jean,R. and Rode, H.N. |
| TITLE | Protein fusions of beta-galactosidase to the ferrichrome-iron receptor of *Escherichia coli* K-12 |
| JOURNAL | J. Bacteriol. 165 (1), 181-192 (1986) |
| PUBMED | 3079747 |
| REFERENCE | 98 |
| AUTHORS | Lee,N., Gielow,W., Martin,R., Hamilton,E. and Fowler,A. |
| TITLE | The organization of the araBAD operon of Escherichia coli |
| JOURNAL | Gene 47 (2-3), 231-244 (1986) |
| PUBMED | 3549454 |
| REFERENCE | 99 |
| AUTHORS | Sekiguchi,T., Ortega-Cesena,J., Nosoh,Y., Ohashi,S., Tsuda,K. and Kanaya,S. |
| TITLE | DNA and amino-acid sequences of 3-isopropylmalate dehydrogenase of *Bacillus coagulans*. Comparison with the enzymes of *Saccharomycescerevisiae* and *Thermus thermophilus* |
| JOURNAL | Biochim. Biophys. Acta 867, 36-44 (1986) |
| REFERENCE | 100 |
| AUTHORS | Chong,P., Hui,I., Loo,T. and Gillam,S. |

| | -continued |
|---|---|
| TITLE | Structural analysis of a new GC-specific insertion element IS186 |
| JOURNAL | FEBS Lett. 192 (1), 47-52 (1985) |
| PUBMED | 2996940 |
| REFERENCE | 101 |
| AUTHORS | Icho,T., Sparrow,C.P. and Raetz,C.R. |
| TITLE | Molecular cloning and sequencing of the gene for CDP-diglyceride synthetase of *Escherichia coli* |
| JOURNAL | J. Biol. Chem. 260 (22), 12078-12083 (1985) |
| PUBMED | 2995358 |
| REFERENCE | 102 |
| AUTHORS | Nomura,T., Aiba,H. and Ishihama,A. |
| TITLE | Transcriptional organization of the convergent overlapping dnaQ-rnh genes of *Escherichia coli* |
| JOURNAL | J. Biol. Chem. 260 (11), 7122-7125 (1985) |
| PUBMED | 2987244 |
| REFERENCE | 103 |
| AUTHORS | Kamio,Y., Lin,C.K., Regue,M. and Wu,H.C. |
| TITLE | Characterization of the ileS-lsp operon in *Escherichia coli*. Identification of an open reading frame upstream of the ileS gene and potential promoter(s) for the ileS-lsp operon |
| JOURNAL | J. Biol. Chem. 260 (9), 5616-5620 (1985) |
| PUBMED | 2985604 |
| REFERENCE | 104 |
| AUTHORS | Cowing,D.W., Bardwell,J.C., Craig,E.A., Woolford,C., Hendrix, R.W. and Gross,C.A. |
| TITLE | Consensus sequence for *Escherichia coli* heat shock gene promoters |
| JOURNAL | Proc. Natl. Acad. Sol. U.S.A. 82 (9), 2679-2683 (1985) |
| PUBMED | 3887408 |
| REFERENCE | 105 |
| AUTHORS | Broome-Smith,J.K., Edelman,A., Yousif,S. and Spratt,B.G. |
| TITLE | The nucleotide sequences of the ponA and ponB genes encoding penicillin-binding protein 1A and 1B of *Escherichia coli* K12 |
| JOURNAL | Eur. J. Biochem. 147 (2), 437-446 (1985) |
| PUBMED | 3882429 |
| REFERENCE | 106 |
| AUTHORS | Becerril,B., Valle,F., Merino,E., Riba,L. and Bolivar,F. |
| TITLE | Repetitive extragenic palindromic (REP) sequences in the *Escherichia coli* gdhA gene |
| JOURNAL | Gene 37 (1-3), 53-62 (1985) |
| PUBMED | 3902576 |
| REFERENCE | 107 |

| | |
|---|---|
| AUTHORS | Friedberg,D., Rosenthal,E.R., Jones,J.W. and Calvo,J.M. |
| TITLE | Characterization of the 3' end of the leucine operon of *Salmonella typhimurium* |
| JOURNAL | Mol. Gen. Genet. 199 (3), 486-494 (1985) |
| PUBMED | 2993799 |
| REFERENCE | 108 |
| AUTHORS | Bouvier,J., Richaud,C., Richaud,F., Patte,J.C. and Stragier,P. |
| TITLE | Nucleotide sequence and expression of the *Escherichia coli* dapB gene |
| JOURNAL | J. Biol. Chem. 259 (23), 14829-14834 (1984) |
| PUBMED | 6094578 |
| REFERENCE | 109 |
| AUTHORS | Richaud,C., Richaud,F., Martin,C., Haziza,C. and Patte,J.C. |
| TITLE | Regulation of expression and nucleotide sequence of the *Escherichia coli* dapD gene |
| JOURNAL | J. Biol. Chem. 259 (23), 14824-14828 (1984) |
| PUBMED | 6094577 |
| REFERENCE | 110 |
| AUTHORS | Nuesch,J. and Schumperli,D. |
| TITLE | Structural and functional organization of the gpt gene region of *Escherichia coli* |
| JOURNAL | Gene 32 (1-2), 243-249 (1984) |
| PUBMED | 6397401 |
| REFERENCE | 111 |
| AUTHORS | Jagadeeswaran,P., Ashman,C.R., Roberts,S. and Langenberg,J. |
| TITLE | Nucleotide sequence and analysis of deletion mutants of the *Escherichia coli* gpt gene in plasmid pSV2 gpt |
| JOURNAL | Gene 31 (1-3), 309-313 (1984) |
| PUBMED | 6396164 |
| REFERENCE | 112 |
| AUTHORS | Deutch,A.H., Rushlow,K.E. and Smith,C.J. |
| TITLE | Analysis of the *Escherichia coli* proBA locus by DNA and protein sequencing |
| JOURNAL | Nucleic Acids Res. 12 (15), 6337-6355 (1984) |
| PUBMED | 6089111 |
| REFERENCE | 113 |
| AUTHORS | Bouvier,J., Patte,J.C. and Stragier,P. |
| TITLE | Multiple regulatory signals in the control region of the *Escherichia coli* carAB operon |
| JOURNAL | Proc. Natl. Acad. Sci. U.S.A. 81 (13), 4139-4143 (1984) |
| PUBMED | 6377309 |
| REFERENCE | 114 |

| | |
|---|---|
| AUTHORS | Innis,M.A., Tokunaga,M., Williams,M.E., Loranger,J.M., Chang,S.Y., Chang,S. and Wu,H.C. |
| TITLE | Nucleotide sequence of the *Escherichia coli* prolipoprotein signal peptidase (lsp) gene |
| JOURNAL | Proc. Natl. Acad. Sci. U.S.A. 81 (12), 3708-3712 (1984) |
| PUBMED | 6374664 |
| REFERENCE | 115 |
| AUTHORS | Bardwell,J.C. and Craig,E.A. |
| TITLE | Major heat shock gene of Drosophila and the *Escherichia coli* heat-inducible dnaK gene are homologous |
| JOURNAL | Proc. Natl. Acad. Sci. U.S.A. 81 (3), 848-852 (1984) |
| PUBMED | 6322174 |
| REFERENCE | 116 |
| AUTHORS | Pratt,D. and Subramani,S. |
| TITLE | Nucleotide sequence of the *Escherichia coli* xanthine-guanine phosphoribosyl transferase gene |
| JOURNAL | Nucleic Acids Res. 11 (24), 8817-8823 (1983) |
| PUBMED | 6324103 |
| REFERENCE | 117 |
| AUTHORS | Richardson,K.K., Fostel,J. and Skopek,T.R. |
| TITLE | Nucleotide sequence of the xanthine guanine phosphoribosyl transferase gene of E. coli |
| JOURNAL | Nucleic Acids Res. 11 (24), 8809-8816 (1983) |
| PUBMED | 6324102 |
| REFERENCE | 118 |
| AUTHORS | Parsot,C., Cossart,P., Saint-Girons,I. and Cohen,G.N. |
| TITLE | Nucleotide sequence of thrC and of the transcription termination region of the threonine operon in *Escherichia coli* K12 |
| JOURNAL | Nucleic Acids Res. 11 (21), 7331-7345 (1983) |
| PUBMED | 6316258 |
| REFERENCE | 119 |
| AUTHORS | Stephens,P.E., Lewis,H.M., Darlison,M.G. and Guest,J.R. |
| TITLE | Nucleotide sequence of the lipoamide dehydrogenase gene of *Escherichia coli* K12 |
| JOURNAL | Eur. J. Biochem. 135 (3), 519-527 (1983) |
| PUBMED | 6352260 |
| REFERENCE | 120 |
| AUTHORS | Stephens,P.E., Darlison,M.G., Lewis,H.M. and Guest,J.R. |
| TITLE | The pyruvate dehydrogenase complex of *Escherichia coli* K12. Nucleotide sequence encoding the dihydrolipoamide acetyltransferase component |
| JOURNAL | Eur. J. Biochem. 133 (3), 481-489 (1983) |
| PUBMED | 6345153 |

-continued

| | |
|---|---|
| REFERENCE | 121 |
| AUTHORS | Stephens,P.E., Darlison,M.G., Lewis,H.M. and Guest,J.R. |
| TITLE | The pyruvate dehydrogenase complex of *Escherichia coli* K12. Nucleotide sequence encoding the pyruvate dehydrogenase component |
| JOURNAL | Eur. J. Biochem. 133 (1), 155-162 (1983) |
| PUBMED | 6343085 |
| REFERENCE | 122 |
| AUTHORS | Kanaya,S. and Crouch,R.J. |
| TITLE | Low levels of RNase H activity in *Escherichia coli* FB2 rnh result from a single-base change in the structural gene of RNase H |
| JOURNAL | J. Bacteriol. 154 (2), 1021-1026 (1983) |
| PUBMED | 6302075 |
| REFERENCE | 123 |
| AUTHORS | Overbeeke,N., Bergmans,H., van Mansfeld,F. and Lugtenberg,B. |
| TITLE | Complete nucleotide sequence of phoE, the structural gene for the phosphate limitation inducible outer membrane pore protein of *Escherichia coli* K12 |
| JOURNAL | J. Mol. Biol. 163 (4), 513-532 (1983) |
| PUBMED | 6341601 |
| REFERENCE | 124 |
| AUTHORS | Gilson,E., Nikaido,H. and Hofnung,M. |
| TITLE | Sequence of the malK gene in *E.coli* K12 |
| JOURNAL | Nucleic Acids Res. 10 (22), 7449-7458 (1982) |
| PUBMED | 6296778 |
| REFERENCE | 125 |
| AUTHORS | Stoner,C.M. and Schleif,R. |
| TITLE | Is the amino acid but not the nucleotide sequence of the *Escherichia coli* araC gene conserved? |
| JOURNAL | J. Mol. Biol. 154 (4), 649-652 (1982) |
| PUBMED | 6283093 |
| REFERENCE | 126 |
| AUTHORS | An,G., Bendiak,D.S., Mamelak,L.A. and Friesen,J.D. |
| TITLE | Organization and nucleotide sequence of a new ribosomal operon in Escherichia coli containing the genes for ribosomal protein S2 and elongation factor Ts |
| JOURNAL | Nucleic Acids Res. 9 (16), 4163-4172 (1981) |
| PUBMED | 6272196 |
| REFERENCE | 127 |
| AUTHORS | Mackie,G.A. |
| TITLE | Nucleotide sequence of the gene for ribosomal protein S20 and its flanking regions |
| JOURNAL | J. Biol. Chem. 256 (15), 8177-8182 (1981) |

| | |
|---|---|
| PUBMED | 6267039 |
| REFERENCE | 128 |
| AUTHORS | Little,J.W., Mount,D.W. and Yanisch-Perron,C.R. |
| TITLE | Purified lexA protein is a repressor of the recA and lexA genes |
| JOURNAL | Proc. Natl. Acad. Sci. U.S.A. 78 (7), 4199-4203 (1981) |
| PUBMED | 7027255 |
| REFERENCE | 129 |
| AUTHORS | Mulligan,R.C. and Berg,P. |
| TITLE | Factors governing the expression of a bacterial gene in mammalian cells |
| JOURNAL | Mol. Cell. Biol. 1 (5), 449-459 (1981) |
| PUBMED | 6100966 |
| REFERENCE | 130 |
| AUTHORS | Lee,N.L., Gielow,W.O. and Wallace,R.G. |
| TITLE | Mechanism of araC autoregulation and the domains of two overlapping promoters, Pc and PBAD, in the L-arabinose regulatory region of *Escherichia coli* |
| JOURNAL | Proc. Natl. Acad. Sci. U.S.A. 78 (2), 752-756 (1981) |
| PUBMED | 6262769 |
| REFERENCE | 131 |
| AUTHORS | Cossart,P., Katinka,M. and Yaniv,M. |
| TITLE | Nucleotide sequence of the thrB gene of *E. coli*, and its two adjacent regions; the thrAB and thrBC junctions |
| JOURNAL | Nucleic Acids Res. 9 (2), 339-347 (1981) |
| PUBMED | 6259626 |
| REFERENCE | 132 |
| AUTHORS | Miyada,C.G., Horwitz,A.H., Cass,L.G., Timko,J. and Wilcox,G. |
| TITLE | DNA sequence of the araC regulatory gene from *Escherichia coli* B/r |
| JOURNAL | Nucleic Acids Res. 8 (22), 5267-5274 (1980) |
| PUBMED | 7008027 |
| REFERENCE | 133 |
| AUTHORS | Katinka,M., Cossart,P., Sibilli,L., Saint-Girons,I., Chalvignac,M.A., Le Bras,G., Cohen,G.N. and Yaniv,M. |
| TITLE | Nucleotide sequence of the thrA gene of *Escherichia coli* |
| JOURNAL | Proc. Natl. Acad. Sci. U.S.A. 77 (10), 5730-5733 (1980) |
| PUBMED | 7003595 |
| REFERENCE | 134 |
| AUTHORS | Ogden,S., Haggerty,D., Stoner,C.M., Kolodrubetz,D. and Schleif,R. |
| TITLE | The *Escherichia coli* L-arabinose operon: binding sites of the regulatory proteins and a mechanism of positive and negative regulation |

| | |
|---|---|
| JOURNAL | Proc. Natl. Acad. Sci. U.S.A. 77 (6), 3346-3350 (1980) |
| PUBMED | 6251457 |
| REFERENCE | 135 |
| AUTHORS | Smith,D.R. and Calvo,J.M. |
| TITLE | Nucleotide sequence of the *E coli* gene coding for dihydrofolate reductase |
| JOURNAL | Nucleic Acids Res. 8 (10), 2255-2274 (1980) |
| PUBMED | 6159575 |
| REFERENCE | 136 |
| AUTHORS | Johnsrud,L. |
| TITLE | DNA sequence of the transposable element IS1 |
| JOURNAL | Mol. Gen. Genet. 169 (2), 213-218 (1979) |
| PUBMED | 375010 |
| REFERENCE | 137 |
| AUTHORS | Smith,B.R. and Schleif,R. |
| TITLE | Nucleotide sequence of the L-arabinose regulatory region of *Escherichia coli* K12 |
| JOURNAL | J. Biol. Chem. 253 (19), 6931-6933 (1978) |
| PUBMED | 357433 |
| REFERENCE | 138 |
| AUTHORS | Greenfield,L., Boone,T. and Wilcox,G. |
| TITLE | DNA sequence of the araBAD promoter in *Escherichia coli* B/r |
| JOURNAL | Proc. Natl. Acad. Sci. U.S.A. 75 (10), 4724-4728 (1978) |
| PUBMED | 368797 |
| REFERENCE | 139 |
| AUTHORS | Young,R.A. and Steitz,J.A. |
| TITLE | Complementary sequences 1700 nucleotides apart form a ribonuclease III cleavage site in *Escherichia coli* ribosomal precursor RNA |
| JOURNAL | Proc. Natl. Acad. Sci. U.S.A. 75 (8), 3593-3597 (1978) |
| PUBMED | 358189 |
| REFERENCE | 140 |
| AUTHORS | Ohtsubo,H. and Ohtsubo,E. |
| TITLE | Nucleotide sequence of an insertion element, IS1 |
| JOURNAL | Proc. Natl. Acad. Sci. U.S.A. 75 (2), 615-619 (1978) |
| PUBMED | 273224 |
| REFERENCE | 141 |
| AUTHORS | Musso,R., Di Lauro,R., Rosenberg,M. and de Crombrugghe,B. |
| TITLE | Nucleotide sequence of the operator-promoter region of the galactose operon of *Escherichia coli* |
| JOURNAL | Proc. Natl. Acad. Sci. U.S.A. 74 (1), 106-110 (1977) |
| PUBMED | 319453 |

```
                       -continued
REFERENCE     142 (bases 1 to 4646332)
CONSRTM       NCBI Genome Project
TITLE         Direct Submission
JOURNAL       Submitted (10-NOV-2005) National Center for Biotechnology
              Information, NIH, Bethesda, MD 20894, USA REFERENCE     143 (bases 1 to 4646332)
AUTHORS       Mori,H., Horiuchi,T. and Hirai,A.
TITLE         Direct Submission
JOURNAL       Submitted (22-AUG-2005) Hirotada Mori, Graduate School of
              Biological Sciences, Nara Institute of Science and Technology;
              8916-5 Takayama, Ikoma, Nara 630-0101, Japan
              (E-mail:hmori@gtc.naist.jp, Tel:81-743-72-5660, Fax:81-743-72-
              5669)

COMMENT       PROVISIONAL REFSEQ: This record has not yet been subject to
              final
              NCBI review. The reference sequence was derived from AP009048.

COMPLETENESS: full length.

FEATURES      Location/Qualifiers source        complement(<1..>5861)
              /organism="Escherichia coli str. K-12 substr. W3110"
              /mol_type="genomic DNA"
              /strain="K-12"
              /sub_strain="W3110"
              /db_xref="taxon:316407"

gene          complement(<1..6)
              /gene="dcuD"

CDS           complement(<1..6)
              /gene="dcuD"
              /note="ECK3216:JW3196:b3227"
              /codon_start=1
              /transl_table=11
              /product="predicted transporter"
              /protein_id="AP 003769.1"
              /db_xref="GI:89109989"
                                                              (SEQ ID NO: 35)
/translation="MFGIIISVIVLITMGYLILKNYKPQVVLAAAGIFLMMCGVWLGF

GGVLDPTKSSGYLIVDIYNEILRMLSNRIAGLGLSIMAVGGYARYMERIGASRAMVSL

LSRPLKLIRSPYIILSATYVIGQIMAQFITSASGLGMLLMVTLFPTLVSLGVSRLSAV

AVIATTMSIEWGILETNSIFAAQVAGMKIATYFFHYQLPVASCVIISVAISHFFVQRA

FDKKDKNINHEQAEQKALDNVPPLYYAILPVMPLILMLGSLFLAHVGLMQSELHLVVV

MLLSLTVTMFVEFFRKHNLRETMDDVQAFFDGMGTQFANVVTLVVAGEIFAKGLTTIG

TVDAVIRGAEHSGLGGIGVMIIMALVIAICAIVMGSGNAPFMSFASLIPNIAAGLHVP

AVVMIMPMHFATTLARAVSPITAVVVVTSGIAGVSPFAVVKRTAIPMAVGFVVNMIAT

ITLFY"

primer        330..348
              /label="ck nanR3 control primer"

gene          386..1177
              /gene="nanR"

CDS           386..1177
              /gene="nanR"
              /note="ECK3215:JW3195:b3226"
              /codon_start=1
              /transl_table=11
              /product="DNA-binding transcriptional dual regulator"
              /protein_id="AP 003768.1"
              /db_xref="GI:89109988"
```

-continued (SEQ ID NO: 36)
/translation="MGLMNAFDSQTEDSSPAIGRNLRSRPLARKKLSEMVEEELEQMI
RRREFGEGEQLPSERELMAFFNVGRPSVREALAALKRKGLVQINNGERARVSRPSADT
IIGELSGMAKDFLSHPGGIAHFEQLRLFFESSLVRYAAEHATDEQIDLLAKALEINSQ
SLDNNAAFIRSDVDFHRVLAEIPGNPIFMAIHVALLDWLIAARPTVTDQALHEHNNVS
YQQHIAIVDAIRRHDPDEADRALQSHLNSVSATWHAFGQTTNKKK"

```
primer          1005..1025
                /label="nanR ck2 control primer"

primer          1126..1146
                /label="nanAFck control primer"

promoter        1178..1278
                /label="nan operon promoter region"

Site            1187..1191
                /site_type="binding site"
                /label="CAP binding"

Site            1198..1202
                /site_type="binding site"
                /label="CAP binding"

promoter        1241..1246
                /label=-10 primer_bind     1252..1301
                /note="for dnanA:: or dnanATE::scar deletions"
                /label="H1-dnanA lambda red primer"
mRNA 1255
                /label=+1 mRNA            1267
                /label=+13 mRNA            1279
                /label=+25 gene            1299..2192
                /gene="nanA"

CDS             1299..2192
                /gene="nanA"
                /note="ECK3214:JW3194:b3225"
                /codon_start=1
                /transl_table=11
                /product="N-acetylneuraminate lyase"
                /protein_id="AP 003767.1"
                /db_xref="GI:89109987"
```

(SEQ ID NO: 37)
/translation="MATNLRGVMAALLTPFDQQQALDKASLRRLVQFNIQQGIDGLYV
GGSTGEAFVQSLSEREQVLEIVAEEAKGKIKLIAHVGCVSTAESQQLAASAKRYGFDA
VSAVTPFYYPFSFEEHCDHYRAIIDSADGLPMVVYNIPALSGVKLTLDQINTLVTLPG
VGALKQTSGDLYQMEQIRREHPDLVLYNGYDEIFASGLLAGADGGIGSTYNIMGWRYQ
GIVKALKEGDIQTAQKLQTECNKVIDLLIKTGVFRGLKTVLHYMDVVSVPLCRKPFGP
VDEKYLPELKALAQQLMQERG"

```
Region          1302..4424
                /label="DELETION nanATE"

primer_bind     complement(2175..2224)
                /label="H2-dnanA lambda red primer"

gene            2301..3791
                /gene="nanT"

CDS             2301..3791
                /gene="nanT"
                /note="ECK3213:JW3193:b3224"
                /codon_start=1
```

```
                    -continued
                    /transl_table=11
                    /product="sialic acid transporter"
                    /protein_id="AP 003766.1"
                    /db_xref="GI:89109986"
                                                                        (SEQ ID NO: 38)
/translation="MSTTTQNIPWYRHLNRAQWRAFSAAWLGYLLDGFDFVLIALVLT

EVQGEFGLTTVQAASLISAAFISRWFGGLMLGAMGDRYGRRLAMVTSIVLFSAGTLAC

GFAPGYITMFIARLVIGMGMAGEYGSSATYVIESWPKHLRNKASGFLISGFSVGAVVA

AQVYSLVVPVWGWRALFFIGILPIIFALWLRKNIPEAEDWKEKHAGKAPVRTMVDILY

RGEHRIANIVMTLAAATALWFCFAGNLQNAAIVAVLGLLCAAIFISFMVQSAGKRWPT

GVMLMVVVLFAFLYSWPIQALLPTYLKTDLAYNPHTVANVLFFSGFGAAVGCCVGGFL

GDWLGTRKAYVCSLLASQLLIIPVFAIGGANVWVLGLLLFFQQMLGQGIAGILPKLIG

GYFDTDQRAAGLGFTYNVGALGGALAPIIGALIAQRLDLGTALASLSFSLTFVVILLI

GLDMPSRVQRWLRPEALRTHDAIDGKPFSGAVPFGSAKNDLVKTKS"

primer           complement(2329..2350)
                 /label="nanARck control primer"

primer_bind      3792..3841
                 /label="H1-dnanE lambda red primer"

gene             3839..4528
                 /gene="nanE"

CDS              3839..4528
                 /gene="nanE"
                 /note="ECK3212:JW3192:b3223"
                 /codon_start=1
                 /transl_table=11
                 /product="predicted N-acetylmannosamine-6-P
                 epimerase"
                 /protein_id="AP 003765.1"
                 /db_xref="GI:89109985"
                                                                        (SEQ ID NO: 39)
/translation="MSLLAQLDQKIAANGGLIVSCQPVPDSPLDKPEIVAAMALAAEQ

AGAVAIRIEGVANLQATRAVVSVPIIGIVKRDLEDSPVRITAYIEDVDALAQAGADII

AIDGTDRPRPVPVETLLARIHHHGLLAMTDCSTPEDGLACQKLGAEIIGTTLSGYTTP

ETPEEPDLALVKTLSDAGCRVIAEGRYNTPAQAADAMRHGAWAVTVGSAITRLEHICQ

WYNTAMKKAVL"

primer_bind      complement(4425..4474)
                 /note="for dnanATE::scar deletion"
                 /label="H2-dnanE lambda red primer"

RBS              4425..4448
                 /label="C-terminal gibberish peptide fused to KD13
                 scar peptide"

RBS              4449..4451
                 /label="NEW STOP gibberish peptide after resolution
                 of cassette"

primer_bind      4486..4530
                 /label="nanK-H1 lambda red primer"

RBS              4515..4520
                 /label="nanK RBS"

gene             4525..5400
                 /gene="nanK"

CDS              4525..5400
                 /gene="nanK"
                 /note="ECK3211:JW5538:b3222"
                 /codon_start=1
                 /transl_table=11
                 /product="predicted N-acetylmannosamine kinase"
```

```
                    /protein_id="AP 003764.1"
                    /db_xref="GI:89109984"
                                                        (SEQ ID NO:40)
/translation="MTTLAIDIGGTKLAAALIGADGQIRDRRELPTPASQTPEALRDA
LSALVSPLQAHAQRVAIASTGIIRDGSLLALNPHNLGGLLHFPLVKTLEQLTNLPTIA
INDAQAAAWAEFQALDGDITDMVFITVSTGVGGGVVSGCKLLTGPGGLAGHIGHTLAD
PHGPVCGCGRTGCVEAIASGRGIAAAAQGELAGADAKTIFTRAGQGDEQAQQLIHRSA
RTLARLIADIKATTDCQCVVVGGSVGLAEGYLALVETYLAQEPAAFHVDLLAAHYRHD
AGLLGAALLAQGEKL"
RBS             4526..4528
                /label="Native Stop for NanE"
primer          complement(5065..5083)
                /label="nanKckl control primer"
primer_bind     complement(5380..5424)
                /label="nanK-H2 lambda red primer"
gene            5397..5861
                /gene="yhcH"
CDS             5397..5861
                /gene="yhcH"
                /note="ECK3210:JW3190:b3221"
                /codon_start=1
                /transl_table=11
                /product="hypothetical protein"
                /protein_id="AP 003763.1"
                /db_xref="GI:89109983"
                                                        (SEQ ID NO: 41)
/translation="MMMGEVQSLPSAGLHPALQDALTLALAARPQEKAPGRYELQGDN
IFMNVMTFNTQSPVEKKAELHEQYIDIQLLLNGEERILFGMAGTARQCEEFHHEDDYQ
LCSTIDNEQAIILKPGMFAVFMPGEPHKPGCVVGEPGEIKKVVVKVKADLMA"
ORIGIN
                                                        (SEQ ID NO: 42)
     1      GAACATTGTT GAACTCCGTG TCAAAAGAAA ACGGTCAATC CCATAAACGG CAGATTGAAA
    61      ACAACGATGT TATATTTTTT GCAAGGCTAT TTATGGTGCG GATGTCGTGT TTTTAATTGT
   121      AGGTGAGGTG ATTTTTCATT AAAAAATATG CGCTTATGAT TATTTTGTAA GAACACATTC
   181      ATAATATTCA TAATGCTCGT GAATAGTCTT ATAAATAATT CAAACGGGAT GTTTTTATCT
   241      GCGTTACATT AATTTTTCGC AATAGTTAAT TATTCCGTTA ATTATGGTAA TGATGAGGCA
   301      CAAAGAGAAA ACCCTGCCAT TTTCCCCTAC TTTCAATCCT GTGATAGGAT GTCACTGATG
   361      ATGTTAATCA CACTGACCTT ACAGAATGGG CCTTATGAAC GCATTTGATT CGCAAACCGA
   421      AGATTCTTCA CCTGCAATTG GTCGCAACTT GCGTAGCCGC CCGCTGGCGC GTAAAAAACT
   481      CTCCGAAATG GTGGAAGAAG AGCTGGAACA GATGATCCGC CGTCGTGAAT TTGGCGAAGG
   541      TGAACAATTA CCGTCTGAAC GCGAACTGAT GGCGTTCTTT AACGTCGGGC GTCCTTCGGT
   601      GCGTGAAGCG CTGGCAGCGT TAAAACGCAA AGGTCTGGTG CAAATAAACA ACGGCGAACG
   661      CGCTCGCGTC TCGCGTCCTT CTGCGGACAC TATCATCGGT GAGCTTTCCG GCATGGCGAA
   721      AGATTTCCTT TCTCATCCCG GTGGGATTGC CCATTTCGAA CAATTACGTC TGTTCTTTGA
   781      ATCCAGTCTG GTGCGCTATG CGGCTGAACA TGCCACCGAT GAGCAAATCG ATTTGCTGGC
   841      AAAAGCACTG GAAATCAACA GTCAGTCGCT GGATAACAAC GCGGCATTCA TTCGTTCAGA
   901      CGTTGATTTC CACCGCGTGC TGGCGGAGAT CCCCGGTAAC CCAATCTTCA TGGCGATCCA
   961      CGTTGCCCTG CTCGACTGGC TTATTGCCGC ACGCCCAACG GTTACCGATC AGGCACTGCA
  1021      CGAACATAAC AACGTTAGTT ATCAACAGCA TATTGCGATC GTTGATGCGA TCCGCCGTCA
```

```
1081        TGATCCTGAC GAAGCCGATC GTGCGTTGCA ATCGCATCTC AACAGCGTCT CTGCTACCTG

1141        GCACGCTTTC GGTCAGACCA CCAACAAAAA GAAATAATGC CACTTTAGTG AAGCAGATCG

1201        CATTATAAGC TTTCTGTATG GGTGTTGCT TAATTGATCT GGTATAACAG GTATAAAGGT

1261        ATATCGTTTA TCAGACAAGC ATCACTTCAG AGGTATTTAT GGCAACGAAT TTACGTGGCG

1321        TAATGGCTGC ACTCCTGACT CCTTTTGACC AACAACAAGC ACTGGATAAA GCGAGTCTGC

1381        GTCGCCTGGT TCAGTTCAAT ATTCAGCAGG GCATCGACGG TTTATACGTG GGTGGTTCGA

1441        CCGGCGAGGC CTTTGTACAA AGCCTTTCCG AGCGTGAACA GGTACTGGAA ATCGTCGCCG

1501        AAGAGGCGAA AGGTAAGATT AAACTCATCG CCCACGTCGG TTGCGTCAGC ACCGCCGAAA

1561        GCCAACAACT TGCGGCATCG GCTAAACGTT ATGGCTTCGA TGCCGTCTCC GCCGTCACGC

1621        CGTTCTACTA TCCTTTCAGC TTTGAAGAAC ACTGCGATCA CTATCGGGCA ATTATTGATT

1681        CGGCGGATGG TTTGCCGATG GTGGTGTACA ACATTCCAGC CCTGAGTGGG GTAAAACTGA

1741        CCCTGGATCA GATCAACACA CTTGTTACAT TGCCTGGCGT AGGTGCGCTG AAACAGACCT

1801        CTGGCGATCT CTATCAGATG GAGCAGATCC GTCGTGAACA TCCTGATCTT GTGCTCTATA

1861        ACGGTTACGA CGAAATCTTC GCCTCTGGTC TGCTGGCGGG CGCTGATGGT GGTATCGGCA

1921        GTACCTACAA CATCATGGGC TGGCGCTATC AGGGGATCGT TAAGGCGCTG AAAGAAGGCG

1981        ATATCCAGAC CGCGCAGAAA CTGCAAACTG AATGCAATAA AGTCATTGAT TTACTGATCA

2041        AAACGGGCGT ATTCCGCGGC CTGAAAACTG TCCTCCATTA TATGGATGTC GTTTCTGTGC

2101        CGCTGTGCCG CAAACCGTTT GGACCGGTAG ATGAAAAATA TCTGCCAGAA CTGAAGGCGC

2161        TGGCCCAGCA GTTGATGCAA GAGCGCGGGT GAGTTGTTTC CCCTCGCTCG CCCCTACCGG

2221        GTGAGGGGAA ATAAACGCAT CTGTACCCTA CAATTTTCAT ACCAAAGCGT GTGGGCATCG

2281        CCCACCGCGG GAGACTCACA ATGAGTACTA CAACCCAGAA TATCCCGTGG TATCGCCATC

2341        TCAACCGTGC ACAATGGCGC GCATTTTCCG CTGCCTGGTT GGGATATCTG CTTGACGGTT

2401        TTGATTTCGT TTTAATCGCC CTGGTACTCA CCGAAGTACA AGGTGAATTC GGGCTGACGA

2461        CGGTGCAGGC GGCAAGTCTG ATCTCTGCAG CCTTTATCTC TCGCTGGTTC GGCGGCCTGA

2521        TGCTCGGCGC TATGGGTGAC CGCTACGGGC GTCGTCTGGC AATGGTCACC AGCATCGTTC

2581        TCTTCTCGGC CGGGACGCTG GCCTGCGGCT TTGCGCCAGG CTACATCACC ATGTTTATCG

2641        CTCGTCTGGT CATCGGCATG GGGATGGCGG GTGAATACGG TTCCAGCGCC ACCTATGTCA

2701        TTGAAAGCTG GCCAAAACAT CTGCGTAACA AAGCCAGTGG TTTTTTGATT TCAGGCTTCT

2761        CTGTGGGGGC CGTCGTTGCC GCTCAGGTCT ATAGCCTGGT GGTTCCGGTC TGGGGCTGGC

2821        GTGCGCTGTT CTTTATCGGC ATTTTGCCAA TCATCTTTGC TCTCTGGCTG CGTAAAAACA

2881        TCCCGGAAGC GGAAGACTGG AAAGAGAAAC ACGCAGGTAA AGCACCAGTA CGCACAATGG

2941        TGGATATTCT CTACCGTGGT GAACATCGCA TTGCCAATAT CGTAATGACA CTGGCGGCGG

3001        CTACTGCGCT GTGGTTCTGC TTCGCCGGTA ACCTGCAAAA TGCCGCGATC GTCGCTGTTC

3061        TTGGGCTGTT ATGCGCCGCA ATCTTTATCA GCTTTATGGT GCAGAGTGCA GGCAAACGCT

3121        GGCCAACGGG CGTAATGCTG ATGGTGGTCG TGTTGTTTGC TTTCCTCTAC TCATGGCCGA

3181        TTCAGGCGCT GCTGCCAACG TATCTGAAAA CCGATCTGGC TTATAACCCG CATACTGTAG

3241        CCAATGTGCT GTTCTTTAGT GGCTTTGGCG CGGCGGTGGG ATGCTGCGTA GGTGGCTTCC

3301        TCGGTGACTG GCTGGGAACC GCAAAGCGT ACGTTTGTAG CCTGCTGGCC TCGCAGCTGC

3361        TGATTATTCC GGTATTTGCG ATTGGCGGCG CAAACGTCTG GGTGCTCGGT CTGTTACTGT

3421        TCTTCCAGCA AATGCTTGGA CAAGGGATCC CCGGGATCTT ACCAAAACTG ATTGGCGGTT

3481        ATTTCGATAC CGACCAGCGT GCAGCGGGCC TGGGCTTTAC CTACAACGTT GGCGCATTGG
```

-continued

```
3541        GCGGTGCACT GGCCCCAATC ATCGGCGCGT TGATCGCTCA ACGTCTGGAT CTGGGTACTG
3601        CGCTGGCATC GCTCTCGTTC AGTCTGACGT TCGTGGTGAT CCTGCTGATT GGGCTGGATA
3661        TGCCTTCTCG CGTTCAGCGT TGGTTGCGCC CGGAAGCGTT GCGTACTCAT GACGCTATCG
3721        ACGGTAAACC ATTCAGCGGT GCCGTGCCGT TTGGCAGCGC CAAAAACGAT TTAGTCAAAA
3781        CCAAAAGTTA ATCCTGTTGC CCGGTCTATG TACCGGGCCT TTCGCTAAGG GAAGATGTAT
3841        GTCGTTACTT GCACAACTGG ATCAAAAAAT CGCTGCTAAC GGTGGCCTGA TTGTCTCCTG
3901        CCAGCCGGTT CCGGACAGCC CGCTCGATAA ACCCGAAATC GTCGCCGCCA TGGCATTAGC
3961        GGCAGAACAG GCGGGCGCGG TTGCCATTCG CATTGAAGGT GTGGCAAATC TGCAAGCCAC
4021        GCGTGCGGTG GTGAGCGTGC CGATTATTGG AATTGTGAAA CGCGATCTGG AGGATTCTCC
4081        GGTACGCATC ACGGCCTATA TTGAAGATGT TGATGCGCTG GCGCAGGCGG GCGCGGACAT
4141        TATCGCCATT GACGGCACCG ACCGCCCGCG TCCGGTGCCT GTTGAAACGC TGCTGGCACG
4201        TATTCACCAT CACGGTTTAC TGGCGATGAC CGACTGCTCA ACGCCGGAAG ACGGCCTGGC
4261        ATGCCAAAAG CTGGGAGCCG AAATTATTGG CACTACGCTT TCTGGCTATA CCACGCCTGA
4321        AACGCCAGAA GAGCCGGATC TGGCGCTGGT GAAAACGTTG AGCGACGCCG ATGTCGGGT
4381        GATTGCCGAA GGGCGTTACA ACACGCCTGC TCAGGCGGCG GATGCGATGC GCCACGGCGC
4441        GTGGGCGGTG ACGGTCGGTT CTGCAATCAC GCGTCTTGAG CACATTTGTC AGTGGTACAA
4501        CACAGCGATG AAAAAGGCGG TGCTATGACC ACACTGGCGA TTGATATCGG CGGTACTAAA
4561        CTTGCCGCCG CGCTGATTGG CGCTGACGGG CAGATCCGCG ATCGTCGTGA ACTTCCTACG
4621        CCAGCCAGCC AGACACCAGA AGCCTTGCGT GATGCCTTAT CCGCATTAGT CTCTCCGTTG
4681        CAAGCTCATG CGCAGCGGGT TGCCATCGCT TCGACCGGGA TAATCCGTGA CGGCAGCTTG
4741        CTGGCGCTTA ATCCGCATAA TCTTGGTGGA TTGCTACACT TTCCGTTAGT CAAAACGCTG
4801        GAACAACTTA CCAATTTGCC GACCATTGCC ATTAACGACG CGCAGGCCGC AGCATGGGCG
4861        GAGTTTCAGG CGCTGGATGG CGATATAACC GATATGGTCT TTATCACCGT TTCCACCGGC
4921        GTTGGCGGCG GTGTAGTGAG CGGCTGCAAA CTGCTTACCG GCCCTGGCGG TCTGGCGGGG
4981        CATATCGGGC ATACGCTTGC CGATCCACAC GGCCCAGTCT GCGGCTGTGG ACGCACAGGT
5041        TGCGTGGAAG CGATTGCTTC TGGTCGCGGC ATTGCAGCGG CAGCGCAGGG GGAGTTGGCT
5101        GGCGCGGATG CGAAAACTAT TTTCACGCGC GCCGGGCAGG GTGACGAGCA GGCGCAGCAG
5161        CTGATTCACC GCTCCGCACG TACGCTTGCA AGGCTGATCG CTGATATTAA AGCCACAACT
5221        GATTGCCAGT GCGTGGTGGT CGGTGGCAGC GTTGGTCTGG CAGAAGGGTA TCTGGCGCTG
5281        GTGGAAACGT ATCTGGCGCA GGAGCCAGCG GCATTTCATG TTGATTTACT GGCGGCGCAT
5341        TACCGCCATG ATGCAGGTTT ACTTGGGGCT GCGCTGTTGG CCCAGGGAGA AAAATTATGA
5401        TGATGGGTGA AGTACAGTCA TTACCGTCTG CTGGGTTACA TCCTGCGTTA CAGGACGCGT
5461        TAACGCTGGC ATTAGCTGCC AGACCGCAAG AAAAAGCGCC GGGTCGTTAC GAATTACAGG
5521        GCGACAATAT CTTTATGAAT GTCATGACGT TTAACACTCA ATCGCCCGTC GAGAAAAAAG
5581        CGGAATTGCA CGAGCAATAC ATTGATATCC AGCTGTTATT AAACGGTGAG GAACGGATTC
5641        TGTTTGGCAT GGCAGGCACT GCGCGTCAGT GTGAAGAGTT CCACCATGAG GATGATTATC
5701        AGCTTTGCAG CACCATTGAT AACGAGCAAG CCATCATCTT AAAACCGGGA ATGTTCGCCG
5761        TGTTTATGCC AGGTGAACCG CATAAACCAG GATGCGTTGT CGGCGAGCCT GGAGAGATTA
5821        AAAAGGTTGT GGTGAAGGTT AAGGCTGATT TAATGGCTTA A
//
```

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

---

What is claimed is:

1. A method for producing a sialylated oligosaccharide in an *Escherichia coli* (*E. coli*) bacterium, wherein said sialylated oligosaccharide comprises 3'-sialyllactose (3'-SL) or 6'-sialyllactose (6'-SL), said method comprising:
   (i) providing an *E. coli* bacterium, said bacterium comprising
      an exogenous sialyl-transferase comprising an α(2,3) sialyl-transferase, an α(2,6) sialyl-transferase, or an α(2,8) sialyltransferase,
      a mutation in an endogenous N-acetylneuraminate lyase gene (nanA), wherein said bacterium comprises an endogenous N-acetylmannosamine kinase gene (nanK) that is not mutated,
      an increased UDP-GlcNAc production capability comprising overexpression of nagC, such that the bacterium produces at least 10% more UDP-GlcNAc than a native *E. coli* bacterium,
      a sialic acid synthetic capability, and
      a functional lactose permease gene,
   and
   (ii) culturing said bacterium in the presence of lactose.

2. The method of claim 1, wherein said bacterium comprises a null mutation in any one of the genes selected from endogenous N-acetylneuraminate lyase gene (nanA), endogenous N-acetylmannosamine-6-phosphate epimerase gene (nanE), and endogenous N-acetylneuraminic acid transporter gene (nanT), or any combination thereof.

3. The method of claim 1, wherein said bacterium comprises a null mutation in an endogenous N-acetylneuraminate lyase gene (nanA).

4. The method of claim 1, wherein said bacterium comprises an endogenous N-acetylmannosamine-6-phosphate epimerase gene (nanE) that is not mutated, and (i) a null mutation in the endogenous N-acetylneuraminate lyase gene (nanA), (ii) a null mutation in an endogenous N-acetylneuraminic acid transporter gene (nanT), or (iii) a null mutation in the endogenous N-acetylneuraminate lyase gene (nanA) and a null mutation in the endogenous N-acetylneuraminic acid transporter gene (nanT).

5. The method of claim 1, wherein said bacterium comprises a null mutation in endogenous N-acetylneuraminate lyase gene (nanA), and a null mutation in endogenous N-acetylmannosamine-6-phosphate epimerase gene (nanE).

6. The method of claim 1, wherein said sialic acid synthetic capability comprises an exogenous CMP-Neu5Ac synthetase gene (neuA), an exogenous sialic acid synthase gene (neuB), and an exogenous UDP-GlcNac 2-epimerase (neuC).

7. The method of claim 1, wherein said α(2,3) sialyl-transferase, α(2,6) sialyl-transferase, or α(2,8) sialyltransferase, comprises a sequence of a *Photobacterium* sp. sialyltransferase, *Campylobacter jejuni* sialyl-transferase, *Neisseria meningitides* sialyl-transferase, or *Neisseria gonorrhoeae* sialyl-transferase.

8. The method claim 1, wherein said sialylated oligosaccharide comprises 6' sialyllactose (6'-SL).

9. The method of claim 1, wherein said bacterium comprises a deleted or inactivated endogenous β-galactosidase gene.

10. The method of claim 9, wherein said deleted or inactivated β-galactosidase gene comprises an *E. coli* lacZ gene.

11. The method of claim 1, wherein said bacterium comprises a recombinant β-galactosidase gene providing a level of β-galactosidase activity between 0.05 and 200 units.

12. The method of claim 1, wherein said bacterium further comprises a deleted, inactivated, or mutated lacA gene.

13. The method of claim 1, wherein said *E. coli* bacterium comprises an increased UDP-GlcNAc production capability, such that it produces at least 20% more UDP-GlcNAc than a native *E. coli* bacterium.

14. The method of claim 1, wherein said increased UDP-GlcNAc production capability further comprises overexpression of a glmS gene, a glmY gene, a glmZ gene or any combination thereof.

15. The method of claim 1, wherein said increased UDP-GlcNAc production capability comprises overexpression of nagC and glmS.

16. The method of claim 1, wherein said increased UDP-GlcNAc production capability comprises overexpression of nagC and glmY.

17. The method of claim 1, wherein said increased UDP-GlcNAc production capability comprises overexpression of nagC and glmZ.

18. A method of purifying a sialylated oligosaccharide produced by the method of claim 1, comprising binding said sialylated oligosaccharide from a bacterial cell lysate or bacterial cell culture supernatant of said bacterium to a carbon column, and eluting said sialylated oligosaccharide from said column.

19. A purified sialylated oligosaccharide produced by the method of claim 1.

20. The method of claim 1, further comprising retrieving said sialylated oligosaccharide from said bacterium or from a culture supernatant of said bacterium.

21. The method of claim 1, wherein said bacterium comprises a mutation in an endogenous N-acetylmannosamine-6-phosphate epimerase gene (nanE).

22. The method of claim 1, wherein said bacterium comprises an endogenous N-acetylneuraminic acid transporter gene (nanT) gene that is not mutated.

23. The method of claim 1, wherein said sialylated oligosaccharide comprises 3'-sialyllactose (3'-SL).

24. The method of claim 1, wherein said mutation is within the coding region of nanA.

25. The method of claim 24, wherein the mutation comprises an amino acid deletion or insertion.

26. The method of claim 25, wherein the mutation causes a loss of function of a nanA gene product or loss of production of a nanA gene product.

* * * * *